United States Patent
Haining et al.

(10) Patent No.: US 11,740,242 B2
(45) Date of Patent: Aug. 29, 2023

(54) MODULATING BIOMARKERS TO INCREASE TUMOR IMMUNITY AND IMPROVE THE EFFICACY OF CANCER IMMUNOTHERAPY

(71) Applicant: Dana-Farber Cancer Institute, Inc., Boston, MA (US)

(72) Inventors: William N. Haining, Newton, MA (US); Robert Manguso, Boston, MA (US); Adrienne Long, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 229 days.

(21) Appl. No.: 16/629,176

(22) PCT Filed: Jul. 16, 2018

(86) PCT No.: PCT/US2018/042243
§ 371 (c)(1),
(2) Date: Jan. 7, 2020

(87) PCT Pub. No.: WO2019/014665
PCT Pub. Date: Jan. 17, 2019

(65) Prior Publication Data
US 2020/0300857 A1    Sep. 24, 2020

Related U.S. Application Data

(60) Provisional application No. 62/532,594, filed on Jul. 14, 2017.

(51) Int. Cl.
*G01N 33/574* (2006.01)
*A01K 67/027* (2006.01)
*C12N 15/113* (2010.01)

(52) U.S. Cl.
CPC ........ *G01N 33/574* (2013.01); *A01K 67/027* (2013.01); *C12N 15/1138* (2013.01); *A01K 2227/105* (2013.01); *A01K 2267/0331* (2013.01); *G01N 2333/70539* (2013.01)

(58) Field of Classification Search
CPC .................................................... G01N 33/574
USPC ......................................................... 435/7.23
See application file for complete search history.

(56) References Cited

U.S. PATENT DOCUMENTS

| 2013/0165504 A1 | 6/2013 | Bancel et al. |
| 2014/0010825 A1 | 1/2014 | Ravindranath et al. |
| 2016/0122829 A1 | 5/2016 | Hammerman |

FOREIGN PATENT DOCUMENTS

| WO | WO-2012/094252 A1 | 7/2012 |
| WO | WO-2019/014665 A1 | 1/2019 |

OTHER PUBLICATIONS

Gooden et al (PNAS, 2011, 108(26): 10656-10661).*
Levy et al (International Journal of Oncology, 2008, 32: 633-641).*
Gonzalez et al (Cancer Biology & Therapy, 2012, 13(): 71-76).*
Wischhusen et al (J Neuropathol Exp Neurol, 2005, 64(6): 523-528).*
Sola et al (Cancer Res, 2016, 76(14_Supp): Abstract 2342).*
Carotta (Frontiers in Immunology, 2016, 7(152): 1-10).*
Yuan et al (Cancer Biology & Therapy, 2010, 9(9): 710-716).*
International Search Report and Written Opinion for International Application No. PCT/US2018/042243 dated Dec. 11, 2018.
Manguso et al., "In vivo CRISPR screening identifies Ptpn2 as a cancer immunotherapy target," Nature, 547:413-418 (2017).
Zhen et al., "HLA-E inhibitor enhances the killing of neuroblastoma stem cells by co-cultured dendritic cells and cytokine-induced killer cells loaded with membrane-based microparticles," American journal of cancer research, 7(2):334-345 (2017).

* cited by examiner

*Primary Examiner* — Sean E Aeder
(74) *Attorney, Agent, or Firm* — Foley Hoag LLP

(57) ABSTRACT

The present invention relates, in part, to methods of treating a cancer in a subject comprising administering to the subject a therapeutically effective amount of an agent that inhibits one or more biomarkers listed in Table 1 in combination with an immunotherapy.

4 Claims, 21 Drawing Sheets

Specification includes a Sequence Listing.

E

F

Gooden et al, PNAS 2011

HNSCC: IR= *ex vivo* immune response

A

Influx of immune cells

B

NKG2A⁺ TIL

C

Enhanced Qa-1 expression on tumor

Also found in B16 model

A

B

A

B

C

D

E

A NKG2A expression on TIL

B ....on CD8 T cells after PD-1 therapy

MODULATING BIOMARKERS TO INCREASE TUMOR IMMUNITY AND IMPROVE THE EFFICACY OF CANCER IMMUNOTHERAPY

CROSS-REFERENCE TO RELATED APPLICATIONS

This application is the U.S. national phase of International Patent Application No. PCT/US2018/042243, filed on 16 Jul. 2018, which claims the benefit of priority to U.S. Provisional Application Ser. No. 62/532,594, filed on 14 Jul. 2017; the entire contents of each of said applications are incorporated herein in their entirety by this reference.

BACKGROUND OF THE INVENTION

The striking clinical success of cancer immunotherapy with checkpoint blockade suggests it is likely to form the foundation of curative therapy for many malignancies (Reck et al. (2016) *N. Engl. J. Med.* 375:1823-1833; Hodi et al. (2010) *N. Engl. J. Med.* 363:711-723; Postow et al. (2015) *N. Engl. J. Med.* 372:2006-2017; Wolchok et al. (2013) *N. Engl. Med.* 369:122-133; Ferris et al. (2016) *N. Engl. J. Med.* 375:1856-1867; Brahmer et al. (2012) *N. Engl. J. Med.* 366:2455-2465; Nghiem et al. (2016) *N. Engl. J. Med.* 374:2542-2552; Topalian et al. (2012) *N. Engl. J. Med.* 366:2443-2454); Motzer et al. (2015) *N. Engl. Med.* 373: 1803-1813). However, despite these successes, checkpoint blockade does not achieve sustained clinical response in most patients (Tumeh et al. (2014) *Nature* 515:568-571; Kelderman et al. (2014) *Mol. Oncol.* 8:1132-1139; Zaretsky et al. (2016) *N. Engl. Med.* 375:819-829). Additional therapeutic strategies are therefore needed to increase the clinical efficacy of immunotherapy. Moreover, the optimal strategy for combining emerging cancer immunotherapies with checkpoint blockade remains uncertain.

A relatively small number of genes, such as PD-L1, that enable tumors to evade the immune system have been discovered and most of these are already the focus of intense efforts to develop new immunotherapies (Freeman et al. (2000) *J. Exp. Med.* 192:1027-1034; Hirano et al. (2005) *Cancer Res.* 65:1089-1096; Dong et al. (2002) *Nat. Med.* 8:793-800; Balachandran et al. (2011) *Nat. Med.* 17:1094-1100; Spranger et al. (2013) *Sci Transl Med.* 5:200ra116; Holmgaard et al. (2013) *J. Exp. Med.* 210:1389-1402; Sockolosky et al. (2016) *Proc. Natl. Acad. Sci. U.S.A.* 113:E2646-654; Liu et al. (2015) *Nat. Med.* 21:1209-1215; Weiskopf et al. (2016) *J. Clin. Invest.* 126:2610-2620; Tseng et al. (2013) *Proc. Natl. Acad. Sci. U.S.A.* 110: 11103-11108; Sica et al. (2003) *Immunity* 18:849-861; Zang et al. (2007) *Proc. Natl. Acad. Sci. U.S.A.* 104, 19458-19463). Although cancer cells could, in theory, express many more genes that regulate their response or resistance to tumor immunity, strategies to systematically discover such genes are lacking.

Loss-of-function genetic screens have been increasingly used to study the functional consequences of gene deletion on tumor cells (Howard et al. (2016) Functional Genomic Characterization of Cancer Genomes. *Cold Spring Harb. Symp. Quant. Biol.* (2016); Ebert et al. (2008) *Nature* 451:335-339; Cowley et al. (2014) *Scientific Data* 1: article number 140035). These approaches include pooled genetic screens using CRISPR-Cas9-mediated genome editing that simultaneously test the role of a large number of genes on tumor cell growth, viability or drug resistance (Wang et al. (2014) *Science* 343:80-84; Shalem et al. (2014) *Science* 343:84-87). However, these screens have generally been conducted in vitro, where the contribution of the immune system is absent, or have studied phenotypes such as metastasis that do not directly evaluate the role of tumor immunity (Hart et al. (2015) *Cell* 163:1515-1526; Yu et al. (2016) *Nat. Biotechnol.* 34:419-423; Chen et al. (2015) *Cell* 160:1246-1260).

Despite the dramatic clinical success of cancer immunotherapy with PD-1 checkpoint blockade, most patients do not experience sustained clinical benefit from treatment. Accordingly a great need in the art exists for additional therapeutic strategies.

SUMMARY OF THE INVENTION

The present invention is based, at least in part, on the discovery that inhibiting or blocking one or more biomarkers listed in Table 1, such as one or more regulators of antigen processing and presentation (e.g., HLA-E, Pdia3, Calr, Tap1, Tap2, Tapbp, and/or Erap1), in combination with an immunotherapy, results in a synergistic therapeutic benefit for treating cancers that is unexpected given the lack of such benefit observed for the immunotherapy alone.

In one aspect, a method of treating a subject afflicted with a cancer comprising administering to the subject a therapeutically effective amount of an agent that inhibits the copy number, the expression level, and/or the activity of one or more biomarkers listed in Table 1 or a fragment thereof, in combination with an immunotherapy, is provided.

Numerous embodiments are further provided that can be applied to any aspect of the present invention and/or combined with any other embodiment described herein. For example, in one embodiment, the agent described herein decreases the copy number, the expression level, and/or the activity of one or more biomarkers in Table 1 (e.g., one or more regulators of antigen processing and presentation (e.g., HLA-E, Pdia3, Calr, Tap1, Tap2, Tapbp, and/or Erap1). In another embodiment, the agent selectively decreases the activity of one or more biomarkers in Table 1, such as decreasing the antigen processing and presentation activity and/or the substrate binding activity of one or more regulators of antigen processing and presentation (e.g., HLA-E, Pdia3, Calr, Tap1, Tap2, Tapbp, and/or Erap1). In still another embodiment, the agent described herein antagonizes NKG2A-HLA-E interaction. In yet another embodiment, the agent described herein decreases the copy number, the expression level, and/or the activity of HLA-E, Pdia3, Calr, Tap1, Tap2, Tapbp, and/or Erap1. In one embodiment, the agent described herein selectively decreases the catalytic activity and/or the substrate binding activity of HLA-E. In still another embodiment, the agent described herein is a small molecule inhibitor, CRISPR single-guide RNA (sgRNA), RNA interfering agent, antisense oligonucleotide, peptide or peptidomimetic inhibitor, aptamer, or intrabody. In another embodiment, the RNA interfering agent is a small interfering RNA (siRNA), CRISPR RNA (crRNA), a small hairpin RNA (shRNA), a microRNA (miRNA), or a piwi-interacting RNA (piRNA). In still another embodiment, the RNA interfering agent is a CRISPR single-guide RNA (sgRNA). In yet another embodiment, the sgRNA comprises a nucleic acid sequence selected from the group consisting of nucleic acid sequence listed in Table 2. In one embodiment, the agent described herein comprises an intrabody, or an antigen binding fragment thereof, which specifically binds to the one or more biomarkers in Table 1 and/or a substrate of the one or more biomarkers in Table 1. In another embodiment, the agent described herein comprises an intrabody, or an antigen binding fragment thereof, which specifically binds to HLA-E and/or a substrate of HLA-E. In still another embodiment, the intrabody, or antigen binding fragment thereof, is murine, chimeric, humanized, composite, or human. In yet another embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In one another embodiment, the intrabody, or antigen binding fragment thereof, is conjugated to a cytotoxic agent. In another embodiment, the cytotoxic agent is selected from the group consisting of a chemotherapeutic agent, a biologic agent, a toxin, and a radioactive isotope. In still another embodiment, the agent described herein increases the sensitivity of the cancer cells to an immunotherapy. In another embodiment, the immunotherapy and/or a cancer therapy is administered before, after, or concurrently with the agent. In still another embodiment, the immunotherapy comprises an anti-cancer vaccine and/or virus. In yet embodiment, the immunotherapy is cell-based. In one embodiment, immunotherapy inhibits an immune checkpoint. In another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR. In still another embodiment, the immune checkpoint is selected from the group consisting of PD-1, PD-L1, and PD-L2. In yet another embodiment, the immune checkpoint is PD-1. In one embodiment, the cancer therapy described herein is selected from the group consisting of radiation, a radiosensitizer, an immunogenic chemotherapy (e.g., 5'-fluorouracil, anthracyclines, such as doxorubicin, and the platinum drug, oxaliplatin) that induce interferon production by the cancer cells or at the site of a tumor, interferon, an interferon-inducing agent, a topical inflammatory agent, and a topical TLR agonist. In still another embodiment, the one or more biomarkers described herein comprise a nucleic acid sequence having at least 95% identity to a nucleic acid sequence listed in Table 1 and/or encode an amino acid sequence having at least 95% identity to an amino acid sequence listed in Table 1. In another embodiment, the HLA-E is a human HLA-E, a mouse H2-T23, a chimeric HLA-E, or a fusion HLA-E. In still another embodiment, the HLA-E comprises an amino acid sequence listed in Table 1, such as an amino acid sequence is selected from the group consisting of SEQ ID Nos: 2, 4, 6, 8, 10, 12, and 14. In yet another embodiment, the HLA-E is encoded by a nucleic acid sequence listed in Table 1, such as a nucleic acid sequence is selected from the group consisting of SEQ ID Nos: 1, 3, 5, 7, 9, 11, and 13. In another embodiment, the agent described herein reduces the number of proliferating cells in the cancer and/or reduces the volume or size of a tumor comprising the cancer cells. In another embodiment, the agent increases the sensitivity of the cancer to the immunotherapy. In still another embodiment, the immunotherapy is T-cell-mediated. In yet another embodiment, the agent increases the amount of CD8+ T cells in a tumor comprising the cancer cells. In another embodiment, the cancer described herein is selected from the group consisting of melanoma and colorectal cancer. In another embodiment, the cancer is melanoma. In still another embodiment, the subject described herein is an animal model of the cancer. In another embodiment, the animal model is a mouse model. In still another embodiment, the subject is a mammal. In yet another embodiment, the mammal is a mouse or a human. In one embodiment, the mammal is a human. In another embodiment, the agent described herein is administered in a pharmaceutically acceptable formulation.

In another aspect, a method of killing cancer cells comprising contacting the cancer cells with an agent that inhibits the copy number, the expression level, and/or the activity of one or more biomarkers listed in Table 1 or a fragment thereof, in combination with an immunotherapy, is provided.

As described above, numerous embodiments are further provided that can be applied to any aspect of the present invention and/or combined with any other embodiment described herein. For example, in one embodiment, the agent described herein decreases the copy number, the expression level, and/or the activity of HLA-E, Pdia3, Calr, Tap1, Tap2, Tapbp, and/or Erap1. In another embodiment, the agent described herein selectively decreases the catalytic activity and/or the substrate binding activity of HLA-E. In still another embodiment, the agent is a small molecule inhibitor, CRISPR single-guide RNA (sgRNA), RNA interfering agent, antisense oligonucleotide, peptide or peptidomimetic inhibitor, aptamer, or intrabody. In yet another embodiment, the RNA interfering agent is a small interfering RNA (siRNA), CRISPR RNA (crRNA), a small hairpin RNA (shRNA), a microRNA (miRNA), or a piwi-interacting RNA (piRNA). In one embodiment, the RNA interfering agent is a CRISPR single-guide RNA (sgRNA). In another embodiment, the sgRNA comprises a nucleic acid sequence selected from the group consisting of nucleic acid sequence listed in Table 2. In still another embodiment, the agent comprises an intrabody, or an antigen binding fragment thereof, which specifically binds to HLA-E and/or a substrate of HLA-E. In yet another embodiment, the intrabody, or antigen binding fragment thereof, is murine, chimeric, humanized, composite, or human. In one embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In another embodiment, the intrabody, or antigen binding fragment thereof, is conjugated to a cytotoxic agent. In still another embodiment, the cytotoxic agent is selected from the group consisting of a chemotherapeutic agent, a biologic agent, a toxin, and a radioactive isotope. In yet another embodiment, the agent described herein increases the sensitivity of the cancer cells to an immunotherapy. In one embodiment, the cancer cells are contacted with an immunotherapy and/or a cancer therapy before, after, or concurrently with the agent. In another embodiment, the immunotherapy comprises an anti-cancer vaccine and/or virus. In still another embodiment, the immunotherapy is cell-based. In yet another embodiment, the immunotherapy inhibits an immune checkpoint. In one embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR. In one embodiment, the cancer therapy is selected from the group consisting of radiation, a radiosensitizer, an immunogenic chemotherapy (e.g., 5'-fluorouracil, anthracyclines, such as doxorubicin, and the platinum drug, oxaliplatin) that induce interferon production by the cancer cells or at the site of a tumor, interferon, an interferon-inducing agent, a topical inflammatory agent, and a topical TLR agonist. In another embodiment, the biomarker comprises a nucleic acid sequence having at least 95% identity to a nucleic acid sequence listed in Table 1 and/or encodes an amino acid sequence having at least 95% identity to an amino acid sequence listed in Table 1. In still another embodiment, the HLA-E is In still another embodiment, a human HLA-E, a mouse H2-T23, a chimeric HLA-E, or a fusion HLA-E. In one embodiment, the HLA-E described herein comprises an amino acid sequence listed in Table 1. In another embodiment, the amino acid sequence described herein. In still another embodiment, is selected from the group consisting of SEQ ID Nos: 2, 4, 6, 8, 10, 12, and 14. In still another embodiment, the HLA-E described herein is encoded by a nucleic acid sequence listed in Table 1. In yet another embodiment, the nucleic acid sequence is selected from the group consisting of SEQ ID Nos: 1, 3, 5, 7, 9, 11, and 13. In another embodiment, the agent reduces the number of proliferating cells in the cancer and/or reduces the volume or size of a tumor comprising the cancer cells. In another embodiment, the agent increases the sensitivity of the cancer to the immunotherapy. In still another embodiment, the immunotherapy is T-cell-mediated. In yet another embodiment, the agent increases the amount of CD8+ T cells in a tumor comprising the cancer cells. In another embodiment, the cancer described herein is selected from the group consisting of melanoma and colorectal cancer. In another embodiment, the cancer is melanoma. In still another embodiment, the agent described herein is administered in a pharmaceutically acceptable formulation.

In still another aspect, a method of determining whether a subject afflicted with a cancer or at risk for developing a cancer would benefit from inhibiting the copy number, amount, and/or activity of at least one biomarker listed in Table 1 is provided, the method comprising a) obtaining a biological sample from the subject; b) determining the copy number, amount, and/or activity of at least one biomarker listed in Table 1; c) determining the copy number, amount, and/or activity of the at least one biomarker in a control; and d) comparing the copy number, amount, and/or activity of the at least one biomarker detected in steps b) and c); wherein the presence of, or a significant increase in, the copy number, amount, and/or activity of, the at least one biomarker listed in Table 1 in the subject sample relative to the control copy number, amount, and/or activity of the at least one biomarker indicates that the subject afflicted with the cancer or at risk for developing the cancer would benefit from inhibiting the copy number, amount, and/or activity of the at least one biomarker listed in Table 1.

As described above, numerous embodiments are further provided that can be applied to any aspect of the present invention and/or combined with any other embodiment described herein. In one embodiment, the method described herein further comprises recommending, prescribing, or administering an agent that inhibits the at least one biomarker listed in Table 1 if the cancer is determined to benefit from the agent. In another embodiment, the method described herein further comprises administering at least one additional cancer therapy. In still another embodiment, the method described herein further comprises recommending, prescribing, or administering cancer therapy other than an agent that inhibits the at least one biomarker listed in Table 1 if the cancer is determined to not benefit from the agent. In yet another embodiment, the cancer therapy is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy (e.g., 5'-fluorouracil, anthracyclines, such as doxorubicin, and the platinum drug, oxaliplatin) that induce interferon production by the cancer cells or at the site of a tumor, interferon, an interferon-inducing agent, a topical inflammatory agent, and a topical TLR agonist. In another embodiment, the control sample described herein is determined from a cancerous or non-cancerous sample from either the patient or a member of the same species to which the patient belongs. In still another embodiment, the control sample comprises cells.

In yet another aspect, a method for predicting the clinical outcome of a subject afflicted with a cancer expressing one or more biomarkers listed in Table 1 or a fragment thereof is provided, the method comprising a) determining the copy number, amount, and/or activity of at least one biomarker listed in Table 1 in a subject sample; b) determining the copy number, amount, and/or activity of the at least one biomarker in a control having a good clinical outcome; and c) comparing the copy number, amount, and/or activity of the at least one biomarker in the subject sample and in the control, wherein the presence of, or a significant increase in, the copy number, amount, and/or activity of, the at least one biomarker listed in Table 1 in the subject sample as compared to the copy number, amount and/or activity in the control, is an indication that the subject has a poor clinical outcome.

In another aspect, a method for monitoring the progression of a cancer in a subject, wherein the subject is administered a therapeutically effective amount of an agent that inhibits the copy number, amount, and/or activity of at least one biomarker listed in Table 1, is provided, the method comprising a) detecting in a subject sample at a first point in time the copy number, amount, and/or activity of at least one biomarker listed in Table 1; b) repeating step a) at a subsequent point in time; and c) comparing the amount or activity of at least one biomarker listed in Table 1 detected in steps a) and b) to monitor the progression of the cancer in the subject.

In still another aspect, a method of assessing the efficacy of an agent that inhibits the copy number, amount, and/or activity of at least one biomarker listed in Table 1 for treating a cancer in a subject is provided, comprising a) detecting in a subject sample at a first point in time the copy number, amount, and/or or activity of at least one biomarker listed in Table 1; b) repeating step a) during at least one subsequent point in time after administration of the agent; and c) comparing the copy number, amount, and/or activity detected in steps a) and b), wherein the absence of, or a significant decrease in, the copy number, amount, and/or activity of, the at least one biomarker listed in Table 1, in the subsequent sample as compared to the copy number, amount, and/or activity in the sample at the first point in time, indicates that the agent treats the cancer in the subject.

As described above, numerous embodiments are further provided that can be applied to any aspect of the present invention and/or combined with any other embodiment described herein. For example, in one embodiment, between the first point in time and the subsequent point in time, as described herein, the subject has undergone treatment, completed treatment, and/or is in remission for the cancer. In another embodiment, the cancer treatment described herein is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy (e.g., 5'-fluorouracil, anthracyclines, such as doxorubicin, and the platinum drug, oxaliplatin) that induce interferon production by the cancer cells or at the site of a tumor, interferon, an interferon-inducing agent, a topical inflammatory agent, and a topical TLR agonist. In still another embodiment, the first and/or at least one subsequent sample is selected from the group consisting of ex vivo and in vivo samples. In yet another embodiment, the first and/or at least one subsequent sample is a portion of a single sample or pooled samples obtained from the subject. In one embodiment, the sample described herein comprises cells, serum, peritumoral tissue, and/or intratumoral tissue obtained from the subject. In another embodiment, the one or more biomarkers listed in Table 1 comprise HLA-E, Pdia3, Calr, Tap1, Tap2, Tapbp, and/or Erap1. In still another embodiment, the one or more biomarkers described herein comprise a nucleic acid sequence having at least 95% identity to a nucleic acid sequence listed in Table 1 and/or encodes an amino acid sequence having at least 95% identity to an amino acid sequence listed in Table 1. In yet another embodiment, the HLA-E is a human HLA-E, a mouse H2-T23, a chimeric HLA-E, or a fusion HLA-E. In one embodiment, the HLA-E comprises an amino acid sequence listed in Table 1, such as an amino acid sequence selected from the group consisting of SEQ ID Nos: 2, 4, 6, 8, 10, 12, and 14. In another embodiment, the HLA-E is encoded by a nucleic acid sequence listed in Table 1, such as a nucleic acid sequence is selected from the group consisting of SEQ ID Nos: 1, 3, 5, 7, 9, 11, and 13. In still another embodiment, the agent described herein reduces the number of proliferating cells in the cancer and/or reduces the volume or size of a tumor comprising the cancer cells. In another embodiment, the agent described herein increases the sensitivity of the cancer to the immunotherapy. In still another embodiment, the immunotherapy is T-cell-mediated. In yet another embodiment, the agent described herein increases the amount of CD8+ T cells in a tumor comprising the cancer cells. In another embodiment, the cancer described herein is selected from the group consisting of melanoma and colorectal cancer. In another embodiment, the cancer is melanoma. In still another embodiment, the agent described herein is administered in a pharmaceutically acceptable formulation. In yet another embodiment, the subject described herein is an animal model of the cancer. In another embodiment, the animal model is a mouse model. In still another embodiment, the subject is a mammal. In yet another embodiment, the mammal is a mouse or a human. In one embodiment, the mammal is a human.

Figure 1:
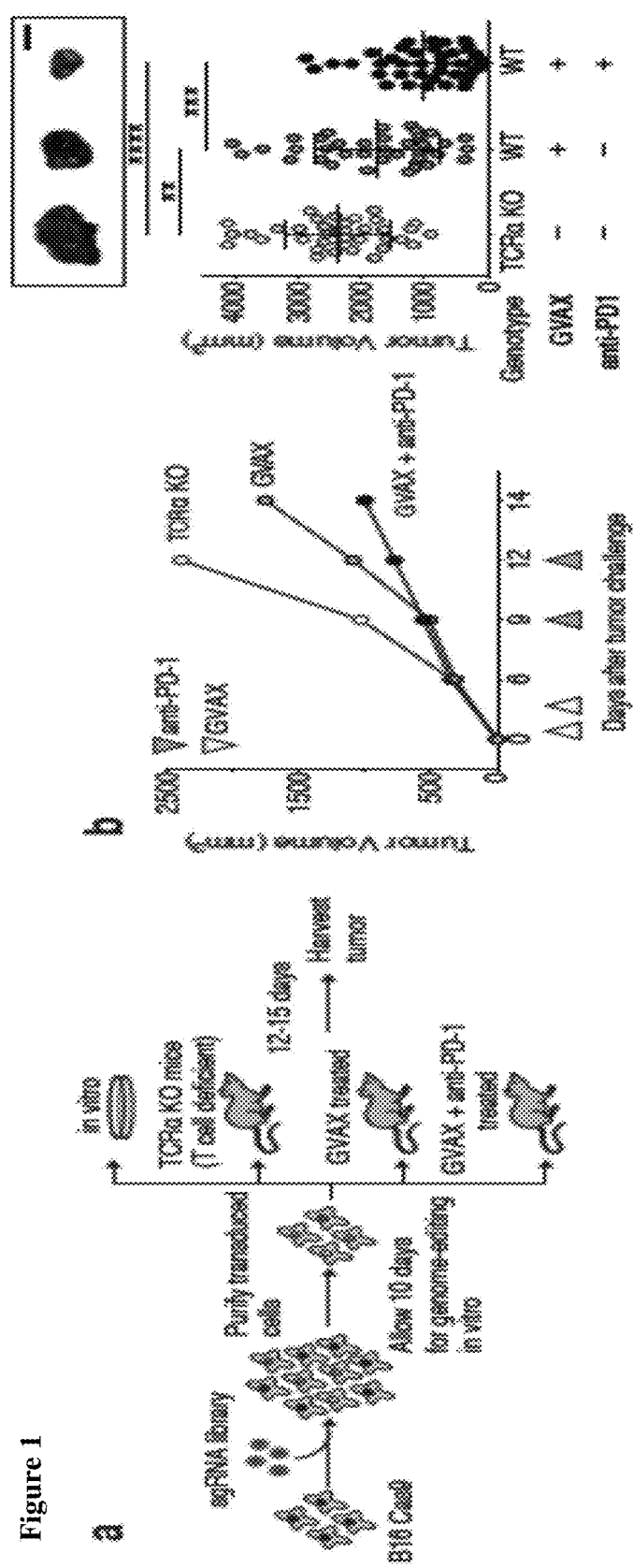
FIG. 1 includes 6 panels, identified as panels A, B, C, D, E, and F, which show that in vivo pooled loss-of-function screening using CRISPR/Cas9 in tumor cells recovers known mediators of immune evasion. Panel A shows a schematic diagram of the in vivo screening system using the B16 transplantable tumor model. Tumor volumes (in mm$^3$) were compared under each conditions, averaged for each group at each time point (Panel B, left) or for individual animals on the day of sacrifice (Panel B, right). Bars represent means, while whiskers represent standard deviation. Enrichment analysis was carried out using a hypergeometric test to show functional classes of genes, (from the Gene Ontology Consortium database (GO)) targeted by sgRNAs, that were enriched or depleted in tumors in animals, including animals treated with irradiated tumor cell vaccine (GVAX) and anti-PD-1 antibody and the TCRα$^{-/-}$ animals (Panel C). Frequency histogram (Panel D, top) and collapsed histograms (Panel D, middle) of enrichment or depletion (normalized as Z scores) are shown for all 9,992 sgRNAs screened. Enrichment/depletion scores are averaged from 10 mice per condition. sgRNAs targeting PD-L1 are indicated by the red lines (Panel D, middle). PD-L1 expression is compared among Cas9-expressing B16 tumor cells transfected with one of the four sgRNAs targeting PD-L1 (red) or a control sgRNA (grey) (Panel D, bottom). Similar to Panel D, Panel E shows the depletion of CD47 by its specific sgRNAs (indicated in red (top and middle)) and CD47 expression after CRISPR editing with sgRNAs targeting CD47 (bottom). Panel F compares tumor volumes over time between CD47 null (red) and control (grey) tumors growing in mice treated with GVAX and PD-1 blockade (average and standard error of the mean; n=10 animals per group).  $p<0.01$; * $p<0.001$; **** $p<0.0001$.
Figure 1:
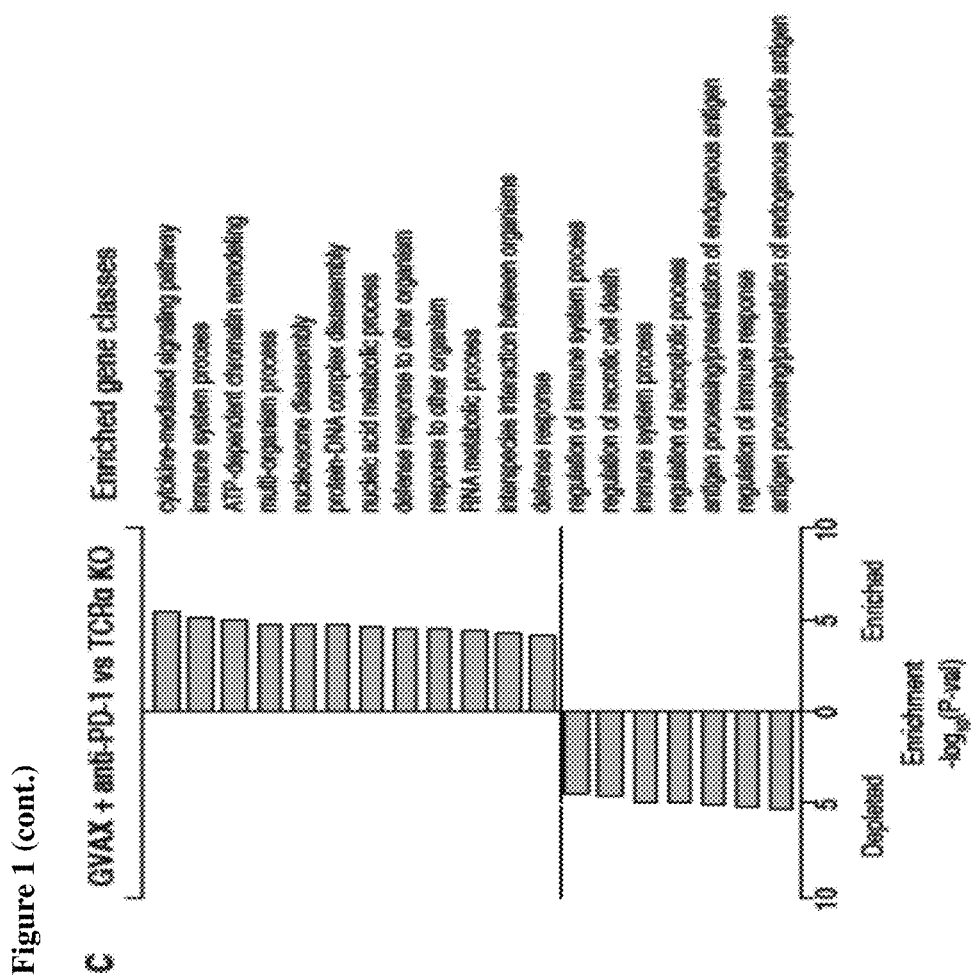
Figure 1:
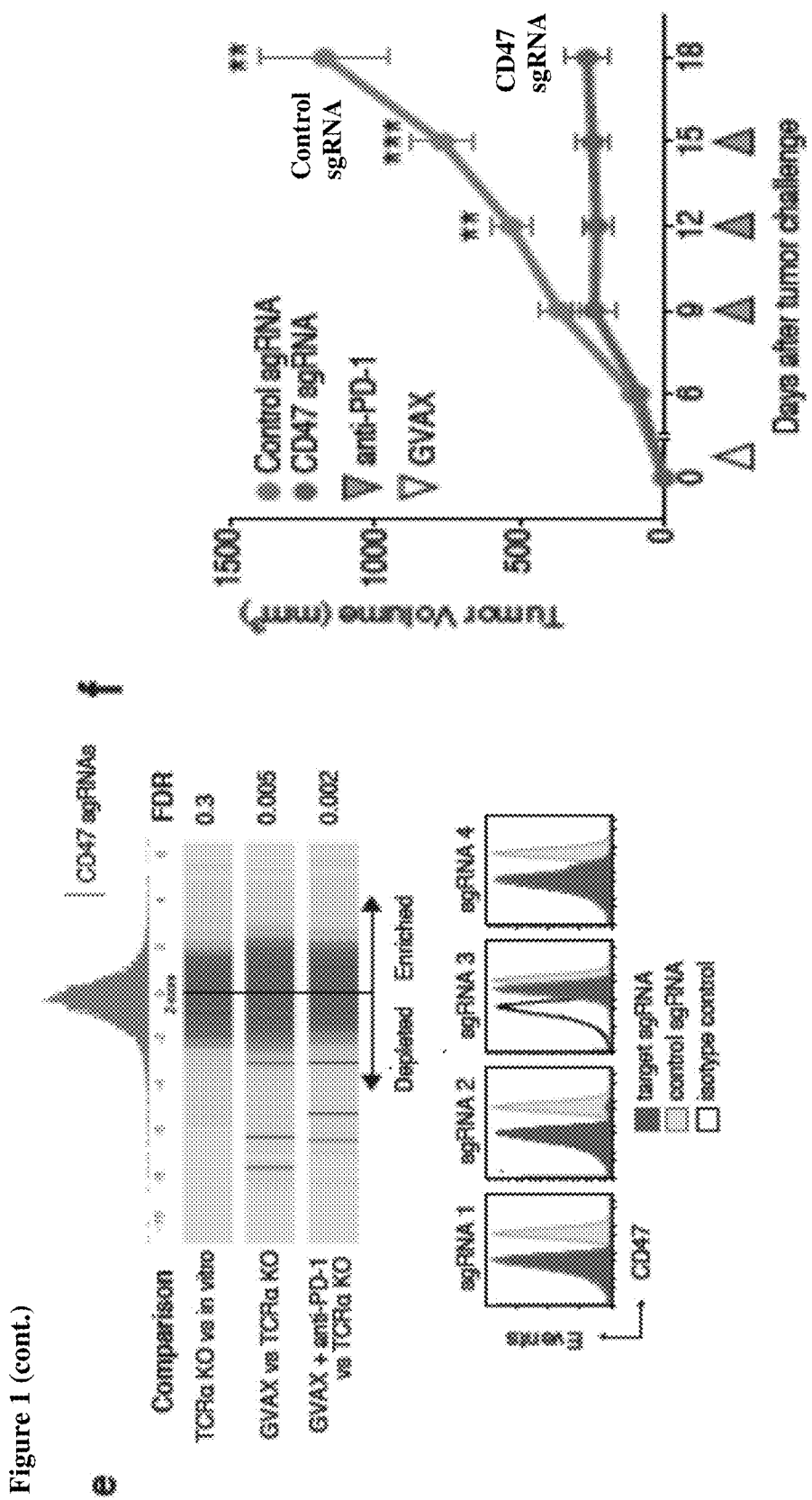

The data in FIGS. 4-12 are adapted from a presentation titled "NKG2A checkpoint receptor expression on tumor-infiltrating CD8+ T cells restrains efficacy of immunotherapy" (Thorbald van Hall et al., AACR Annual Meeting 2017 dated Apr. 3, 2017).

DETAILED DESCRIPTION OF THE INVENTION

It has been determined herein that negative regulators of one or more biomarkers listed in Table 1, such as one or more proteins modulating antigen processing and presentation (e.g., HLA-E, Pdia3, Calr, Tap1, Tap2, Tapbp, Erap1, etc.) can be used to increase interferon sensing by tumor cells and augment tumor immunity and immunotherapies. Thus, the instant disclosure provides at least a method of treating cancers, e.g., those cancer types otherwise not responsive or weakly responsive to immunotherapies, with a combination of a negative regulator of one or more biomarkers listed in Table 1, such as one or more proteins modulating antigen processing and presentation (e.g., HLA-E, Pdia3, Calr, Tap1, Tap2, Tapbp, Erap1, etc.) and another immunotherapy. The results described herein are unexpected given that analyses of such regulator function has heretofore been largely confined to hematopoietic cells and not examined in cancer cells, as well as the fact that modulating sensitivity to interferon signaling is critical for immunotherapy effects rather than simply modulating interferon availability since interferon therapy is known to not significantly augment immunotherapy effects. Accordingly, the present invention provides exemplary RNA interfering agents inhibiting such regulators, which may be used in the combination therapy and other methods described herein, such as agents that inhibit the function and/or its ability of one or more biomarkers listed in Table 1 to interact/bind to its substrates described herein, or by increasing its degradation and/or stability and/or interaction/binding to its inhibitors. Similarly, methods of screening for inhibitors of such regulators and methods of diagnosing, prognosing, and monitoring cancer involving such inhibitors/immunotherapy combination therapies are provided.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" refers to antigen-binding portions adaptable to be expressed within cells as "intracellular antibodies." (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

Antibodies may be polyclonal or monoclonal; xenogeneic, allogeneic, or syngeneic;

or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of effects of combinatorial therapies comprising one or more inhibitors of one or more biomarkers listed in Table 1, such as one or more proteins modulating antigen processing and presentation regulators (e.g., HLA-E, Pdia3, Calr, Tap1, Tap2, Tapbp, Erap1, etc., or the corresponding proteins) and immunotherapy (e.g., immune checkpoint inhibitors) on a cancer. Biomarkers can include, without limitation, nucleic acids and proteins, including those shown in the Tables, the Examples, the Figures, and otherwise described herein. As described herein, any relevant characteristic of a biomarker can be used, such as the copy number, amount, activity, location, modification (e.g., phosphorylation), and the like.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such cells exhibit such characteristics in part or in full due to the expression and activity of signaling pathways regulated by one or more biomarkers listed in Table 1, such as one or more regulators of antigen processing and presentation described herein (e.g., HLA-E, Pdia3, Calr, Tap1, Tap2, Tapbp, Erap1, etc.)

(e.g., NF-kappaB Signaling pathway, MAP kinase pathway, JAK-STAT signaling pathway, or other signaling pathways involving receptor tyrosine kinases, non-receptor tyrosine kinases, Src family kinases, and/or signal transducer and activator of transcription (STAT) proteins). In certain embodiments, the cancer cells are capable of responding to interferon because they express functional proteins of the type I interferon signaling pathway and/or type II interferon signaling pathway, such as those shown in panel E of FIG. 11. In some embodiments, the cancer cells described herein are not sensitive to at least one of immunotherapies. Such insensitivity, without limitation, may be related to the inactivation or decreased activation, compared to control cells (e.g., normal and/or wild-type non-cancer cells, and/or cancer cells without this insensitivity to immunotherapies), of interferon signaling (e.g., IFNγ signaling) in such cancer cells and/or other surrounding cells and/or cells localized near to such cancer cells. Such inactivation or decreased activation of interferon signaling, without limitation, may be related to the inhibition of interferon signaling by regulators of antigen processing and presentation described herein (e.g., by overexpression and/or gain-of-function of the gene, RNA transcript, and/or protein, and/or by reduced expression and/or loss-of-function of endogenous negative regulator(s) for such regulators). In some embodiments, the cancer cells are treatable with an agent capable of antagonizing regulators of antigen processing and presentation described herein, such as inhibiting expression and/or function, as described herein. An exemplary agent, without limitation, may relieve the inhibition of signaling by such regulators described herein in such cancer cells and/or other cells surrounding or localized near such cancer cells, thus restoring the IFNγ signaling and the sensitivity of such cancer cells to immunotherapies, especially those immunotherapies related to interferon signaling pathways. In some embodiments, the treatment with the agent antagonizing such regulators of antigen processing and presentation as described herein would increase IFNγ signaling in such cancer cells, compared to pre-treatment situations, or would restore IFNγ signaling in such cancer cells to at least comparable to the levels in control cells, so that such cancer cells would regain sensitivity to immunotherapies. The term "interferon signaling" or "IFNγ signaling" used herein refers to any cell signaling downstream and/or related to the interaction of interferon (e.g., IFNγ) and their receptor(s).

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer encompasses colorectal cancer (e.g., colorectal carcinoma).

The term "colorectal cancer" as used herein, is meant to include cancer of cells of the intestinal tract below the small intestine (e.g., the large intestine (colon), including the cecum, ascending colon, transverse colon, descending colon, and sigmoid colon, and rectum). Additionally, as used herein, the term "colorectal cancer" is meant to further include cancer of cells of the duodenum and small intestine (jejunum and ileum). Colorectal cancer also includes neoplastic diseases involving proliferation of a single clone of cells of the colon and includes adenocarcinoma and carcinoma of the colon whether in a primary site or metastasized.

Colorectal cancer (CRC) is the third most commonly diagnosed cancer and ranks second in cancer mortality. Extensive genetic and genomic analysis of human CRC has uncovered germline and somatic mutations relevant to CRC biology and malignant transformation (Fearon et al. (1990) *Cell* 61, 759-767). These mutations have been linked to well-defined disease stages from aberrant crypt proliferation or hyperplasic lesions to benign adenomas, to carcinoma in situ, and finally to invasive and metastatic disease, thereby establishing a genetic paradigm for cancer initiation and progression. Genetic and genomic instability are catalysts for colon carcinogenesis (Lengauer et al. (1998) *Nature* 396:643-649). CRC can present with two distinct genomic profiles that have been termed (i) chromosomal instability neoplasia (CIN), characterized by rampant structural and numerical chromosomal aberrations driven in part by telomere dysfunction (Artandi et al. (2000) *Nature* 406:641-645; Fodde et al. (2001) *Nat. Rev. Cancer* 1:55-67; Maser and DePinho (2002) *Science* 297:565-569; Rudolph et al. (2001) *Nat. Genet.* 28:155-159) and mitotic aberrations (Lengauer et al. (1998) *Nature* 396:643-649) and (ii) microsatellite instability neoplasia (MIN), characterized by near diploid karyotypes with alterations at the nucleotide level due to mutations in mismatch repair (MMR) genes (Fishel et al. (1993) *Cell* 75:1027-1038; Ilyas et al. (1999) *Eur. 1 Cancer* 35:335-351; Modrich (1991) *Annu. Rev. Genet.* 25:229-253; Parsons et al. (1995) *Science* 268:738-740; Parsons et al. (1993) *Cell* 75:1227-1236). Germline MMR mutations are highly penetrant lesions which drive the MIN phenotype in hereditary nonpolyposis colorectal cancers, accounting for 1-5% of CRC cases (de la Chapelle (2004) *Nat. Rev. Cancer* 4:769-780; Lynch and de la Chapelle (1999) *J. Med. Genet.* 36:801-818; Umar et al. (2004) *Nat. Rev. Cancer* 4:153-158). While CIN and MIN are mechanistically distinct, their genomic and genetic consequences emphasize the requirement of dominant mutator mechanisms to drive intestinal epithelial cells towards a threshold of oncogenic changes needed for malignant transformation.

A growing number of genetic mutations have been identified and functionally validated in CRC pathogenesis. Activation of the WNT signaling pathway is an early requisite event for adenoma formation. Somatic alterations are present in APC in greater than 70% of nonfamilial sporadic cases and appear to contribute to genomic instability and induce the expression of c-myc and Cyclin D1 (Fodde et al. (2001) *Nat. Rev. Cancer* 1:55-67), while activating β-catenin mutations represent an alternative means of WNT pathway deregulation in CRC (Morin (1997) *Science* 275:1787-1790). K-Ras mutations occur early in neoplastic progression and are present in approximately 50% of large adenomas (Fearon and Gruber (2001) Molecular abnormalities in colon and rectal cancer, ed. J. Mendelsohn, P. H., M. Israel, and L. Liotta, W. B. Saunders, Philadelphia). The BRAF serine/threonine kinase and PIK3CA lipid kinase are mutated in 5-18% and 28% of sporadic CRCs, respectively (Samuels et al. (2004) *Science* 304:554; Davies et al. (2002) *Nature* 417:949-954; Rajagopalan et al. (2002) *Nature* 418: 934; Yuen et al. (2002) *Cancer Res.* 62:6451-6455). BRAF and K-ras mutations are mutually exclusive in CRC, suggesting over-lapping oncogenic activities (Davies et al. (2002) *Nature* 417:949-954; Rajagopalan et al. (2002) *Nature* 418:934). Mutations associated with CRC progression, specifically the adenoma-to-carcinoma transition, target the TP53 and the TGF-β pathways (Markowitz et al. (2002) *Cancer Cell* 1:233-236). Greater than 50% of CRCs harbor TP53 inactivating mutations (Fearon and Gruber (2001) Molecular abnormalities in colon and rectal cancer, ed. J. Mendelsohn, P. H., M. Israel, and L. Liotta, W. B. Saunders, Philadelphia) and 30% of cases possess TGFβ-RII mutations (Markowitz (2000) *Biochim. Biophys. Acta* 1470: M13-M20; Markowitz et al. (1995) *Science* 268:1336-1338). MIN cancers consistently inactivate TGFβ-RII by frameshift mutations, whereas CIN cancers target the pathway via inactivating somatic mutations in the TGFβ-RII kinase domain (15%) or in the downstream signaling components of the pathway, including SMAD4 (15%) or SMAD2 (5%) transcription factors (Markowitz (2000) *Biochim. Biophys. Acta* 1470:M13-M20). In some embodiments, the colorectal cancer is microsatellite instable (MSI) colorectal cancer (Llosa et al. (2014) *Cancer Disc.* CD-14-0863; published online Oct. 30, 2014). MSI represents about 15% of sporadic CRC and about 5-6% of stage IV CRCs. MSI is caused by epigenetic silencing or mutation of DNA mismatch repair genes and typically presents with lower stage disease than microsatellite stable subset (MSS) CRC. MSI highly express immune checkpoints, such as PD-1, PD-L1, CTLA-4, LAG-3, and IDO. In other embodiments, the colorectal cancer is MSS CRC.

In certain embodiments, the cancer encompasses melanoma. The term "melanoma" as used herein, is generally meant to include cancers that develop from the pigment-containing cells, known as melanocytes, in the basal layer of the epidermis. Melanomas typically occur in the skin but may rarely occur in the mouth, intestines, or eye. In women they most commonly occur on the legs, while in men they are most common on the back. Sometimes they develop from a mole with concerning changes including an increase in size, irregular edges, change in color, itchiness, or skin breakdown. Thus, the term "melanoma" also includes cancers developing from these cells, tissues, and organs.

Melanomas are among the most dangerous forms of skin cancer and develop when unrepaired DNA damage to skin cells (most often caused by ultraviolet radiation from sunshine or tanning beds) triggers gene mutations that lead the skin cells to multiply rapidly and form malignant tumors. The primary cause of melanoma is ultraviolet light (UV) exposure in those with low levels of skin pigment. Melanomas often resemble moles; some develop from moles. Those with many moles, a history of affected family members, and who have poor immune function are at greater risk. A number of rare genetic defects such as xeroderma pigmentosum also increase risk (Azoury and Lange, 2014 *Surg Clin North Am.* 2014 94:945-962).

Melanoma can be divided into different types, including, at least, lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, uveal melanoma, etc. (see James, et al., 2006 *Andrews' Diseases of the Skin: clinical Dermatology.* Saunders Elsevier. pp. 694-9)

Diagnosis is by biopsy of any concerning skin lesion, including, at least, shave (tangential) biopsy, punch biopsy, incisional and excisional biopsies, "optical" biopsies (e.g., by reflectance confocal microscopy (RCM)), fine needle aspiration (FNA) biopsy, surgical lymph node biopsy, sentinel lymph node biopsy, etc. In addition, visual inspection may also be used for diagnosis, such as a popular method for the signs and symptoms of melanoma as mnemonic "ABCDE": Asymmetrical skin lesion, Border of the lesion is irregular, Color: melanomas usually have multiple colors, Diameter: moles greater than 6 mm are more likely to be melanomas than smaller moles, and Enlarging: Enlarging or evolving. Another method as the "ugly duckling sign" is also known in the art (Mascaro and Mascaro, 1998 *Arch Dermatol.* 134: 1484-1485).

Treatment of melanoma includes surgery, chemotherapy (such as temozolomide, dacarbazine (also termed DTIC), etc.), radiation therapy, oncolytic virotherapy (e.g., see Forbes et al., 2013 *Front. Genet.* 4:184), and immunotherapy (e.g., interleukin-2 (IL-2), interferon, etc.). Targeted therapies (e.g., as in Maverakis et al., 2015 *Acta Derm Venereol.* 95: 516-524) may include: 1) adoptive cell therapy (ACT) using TILs immune cells (tumor infiltrating lymphocytes) isolated from a person's own melanoma tumor). Cells are grown in large numbers in a laboratory and returned to the patient after a treatment that temporarily reduces normal T cells in the patient's body. TIL therapy following lymphodepletion can result in durable complete response in a variety of setups (Besser et al., 2010 *Clin. Cancer Res.* 16:2646-2655); and 2) adoptive transfer of genetically altered (expressing T cell receptors (TCRs)) autologous lymphocytes into patient's lymphocytes, where the altered lymphocytes recognize and bind to the surface of melanoma cells and kill them. Other therapies include, at least, B-Raf inhibitors (such as vemurafenib, see Chapman et al., 2011 *N. Engl. J. Med.* 364:2507-2516) and ipilimumab (alone or in combination with dacarbazine, see, e.g., Robert et al. (2011) *N. Engl. J. Med.* 364:2517-2526).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of one or more coordinately expressed biomarkers related to a measured phenotype. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immunotherapy" or "immunotherapies" refer to any treatment that uses certain parts of a subject's immune system to fight diseases such as cancer. The subject's own immune system is stimulated (or suppressed), with or without administration of one or more agent for that purpose. Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "immunogenic chemotherapy" refers to any chemotherapy that has been demonstrated to induce immunogenic cell death, a state that is detectable by the release of one or more damage-associated molecular pattern (DAMP) molecules, including, but not limited to, calreticulin, ATP and HMGB1 (Kroemer et al. (2013), *Annu. Rev. Immunol.*, 31:51-72). Specific representative examples of consensus immunogenic chemotherapies include 5'-fluorouracil, anthracyclines, such as doxorubicin, and the platinum drug, oxaliplatin, among others.

In some embodiments, immunotherapy comprises inhibitors of one or more immune checkpoints. The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein. In one embodiment, the immune checkpoint is PD-1.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 *EMBO J* 11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well-known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027-1034) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels in murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MEW molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S. The second form is a cell-associated polypeptide, i.e., having a transmembrane and cytoplasmic domain, referred to herein as PD-L1M. The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of PD-L1S is shown from about amino acid 1 to about amino acid 18. The signal sequence of PD-L1M is shown: from about amino acid 1 to about amino acid 18. The IgV domain of PD-L1S is shown from about amino acid 19 to about amino acid 134 and the IgV domain of PD-L1M is shown from about amino acid 19 to about amino acid 134. The IgC domain of PD-L1S is shown from about amino acid 135 to about amino acid 227 and the IgC domain of PD-L1M is shown from about amino acid 135 to about amino acid 227. The hydrophilic tail of the PD-L1 exemplified in PD-L1S comprises a hydrophilic tail shown from about amino acid 228 to about amino acid 245. The PD-L1 polypeptide exemplified in PD-L1M comprises a transmembrane domain shown from about amino acids 239 to about amino acid 259 and a cytoplasmic domain shown from about 30 amino acid 260 to about amino acid 290. In addition, nucleic acid and polypeptide sequences of PD-L1 orthologs in organisms other than humans are well-known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers are well-known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of PD-L2 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two ß sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well-known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "HLA-E," also known as HLA class I histocompatibility antigen (alpha chain E) and Major Histocompatibility Complex (MHC) class I antigen E, refers to a member of a group of proteins in the non-classical MHC class I that are characterized by a limited polymorphism and a lower cell surface expression than the classical paralogues. The functional homolog in mice is called Qa-1b, officially known as H2-T23. HLA-E has a very specialized role in cell recognition by natural killer cells (NK cells) (Braud et al. (1998) Nature 391:795-799). HLA-E binds a restricted subset of peptides derived from signal peptides of classical MHC class I molecules, namely HLA-A, B, C, G (Braud et al. (1997) Eur. J. Immunol. 27:1164-1169). These peptides are released from the membrane of the endoplasmic reticulum (ER) by the signal peptide peptidase and trimmed by the cytosolic proteasome (Lemberg et al. (2001) J. Immunol. 167:6441-6446; Bland et al. (2003) J. Biol. Chem. 278: 33747-33752). Upon transport into the ER lumen by the transporter associated with antigen processing (TAP), these peptides bind to a peptide binding groove on the HLA-E molecule (Braud et al. (1998) Curr. Biol. 8:1-10). This allows HLA-E to assemble correctly and to be expressed on the cell surface. NK cells recognize the HLA-E+peptide complex using the heterodimeric inhibitory receptor CD94/NKG2A/B/C (Braud et al. (1998) Nature 391:795-799). When CD94/NKG2A or CD94/NKG2B is engaged, it produces an inhibitory effect on the cytotoxic activity of the NK cell to prevent cell lysis. However, binding of HLA-E to CD94/NKG2C results in NK cell activation. This interaction has been shown to trigger expansion of NK cell subsets in antiviral responses (Rölle et al. (2014) J. Clin. Invest. 124:5305-5316). HLA-E is involved in pathways such as allograft rejection (e.g., Type I diabetes mellitus, graft-versus-host disease, autoimmune thyroid disease, viral myocarditis, viral carcinogenesis, viral infection (such as Epstein-Barr virus infection, herpes simplex infection, HTLV-I infection, etc.), interferon gamma signaling, CTL-mediated apoptosis, antigen processing and presentation, etc.), immune response role of DAP12 receptors in NK cells (e.g., CD16 signaling in NK cells, NK cell-mediated cytotoxicity, etc.), antigen processing-cross presentation (e.g., ER-phagosome pathway, endosomal/vacuolar pathway, etc.), class I MHC mediated antigen processing and presentation, and RET signaling (e.g., DAP12 signaling, etc.). HLA-E preferably binds to a peptide derived from the signal sequence of most HLA-A, -B, -C and -G molecules, as well as beta-2-microglobulin (B2M), MHC class I protein, Major Histocompatibility Complex, Class II, DR Beta 1 (HLA-DRB1), NK cell lectin-like receptor, and other other peptide antigens.

The nucleic acid and amino acid sequences of a representative human HLA-E is available to the public at the GenBank database (Gene ID 3133) and is shown in Table 1 (e.g., GenBank database numbers NM_005516.5 and NP_005507.3). HLA-E belongs to the HLA class I heavy chain paralogues. This class I molecule is a heterodimer consisting of a heavy chain and a light chain (beta-2 microglobulin). The heavy chain is anchored in the membrane. HLA-E binds a restricted subset of peptides derived from the leader peptides of other class I molecules. The heavy chain is approximately 45 kDa and its gene contains 8 exons. Exon one encodes the leader peptide, exons 2 and 3 encode the alpha1 and alpha2 domains, which both bind the peptide, exon 4 encodes the alpha3 domain, exon 5 encodes the transmembrane region, and exons 6 and 7 encode the cytoplasmic tail. The domain structure of HLA-E polypeptide is well known and accessible in UniProtKB database under the accession number P13747, including, in the order from the 5' terminus to the 3' terminus, a signal peptide comprising, e.g., amino acid positions 1-21 of NP_005507.3, an extracellular domain comprising, e.g., amino acid positions 22-305 of NP_005507.3, a transmembrane domain comprising, e.g., amino acid positions 306-329 of NP_005507.3, and a cytoplasmic domain comprising, e.g., amino acid positions 330-358 of NP_005507.3. The extracellular domain further comprises an Alpha-1 region (e.g., amino acid positions 22-111 of NP_005507.3), an Alpha-2 region (e.g., amino acid positions 112-203 of NP_005507.3), an Alpha-3 region (e.g., amino acid positions 204-295 of NP_005507.3, including an Ig-like C1-type domain comprising, e.g., amino acid positions 206-294 of NP_005507.3), and a connecting peptide (e.g., amino acid positions 296-305 of NP_005507.3).

Nucleic acid and polypeptide sequences of HLA-E orthologs in organisms other than humans are well-known and include, for example, chimpanzee (Pan troglodytes) PATR-E (NM_001045498.1 and NP_001038963.1), Rhesus monkey MAMU-E (NM_001114966.1 and NP_001108438.1), mouse H2-T23 (NM_010398.3 and NP_034528.1, and NM_001271005.1 and NP_001257934.1), and Norway rat (Rattus norvegicus) RT1-S3 (NM_001008886.2 and NP_001008886.2).

The term "HLA-E activity" includes the ability of an HLA-E polypeptide (and its fragments, domains, and/or motifs thereof, discussed herein) to bind its substrate and/or catalyze serine/threonine-protein kinase activity. HLA-E activity may also include one or more of functions, such as those disclosed herein in the NF-κB pathway, autoimmune response, antigen presentation, and viral infection. For example, HLA-E may interact with various proteins disclosed herein, such as HLA-A, -B, -C and -G molecules and other binding partners including multiple antigens and receptors, for it functions in signalings. HLA-E may also be proteolyticly modified, such as being glycosylated, or otherwise disclosed herein, for it funcations.

The term "HLA-E substrate(s)" refers to binding partners of a HLA-E polypeptide (and its fragments, domains, and/or motifs thereof, discussed herein), e.g., the proteins listed herein. Furthermore, HLA-E substates may refer to downstream members in the signaling pathways where HLA-E has a functional role.

The term "HLA-E-regulated signaling pathway(s)" includes signaling pathways in which HLA-E (and its fragments, domains, and/or motifs thereof, discussed herein) binds to at least one of its substrate, through which at least one cellular function and/or activity and/or cellular protein profiles is changed (e.g., antigen processing and presentation). In some embodiments, HLA-E promotes antigen presentation (including autoimmune responses) for at least one of its substates (e.g., antigens) which bind to it. HLA-E-regulated signaling pathways include at least those described herein, such as allograft rejection, antigen processing-cross presentation, class I MHC mediated antigen processing and presentation, and RET signaling, etc.

The term "HLA-E inhibitor(s)" includes any natural or non-natural agent prepared, synthesized, manufactured, and/or purified by human that is capable of reducing, inhibiting, blocking, preventing, and/or that inhibits the ability of an HLA-E polypeptide (and its fragments, domains, and/or motifs thereof, discussed herein). In one embodiment, such inhibitors may reduce or inhibit the binding/interaction between HLA-E and its substrates or other binding partners. In another embodiment, such inhibitors may reduce or inhibit HLA-E as an MHC molecule for antigen presentation and/or other immune responses. In still another embodiment, such inhibitors may increase or promote the turnover rate, reduce or inhibit the expression and/or the stability (e.g., the half-life), and/or change the cellular localization of HLA-E, resulting in at least a decrease in HLA-E levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to HLA-E or also inhibit at least one of other serine/threonine-protein kinases. RNA interference for HLA-E polypepitdes are well known and commercially available (e.g., human or mouse shRNA (Cat. #TF312402, TG312402, TL312402, TL312402V, and TR312402) products from Origene (Rockville, Md.), siRNA/shRNA products (Cat. #sc-62470, sc-62471, and sc-42922) and human or mouse gene knockout kit via CRISPR (Cat. #sc-403124 and sc-437133) from Santa Cruz Biotechonology (Dallas, Tex.), and Ready-to-package AAV shRNA clones from Vigene Biosciences (Rockville, Md., Cat. #SH888322), etc.). Methods for detection, purification, and/or inhibition of HLA-E (e.g., by anti-HLA-E antibodies) are also well known and commercially available (e.g., multiple anti-HLA-E antibodies from Origene (Cat. #TA320346, AM03010BT-N, SM3053P, SM3053A, and others), Novus Biologicals (Littleton, Colo., Cat. #NBP2-47435, NBP1-43124, NB500-310, etc.), abcam (Cambridge, Mass., Cat. #ab2216, ab11820, ab11821, ab88090, ab203082, etc.), Santa Cruz Biotechnology (Cat. #sc-71262, sc-51621, sc-51622, and sc-51624), etc.). HLA-E knockout human cell lines are also well known and available at the Horizon (Cambridge, UK, Cat. #HZGHC3133).

The term "PDIA3," also known as protein disulfide-isomerase A3 and glucose-regulated protein, 58-kD (GRP58), refers to a member of a group of isomerase enzymes which localize to the endoplasmic reticulum (ER) and interacts with lectin chaperones calreticulin and calnexin (CNX) to modulate folding of newly synthesized glycoproteins. Complexes of lectins and this protein mediate protein folding by promoting formation of disulfide bonds in their glycoprotein substrates. The PDIA3 protein is a thiol oxidoreductase that has protein disulfide isomerase activity (Koivunen et al. (1996) Biochem. J. 316:599-605; Dong et al. (2009) Immunity 30:21-32). PDIA3 is also part of the major histocompatibility complex (MHC) class I peptide loading complex, which is essential for formation of the final antigen conformation and export from the endoplasmic reticulum to the cell surface (Dong et al. (2009), supra; Garbi et al. (2006) Nat. Immunol. 7:93-102). This protein of the endoplasmic reticulum interacts with lectin chaperones such as calreticulin and CNX in order to modulate the folding of proteins that are newly synthesized. PDIA3 plays a role in protein folding by promoting the formation of disulfide bonds, and that CNX facilitates the positioning substrates next to the catalytic cysteines. This function allows it to serve as a redox sensor by activating mTORC1, which then mediates mTOR complex assembly to adapt cells to oxidative damage. Thus, PDIA3 regulates cell growth and death according to oxygen concentrations, such as in the hypoxic microenvironment of bones. Additionally, PDIA3 activates cell anchorage in bones by associating with cell division and cytoskeleton proteins, such as beta-actin and vimentin, to form a complex which controls TUBB3 folding and proper attachment of the microtubules to the kinetochore. PDIA3 also plays a role in cytokine-dependent signal transduction, including STAT3 signaling (Santana-Codina et al. (2013) Mol. Cell. Proteomics 12:2111-2125). PDIA3 is involved in pathways such as antigen processing-cross presentation (e.g., ER-phagosome pathway), Class I MHC mediated antigen processing and presentation, calnexin/calreticulin cycle, protein metabolisms (e.g., post-translational protein modification), and allograft rejection. It has been demonstrated that the downregulation of PDIA3 expression is correlated with poor prognosis in early-stage cervical cancer (Chung et al. (2013) Biomarkers 18:573-579). It has also been demonstrated that ERp57/PDIA3 binds specific DNA fragments in a melanoma cell line (Aureli et al. (2013) Gene 524:390-395). PDIA3 is also involved in bone metastasis, which is the most common source of distant relapse in breast cancer (Santana-Codina et al. (2013), supra). In addition to cancer, overexpression of PDIA3 is linked to renal fibrosis, which is characterized by excess synthesis and secretion of ECM leading to ER stress (Dihazi et al. (2013) J. Cell Sci. 126:3649-3663). PDIA3 has been related to maxillary sinus squamous cell carcinoma, maxillary sinus cancer, and paranasal sinus cancer (Ogino et al. (2003) Clin. Cancer Res. 9:4043-4051).

The nucleic acid and amino acid sequences of a representative human PDIA3 is available to the public at the GenBank database (Gene ID 2923) and is shown in Table 1 (e.g., GenBank database numbers NM_005313.4 and NP_005304.3). The PDIA3 protein consists of four thioredoxin-like domains: a, b, b', and a'. The a and a' domains have Cys-Gly-His-Cys active site motifs (C57-G58-H59-C60 and C406-G407-H408-C409) and are catalytically active (Dong et al. (2009), supra; Kozlov et al. (2006) Structure 14:1331-1339). The bb' domains contain a CNX binding site, which is composed of positively charged, highly conserved residues (K214, K274, and R282) that interact with the negatively charged residues of the CNX P domain. The b' domain comprises the majority of the binding site, but the β4-β5 loop of the b domain provides additional contact (K214) to strengthen the interaction. A transient disulfide bond forms between the N-terminal cysteine in the catalytic motif and a substrate, but in a step called "escape pathway", the bond is disrupted as the C-terminal cysteine attacks the N-terminal cysteine to release the substrate. The domain structure of PDIA3 polypeptide is well known and accessible in UniProtKB database under the accession number P30101, including, in the order from the 5' terminus to the 3' terminus, a Thioredoxin domain 1 comprising, e.g., amino acid positions 25-133 of NP_005304.3, a Thioredoxin domain 2 comprising, e.g., amino acid positions 343-485 of NP_005304.3, and a C-terminal motif to prevent secretion from ER (e.g., amino acid positions 502-505 of NP_005304.3). Known binding partners of PDIA3 include, e.g., BACE1 (Leach et al. (2002) J. Biol. Chem. 277:29686-29697), ERP27 (Alanen et al. (2006) J. Biol. Chem. 281:33727-33738), tapasin (Leach et al. (2002), supra), CRT, and CNX.

Nucleic acid and polypeptide sequences of PDIA3 orthologs in organisms other than humans are well-known and include, for example, chimpanzee (Pan troglodytes) PDIA3 (NM_001246452.1 and NP_001233381.1), Rhesus monkey PDIA3 (NM_001195716.1 and NP_001182645.1), dog PDIA3 (XM_535453.5 and XP_535453.3), cattle PDIA3 (NM_174333.3 and NP_776758.2), mouse PDIA3 (NM_007952.2 and NP_031978.2), chicken PDIA3 (NM_204110.3 and NP_989441.1), tropical clawed frog PDIA3 (NM_203998.1 and NP_989329.1), fruit fly ERp60 (NM_165849.3 and NP_725084.2), Norway rat (*Rattus norvegicus*) PDIA3 (NM_017319.1 and NP_059015.1) and zebrafish PDIA3 (NM_001199737.1 and NP_001186666.1).

The term "PDIA3 activity" includes the ability of a PDIA3 polypeptide (and its fragments, domains, and/or motifs thereof, discussed herein) to bind its substrate and/or catalyze thiol oxidoreductase activity. PDIA3 activity may also include one or more of functions, such as those disclosed herein in antigen processing-cross presentation (e.g., ER-phagosome pathway), Class I MHC mediated antigen processing and presentation, calnexin/calreticulin cycle, protein metabolisms (e.g., post-translational protein modification), and allograft rejection. For example, PDIA3 may interact with various proteins disclosed herein, such as BACE1, ERP27, tapasin, CRT, and CNX and other binding partners including multiple antigens and receptors, for it functions in signalings. PDIA3 may also be proteolyticly modified, such as being glycosylated, or otherwise disclosed herein, for it funcations.

The term "PDIA3 substrate(s)" refers to binding partners of a PDIA3 polypeptide (and its fragments, domains, and/or motifs thereof, discussed herein), e.g., the proteins listed herein. Furthermore, PDIA3 substates may refer to downstream members in the signaling pathways where PDIA3 has a functional role.

The term "PDIA3-regulated signaling pathway(s)" includes signaling pathways in which PDIA3 (and its fragments, domains, and/or motifs thereof, discussed herein) binds to at least one of its substrate, through which at least one cellular function and/or activity and/or cellular protein profiles is changed (e.g., antigen processing and presentation). In some embodiments, PDIA3 promotes antigen presentation (including autoimmune responses) for at least one of its substates (e.g., antigens) which bind to it. PDIA3-regulated signaling pathways include at least those described herein, such as antigen processing-cross presentation (e.g., ER-phagosome pathway), Class I MHC mediated antigen processing and presentation, calnexin/calreticulin cycle, protein metabolisms (e.g., post-translational protein modification), and allograft rejection, etc.

The term "PDIA3 inhibitor(s)" includes any natural or non-natural agent prepared, synthesized, manufactured, and/or purified by human that is capable of reducing, inhibiting, blocking, preventing, and/or that inhibits the ability of a PDIA3 polypeptide (and its fragments, domains, and/or motifs thereof, discussed herein). In one embodiment, such inhibitors may reduce or inhibit the binding/interaction between PDIA3 and its substrates or other binding partners. In another embodiment, such inhibitors may reduce or inhibit PDIA3 as a protein disulfide isomerase and as an MHC molecule for antigen presentation and/or other immune responses. In still another embodiment, such inhibitors may increase or promote the turnover rate, reduce or inhibit the expression and/or the stability (e.g., the half-life), and/or change the cellular localization of PDIA3, resulting in at least a decrease in PDIA3 levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to PDIA3 or also inhibit at least one of other serine/threonine-protein kinases. RNA interference for PDIA3 polypepitdes are well known and commercially available (e.g., human or mouse shRNA products (Cat. #TL310527) and siRNA products (Cat #SR301974) and CRISPR knockout products (Cat. #KN205940 and KN313044) from Origene (Rockville, Md.), siRNA/shRNA products (Cat. #sc-35341, sc-44299, sc-42876) and human or mouse gene knockout kit via CRISPR (Cat. #sc-420698) from Santa Cruz Biotechonology (Dallas, Tex.), and Ready-to-package AAV shRNA clones from Vigene Biosciences (Rockville, Md., Cat. #SH814529), etc.). Methods for detection, purification, and/or inhibition of PDIA3 (e.g., by anti-PDIA3 antibodies) are also well known and commercially available (e.g., multiple anti-PDIA3 antibodies from Origene (Cat. #AP16091PU-T, AP17626PU-N, TA504995BM, and others), Novus Biologicals (Littleton, Colo., Cat. #NBP1-84796, NBP2-36765, NBP2-36766, etc.), abcam (Cambridge, Mass., Cat. #ab13506, ab154191, ab183398, ab183397, etc.), Santa Cruz Biotechnology (Cat. #sc-136522, sc-71075, sc-166680, sc-80648, etc.), etc.). PDIA3 knockout human cell lines are also well known and available at the Horizon (Cambridge, UK, Cat. #HZGHC2923).

The term "CALR," also known as calreticulin, calregulin, CRP55, CaBP3, calsequestrin-like protein, and endoplasmic reticulum resident protein 60 (ERp60) glucose-regulated protein, 58-kD (GRP58), refers to a member of a group of multifunctional proteins that bind and inactivate (as a chaperone to store calcium in ER) $Ca^{2+}$ ions (a second messenger in signal transduction). Calreticulin locates in the lumen of the endoplasmic reticulum and sarcoplasmic reticulum. It is also found in the nucleus, suggesting that it may have a role in transcription regulation. Calreticulin binds to the synthetic peptide KLGFFKR, which is almost identical to an amino acid sequence in the DNA-binding domain of the superfamily of nuclear receptors. CALR promotes folding, oligomeric assembly and quality control in the endoplasmic reticulum (ER) via the calreticulin/calnexin cycle. Calreticulin binds to misfolded proteins and prevents them from being exported from the endoplasmic reticulum to the Golgi apparatus. Calreticulin binds to antibodies in certain sera of systemic lupus and Sjogren patients which contain anti-Ro/SSA antibodies. Calreticulin is highly conserved among species. The amino terminus of calreticulin interacts with the DNA-binding domain of the glucocorticoid receptor and prevents the receptor from binding to its specific glucocorticoid response element. Calreticulin can inhibit the binding of androgen receptor to its hormone-responsive DNA element and can inhibit androgen receptor and retinoic acid receptor transcriptional activities in vivo, as well as retinoic acid-induced neuronal differentiation. Thus, calreticulin can act as an important modulator of the regulation of gene transcription by nuclear hormone receptors. Systemic lupus erythematosus is associated with increased autoantibody titers against calreticulin but calreticulin is not currently considered as a Ro/SS-A antigen. Increased autoantibody titer against human calreticulin is found in infants with complete congenital heart block of both the IgG and IgM classes. Diseases associated with CALR include myelofibrosis with myeloid metaplasia, somatic and thrombocythemia 1. CALR mutations are the second most common in myeloproliferative neoplasms. All mutations (insertions or deletions) affected the last exon, generating a reading frame shift of the resulting protein, that creates a novel terminal peptide and causes a loss of endoplasmic reticulum KDEL retention signal (Nangalia et al. (2013) *N. Engl. J. Med.* 369:2391-2405; Klampfl et al. (2013) *N. Engl. J. Med.* 369:2379-2390). CALR-related pathways include HTLV-I infection and transport to the Golgi and subsequent modification. GO annotations related to this gene include poly(A) RNA binding and ubiquitin protein ligase binding. CALR interacts transiently with almost all of the monoglucosylated glycoproteins that are synthesized in the ER. It interacts with the DNA-binding domain of NR3C1 and mediates its nuclear export. CALR is involved in maternal gene expression regulation and may participate in oocyte maturation via the regulation of calcium homeostasis. Calreticulin has been shown to interact with perforin (Andrin et al. (1998) *Biochemistry* 37:10386-10394) and NK2 homeobox 1 (Perrone et al. (1999) *J. Biol. Chem.* 274:4640-4645).

The nucleic acid and amino acid sequences of a representative human CALR is available to the public at the GenBank database (Gene ID 811) and is shown in Table 1 (e.g., GenBank database numbers NM_004343.3 and NP_004334.1). The domain structure of CALR polypeptide is well known and accessible in UniProtKB database under the accession number P27797, including, in the order from the 5' terminus to the 3' terminus, a signal peptide comprising, e.g., amino acid positions 1-17 of NP_004334.1, a N-terminal globular domain (containing zinc binding sites) comprising, e.g., amino acid positions 18-197 of NP_004334.1, a proline-rich P-domain forming an elongated arm-like structure comprising, e.g., amino acid positions 198-308 of NP_004334.1, and a C-terminal acidic domain comprising, e.g., amino acid positions 309-417 of NP_004334.1. In addition, other regions are indicated on CALR, including 4× approximate repeats comprising, e.g., amino acid positions 191-255 of NP_004334.1, a domain interacting with PPIB comprising, e.g., amino acid positions 237-270 of NP_004334.1, and 3× approximate repeats comprising, e.g., amino acid positions 259-297 of NP_004334.1. The P-domain binds one molecule of calcium with high affinity, whereas the acidic C-domain binds multiple calcium ions with low affinity. The tip of the extended arm formed by the P-domain also associates with PDIA3.

Nucleic acid and polypeptide sequences of CALR orthologs in organisms other than humans are well-known and include, for example, chimpanzee CALR (XM_016935207.1 and XP_016790696.1), Rhesus monkey CALR (NM_001261131.1 and NP_001248060.1), dog CALR (XM_862217.4 and XP_867310.2), cattle CALR (NM_174000.2 and NP_776425.1), mouse CALR (NM_007591.3 and NP_031617.1), chicken CALR (NM_001348545.1 and NP_001335474.1), tropical clawed frog CALR (NM_001001253.1 and NP_001001253.1), fruit fly CALR (NM_001275501.1 and NP_001262430.1, and NM_079569.5 and NP_524293.2), rat CALR (NM_022399.2 and NP_071794.1), and zebrafish CALR (NM_199713.2 and NP_956007.2).

The term "CALR activity" includes the ability of a CALR polypeptide (and its fragments, domains, and/or motifs thereof, discussed herein) to bind its substrate and/or catalyze thiol oxidoreductase activity. CALR activity may also include one or more of functions, such as those disclosed herein in calcium-binding, folding/assembly/quality control in the ER, interaction with glycoproteins in the ER and/or with NR3C1 for its nuclear export, maternal gene expression regulation, oocyte maturation via the regulation of calcium homeostasis.

The term "CALR substrate(s)" refers to binding partners of a CALR polypeptide (and its fragments, domains, and/or motifs thereof, discussed herein), e.g., the glycoproteins, NR3C1, perforin, NK2 homeobox 1, and PDIA3, as disclosed herein. Furthermore, CALR substates may refer to downstream members in the signaling pathways where CALR has a functional role.

The term "CALR-regulated signaling pathway(s)" includes signaling pathways in which CALR (and its fragments, domains, and/or motifs thereof, discussed herein) binds to at least one of its substrate, through which at least one cellular function and/or activity and/or cellular protein profiles is changed (e.g., antigen processing and presentation). In some embodiments, CALR promotes antigen presentation (including ER-Phagosome pathway), unfolded protein response (UPR), calnexin/calreticulin cycle, binding and uptake of ligands by savenger receptors, Class I MHC mediated antigen processing and presentation, and/or virus assembly and release.

The term "CALR inhibitor(s)" includes any natural or non-natural agent prepared, synthesized, manufactured, and/or purified by human that is capable of reducing, inhibiting, blocking, preventing, and/or that inhibits the ability of a CALR polypeptide (and its fragments, domains, and/or motifs thereof, discussed herein). In one embodiment, such inhibitors may reduce or inhibit the binding/interaction between CALR and its substrates or other binding partners. In another embodiment, such inhibitors may reduce or inhibit CALR functions. In one embodiment, such inhibitors may increase or promote the turnover rate, reduce or inhibit the expression and/or the stability (e.g., the half-life), and/or change the cellular localization of CALR, resulting in at least a decrease in CALR levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to CALR or also inhibit at least one of other related proteins (e.g., calcium-binding chaperons). RNA interference for CALR polypepitdes are well known and commercially available (e.g., human or mouse shRNA products (Cat. #TL314216 and TG500254) and siRNA products (Cat #SR413808, SR300567, SR509128, etc.) and CRISPR knockout products (Cat. #KN203222 and KN302469) from Origene (Rockville, Md.), siRNA/shRNA products (Cat. #sc-29234, sc-29895, and sc-63293) and human or mouse gene knockout kit via CRISPR (Cat. #sc-419428) from Santa Cruz Biotechonology (Dallas, Tex.), and Ready-to-package AAV shRNA clones from Vigene Biosciences (Rockville, Md., Cat. #SH855911), etc.). Methods for detection, purification, and/or inhibition of CALR (e.g., by anti-CALR antibodies) are also well known and commercially available (e.g., multiple anti-CALR antibodies from Origene (Cat. #TA336776, AM06211SU-N, TA326909, etc.), Novus Biologicals (Littleton, Colo., Cat. #NBP1-47518, NB600-101, NB600-103, etc.), abcam (Cambridge, Mass., Cat. #ab2907, ab22683, ab204990, etc.), Santa Cruz Biotechnology (Cat. #sc-101436, sc-166837, sc-373863, etc.), etc.). CALR knockout human cell lines are also well known and available at the Horizon (Cambridge, UK, Cat. #HZGHC018222c012, HZGHC018222c019, etc.).

The term "TAP1," also known as transporter 1, ATP Binding Cassette Subfamily B (MDR/TAP) member and transporter associated with antigen processing 1, refers to a member of a group of membrane-bound proteins of the superfamily of ATP-binding cassette (ABC) transporters. ABC proteins transport various molecules across extra- and intra-cellular membranes to the endoplasmic reticulum for association with WIC class I molecules. ABC genes are divided into seven distinct subfamilies (ABC1, MDR/TAP, MRP, ALD, OABP, GCN20, White). Members of the MDR/TAP subfamily are involved in multidrug resistance. TAP1 is involved in the pumping of degraded cytosolic peptides across the endoplasmic reticulum into the membrane-bound compartment where class I molecules assemble. TAP1 also acts as a molecular scaffold for the final stage of MHC class I folding. Nascent MHC class I molecules associate with TAP via tapasin. TAP1 is inhibited by the covalent attachment of herpes simplex virus ICP47 protein, which blocks the peptide-binding site of TAP. TAP1 is also inhibited by human cytomegalovirus US6 glycoprotein, which binds to the lumenal side of the TAP complex and inhibits peptide translocation by specifically blocking ATP-binding to TAP1 and prevents the conformational rearrangement of TAP induced by peptide binding. TAP1 is further inhibited by human adenovirus E3-19K glycoprotein, which binds the TAP complex and acts as a tapasin inhibitor, preventing WIC class I/TAP association. Expression of TAP1 is down-regulated by human Epstein-Barr virus vIL-10 protein, thereby affecting the transport of peptides into the endoplasmic reticulum and subsequent peptide loading by MHC class I molecules. Mutations in Tap1 may be associated with ankylosing spondylitis, insulin-dependent diabetes mellitus, celiac disease, Bare Lymphocyte Syndrome (BLS), Type I, herpes simplex infection, autosomal recessive inheritance, bronchiectasis, bronchiolitis, chronic otitis media, chronic sinusitis, etc. TAP1-related pathways include, e.g., antigen processing-cross presentation (such as ER-Phagosome pathway), Class I MHC mediated antigen processing and presentation, regulation of activated PAK-2p34 by proteasome mediated degradation, allograft rejection, Influenza A infection, immune System and Type II interferon signaling (IFNG), and NF-kappaB signaling. TAP1 has been shown to interact with HLA-A (Paulsson et al. (2002) *J. Biol. Chem.* 277:18266-18271), and Tapasin (Raghuraman et al. (2002) *J. Biol. Chem.* 277:41786-41794). TAP1 also forms heterodimers with TAP2 and interacts with Epstein-Barr virus BNLF2a, herpes simplex virus ICP47, PSMB5, and PSMB8 (Fruh et al. (1995) *Nature* 375:415-418; Begley et al. (2005) *Mol. Immunol.* 42:137-141; Horst et al. (2009) *J. Immunol.* 182:2313-2324).

The nucleic acid and amino acid sequences of a representative human TAP1 is available to the public at the GenBank database (Gene ID 6890) and is shown in Table 1 (e.g., GenBank database numbers NM_000593.5 and NP_000584.2, which represent the longer transcript variant 1 and the encoded longer isoform 1; and NM_001292022.1 and NP_001278951.1, which represent the shorter transcript variant 2, which differs in the 5'UTR and coding sequence compared to variant 1, and the encode isoform 2 shorter at the N-terminus compared to isoform 1). The domain structure of TAP1 polypeptide is well known and accessible in UniProtKB database under the accession number Q03518, including, in the order from the 5' terminus to the 3' terminus, a type I ABC transmembrane domain, e.g., amino acid positions 247-530 of NP_000584.2, and an ABC transporter domain comprising, e.g., amino acid positions 563-802 of NP_000584.2.

Nucleic acid and polypeptide sequences of TAP1 orthologs in organisms other than humans are well-known and include, for example, chimpanzee TAP1 (XM_001166911.5 and XP_001166911.2), Rhesus monkey TAP1 (XM_001115506.3 and XP_001115506.1), dog TAP1 (NM_001284496.2 and NP_001271425.1), cattle TAP1 (NM_001098058.1 and NP_001091527.1), mouse TAP1 (NM_013683.2 and NP_038711.2, representing the longer transcript variant 1 and the encoded longer isoform 1; and NM_001161730.1 and NP_001155202.1, representing the shorter transcript variant 2 lacking an alternate in-frame segment compared to variant 1 and the encoded isoform 2 with the same N- and C-termini but being shorter compared to isoform 1), chicken TAP1 (NM_001135968.1 and NP_001129440.1), rat TAP1 (NM_032055.4 and NP_114444.2), and zebrafish TAP1 (XM_002665007.2 and XP_002665053.1).

The term "TAP1 activity" includes the ability of a TAP1 polypeptide (and its fragments, domains, and/or motifs thereof, discussed herein) to bind its substrate (e.g., ATP, HLA-A, Tapasin, TAP2, etc.) and/or catalyze antigen presentation activity. TAP1 activity may also include one or more of functions, such as those disclosed herein in MHC class I folding, dimerization with TAP2, and other signaling pathways.

The term "TAP1 substrate(s)" refers to binding partners of a TAP1 polypeptide (and its fragments, domains, and/or motifs thereof, discussed herein), e.g., ATP, HLA-A, Tapasin, TAP2, and others as disclosed herein. Furthermore, TAP1 substates may refer to downstream members in the signaling pathways where TAP1 has a functional role.

The term "TAP1-regulated signaling pathway(s)" includes signaling pathways in which TAP1 (and its fragments, domains, and/or motifs thereof, discussed herein) binds to at least one of its substrate, through which at least one cellular function and/or activity and/or cellular protein profiles is changed (e.g., antigen processing and presentation). In some embodiments, TAP1 promotes antigen presentation (including ER-Phagosome pathway), regulation of activated PAK-2p34 by proteasome mediated degradation (e.g., ABC transporters), Class I MHC mediated antigen processing and presentation, allograft rejection, and/or virus assembly and release.

The term "TAP1 inhibitor(s)" includes any natural or non-natural agent prepared, synthesized, manufactured, and/or purified by human that is capable of reducing, inhibiting, blocking, preventing, and/or that inhibits the ability of a TAP1 polypeptide (and its fragments, domains, and/or motifs thereof, discussed herein). In one embodiment, such inhibitors may reduce or inhibit the binding/interaction between TAP1 and its substrates or other binding partners. In another embodiment, such inhibitors may reduce or inhibit TAP1 functions. In one embodiment, such inhibitors may increase or promote the turnover rate, reduce or inhibit the expression and/or the stability (e.g., the half-life), and/or change the cellular localization of TAP1, resulting in at least a decrease in TAP1 levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to TAP1 or also inhibit at least one of other related proteins (e.g., ATP-binding cassette (ABC) transporters). For example, Gromme et al. ((1997) *Eur. J. Immunol.* 27:898-904) teach rational design of TAP inhibitors by peptide substrate modification and peptidomimetics. RNA interference for TAP1 polypepitdes are well known and commercially available (e.g., human or mouse shRNA products (Cat. #TG308949, TR502210, TF711649, etc.) and siRNA products (Cat #SR321961, SR417657, SR504188, etc.) and CRISPR knockout products (Cat. #KN204242 and KN317175) from Origene (Rockville, Md.), siRNA/shRNA products (Cat. #sc-42981 and sc-42982) and human or mouse gene knockout kit via CRISPR (Cat. #sc-423265 and sc-405210) from Santa Cruz Biotechonology (Dallas, Tex.), and Ready-to-package AAV shRNA clones from Vigene Biosciences (Rockville, Md., Cat. #SH807891), etc.). Methods for detection, purification, and/or inhibition of TAP1 (e.g., by anti-TAP1 antibodies) are also well known and commercially available (e.g., multiple anti-TAP1 antibodies from Origene (Cat. #AP13226PU-N, R1028, TA311131, TA332358, etc.), Novus Biologicals (Littleton, Colo., Cat. #NBP1-54435, H00006890-M01, H00006890-M04, NBP2-55934, etc.), abcam (Cambridge, Mass., Cat. #ab13516, ab83817, ab10356, ab66074, etc.), Santa Cruz Biotechnology (Cat. #sc-376796, sc-20930, sc-11465, etc.), etc.). TAP1 knockout human cell lines are also well known and available at the Horizon (Cambridge, UK, Cat. #HZGHC6890, etc.).

The term "TAP2," also known as transporter 2, ATP Binding Cassette Subfamily B (MDR/TAP) Member, and transporter associated with antigen processing 2, refers to a member of a group of membrane-bound proteins of the superfamily of ATP-binding cassette (ABC) transporters. ABC proteins transport various molecules across extra- and intra-cellular membranes to the endoplasmic reticulum for association with MHC class I molecules. ABC genes are divided into seven distinct subfamilies (ABC1, MDR/TAP, MRP, ALD, OABP, GCN20, White). TAP2, same as TAP1, is a member of the MDR/TAP subfamily, involved in multidrug resistance and antigen presentation. Tap2 is located 7 kb telomeric to gene family member ABCB2 (Tap1). TAP2 forms a heterodimer with TAP1 in order to transport peptides from the cytoplasm to the endoplasmic reticulum. Mutations in TAP2 may be associated with ankylosing spondylitis, insulin-dependent diabetes mellitus, schizophrenia, and celiac disease (Yu et al. (2014) *J. Psychiatr. Res.* 50:73-78). Alternative splicing of Tap2 produces two products which differ in peptide selectivity and level of restoration of surface expression of MHC class I molecules. TAP2 is involved in the transport of antigens from the cytoplasm to the endoplasmic reticulum for association with MHC class I molecules. TPA2 also acts as a molecular scaffold for the final stage of MHC class I folding. Nascent MHC class I molecules associate with TAP via tapasin. TAP2 is inhibited by the covalent attachment of herpes simplex virus ICP47 protein, which blocks the peptide-binding site of TAP. TAP2 is also inhibited by human cytomegalovirus US6 glycoprotein, which binds to the lumenal side of the TAP complex and inhibits peptide translocation by specifically blocking ATP-binding to TAP1 and prevents the conformational rearrangement of TAP induced by peptide binding. TAP2 is also inhibited by human adenovirus E3-19K glycoprotein, which binds the TAP complex and acts as a tapasin inhibitor, preventing MHC class I/TAP association. Mutations in Tap2 may be associated with ankylosing spondylitis, insulin-dependent diabetes mellitus, celiac disease, Bare Lymphocyte Syndrome (BLS), Type I, herpes simplex infection, spondylitis, cardiac sarcoidosis, and posterior uveal melanoma. TAP2-related pathways include, e.g., antigen processing-cross presentation (such as ER-Phagosome pathway), Class I MHC mediated antigen processing and presentation, regulation of activated PAK-2p34 by proteasome mediated degradation (e.g., ABC transporters), allograft rejection, Influenza A infection, and NF-kappaB signaling. TAP2 interacts with, at least, TAP1, BLNF2a, ICP47, HLA-C, TAPBP, ABCA1, and ABCB7.

The nucleic acid and amino acid sequences of a representative human TAP2 is available to the public at the GenBank database (Gene ID 6891) and is shown in Table 1 (e.g., GenBank database numbers NM_000544.3 and NP_000535.3, which represent the longer transcript variant 1 (B allele) and the encoded longest isoform 1; NM_001290043.1 and NP_001276972.1, which represent transcript variant 1 (A allele), which differs at 3 nt positions compared to variant 1, B allele, and the encoded isoform 2, which is shorter at the C-terminus compared to isoform 1; and NM_018833.2 and NP_061313.2, which represent transcript variant 2, which differs in the 5' UTR and coding region compared to variant 1, and the encoded isoform 3, which is shorter and has a distinct C-terminus compared to isoform 1). The domain structure of TAP2 polypeptide is well known and accessible in UniProtKB database under the accession number Q03519, including, in the order from the 5' terminus to the 3' terminus, a type I ABC transmembrane domain comprising, e.g., amino acid positions 152-435 of NP_000535.3, and an ABC transporter domain comprising, e.g., amino acid positions 468-686 of NP_000535.3.

Nucleic acid and polypeptide sequences of TAP2 orthologs in organisms other than humans are well-known and include, for example, chimpanzee TAP2 (XM_009450990.2 and XP_009449265.2), tropical clawed frog TAP2 (XM_002942603.4 and XP_002942649.3), dog TAP2 (NM_001284495.1 and NP_001271424.1), cattle TAP2 (NM_174222.2 and NP_776647.1), mouse TAP2 (NM_011530.3 and NP_035660.3), chicken TAP2 (NM_001099357.1 and NP_001092827.1), rat TAP2 (NM_032056.3 and NP_114445.2), and zebrafish TAP2 (NM_001006594.1 and NP_001006594.1).

The term "TAP2 activity" includes the ability of a TAP2 polypeptide (and its fragments, domains, and/or motifs thereof, discussed herein) to bind its substrate (e.g., ATP, BLNF2a, ICP47, HLA-C, TAPBP, ABCA1, ABCB7, etc.) and/or catalyze antigen presentation activity. TAP2 activity may also include one or more of functions, such as those disclosed herein in MHC class I folding, dimerization with TAP1, and other signaling pathways.

The term "TAP2 substrate(s)" refers to binding partners of a TAP2 polypeptide (and its fragments, domains, and/or motifs thereof, discussed herein), e.g., ATP, BLNF2a, ICP47, HLA-C, TAPBP, ABCA1, ABCB7, and others as disclosed herein. Furthermore, TAP2 substates may refer to downstream members in the signaling pathways where TAP2 has a functional role.

The term "TAP2-regulated signaling pathway(s)" includes signaling pathways in which TAP2 (and its fragments, domains, and/or motifs thereof, discussed herein) binds to at least one of its substrate, through which at least one cellular function and/or activity and/or cellular protein profiles is changed (e.g., antigen processing and presentation). In some embodiments, TAP2 promotes antigen presentation (including ER-Phagosome pathway), regulation of activated PAK-2p34 by proteasome mediated degradation (e.g., ABC transporters), Class I MHC mediated antigen processing and presentation, allograft rejection, virus assembly and release, and NF-kappaB signaling.

The term "TAP2 inhibitor(s)" includes any natural or non-natural agent prepared, synthesized, manufactured, and/or purified by human that is capable of reducing, inhibiting, blocking, preventing, and/or that inhibits the ability of a TAP2 polypeptide (and its fragments, domains, and/or motifs thereof, discussed herein). In one embodiment, such inhibitors may reduce or inhibit the binding/interaction between TAP2 and its substrates or other binding partners. In another embodiment, such inhibitors may reduce or inhibit TAP2 functions. In one embodiment, such inhibitors may increase or promote the turnover rate, reduce or inhibit the expression and/or the stability (e.g., the half-life), and/or change the cellular localization of TAP2, resulting in at least a decrease in TAP2 levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to TAP2 or also inhibit at least one of other related proteins (e.g., ATP-binding cassette (ABC) transporters). For example, Gromme et al. ((1997) *Eur. J. Immunol.* 27:898-904) teach rational design of TAP inhibitors by peptide substrate modification and peptidomimetics. RNA interference for TAP2 polypepitdes are well known and commercially available (e.g., human or mouse shRNA products (Cat. #TF301249, TR516069, etc.) and siRNA products (Cat #SR503075, SR304711, SR316944, SR427405, etc.) and CRISPR knockout products (Cat. #KN222611 and KN317176) from Origene (Rockville, Md.), siRNA/shRNA products (Cat. #sc-42983 and sc-42984) and human or mouse gene knockout kit via CRISPR (Cat. #sc-423266 and sc-404218-KO-2) from Santa Cruz Biotechonology (Dallas, Tex.), and Ready-to-package AAV shRNA clones from Vigene Biosciences (Rockville, Md., Cat. #SH836791 and SH812040), etc.). Methods for detection, purification, and/or inhibition of TAP2 (e.g., by anti-TAP2 antibodies) are also well known and commercially available (e.g., multiple anti-TAP2 antibodies from Origene (Cat. #TA317404, TA327099, TA351786, TA351787, etc.), Novus Biologicals (Littleton, Colo., Cat. #NBP1-54436, NBP1-89312, NBP1-40335, etc.), abcam (Cambridge, Mass., Cat. #ab180611, ab130414, ab191067, etc.), Santa Cruz Biotechnology (Cat. #sc-25612, sc-515576, etc.), etc.). TAP2 knockout human cell lines are also well known and available at the Horizon (Cambridge, UK, Cat. #HZGHC6891, etc.).

The term "TAPBP," also known as TAP binding protein and Tapasin, refers to a member of a group of transmembrane glycoproteins which are present in the luman of the endoplasmic reticulum and mediate interaction between newly assembled major histocompatibility complex (MHC) class I molecules and the transporter associated with antigen processing (TAP), which is required for the transport of antigenic peptides across the endoplasmic reticulum membrane. This interaction facilitates optimal peptide loading on the MHC class I molecule. Up to four complexes of MHC class I and tapasin may be bound to a single TAP molecule. The peptide-loading complex consists of TAP, tapasin, MHC class I, calreticulin, and ERp57. Tapasin recruits MHC class I molecules to the TAP peptide transporter, and also enhances loading of MHC class I with high-affinity peptides. Following loading of MEW class I with a high-affinity ligand, the interaction between tapasin and MEW class I disappears (Zhang and Williams (2006) *Immunol. Res.* 35:151-162). Tapasin contains a C-terminal double-lysine motif (KKKAE) known to maintain membrane proteins in the endoplasmic reticulum. In humans, the tapasin gene lies within the major histocompatibility complex on chromosome 6. Alternative splicing results in three transcript variants encoding different isoforms. Tapasin has been shown to interact with HLA-A (Paulsson et al. (2002) *J. Biol. Chem.* 277:18266-18271), and TAP1 (Raghuraman et al. (2002) *J. Biol. Chem.* 277:41786-41794). Other predicted interacting partners for TAPBP include HLA-B, HLA-C, and PDIA3. Diseases associated with Tapasin/TAPBP include Bare Lymphocyte Syndrome, Type I, maxillary sinus squamous cell carcinoma, paranasal sinus cancer (e.g., adenoid cystic carcinoma of accessory sinus), and orbital melanoma. Among its related pathways are antigen processing-cross presentation (such as ER-Phagosome pathway), Class I MEW mediated antigen processing and presentation, and immune system and allograft rejection. An important paralog of this gene is TAPBPL.

The nucleic acid and amino acid sequences of a representative human TAPBP is available to the public at the GenBank database (Gene ID 6892) and is shown in Table 1 (e.g., GenBank database numbers NM_003190.4 and NP_003181.3, which represent the transcript variant 1 and the encoded isoform 1; NM_172208.2 and NP_757345.2, which represent the transcript variant 2, which differs in the 3' coding region and 3' UTR, compared to variant 1, and the encoded isoform 2 having a distinct C-terminus than isoform 1; and NM_172209.2 and NP_757346.2, which represent the transcript variant 3, which lacks an alternate in-frame exon in the central coding region, compared to variant 1, and the encoded isoform 3 that is shorter than isoform 1). The domain structure of TAPBP polypeptide is well known and accessible in UniProtKB database under the accession number 015533, including, in the order from the 5' terminus to the 3' terminus, a signal peptide comprising, e.g., amino acid positions 1-20 of NP_003181.3, and a Tapasin domain comprising, e.g., amino acid positions 21-448 of NP_003181.3.

Nucleic acid and polypeptide sequences of TAPBP orthologs in organisms other than humans are well-known and include, for example, chimpanzee TAPBP (XM_009451012.2 and XP_009449287.1, XM_009451014.2 and XP_009449289.1, XM_009451016.2 and XP_009449291.1, XM_009451017.2 and XP_009449292.1, and XM_001170532.4 and XP_001170532.1), Rhesus monkey TAPBP (NM_001261727.2 and NP_001248656.1), dog TAPBP (NM_001048101.2 and NP_001041566.1), cattle TAPBP (NM_001045885.1 and NP_001039350.1), mouse TAPBP (NM_001025313.1 and NP_001020484.1, representing the longer transcript variant 1 and the encoded longer isoform 1; and NM_009318.2 and NP_033344.1, representing the shorter transcript variant 2 with an alternate splice site in the coding region and the encoded isoform 2 lacks an internal aa, compared to isoform 1), chicken TAPBP (NM_001034816.3 and NP_001029988.2, and NM_001206611.2 and NP_001193540.1), tropical clawed frog TAPBP (XM_002938682.4 and XP_002938728.2), rat TAPBP (NM_033098.2 and NP_149089.1), and zebrafish TAPBP (NM_130974.1 and NP_571049.1).

The term "TAPBP activity" includes the ability of a TAPBP polypeptide (and its fragments, domains, and/or motifs thereof, discussed herein) to bind its substrate (e.g., TAP1, HLA-A, HLA-B, HLA-C, PDIA3, etc.) and/or catalyze antigen presentation activity. TAPBP activity may also include one or more of functions, such as those disclosed herein in antigen processing-cross presentation (such as ER-Phagosome pathway), Class I MHC mediated antigen processing and presentation, and immune system and allograft rejection and other signaling pathways.

The term "TAPBP substrate(s)" refers to binding partners of a TAPBP polypeptide (and its fragments, domains, and/or motifs thereof, discussed herein), e.g., TAP1, HLA-A, HLA-B, HLA-C, PDIA3, and others as disclosed herein. Furthermore, TAPBP substates may refer to downstream members in the signaling pathways where TAPBP has a functional role.

The term "TAPBP-regulated signaling pathway(s)" includes signaling pathways in which TAPBP (and its fragments, domains, and/or motifs thereof, discussed herein) binds to at least one of its substrate, through which at least one cellular function and/or activity and/or cellular protein profiles is changed (e.g., antigen processing and presentation). In some embodiments, TAPBP promotes antigen processing-cross presentation (such as ER-Phagosome pathway), Class I MHC mediated antigen processing and presentation, immune system and allograft rejection, and other signaling pathways.

The term "TAPBP inhibitor(s)" includes any natural or non-natural agent prepared, synthesized, manufactured, and/or purified by human that is capable of reducing, inhibiting, blocking, preventing, and/or that inhibits the ability of a TAPBP polypeptide (and its fragments, domains, and/or motifs thereof, discussed herein). In one embodiment, such inhibitors may reduce or inhibit the binding/interaction between TAPBP and its substrates or other binding partners. In another embodiment, such inhibitors may reduce or inhibit TAPBP functions. In one embodiment, such inhibitors may increase or promote the turnover rate, reduce or inhibit the expression and/or the stability (e.g., the half-life), and/or change the cellular localization of TAPBP, resulting in at least a decrease in TAPBP levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to TAPBP or also inhibit at least one of other related proteins (e.g., TAP-associated proteins). RNA interference for TAPBP polypeptides are well known and commercially available (e.g., human or mouse shRNA products (Cat. #TF301248) and siRNA products (Cat #SR304712, SR324363, SR426898, etc.) and CRISPR knockout products (Cat. #KN317177 and KN217968) from Origene (Rockville, Md.), siRNA/shRNA products (Cat. #sc-42986 and sc-42987) and human or mouse gene knockout kit via CRISPR (Cat. #sc-423267) from Santa Cruz Biotechonology (Dallas, Tex.), and Ready-to-package AAV shRNA clones from Vigene Biosciences (Rockville, Md., Cat. #SH846826 and SH829641), etc.). Methods for detection, purification, and/or inhibition of TAPBP (e.g., by anti-TAPBP antibodies) are also well known and commercially available (e.g., multiple anti-TAPBP antibodies from Origene (Cat. #TA332478 and AP46045PU-N), Novus Biologicals (Littleton, Colo., Cat. #NBP1-59071, NBP1-59070, NBP1-59938, etc.), abcam (Cambridge, Mass., Cat. #ab13518, ab196764, and ab104806), Santa Cruz Biotechnology (Cat. #sc-136435), etc.). TAPBP knockout human cell lines are also well known and available at the Horizon (Cambridge, UK, Cat. #HZGHC6892, etc.).

The term "ERAP1," also known as ER aminopeptidase 1 and Type 1 tumor necrosis factor receptor shedding aminopeptidase regulator or endoplasmic reticulum aminopeptidase 1 (ARTS-1), refers to a member of group of aminopeptidase involved in trimming HLA class I-binding precursors so that they can be presented on MHC class I molecules. ERAP1 acts as a monomer or as a heterodimer with ERAP2. It may also be involved in blood pressure regulation by inactivation of angiotensin II. Three transcript variants encoding two different isoforms have been found for Erap1. ERAP1 is an aminopeptidase that plays a central role in peptide trimming, a step required for the generation of most HLA class I-binding peptides. Peptide trimming is essential to customize longer precursor peptides to fit them to the correct length required for presentation on MHC class I molecules. ERAP1 strongly prefers substrates 9-16 residues long and rapidly degrades 13-mer to a 9-mer and then stops. ERAP1 preferentially hydrolyzes the residue Leu and peptides with a hydrophobic C-terminus, while it has weak activity toward peptides with charged C-terminus, including Met, Cys, and Phe (Nguyen et al. (2011) *Nat. Struct. Mol. Biol.* 18:604-613). In addition, ERAP1 cleaves several cytokine receptors on the surface of cells and reduces their ability to transmit chemical signals into the cell, which affects the process of inflammation. ERAP1/ARTS-1 is a member of the M1 family of zinc metallopeptidases which acts as an aminopeptidase that degrades oligopeptides by cleavage starting at the amino terminus. One of the functions of aminopeptidases is to degrade potentially toxic peptides in the cytosol. ERAP1/ARTS-1 is a transmembrane protein that is localized to the endoplasmic reticulum. ERAP1 may play a role in the inactivation of peptide hormones and may be involved in the regulation of blood pressure through the inactivation of angiotensin II and/or the generation of bradykinin in the kidney. Mutations in the ERAP1/ARTS-1 have been linked to an increased risk of ankylosing spondylitis but only in HLA-B27 positive patients (Brionez and Reveille (2008) *Curr. Opin. Rheumatol.* 20:384-391). Other related diseases and disorders include, e.g., birdshot chorioretinopathy, behcet syndrome, spondylitis, and essential hypertension. Tapasin has been suggested to interact with HIST3H3, HLA-B, IL6R, TNFRSF1A, and ACO2. Among its related pathways are antigen processing-cross presentation (folding, assembly, and peptide loading of class I MHC), Class 1 MHC mediated antigen processing and presentation, TNFR1 pathway (e.g., apoptosis and survival TNFR1 signaling), and immune system rejection.

The nucleic acid and amino acid sequences of a representative human ERAP1 is available to the public at the GenBank database (Gene ID 51752) and is shown in Table 1 (e.g., GenBank database numbers NM_016442.4 and NP_057526.3, which represent the longest transcript variant 1 and the encoded longer isoform a; NM_001349244.1 and NP_001336173.1, which represent the transcript variant 4, which differs in the 5' UTR, compared to variant 1, and the encoded same isoform a; NM_001040458.2 and NP_001035548.1, which represent the transcript variant 2, which differs in the 3' UTR and coding sequence compared to variant 1, and the encoded isoform b with a shorter and distinct C-terminus compared to isoform a; and NM_001198541.2 and NP_001185470.1, representing the transcript variant 3, which differs in the 3' UTR and coding sequence and in the 5' UTR compared to variant 1, and the same encoded isoform b). The domain structure of ERAP1 polypeptide is well known and accessible in UniProtKB database under the accession number Q9NZ08, including, in the order from the 5' terminus to the 3' terminus, a transmembrane region comprising, e.g., amino acid positions 2-21 of NP_057526.3, a peptidase M1 region comprising, e.g., amino acid positions 53-441 of NP_057526.3, and an ERAP1-like C-terminal domain comprising, e.g., amino acid positions 598-914 of NP_057526.3.

Nucleic acid and polypeptide sequences of ERAP1 orthologs in organisms other than humans are well-known and include, for example, chimpanzee ERAP1 (XM_009449387.2 and XP_009447662.2, XM_003310766.4 and XP_003310814.2, XM_016953521.1 and XP_016809010.1, XM_016953519.1 and XP_016809008.1, XM_016953520.1 and XP_016809009.1, XM_009449383.2 and XP_009447658.2, XM_009449384.2 and XP_009447659.2, XM_016953523.1 and XP_016809012.1, and XM_016953522.1 and XP_016809011.1), Rhesus monkey ERAP1 (XM_001094790.3 and XP_001094790.2), dog ERAP1 (XM_546015.5 and XP_546015.3, XM_005618086.2 and XP_005618143.1, XM_005618087.2 and XP_005618144.1, and XM_005618085.2 and XP_005618142.1), cattle ERAP1

(NM_001102003.1 and NP_001095473.1), mouse ERAP1 (NM_030711.4 and NP_109636.1), chicken ERAP1 (XM_001232417.4 and XP_001232418.2), tropical clawed frog ERAP1 (XM_002933429.2 and XP_002933475.2, and XM_012968052.2 and XP_012823506.1), and rat ERAP1 (NM_030836.1 and NP_110463.1).

The term "ERAP1 activity" includes the ability of an ERAP1 polypeptide (and its fragments, domains, and/or motifs thereof, discussed herein) to bind its substrate (e.g., ERAP2, HIST3H3, HLA-B, IL6R, TNFRSF1A, ACO2, etc.) and/or catalyze antigen presentation activity. ERAP1 activity may also include one or more of functions, such as those disclosed herein in antigen processing-cross presentation (folding, assembly, and peptide loading of class I MHC), Class I MHC mediated antigen processing and presentation, TNFR1 pathway (e.g., apoptosis and survival TNFR1 signaling), immune system rejection, and other signaling pathways.

The term "ERAP1 substrate(s)" refers to binding partners of an ERAP1 polypeptide (and its fragments, domains, and/or motifs thereof, discussed herein), e.g., ERAP2, HIST3H3, HLA-B, IL6R, TNFRSF1A, ACO2, and others as disclosed herein. Furthermore, ERAP1 substates may refer to downstream members in the signaling pathways where ERAP1 has a functional role.

The term "ERAP1-regulated signaling pathway(s)" includes signaling pathways in which ERAP1 (and its fragments, domains, and/or motifs thereof, discussed herein) binds to at least one of its substrate, through which at least one cellular function and/or activity and/or cellular protein profiles is changed (e.g., antigen processing and presentation). In some embodiments, ERAP1 promotes antigen processing-cross presentation (folding, assembly, and peptide loading of class I MEW), Class I MEW mediated antigen processing and presentation, TNFR1 pathway (e.g., apoptosis and survival TNFR1 signaling), immune system rejection, and other signaling pathways.

The term "ERAP1 inhibitor(s)" includes any natural or non-natural agent prepared, synthesized, manufactured, and/or purified by human that is capable of reducing, inhibiting, blocking, preventing, and/or that inhibits the ability of an ERAP1 polypeptide (and its fragments, domains, and/or motifs thereof, discussed herein). In one embodiment, such inhibitors may reduce or inhibit the binding/interaction between ERAP1 and its substrates or other binding partners. In another embodiment, such inhibitors may reduce or inhibit ERAP1 functions. In one embodiment, such inhibitors may increase or promote the turnover rate, reduce or inhibit the expression and/or the stability (e.g., the half-life), and/or change the cellular localization of ERAP1, resulting in at least a decrease in ERAP1 levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to ERAP1 or also inhibit at least one of other related proteins (e.g., aminopeptidases). For example, Węglarz-Tomczaka et al. teach discovery of multiple compound inhibitors for ERAP1 and ERAP2 by screening libraries of phosphorus-containing amino acid and dipeptide analogues (Węglarz-Tomczaka et al. (2016) *Bioorg. Med. Chem. Lett.* 26:4122-4126). RNA interference for ERAP1 polypepitdes are well known and commercially available (e.g., human or mouse shRNA products (Cat. #TG307017, TF505369, TF711082, etc.) and siRNA products (Cat #SR309948, SR421275, SR505552, etc.) and CRISPR knockout products (Cat. #KN205249) from Origene (Rockville, Md.), siRNA/shRNA products (Cat. #sc-43577 and sc-44435) and human or mouse gene knockout kit via CRISPR (Cat. #sc-429840) from Santa Cruz Biotechonology (Dallas, Tex.), and Ready-to-package AAV shRNA clones from Vigene Biosciences (Rockville, Md., Cat. #SH838580 and SH865692, etc.). Methods for detection, purification, and/or inhibition of ERAP1 (e.g., by anti-ERAP1 antibodies) are also well known and commercially available (e.g., multiple anti-ERAP1 antibodies from Origene (Cat. #TA350992, TA315501, TA341243, etc.), Novus Biologicals (Littleton, Colo., Cat. #MAB2334, AF2334, NBP2-41232, H00051752-M01, etc.), abcam (Cambridge, Mass., Cat. #ab124669, ab181390, ab150627, etc.), Santa Cruz Biotechnology (Cat. #sc-100727 and sc-271823), etc.). ERAP1 knockout human cell lines are also well known and available at the Horizon (Cambridge, UK, Cat. #HZGHC51752, etc.).

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM, IgG1, IgG2C, and the like) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as inhibitor(s) of the regulators of one or more biomarkers listed in Table 1, such as one or more antigen processing and presentation as described herein/immunotherapy combination therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or underactivity, emergence, expression, growth, remission, recurrence or resistance of tumors before, during or after therapy, for determining the likelihood of response of a cancer to inhibitor(s) of one or more biomarkers listed in Table 1, such as one or more regulators of antigen processing and presentation as described herein/immunotherapy combination therapy (e.g., treatment with a combination of such inhibitor and an immunotherapy, such as an immune checkpoint inhibitor). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular inhibitor/immunotherapy combination therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

The term "response to immunotherapy" or "response to inhibitor(s) of one or more biomarkers listed in Table 1, such as one or more regulators of antigen processing and presentation as described herein/immunotherapy combination therapy" relates to any response of the hyperproliferative disorder (e.g., cancer) to an anti-cancer agent, such as an inhibitor of one or more biomarkers listed in Table 1, such as one or more regulators of antigen processing and presentation as described herein (e.g., HLA-E, Pdia3, Calr, Tap1, Tap2, Tapbp, Erap1, etc.), and an immunotherapy, preferably to a change in tumor mass and/or volume after initiation of neoadjuvant or adjuvant therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) J. Virol. 76:9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the therapies. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "subject" refers to any healthy animal, mammal or human, or any animal, mammal or human afflicted with a cancer, e.g., brain, lung, ovarian, pancreatic, liver, breast, prostate, and/or colorectal cancers, melanoma, multiple myeloma, and the like. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "synergistic effect" refers to the combined effect of two or more anti-cancer agents (e.g., inhibitor(s) of one or more biomarkers listed in Table 1, such as one or more regulators of antigen processing and presentation as described herein/immunotherapy combination therapy) can be greater than the sum of the separate effects of the anti-cancer agents/therapies alone.

The term "T cell" includes CD4$^+$ T cells and CD8$^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) Science 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Tables 1 and 2) are well-known in the art and readily available on publicly available databases, such as the National Center for Biotechnology Information (NCBI). For example, exemplary nucleic acid and amino acid sequences derived from publicly available sequence databases are provided below and include, for example, PCT Publ. WO 2014/022759, which is incorporated herein in its entirety by this reference.

TABLE 1

```
SEQ ID NO: 1 Human HLA-E cDNA Sequence (NM_005516.5, CDS region
from position 127-1203)
     1      gcagactcag ttctcattcc caatgggtgt cgggtttcta gagaagccaa tcagcgtcgc 61      cacgactccc gactataaag tcccatccg  gactcaagaa gttctcagga ctcagaggct 121      gggatcatgg tagatggaac cctcctttta ctcctctcgg aggccctggc ccttacccag 181      acctgggcgg gctcccactc cttgaagtat ttccacactt ccgtgtcccg gcccggccgc 241      ggggagcccc gcttcatctc tgtgggctac gtggacgaca cccagttcgt gcgcttcgac 301      aacgacgccg cgagtccgag gatggtgccg cgggcgccgt ggatggagca ggaggggtca 361      gagtattggg accgggagac acggagcgcc agggacaccg cacagatttt ccgagtgaat 421      ctgcggacgc tgcgcggcta ctacaatcag agcgaggccg ggtctcacac cctgcagtgg 481      atgcatggct gcgagctggg gcccgacggg cgcttcctcc gcgggtatga acagttcgcc 541      tacgacggca aggattatct caccctgaat gaggacctgc gctcctggac cgcggtggac 601      acggcggctc agatctccga gcaaaagtca aatgatgcct ctgaggcgga gcaccagaga 661      gcctacctgg aagacacatg cgtggagtgg ctccacaaat acctggagaa ggggaaggag 721      acgctgcttc acctggagcc cccaaagaca cacgtgactc accaccccat ctctgaccat 781      gaggccaccc tgaggtgctg ggccctgggc ttctaccctg cggagatcac actgacctgg 841      cagcaggatg gggagggcca tacccaggac acggagctcg tggagaccag gcctgcaggg 901      gatggaacct tccagaagtg ggcagctgtg gtggtgcctt ctggagagga gcagagatac 961      acgtgccatg tgcagcatga ggggctaccc gagcccgtca ccctgagatg gaagccggct 1021      tcccagccca ccatccccat cgtgggcatc attgctggcc tggttctcct tggatctgtg 1081      gtctctggag ctgtggttgc tgctgtgata tggaggaaga agagctcagg tggaaaagga 1141      gggagctact ctaaggctga gtggagcgac agtgcccagg ggtctgagtc tcacagcttg 1201      taaagcctga gacagctgcc ttgtgtgcga ctgagatgca cagctgcctt gtgtgcgact 1261      gagatgcagg atttcctcac gcctcccta tgtgtcttag gggactctgg cttctctttt 1321      tgcaagggcc tctgaatctg tctgtgtccc tgttagcaca atgtgaggag gtagagaaac 1381      agtccacctc tgtgtctacc atgaccccct tctcacact gacctgtgtt ccttccctgt 1441      tctcttttct attaaaaata agaacctggg cagagtgcgg cagctcatgc ctgtaatccc 1501      agcacttagg gaggccgagg agggcagatc acgaggtcag gagatcgaaa ccatcctggc 1561      taacacggtg aaaccccgtc tctactaaaa aatacaaaaa attagctggg cgcagaggca 1621      cgggcctgta gtcccagcta ctcaggaggc tgaggcagga gaatggcgtc aacccgggag
```

TABLE 1-continued

```
1681    gcggaggttg cagtgagcca ggattgtgcg actgcactcc agcctgggtg acagggtgaa
1741    acgccatctc aaaaaataaa aattgaaaaa taaaaaaaga acctggatct caatttaatt
1801    tttcatattc ttgcaatgaa atggacttga ggaagctaag atcatagcta gaaatacaga
1861    taattccaca gcacatctct agcaaattta gcctattcct attctctagc ctattcctta
1921    ccacctgtaa tcttgaccat ataccttgga gttgaatatt gttttcatac tgctgtggtt
1981    tgaatgttcc ctccaacact catgttgaga cttaatccct aatgtggcaa tactgaaagg
2041    tggggccttt gagatgtgat tggatcgtaa ggctgtgcct tcattcatgg gttaatggat
2101    taatgggtta tcacaggaat gggactggtg gctttataag aagaggaaaa gagaactgag
2161    ctagcatgcc cagcccacag agagcctcca ctagagtgat gctaagtgga aatgtgaggt
2221    gcagctgcca cagagggccc ccaccaggga aatgtctagt gtctagtgga tccaggccac
2281    aggagagagt gccttgtgga gcgctgggag caggacctga ccaccaccag gaccccagaa
2341    ctgtggagtc agtggcagca tgcagcgccc ccttgggaaa gctttaggca ccagcctgca
2401    acccattcga gcagccacgt aggctgcacc cagcaaagcc acaggcacgg ggctacctga
2461    ggccttgggg gcccaatccc tgctccagtg tgtccgtgag gcagcacacg aagtcaaaag
2521    agattattct cttcccacag ataccttttc tctcccatga cccttttaaca gcatctgctt
2581    cattccctc accttccag gctgatctga ggtaaacttt gaagtaaaat aaaagctgtg
2641    tttgagcatc atttgtattt caaaaaaaaa aaaaaaaa
```

SEQ ID NO: 2 Human HLA-E Amino Acid Sequence (NP_005507.3)
```
  1    mvdgtlllll sealaltqtw agshslkyfh tsvsrpgrge prfisvgyvd dtqfvrfdnd
 61    aasprmvpra pwmeqegsey wdretrsard taqifrvnlr tlrgyynqse agshtlqwmh
121    gcelgpdgrf lrgyeqfayd gkdyltlned lrswtavdta aqiseqksnd aseaehqray
181    ledtcvewlh kylekgketl lhleppkthv thhpisdhea tlrcwalgfy paeitltwqg
241    dgeghtqdte lvetrpagdg tfqkwaavvv psgeeqrytc hvqheglpep vtlrwkpasq
301    ptipivgiia glvllgsvvs gavvaaviwr kkssggkggs yskaewsdsa qgseshsl
```

SEQ ID NO: 3 Mouse H2-T23 cDNA Sequence (NM_010398.3, CDS region from position 33-1106)
```
  1    attcaggttc ctcacagacc caggggtga ggatgttgct ttttgcccac ttgcttcagc
 61    tgctggtcag cgccacagtc ccgacccaga gtagcccaca ctcgctgcgg tatttcacca
121    ccgccgtgtc ccggcccggc ctcggggagc cccggttcat cattgtcggc tacgtggacg
181    acacgcagtt cgtgcgcttc gacagcgacg cggaaaatcc gaggatggag cctcgggcgc
241    ggtggattga gcaggagggg ccggagtatt gggagcggga gacttggaaa gccagggaca
301    tggggaggaa cttcagagta aacctgagga ccctgctcgg ctactacaat cagagtaacg
361    acgaatctca cacgctgcag tggatgtacg gctgcgacgt ggggcccgat gggcgcctgc
421    tccgcgggta ttgtcaggag gcctacgatg ccaggattta catctccctg aacgaggacc
481    tgcgttcctg gaccgcgaat gacatagcct cacagatctc taagcacaag tcagaggcag
541    tcgatgaggc caccaacaga gggcatacc tgcaaggtcc ttgcgtggag tggctccata
601    gatacctacg gctgggaaat gagacactgc agcgctcaga ccctccaaag gcacatgtga
661    cccatcaccc tagatctgaa gatgaagtca ccctgaggtg ctgggccctg gcttctacc
721    ctgctgacat caccctgacc tggcagttga tggggagga gctgaccag gacatggagc
781    ttgtggagac caggcctgca gggatggaa ccttccagaa gtggcagct gtcgtggtgc
841    ctcttgggaa ggagcagtat tacacatgcc atgtgtacca tgaggggctg cctgagcccc
901    tcaccctgag atgggagcct cctccatcca ctgtctccaa catggtaatc atagctgttc
```

TABLE 1-continued

```
 961    tggttgtcct tggagctgtg atcatccttg gagctgtggt ggcttttgtg atgaagagga
1021    ggagacacat aggtgtaaaa ggatgctatg ctcatgttct aggcagcaag agcttccaga
1081    cctctgactg gcctcagaag gcatgaaaat ccctgggggg gctggtgaga tggctcagtg
1141    ggtaagagca ctgactgctc ttctgaaggt ccagagttca atcccagca accacatggt
1201    ggctcacaac catccgtaac gagatctgac tccctcttct ggagtgtctg aagacagcta
1261    caatgtactt acatataata aataaataaa taaataaata aataaataaa taaataa
```

SEQ ID NO: 4 Mouse H2-T23 Amino Acid Sequence (NP_034528.1)
```
  1    mllfahllql lvsatvptqs sphslryftt avsrpglgep rfiivgyvdd tqfvrfdsda
 61    enprmeprar wieqegpeyw eretwkardm grnfrvnlrt llgyynqsnd eshtlqwmyg
121    cdvgpdgrll rgycqeaydg qdyislnedl rswtandias qiskhkseav deahqqrayl
181    qgpcvewlhr ylrlgnetlq rsdppkahvt hhprsedevt lrcwalgfyp aditltwqln
241    geeltqdmel vetrpagdgt fqkwaavvvp lgkeqyytch vyheglpepl tlrwepppst
301    vsnmviiavl vvlgaviilg avvafvmkrr rhigvkgcya hvlgsksfqt sdwpqka
```

SEQ ID NO: 5 Mouse HLA-E/H2-T23 Pseudogene cDNA Sequence
(NM_001271005.1, CDS region from position 20-1024)
```
  1    acagacccag ggagtgagga tgttgctttt tgcccacttg ctccagctgc tggtcagcgc
 61    cacagtcccg acccagagta gctcacactc gctgcggtat ttccacaccg tcgtatcccg
121    gcccggcctc ggagagcccc ggttcatcat tgtcggctac gtggacgaca cgcagttcgt
181    gcgcttcgac agcgactcgg agaatccgag gatggagcct cgggcgcggt ggattgagca
241    ggagggccg gagtattggg agcgggagac tcggaaagcc agggacatgg gaggaacttt
301    cagagtaaac ctgaggaccc tgctcggcta ctacaatcag agtaaggacg aatctcacac
361    gctgcagtgg atgtacggct gcgacgtggg gcccgatggg cgcctgctcc gcgggtattg
421    tcaggaggcc tatgatggcc aggattacat ctccctgaac gaagacctgc gctcctggac
481    cgcgaccaac ttagcctcgc atatctctaa gtgcaagtca gaggcggtcg atgaggccca
541    ccaacagagg gcatacctgc aaggtccttg cgtggagtgg ctccatacat acctacagct
601    gggaagtgag acactgctgc gctcagaccc tccaaaggca catgtgaccc gtcaccccag
661    acctgaaggt gatgtcaccc tgaggtgctg ggccctgggc ttctatcctg ctgacatcac
721    cctgacctgg cagttgaatg gggaggagct gacccaggac atggagtttg tggagaccag
781    gcctgcaggg gatggaacct tccagaagtg gcatctgtg tggtgcctc ttgggaagga
841    gcagaattac acatgccatg tgtaccatga ggggctgcct gagcccctca ccctgagatg
901    ggagcctcct ccatccactg tctccaacat ggtaatcatt gctgttctgg ttgtccttgg
961    agctgtgata gtcattgttg ctgtggtggc ttttgtaatg aagaggagga aaacacaggt
1021    gtaaaaggat gctatgctca tgttctaggc agcaagagct tccagacctc tgactggcct
1081    cagaaggcat gacaatccct ggggcctgg gactggacct gaggcacaag ggagaccggg
1141    gttcaattcc tagcactgac atggcaggtg tctgttacta gtaacaaaca gttcatgtct
1201    catgaatgta gacatgaatg cagctaaagc accaacatac ataatattaa acctttaaaa
1261    aaataaaagg tgtatgagct ggacaaaca
```

SEQ ID NO: 6 Mouse HLA-E/H2-T23 Pseudogene Amino Acid Sequence
(NP_001257934.1)
```
  1    mllfahllql lvsatvptqs sshslryfht vvsrpglgep rfiivgyvdd tqfvrfdsds
 61    enprmeprar wieqegpeyw eretrkardm grnfrvnlrt llgyynqskd eshtlqwmyg
121    cdvgpdgrll rgycqeaydg qdyislnedl rswtatnlas hiskckseav deahqqrayl
181    qgpcvewlht ylqlgsetll rsdppkahvt rhprpegdvt lrcwalgfyp aditltwqln
```

TABLE 1-continued

```
241  geeltqdmef vetrpagdgt fqkwasvvvp lgkeqnytch vyheglpepl tlrwepppst
301  vsnmviiavl vvlgaviviv avvafvmkrr ktqv
```

SEQ ID NO: 7 Human PDIA3 cDNA Sequence (NM_005313.4, CDS region from position 149-1666)

```
   1  gccgggtttg ggggttggga cctccggctg caggtccgcc tgggccagac gcgcgagcgc
  61  aagcagcggg ttagtggtcg cgcgcccgac ctccgcagtc ccagccgagc gcgacccctt
 121  ccggccgtcc caccccacc tcgccgccat gcgcctccgc cgcctagcgc tgttcccggg
 181  tgtggcgctg cttcttgccg cggcccgcct cgccgctgcc tccgacgtgc tagaactcac
 241  ggacgacaac ttcgagagtc gcatctccga cacgggctct gcgggcctca tgctcgtcga
 301  gttcttcgcc ccctggtgtg acactgcaa gagacttgca cctgagtatg aagctgcagc
 361  taccagatta aaaggaatag tcccattagc aaaggttgat tgcactgcca acactaacac
 421  ctgtaataaa tatggagtca gtggatatcc aaccctgaag atatttagag atggtgaaga
 481  agcaggtgct tatgatggac ctaggactgc tgatggaatt gtcagccact gaagaagca
 541  ggcaggacca gcttcagtgc ctctcaggac tgaggaagaa tttaagaaat tcattagtga
 601  taaagatgcc tctatagtag gttttttcga tgattcattc agtgaggctc actccgagtt
 661  cctaaaagca gccagcaact tgagggataa ctaccgattt gcacatacga atgttgagtc
 721  tctggtgaac gagtatgatg ataatggaga gggtatcatc ttatttcgtc cttcacatct
 781  cactaacaag tttgaggaca agactgtggc atatacagag caaaaaatga ccagtggcaa
 841  aattaaaaag tttatccagg aaaacatttt tggtatctgc cctcacatga cagaagacaa
 901  taaagatttg atacagggca aggacttact tattgcttac tatgatgtgg actatgaaaa
 961  gaacgctaaa ggttccaact actgggagaaa cagggtaatg atggtggcaa agaaattcct
1021  ggatgctggg cacaaactca actttgctgt agctagccgc aaaacccttta gccatgaact
1081  ttctgatttt ggcttggaga gcactgctgg agagattcct gttgttgcta tcagaactgc
1141  taaaggagag aagtttgtca tgcaggagga gttctcgcgt gatgggaagg ctctggagag
1201  gttcctgcag gattactttg atggcaatct gaagagatac ctgaagtctg aacctatccc
1261  agagagcaat gatgggcctg tgaaggtagt ggtagcagag aattttgatg aaatagtgaa
1321  taatgaaaat aaagatgtgc tgattgaatt ttatgccct tggtgtggtc actgtaagaa
1381  cctggagccc aagtataaag aacttggcga aagctcagc aaagacccaa atatcgtcat
1441  agccaagatg gatgccacag ccaatgatgt gccttctcca tatgaagtca gaggttttcc
1501  taccatatac ttctctccag ccaacaagaa gctaaatcca agaaatatg aaggtggccg
1561  tgaattaagt gattttatta gctatctaca aagagaagct acaaaccccc ctgtaattca
1621  agaagaaaaa cccaagaaga agaagaaggc acaggaggat ctctaaagca gtagccaaac
1681  accactttgt aaaaggactc ttccatcaga gatgggaaaa ccattgggga ggactaggac
1741  ccatatggga attattaccct ctcagggccg agaggacaga atggatataa tctgaatcct
1801  gttaaatttt ctctaaactg tttcttagct gcactgttta tggaaatacc aggaccagtt
1861  tatgtttgtg gttttgggaa aaattatttg tgttggggga atgttgtgg gggtggggtt
1921  gagttggggg tattttctaa tttttttgt acatttggaa cagtgacaat aaatgagacc
1981  cctttaaact gtcttatttt ccaccagatt gagaaccaga tgttctctac acactatcac
2041  tgttcaatag agcttcttc agtgatggaa atgctctgta atctacactg ttcagtacag
2101  gtagctacgg agcatctgaa atatggctag aaactacatt tttgttttga ttaatttaaa
2161  tagccataca gttgctacca tactggtcac ggcagctgta gactgactgg gtccatagtt
```

TABLE 1-continued

```
2221  catcacctca aaattctttc aaaatttatt atctctttct ctccttacat gtttatttcc
2281  caggcctacc ctggtgatta gaacagctga agggccttc ttgttaggct gtccatgccc
2341  taaggatggg ttcctgttta tccttgccac gcagctgagc ttactgcatg tttatatctc
2401  ccaaggactg ttctctgctc agaaatgccc tgtcaagggg gtggcatcac gcagtttcat
2461  ccaagttgtt tcaggaattg ctgacactgc tgggtgcagt tctatcccct aaagcctagg
2521  gtgtggccct taacttccc cttcagtaga actgggaaag gcagtaccat tcctagttat
2581  gagtgaagca tccactttct tttgtaacaa tgaggaacag aaaggataag actgaagagt
2641  gatcttttgt ccaactaaac catttatctc cttttgtagg taaattcaaa tcctgcccag
2701  ttatagtttt cagtcactgg agaattccag gtaggagccc tactttaggt gatcctagga
2761  actcctatgt tcagaaaaga atttcttcc tactatataa ttacagtatt tagctgtcaa
2821  ttttaagatg aatttggtag agccttatag taaagtatgt atcttggtca cacacaaagc
2881  ttggaaaaag taaaagatgt ctaaaccata atcttgtaac tcataacatc tgggctgggg
2941  cccggggatc taattgttta gagagcccca aaagtggctc agatgtaaag ccagggttaa
3001  gaaccatctg ccttggaaga tttaagggaa acatataaac ttgtacaaag gacaaaaaaa
```

SEQ ID NO: 8 Human PDIA3 Amino Acid Sequence (NP_005304.3)
```
  1  mrlrrlalfp gvalllaaar laaasdvlel tddnfesris dtgsaglmlv effapwcghc
 61  krlapeyeaa atrlkgivpl akvdctantn tcnkygvsgy ptlkifrdge eagaydgprt
121  adgivshlkk qagpasvplr teeefkkfis dkdasivgff ddsfseahse flkaasnlrd
181  nyrfahtnve slvneyddng egiilfrpsh ltnkfedktv ayteqkmtsg kikkfiqeni
241  fgicphmted nkdliqgkdl liayydvdye knakgsnywr nrvmmvakkf ldaghklnfa
301  vasrktfshe lsdfglesta geipvvairt akgekfvmqe efsrdgkale rflqdyfdgn
361  lkrylksepi pesndgpvkv vvaenfdeiv nnenkdvlie fyapwcghck nlepkykelg
421  eklskdpniv lakmdatand vpspyevrgf ptiyfspank klnpkkyegg relsdfisyl
481  qreatnppvi qeekpkkkkk agedl
```

SEQ ID NO: 9 Mouse PDI43 cDNA Sequence (NM_007952.2, CDS region from position 138-1655)
```
  1  cgagcaggcc taggggttg ggacctcggc agcgggtctg cccgggccag acgcgcgagc
 61  gcaggcaagc ggctgcagat tgcgggctct cccatctcat ttctccggtc ccggcccctcc
121  gaccgcgacc cgccgccatg cgcttcagct gcctagctct gctccccggc gtggcgctgc
181  tgctcgcctc ggcccgtctc gccgccgcct ccgatgtgtt ggaactgacg gacgaaaact
241  tcgagagtcg cgtctccgac acgggctcgg cggggctcat gctagtcgag ttcttcgccc
301  cctggtgtgg acattgcaag aggcttgccc ctgagtatga agctgcagca accagattaa
361  aaggaatagt cccattagca aaggtggatt gcactgccaa cacaaacacc tgtaataagt
421  atgggggtcag tggctaccca actcttaaga tctttagaga tggtgaagaa gcgggtgctt
481  atgatgggcc taggactgct gatggaattg tcagccactt gaagaaacaa gcaggaccag
541  cttcagttcc tctcaggact gaggaagaat ttaagaagtt cattagtgat aaagatgcct
601  cagtggtggg tttttcagg gatttattca gtgatgggca ctctgaattc ctaaaagcag
661  ccagcaactt gagagataac taccgatttg cacacaccaa cattgagtct ctggtgaagg
721  agtacgatga taatggagag ggatcacta tattccgtcc attacatctt gctaacaagt
781  ttgaagacaa aactgtggca tatactgaaa agaaaatgac cagtggcaag atcaagaaat
841  ttattcagga tagcattttt ggtctctgtc ctcatatgac ggaagataat aaagatttga
901  tacaaggcaa ggacttactc accgcttact atgatgtgga ctatgaaaag aatgctaaag
```

TABLE 1-continued

```
 961  gttctaacta ctggagaaac agggtcatga tggtggcaaa gaaattcctt gatgctggac
1021  acaaactcaa ctttgctgta gctagccgta aaacctttag ccatgaactg tcagattttg
1081  gcttagaaag cactactgga gaggttcctg ttgtggctat cagaactgct aaaggagaga
1141  agtttgtcat gcaggaggag ttctcgcgag atggcaaggc tcttgaacag ttcctgcaag
1201  aatactttga tggcaacttg aagagatacc tgaagtctga acccatccca gagtccaacg
1261  aagggcctgt caaggttgtg gtagcagaga attttgatga catagtgaat gaagaagata
1321  aggacgtgct gattgaattt tacgcccctt ggtgtggcca ctgtaagaat ctggaaccca
1381  agtataaaga gctgggagaa aaactcagca agatcccaaa tattgtcata gccaagatgg
1441  atgccacagc caatgatgtg ccttctccat atgaagtcaa gggttttcct accatctact
1501  tctcaccagc caacaagaag ctaactccaa agaagtatga aggtggccgt gaattaaatg
1561  attttattag ctatctacaa cgagaagcta caaaccccc tataattcaa gaagaaaaac
1621  ctaagaagaa gaagaaggca caagaggacc tctaaagcaa cagccaaatg caccacttta
1681  taaaaggact cttacaccag agaaggcaaa accagagagg acagaatgga tatactctga
1741  atcctgttaa attttctcta aactgtttct tagctgcact gtttgaaaat acaaggacca
1801  gtttatgttt gtggttttgg gagaaaatta tttgtgttgg aagaatgtt gtggggtgg
1861  ggggaattga gttggggggt tattttctaa ttttttttgt acatttgaa cagtgacaat
1921  aaatgtgccc cctttatact gtcgttttt tcccctcatg ggatggagaa tcagggtctc
1981  taaactgtaa tacagtaata gatagaagtg tttgagctat gctgttcaat gctgtagcta
2041  aaccagatat gttatctcct ataatcgcaa cacttgggag gtgcaggcaa gagatctcaa
2101  gttcaagatc ttccatggct acatagcagg ttttgaggct agcatcttaa acaggtttga
2161  tcttcaaa acaaagaaaa ccagctatgc tgattcctgt aacttgagac tgaataggtc
2221  cagttaccat ctccaaattg tataatttat tagtttcttt ctgtagctca agctgtcctt
2281  gaacttgtga tggtctccct ccctggccct gagatactga tgacagtt gtttctagcc
2341  tcattcatgt cctaaaggtg aatgcttact cttgccacac agccaagctt tctgcatgtg
2401  catgcctcct gaggatggtt ctctgcccag aaatgccctg tgtgagtgac agcagtttgg
2461  ggttccatcc aatttttagga attattgaaa ctgctgggtg cagctctccc caaatcattg
2521  ggtgtagcca tttacttccc tccagtgaac agggaaacag tatcaatcgc tggcaagaac
2581  aagaacccac agagatgttt tcttttgaat ggattaaagt attgccctcc ttttatagct
2641  aaaaaaaaaa aaaaaaaa
```

SEQ ID NO: 10 Mouse PDI43 Amino Acid Sequence (NP_031978.2)

```
  1  mrfsclallp gvalllasar laaasdvlel tdenfesrvs dtgsaglmlv effapwcghc
 61  krlapeyeaa atrlkgivpl akvdctantn tcnkygvsgy ptlkifrdge eagaydgprt
121  adgivshlkk qagpasvplr teeefkkfis dkdasvvgff rdlfsdghse flkaasnlrd
181  nyrfahtnie slvkeyddng egitifrplh lankfedktv aytekkmtsg kikkfiqdsi
241  fglcphmted nkdliqgkdl ltayydvdye knakgsnywr nrvmmvakkf ldaghklnfa
301  vasrktfshe lsdfglestt gevpvvairt akgekfvmqe efsrdgkale qflgeyfdgn
361  lkrylksepi pesnegpvkv vvaenfddiv needkdvlie fyapwcghck nlepkykelg
421  eklskdpniv iakmdatand vpspyevkgf ptiyfspank kltpkkyegg relndfisyl
481  qreatnppii qeekpkkkkk agedl
```

TABLE 1-continued

SEQ ID NO: 11 Human CALR cDNA Sequence (NM_004343.3, CDS region from position 81-1334)

```
   1  gcggcgtccg tccgtactgc agagccgctg ccggagggtc gttttaaagg gcccgcgcgt
  61  tgccgccccc tcggcccgcc atgctgctat ccgtgccgct gctgctcggc ctcctcggcc
 121  tggccgtcgc cgagcctgcc gtctacttca aggagcagtt tctggacgga cgggtggac
 181  cttcccgctg gatcgaatcc aaacacaagt cagattttgg caaattcgtt ctcagttccg
 241  gcaagttcta cggtgacgag gagaagata aaggtttgca gacaagccag gatgcacgct
 301  tttatgctct gtcggccagt ttcgagcctt tcagcaacaa aggccagacg ctggtggtgc
 361  agttcacggt gaaacatgag cagaacatcg actgtggggg cggctatgtg aagctgtttc
 421  ctaatagttt ggaccagaca gacatgcacg gagactcaga atacaacatc atgtttggtc
 481  ccgacatctg tggccctggc accaagaagg ttcatgtcat cttcaactac aagggcaaga
 541  acgtgctgat caacaaggac atccgttgca aggatgatga gtttacacac ctgtacacac
 601  tgattgtgcg gccagacaac acctatgagg tgaagattga caacagccag gtggagtccg
 661  gctccttgga agacgattgg gacttcctgc cacccaagaa gataaaggat cctgatgctt
 721  caaaaccgga agactgggat gagcgggcca gatcgatga tcccacagac tccaagcctg
 781  aggactggga caagcccgag catatccctg accctgatgc taagaagccc gaggactggg
 841  atgaagagat ggacggagag tgggaacccc cagtgattca gaaccctgag tacaagggtg
 901  agtggaagcc ccggcagatc gacaacccag attacaaggg cacttggatc cacccagaaa
 961  ttgacaaccc cgagtattct cccgatccca gtatctatgc ctatgataac tttggcgtgc
1021  tgggcctgga cctctggcag gtcaagtctg gcaccatctt tgacaacttc ctcatcacca
1081  acgatgaggc atacgctgag gagtttggca cgagacgtg gggcgtaaca aaggcagcag
1141  agaaacaaat gaaggacaaa caggacgagg agcagaggct taaggaggag gaagaagaca
1201  agaaacgcaa agaggaggag gaggcagagg acaaggagga tgatgaggac aaagatgagg
1261  atgaggagga tgaggaggac aaggaggaag atgaggagga agatgtcccc ggccaggcca
1321  aggacgagct gtagagaggc ctgcctccag gctggactg aggcctgagc gctcctgccg
1381  cagagctggc cgcgccaaat aatgtctctg tgagactcga aactttcat tttttttccag
1441  gctggttcgg atttggggtg gattttggtt ttgttcccct cctccactct ccccaccc
1501  ctcccccgccc ttttttttttt tttttttttaa actggtattt tatctttgat tctccttcag
1561  ccctcacccc tggttctcat ctttcttgat caacatcttt tcttgcctct gtcccttct
1621  ctcatctctt agctcccctc caacctgggg ggcagtggtg tggagaagcc acaggcctga
1681  gatttcatct gctctccttc ctggagccca gaggagggca gcagaagggg gtggtgtctc
1741  caacccccca gcactgagga agaacggggc tcttctcatt tcacccctcc ctttctcccc
1801  tgccccagg actgggccac ttctgggtgg ggcagtgggt cccagattgg ctcacactga
1861  gaatgtaaga actacaaaca aaatttctat taaattaaat tttgtgtctc caaaaaaaa
1921  aaaaaaaaa
```

SEQ ID NO: 12 Human CALR Amino Acid Sequence (NP_004334.1)

```
   1  mllsvplllg llglavaepa vyfkeqfldg dgwtsrwies khksdfgkfv lssgkfygde
  61  ekdkglqtsq darfyalsas fepfsnkgqt lvvqftvkhe gnidcgggyv klfpnsldqt
 121  dmhgdseyni mfgpdicgpg tkkvhvifny kgknvlinkd irckddefth lytlivrpdn
 181  tyevkidnsq vesgsleddw dflppkkikd pdaskpedwd erakiddptd skpedwdkpe
 241  hipdpdakkp edwdeemdge weppviqnpe ykgewkprqi dnpdykgtwi hpeidnpeys
```

TABLE 1-continued

```
301    pdpsiyaydn fgvlgldlwq vksgtifdnf litndeayae efgnetwgvt kaaekqmkdk
361    qdeeqrlkee eedkkrkeee eaedkedded kdedeedeed keedeeedvp gqakdel
```

SEQ ID NO: 13 Mouse CALR cDNA Sequence (NM_007591.3, CDS region from position 134-1384)
```
   1   ggctgtgtca ggttcgggtg agaggtaggt gaatataaat tgaagcggcg gtggccgcgt
  61   ccgtcaatac cgcagagccg ctgcctgaag atcgtcttaa aaggcctgtg tgccgccgcc
 121   ccctcggccc gccatgctcc tttcggtgcc gctcctgctt ggcctcctcg gctggccgc
 181   cgcagaccct gccatctatt tcaaagagca gttcttggac ggagatgcct ggaccaaccg
 241   ctgggtcgaa tccaaacata agtccgattt tggcaaattt gtcctcagtt ctggcaaatt
 301   ttacggggac ctggagaagg ataaagggct gcagacaagc caagatgccc gattttacgc
 361   actgtccgcc aaattcgaac ccttcagcaa taagggccag acactggtgg tacagttcac
 421   ggtgaagcat gagcagaata tcgactgtgg gggcggctac gtgaagctgt ttccgagtgg
 481   tttggaccag aaggacatgc atggagactc agaatataac atcatgtttg gtccggacat
 541   ctgcggtcct ggcaccaaga aggttcatgt catctttaac tacaagggca agaatgtgct
 601   gatcaacaag gatatccggt gtaaggatga tgaattcaca cacctataca cactgattgt
 661   gcggccagac aacacctatg aggtgaaaat tgacaacagc caggtggagt caggctcctt
 721   ggaggatgat tgggactttc tgccacccaa gaagataaag gaccctgatg ctgccaagcc
 781   ggaagactgg gatgaacgag ccaagatcga tgacccaca gattccaagc ctgaggactg
 841   ggacaagcca gagcacatcc ctgaccctga tgctaagaag cctgaggact gggatgaaga
 901   gatggatgga gagtgggaac caccagtgat tcaaaatcct gaatacaagg gcgagtggaa
 961   accacgtcaa attgacaacc cagattacaa gggtacctgg atacacccag aaattgacaa
1021   ccctgaatac tcccccgatg caaatatcta tgcctatgat gttttgctg tactgggcct
1081   agatctctgg caggtcaagt ccgggacaat ctttgacaat ttcctcatca ccaatgatga
1141   ggcctatgca gaggagtttg gcaatgagac gtggggtgtt accaaggctg cagagaagca
1201   gatgaaggac aagcaggatg aggagcagag gcttaaggaa gaagagagg acaagaagcg
1261   taaagaggaa gaagaagctg aggataaaga ggatgatgat gacagagatg aagatgagga
1321   cgaagaagat gagaaggagg aagatgagga gaatcccct ggccaagcca aggatgagct
1381   gtagaggcca caccacctgc cttcagggct ggactgaggc ctgaacaccc tgccgcagag
1441   ctggctgctc ccaataatgt ctctatgaga ctcaagaact tttcattttt tccaggcagg
1501   ttcagatctg gggtagattc tgattttgtt ccctgcctc ccattacc ccccccctt
1561   tttttttta ctggtgtttg tctttaattc tccttcagcc ctcatctggt ttctcatttt
1621   tgaatcaaca tctttccctt ctgtccctcc ctttctccat cttttggtca ctaccctcca
1681   actctaggaa caggggtgta gaggagaagc cctaggcttg agatttcatc tgctctcctt
1741   cctgcatctc agaggagggc aggagaaggg ggtggtgttt tccctcccc cgcactgagg
1801   aagaatgggg ctcttctcat ccccttttctc ccttgccccc aggactgggc cacttgtggg
1861   gcagccagtt ctagcacagc tcacactgag agtgtaagaa ctacaaacaa aatttctatt
1921   aaattaagtt ttgtgtcttc cct
```

SEQ ID NO: 14 Mouse CALR Amino Acid Sequence (NP_031617.1)
```
   1   mllsvplllg llglaaadpa iyfkeqfldg dawtnrwves khksdfgkfv lssgkfygdl
  61   ekdkglqtsq darfyalsak fepfsnkgqt lvvqftvkhe qnidcgggyv klfpsgldqk
 121   dmhgdseyni mfgpdicpg tkkvhvifny kgknvlinkd irckddefth lytlivrpdn
 181   tyevkidnsq vesgsleddw dflppkkikd pdaakpedwd erakiddptd skpedwdkpe
```

TABLE 1-continued

```
241  hipdpdakkp edwdeemdge weppviqnpe ykgewkprqi dnpdykgtwi hpeidnpeys 301  pdaniyayds favlgldlwq vksgtifdnf litndeayae efgnetwgvt kaaekqmkdk 361  qdeeqrlkee eedkkrkeee eaedkedddd rdededeede keedeeespg qakdel
```

SEQ ID NO: 15 Human Tap1 cDNA Variant 1 Sequence (NM_000593.5, CDS region from position 156-2582)

```
   1  gtgtgcgtga tggagaaaat tgggcaccag ggctgctccc gagattctca gatctgattt 61  ccacgcttgc taccaaaata gtctgggcag ccacttttg gaagtaggcg ttatctagtg 121  agcaggcggc cgctttcgat ttcgctttcc cctaaatggc tgagcttctc gccagcgcag 181  gatcagcctg ttcctgggac tttccgagag ccccgccctc gttccctccc cagccgcca 241  gtaggggagg actcggcggt acccggagct tcaggcccca ccggggcgcg gagagtccca 301  ggcccggccg ggaccgggac ggcgtccgag tgccaatggc tagctctagg tgtcccgctc 361  cccgcgggtg ccgctgcctc cccggagctt ctctcgcatg gctggggaca gtactgctac 421  ttctcgccga ctgggtgctg ctccggaccg cgctgccccg catattctcc ctgctggtgc 481  ccaccgcgct gccactgctc cgggtctggg cggtgggcct gagccgctgg gccgtgctct 541  ggctggggc ctgcgggtc ctcagggcaa cggttggctc caagagcgaa aacgcaggtg 601  cccagggctg gctggctgct ttgaagccat tagctgcggc actgggcttg gccctgccgg 661  gacttgcctt gttccgagag ctgatctcat ggggagcccc cgggtccgcg gatagcacca 721  ggctactgca ctggggaagt caccctaccg ccttcgttgt cagttatgca gcggcactgc 781  ccgcagcagc cctgtggcac aaactcggga gcctctgggt gcccggcggt cagggcggct 841  ctggaaaccc tgtgcgtcgg cttctaggct gcctgggctc ggagacgcgc cgcctctcgc 901  tgttcctggt cctggtggtc ctctcctctc ttggggagat ggccattcca ttctttacgg 961  gccgcctcac tgactggatt ctacaagatg gctcagccga taccttcact cgaaacttaa 1021  ctctcatgtc cattctcacc atagccagtg cagtgctgga gttcgtgggt gacgggatct 1081  ataacaacac catgggccac gtgcacagcc acttgcaggg agaggtgttt ggggctgtcc 1141  tgcgccagga gacggagttt tccaacaga accagacagg taacatcatg tctcgggtaa 1201  cagaggacac gtccaccctg agtgattctc tgagtgagaa tctgagctta tttctgtggt 1261  acctggtgcg aggcctatgt ctcttgggga tcatgctctg gggatcagtg tccctcacca 1321  tggtcaccct gatcaccctg cctctgcttt ccttctgcc caagaaggtg ggaaaatggt 1381  accagttgct ggaagtgcag gtgcgggaat ctctggcaaa gtccagccag gtggccattg 1441  aggctctgtc ggccatgcct acagttcgaa gctttgccaa cgaggagggc gaagcccaga 1501  agtttaggga aaagctgcaa gaaataaaga cactcaacca gaaggaggct gtggcctatg 1561  cagtcaactc ctggaccact agtatttcag gtatgctgct gaaagtggga atcctctaca 1621  ttggtgggca gctggtgacc agtggggctg taagcagtgg gaaccttgtc acatttgttc 1681  tctaccagat gcagttcacc caggctgtgg aggtactgct ctccatctac cccagagtac 1741  agaaggctgt gggctcctca gagaaaatat ttgagtacct ggaccgcacc ctcgctgcc 1801  cacccagtgg tctgttgact cccttacact ggagggcct tgtccagttc caagatgtct 1861  ccttttgccta cccaaaccgc ccagatgtct tagtgctaca ggggctgaca ttcacccctac 1921  gccctggcga ggtgacggcg ctggtgggac ccaatgggtc tgggaagagc acagtggctg 1981  ccctgctgca gaatctgtac cagcccaccg ggggacagct gctgttggat gggaagcccc 2041  ttccccaata tgagcaccgc tacctgcaca gcaggtggc tgcagtggga caagagccac 2101  aggtatttgg aagaagtctt caagaaaata ttgcctatgg cctgacccag aagccaacta
```

TABLE 1-continued

```
2161    tggaggaaat cacagctgct gcagtaaagt ctggggccca tagtttcatc tctggactcc
2221    ctcagggcta tgacacagag gtagacgagg ctgggagcca gctgtcaggg ggtcagcgac
2281    aggcagtggc gttggcccga gcattgatcc ggaaaccgtg tgtacttatc ctggatgatg
2341    ccaccagtgc cctggatgca aacagccagt tacaggtgga gcagctcctg tacgaaagcc
2401    ctgagcggta ctcccgctca gtgcttctca tcacccagca cctcagcctg gtggagcagg
2461    ctgaccacat cctctttctg gaaggaggcg ctatccggga gggggggaacc caccagcagc
2521    tcatggagaa aaaggggtgc tactgggcca tggtgcaggc tcctgcagat gctccagaat
2581    gaaagccttc tcagacctgc gcactccatc tccctccctt ttcttctctc tgtggtggag
2641    aaccacagct gcagagtagg cagctgcctc caggatgagt tacttgaaat ttgccttgag
2701    tgtgttacct cctttccaag ctcctcgtga taatgcagac ttcctggagt acaaacacag
2761    gatttgtaat tccttactgt aacgagtttt agagccaggg ctgatgcttt ggtgtggcca
2821    gcactctgaa actgagaaat gttcagaatg tacggaaaga tgatcagcta ttttcaacat
2881    aactgaaggc atatgctggc ccataaacac cctgtaggtt cttgatattt ataataaaat
2941    tggtgttttg taaaaaaaaa aaaaaaaaaa aaaa
```

SEQ ID NO: 16 Human TAP1 Isoform 1 Amino Acid Sequence (NP_000584.2)
```
  1     maellasags acswdfprap psfpppaasr gglggtrsfr phrgaesprp grdrdgvrvp
 61     massrcpapr gcrclpgasl awlgtvlll1 adwvllrtal prifsllvpt alpllrvwav
121     glsrwavlwl gacgvlratv gsksenagaq gwlaalkpla aalglalpgl alfreliswg
181     apgsadstrl lhwgshptaf vvsyaaalpa aalwhklgsl wvpggqggsg npvrrllgcl
241     gsetrrlslf lvlvvlsslg emaipfftgr ltdwilqdgs adtftrnltl msiltiasav
301     lefvgdgiyn ntmghvhshl qgevfgavlr qeteffqqnq tgnimsrvte dtstlsdsls
361     enlslflwyl vrglcllgim lwgsysltmv tlitlpllfl lpkkvgkwyq llevqvresl
421     akssqvaiea lsamptvrsf aneegeaqkf reklqeiktl nqkeavayav nswttsisgm
481     llkvgilyig gqlvtsgavs sgnlvtfvly qmqftqavev llsiyprvqk avgssekife
541     yldrtprcpp sglltplhle glvqfqdvsf aypnrpdvlv lqgltftlrp gevtalvgpn
601     gsgkstvaal lqnlygptgg qllldgkplp qyehrylhrq vaavgqepqv fgrslgenia
661     ygltqkptme eitaaavksg ahsfisglpq gydtevdeag sqlsggqrqa valaralirk
721     pcvlildddat saldansqlq veqllyespe rysrsvllit qhlslveqad hilfleggai
781     reggthqqlm ekkgcywamv qapadape
```

SEQ ID NO: 17 Human Tap1 cDNA Variant 2 Sequence (NM_001292022.1, CDS
region from position 199-1842)
```
  1     gctctggggc cgaagggcgg ggcatcctca tctctaacag gaggcttttc tacttcatga
 61     tctccagcct tcctaataaa atcctgaaag ttctggtaga gcaaccacag ggtagtgagt
121     tccagggcag cctatttagg ttcgggattg agacgtcagt gtttcctttc tgctgatgcc
181     ctccaggata atggggagat ggccattcca ttctttacgg gccgcctcac tgactggatt
241     ctacaagatg gctcagccga taccttcact cgaaacttaa ctctcatgtc cattctcacc
301     atagccagtg cagtgctgga gttcgtgggt gacgggatct ataacaacac catgggccac
361     gtgcacagcc acttgcaggg agaggtgttt gggctgtcc tgcgccagga gacggagttt
421     ttccaacaga accagacagg taacatcatg tctcgggtaa cagaggacac gtccaccctg
481     agtgattctc tgagtgagaa tctgagctta tttctgtggt acctggtgcg aggcctatgt
541     ctcttgggga tcatgctctg gggatcagtg tccctcacca tggtcaccct gatcaccctg
601     cctctgcttt tccttctgcc caagaaggtg ggaaaatggt accagttgct ggaagtgcag
```

TABLE 1-continued

```
 661   gtgcgggaat ctctggcaaa gtccagccag gtggccattg aggctctgtc ggccatgcct
 721   acagttcgaa gctttgccaa cgaggagggc gaagcccaga agtttaggga aaagctgcaa
 781   gaaataaaga cactcaacca gaaggaggct gtggcctatg cagtcaactc ctggaccact
 841   agtatttcag gtatgctgct gaaagtggga atcctctaca ttggtgggca gctggtgacc
 901   agtggggctg taagcagtgg gaaccttgtc acatttgttc tctaccagat gcagttcacc
 961   caggctgtgg aggtactgct ctccatctac cccagagtac agaaggctgt gggctcctca
1021   gagaaaatat ttgagtacct ggaccgcacc cctcgctgcc cacccagtgg tctgttgact
1081   cccttacact tggagggcct tgtccagttc caagatgtct cctttgccta cccaaaccgc
1141   ccagatgtct tagtgctaca ggggctgaca ttcaccctac gccctggcga ggtgacggcg
1201   ctggtgggac ccaatgggtc tgggaagagc acagtggctg ccctgctgca gaatctgtac
1261   cagcccaccg ggggacagct gctgttggat gggaagcccc ttccccaata tgagcaccgc
1321   tacctgcaca gcaggtggc tgcagtggga caagagccac aggtatttgg aagaagtctt
1381   caagaaaata ttgcctatgg cctgacccag aagccaacta tggaggaaat cacagctgct
1441   gcagtaaagt ctggggccca tagtttcatc tctggactcc ctcagggcta tgacacagag
1501   gtagacgagg ctgggagcca gctgtcaggg ggtcagcgac aggcagtggc gttggcccga
1561   gcattgatcc ggaaaccgtg tgtacttatc ctggatgatg ccaccagtgc cctggatgca
1621   aacagccagt tacaggtgga gcagctcctg tacgaaagcc ctgagcgta ctcccgctca
1681   gtgcttctca tcacccagca cctcagcctg gtggagcagg ctgaccacat cctctttctg
1741   gaaggaggcg ctatccggga gggggaacc caccagcagc tcatggagaa aaagggtgc
1801   tactgggcca tggtgcaggc tcctgcagat gctccagaat gaaagccttc tcagacctgc
1861   gcactccatc tccctccctt ttcttctctc tgtggtggag aaccacagct gcagagtagg
1921   cagctgcctc caggatgagt tacttgaaat ttgccttgag tgtgttacct cctttccaag
1981   ctcctcgtga taatgcagac ttcctggagt acaaacacag gatttgtaat tccttactgt
2041   aacggagttt agagccaggg ctgatgcttt ggtgtggcca gcactctgaa actgagaaat
2101   gttcagaatg tacggaaaga tgatcagcta ttttcaacat aactgaaggc atatgctggc
2161   ccataaacac cctgtaggtt cttgatattt ataataaaat tggtgttttg taaaaaaaaa
2221   aaaaaaaaaa aaaa
```

SEQ ID NO: 18 Human TAP1 Isoform 2 Amino Acid Sequence (NP_001278951)

```
   1   maipfftgrl tdwilqdgsa dtftrnltlm siltiasavl efvgdglynn tmghvhshlq
  61   gevfgavlrq eteffqqnqt gnimsrvted tstlsdslse nlslflwylv rglcllgiml
 121   wgsvsltmvt litlpllfll pkkvgkwyql levqvresla kssqvaieal samptvrsfa
 181   neegeaqkfr eklqeiktln qkeavayavn swttsisgml lkvgilyigg qlvtsgavss
 241   gnlvtfvlyq mqftgavevl lsiyprvqka vgssekifey ldrtprcpps glltplhleg
 301   lvqfqdvsfa ypnrpdvlvl qgltftlrpg evtalvgpng sgkstvaall qnlygptggq
 361   llldgkplpq yehrylhrqv aavgqepqvf grslqeniay gltqkptmee itaaavksga
 421   hsfisglpqg ydtevdeags qlsggqrqav alaralirkp cvlilddats aldansqlqv
 481   eqllyesper ysrsvllitq hlslveqadh ilfleggair eggthqqlme kkgcywamvq
 541   apadape
```

SEQ ID NO: 19 Mouse Tap1 cDNA Variant 1 Sequence (NM_013683.2, CDS region from position 325-2499)

```
   1   gaggagaatg agattcatgg agaagaacac gacaggccag ggctgctagg cagaactcca
  61   actacagctt cagcggcagc ttccagaaca gcctgagcaa gccagtctca gaaggaggcg
```

TABLE 1-continued

```
 121   tgtctagtga ttcgaggtcg gctttcggtt tcttcttcct ctaaacgcca gcacttctag
 181   tcagctccac cagctcgagc gggttcccgg gactttacgc gcacgccctc ggacccgccc
 241   ttcttccttc cccacggaga ctcctgtgca gcgcggacgt cgagagtccc aggctaggac
 301   cagactctgg acagctcacg ctcgatggct gcgcacgtct ggctggcggc cgccctgctc
 361   cttctggtgg actggctgct gctgcggccc atgctcccgg gaatcttctc cctgttggtt
 421   cccgaggtgc cgctgctccg ggtctgggtg gtgggcctga gtcgctgggc catcctagga
 481   ctaggggtcc gcggggtcct cggggtcacc gcaggagccc atggctggct ggctgctttg
 541   cagccgctgg tggccgcact gagtttggcc ctgcctggac ttgccttgtt ccgagagctg
 601   gccgcctggg aacactccg ggagggtgac agcgctggat tactgtactg aacagtcgt
 661   ccagatgcct tcgctatcag ttatgtggca gcattgcccg cagccgccct gtggcacaag
 721   ttggggagcc tctgggcgcc cagcggcaac agggacgctg agacatgct gtgtcggatg
 781   ctgggcttcc tgggccctaa gaagagacgt ctctacctgg ttctggttct cttgattctc
 841   tcttgccttg gggaaatggc cattcccttc ttcacgggcc gcatcactga ctggattctt
 901   caggataaga cagttcctag cttcacccgc aacatatggc tcatgtccat tctcaccata
 961   gccagcacag cgctggagtt tgcaagtgat ggaatctaca acatcaccat gggacacatg
1021   cacggccgtg tgcacagaga ggtgtttcgg ccgtccttc gccaggagac agggttttc
1081   ctgaagaacc cagcaggttc catcacatct cgggtgactg aggacacagc caacgtgtgc
1141   gagtccatta gtggcacgct gagcctgctg ctgtggtacc tggggcgagc cctgtgtctc
1201   ttggtgttca tgttttgggg gtcaccgtac ctcactctgg tcaccctgat caacctgccc
1261   ctgcttttc ttttgcctaa gaagctggga aaagtgcatc agtcactggc agtgaaggtg
1321   caggagtctc tagcaaagtc cacgcaggtg gcccttgagg cttatcggc gatgcctact
1381   gtgcggagct ttgccaacga ggagggtgag gcccagaagt tcaggcagaa gttggaagaa
1441   atgaagactc taaacaagaa ggaggccttg gcttacgtgg ctgaagtctg gaccacgagt
1501   gtctcgggaa tgctgctgaa ggtgggaatt ctgtacctgg gcgggcagct ggtgatcaga
1561   ggggctgtca gcagcggcaa ccttgtctca ttcgttctct accagcttca gttcacccag
1621   gctgttcagg tcctgctctc cctctacccc tccatgcaga aggctgtggg ctcctcagag
1681   aaaatattcg aatacttgga ccggactcct gctctccac tcagtggctc gttggcaccc
1741   tcaaacatga aaggccttgt ggagttccaa gatgtctctt ttgcctaccc aaaccagccc
1801   aaagtccagg tgcttcaggg gctgacgttc accctgcatc ctggaacggt gacagcgttg
1861   gtgggaccca atggatcagg gaagagcacc gtggctgccc tgctgcagaa cctgtaccag
1921   cccaccgggg ccagctgct gctgatggc cagtgcctgg tccagtatga tcaccattac
1981   ctgcacactc aggtggccgc agtgggacaa gagccgctgc tatttggaag aagctttcga
2041   gaaaatattg cgtatggcct gaaccggact ccaaccatgg aggaaatcac agctgtggcc
2101   gtggagtctg gagcccacga tttcatctct gggttccctc agggctatga cacagaggta
2161   ggtgagactg gaaccagct gtcaggaggt cagcgacagg cagtggcctt ggcccgagcc
2221   ttgatccgga agccactcct gcttatcttg gatgatgcca ccagtgccct ggatgctggc
2281   aaccagctac gggtccagcg gctcctgtat gagagcccca gcgggcttc tcggacggtt
2341   cttcttatca cccagcagct cagcctggca gagcaggccc accacatcct ctttctcaga
2401   gaaggctctg tcggcgagca gggcacccac ctgcagctca tgaagagagg agggtgctac
2461   cgggccatgg tagaggctct tgcggctcct gcagactgac aaggcctctg gactgcacac
```

TABLE 1-continued

| | |
|---|---|
| 2521 | tgcgtgctgt ccccctcctg tcctctactc tgtgtgacag agaacctggg agcaaagata |
| 2581 | ttaccacacc cacgagaca gttgaggagc ggaggtgctt gttacatgag aaaatgtaaa |
| 2641 | ctctaggaga tacccggaat ttaccacgaa tgtgtttccc cgacccgctc cctattagac |
| 2701 | ggggtttcag gtacctcaca ccaacactga gctgctaaat ctccggtctc caccctcccg |
| 2761 | gtgctgagct tgtatcacag catgcacaca caaacctggt ttatgtggcg ttgtgataga |
| 2821 | atgagaagaa acgcccaaag tgtacagaga gaaaggacaa gcagcttgca attaaccaaa |
| 2881 | ggcataggct ggcatttggg tgttctatgg gtgtttgata tttgtaataa aactggtgtt |
| 2941 | ttgtactgtg |

SEQ ID NO: 20 Mouse TAP1 Isoform 1 Amino Acid Sequence (NP_038711.2)

| | |
|---|---|
| 1 | maahvwlaaa llllvdwlll rpmlpgifsl lvpevpllrv wvvglsrwal lglgvrgvlg |
| 61 | vtagahgwla alqplvaals lalpglalfr elaawgtlre gdsagllywn srpdafaisy |
| 121 | vaalpaaalw hklgslwaps gnrdagdmlc rmlgflgpkk rrlylvlvll ilsclgemai |
| 181 | pfftgritdw ilqdktvpsf trniwlmsil tiastalefa sdgiynitmg hmhgrvhrev |
| 241 | fravlrqetg fflknpagsi tsrvtedtan vcesisgtls lllwylgral cllvfmfwgs |
| 301 | pyltlvtlin lpllfllpkk lgkvhqslav kvqeslakst qvalealsam ptvrsfanee |
| 361 | geaqkfrqkl eemktlnkke alayvaevwt tsvsgmllkv gilylggqlv irgavssgnl |
| 421 | vsfvlyqlqf tqavqvllsl ypsmqkavgs sekifeyldr tpcsplsgsl apsnmkglve |
| 481 | fqdvsfaypn qpkvqvlqgl tftlhpgtvt alvgpngsgk stvaallqnl ygptggqlll |
| 541 | dggclvqydh hylhtqvaav gqepllfgrs freniaygln rtptmeeita vavesgandf |
| 601 | isgfpqgydt evgetgnqls ggqrqavala ralirkplll ilddatsald agnqlrvqrl |
| 661 | lyespkrasr tvllitqqls laeqahhilf lregsvgeqg thlqlmkrgg cyramveala |
| 721 | apad |

SEQ ID NO: 21 Mouse Tap1 cDNA Variant 2 Sequence (NM_001161730.1, CDS region from position 325-2415)

| | |
|---|---|
| 1 | gaggagaatg agattcatgg agaagaacac gacaggccag ggctgctagg cagaactcca |
| 61 | actacagctt cagcggcagc ttccagaaca gcctgagcaa gccagtctca gaaggaggcg |
| 121 | tgtctagtga ttcgaggtcg gctttcggtt tcttcttcct ctaaacgcca gcacttctag |
| 181 | tcagctccac cagctcgagc gggttcccgg gactttacgc gcacgccctc ggacccgccc |
| 241 | ttcttccttc cccacggaga ctcctgtgca gcgcggacgt cgagagtccc aggctaggac |
| 301 | cagactctgg acagctcacg ctcgatggct gcgcacgtct ggctggcggc cgccctgctc |
| 361 | cttctggtgg actggctgct gctgcggccc atgctcccgg gaatcttctc cctgttggtt |
| 421 | cccgaggtgc cgctgctccg gtctgggtg gtgggcctga gtcgctgggc catcctagga |
| 481 | ctagggtcc gcggggtcct cggggtcacc gcaggagccc atggctggct ggctgctttg |
| 541 | cagccgctgg tggccgcact gagtttggcc ctgcctggac ttgccttgtt ccgagagctg |
| 601 | gccgcctggg gaacactccg ggagggtgac agcgctggat tactgtactg gaacagtcgt |
| 661 | ccagatgcct tcgctatcag ttatgtggca gcattgcccg cagccgccct gtggcacaag |
| 721 | ttggggagcc tctgggcgcc cagcggcaac agggacgctg agacatgct gtgtcggatg |
| 781 | ctgggcttcc tgggccctaa gaagagacgt ctctacctgg ttctggttct cttgattctc |
| 841 | tcttgccttg gggaaatggc cattcccttc ttcacgggcc gcatcactga ctggattctt |
| 901 | caggataaga cagttcctag cttcacccgc aacatatggc tcatgtccat tctcaccata |
| 961 | gccagcacag cgctggagtt tgcaagtgat ggaatctaca acatcaccat gggacacatg |
| 1021 | cacggccgtg tgcacagaga ggtgtttcgg gccgtccttc gccaggagac agggtttttc |

TABLE 1-continued

```
1081  ctgaagaacc cagcaggttc catcacatct cgggtgactg aggacacagc aacgtgtgc
1141  gagtccatta gtggcacgct gagcctgctg ctgtggtacc tggggcgagc cctgtgtctc
1201  ttggtgttca tgttttgggg gtcaccgtac ctcactctgg tcaccctgat caacctgccc
1261  ctgcttttc ttttgcctaa gaagctggga aaagtgcatc agtcactggc agtgaaggtg
1321  caggagtctc tagcaaagtc cacgcaggtg gcccttgagg ccttatcggc gatgcctact
1381  gtgcggagct tgccaacga ggagggtgag cccagaagt tcaggcagaa gttggaagaa
1441  atgaagactc taaacaagaa ggaggccttg gcttacgtgg ctgaagtctg gaccacgagt
1501  gtctcgggaa tgctgctgaa gcttcagttc acccaggctg ttcaggtcct gctctccctc
1561  tacccctcca tgcagaaggc tgtgggctcc tcagagaaaa tattcgaata cttggaccgg
1621  actccttgct ctccactcag tggctcgttg gcaccctcaa acatgaaagg ccttgtggag
1681  ttccaagatg tctcttttgc ctacccaaac cagcccaaag tccaggtgct tcagggctg
1741  acgttcaccc tgcatcctgg aacggtgaca cgttggtgg acccaatgg atcagggaag
1801  agcaccgtgg ctgccctgct gcagaacctg taccagccca ccgggggcca gctgctgctg
1861  gatggccagt gcctggtcca gtatgatcac cattacctgc acactcaggt ggccgcagtg
1921  ggacaagagc cgctgctatt tggaagaagc tttcgagaaa atattgcgta tggcctgaac
1981  cggactccaa ccatggagga atcacagct gtggccgtgg agtctggagc ccacgatttc
2041  atctctgggt tccctcaggg ctatgacaca gaggtaggtg agactgggaa ccagctgtca
2101  ggaggtcagc gacaggcagt ggccttggcc cgagccttga tccggaagcc actcctgctt
2161  atcttggatg atgccaccag tgccctggat gctggcaacc agctacgggt ccagcggctc
2221  ctgtatgaga gcccaagcg ggcttctcgg acggttcttc ttatcaccca gcagctcagc
2281  ctggcagagc aggcccacca catcctcttt tcagagaag gctctgtcgg cgagcagggc
2341  acccacctgc agctcatgaa gagaggaggg tgctaccggg ccatggtaga ggctcttgcg
2401  gctcctgcag actgacaagg cctctggact gcacactgcg tgctgtcccc tcctgtcct
2461  ctactctgtg tgacagaaa cctgggagca aagatattac cacacccacg gagacagttg
2521  aggagcggag gtgcttgtta catgagaaaa tgtaaactct aggagatacc cggaatttac
2581  cacgaatgtg tttccccgac ccgctcccta ttagacgggg tttcaggtac ctcacaccaa
2641  cactgagctg ctaaatctcc ggtctccacc ctcccggtgc tgagcttgta tcacagcatg
2701  cacacacaaa cctggtttat gtggcgttgt gatagaatga aagaaacgc ccaaagtgta
2761  cagagagaaa ggacaagcag cttgcaatta accaaaggca taggctggca tttgggtgtt
2821  ctatgggtgt ttgatatttg taataaaact ggtgttttgt actgtg
```

SEQ ID NO: 22 Mouse TAP1 Isoform 2 Amino Acid Sequence (NP_001155202.1)
```
  1  maahvwlaaa llllvdwlll rpmlpgifsl lvpevpllrv wvvglsrwal lglgvrgvlg
 61  vtagahgwla alqplvaals lalpglalfr elaawgtlre gdsagllywn srpdafaisy
121  vaalpaaalw hklgslwaps gnrdagdmlc rmlgflgpkk rrlylvlvll ilsclgemai
181  pfftgritdw ilqdktvpsf trniwlmsil tiastalefa sdglynitmg hmhgrvhrev
241  fravlrqetg fflknpagsi tsrvtedtan vcesisgtls lllwylgral cllvfmfwgs
301  pyltlvtlin lpllfllpkk lgkvhqslav kvqeslakst qvalealsam ptvrsfanee
361  geaqkfrqkl eemktlnkke alayvaevwt tsvsgmllkl qftqavqvll slypsmqkav
421  gssekifeyl drtpcsplsg slapsnmkgl vefqdvsfay pnqpkvqvlq gltftlhpgt
481  vtalvgpngs gkstvaallq nlygptggql lldgqclvqy dhhylhtqva avgqepllfg
541  rsfreniayg lnrtptmeel tavavesgah dfisgfpqgy dtevgetgnq lsggqrgava
```

TABLE 1-continued

| | |
|---|---|
| 601 | laralirkpl llilddatsa ldagnqlrvq rllyespkra srtvllitqq lslaegahhi |
| 661 | lflregsvge qgthlqlmkr ggcyramvea laapad |

SEQ ID NO: 23 Human TAP2 cDNA Variant 1, B allele Sequence (NM_000544.3, CDS region from position 123-2234)

| | |
|---|---|
| 1 | gcccgccctg gccgagcgta gctggcggac cagagccggt agcgaggttg ggagagacgg |
| 61 | agcggacctc agcgctgaag cagaagtccc cggagctgcg gtctcccgc cgcggctgag |
| 121 | ccatgcggct ccctgacctg agaccctgga cctccctgct gctggtggac gcggctttac |
| 181 | tgtggctgct tcagggccct ctggggactt tgcttcctca agggctgcca ggactatggc |
| 241 | tggaggggac cctgcgcctg ggagggctgt ggggctgct aaagctaaga gggctgctgg |
| 301 | gatttgtggg gacactgctg ctcccgctct gtctggccac ccccctgact gtctccctga |
| 361 | gagccctggt cgcggggggcc tcacgtgctc cccagccag agtcgcttca gccccttgga |
| 421 | gctggctgct ggtggggtac ggggctgcgg ggctcagctg gtcactgtgg gctgttctga |
| 481 | gccctcctgg agcccaggag aaggagcagg accaggtgaa caacaaagtc ttgatgtgga |
| 541 | ggctgctgaa gctctccagg ccggacctgc ctctcctcgt gccgccttc ttcttccttg |
| 601 | tccttgctgt tttgggtgag acattaatcc ctcactattc tggtcgtgtg attgacatcc |
| 661 | tgggaggtga ttttgacccc catgcctttg ccagtgccat cttcttcatg tgcctcttct |
| 721 | cctttggcag ctcactgtct gcaggctgcc gaggaggctg cttcacctac accatgtctc |
| 781 | gaatcaactt gcggatccgg gagcagcttt tctcctccct gctgcgccag gacctcggtt |
| 841 | tcttccagga gactaagaca ggggagctga actcacggct gagctcggat accaccctga |
| 901 | tgagtaactg gcttcctta aatgccaatg tgctcttgcg aagcctggtg aaagtggtgg |
| 961 | ggctgtatgg cttcatgctc agcatatcgc ctcgactcac cctccttctt ctgctgcaca |
| 1021 | tgcccttcac aatagcagcg agaaggtgt acaacacccg ccatcaggaa gtgcttcggg |
| 1081 | agatccagga tgcagtggcc agggcgggc aggtggtgcg ggaagccgtt ggagggctgc |
| 1141 | agaccgttcg cagttttggg gccgaggagc atgaagtctg tcgctataaa gaggcccttg |
| 1201 | aacaatgtcg gcagctgtat tggcggagag acctggaacg cgccttgtac ctgctcgtaa |
| 1261 | ggagggtgct gcacttgggg gtgcagatgc tgatgctgag ctgtgggctg cagcagatgc |
| 1321 | aggatgggga gctcacccag ggcagcctgc tttcctttat gatctaccag agagcgtgg |
| 1381 | ggagctatgt gcagaccctg gtatacatat atgggggatat gctcagcaac gtgggagctg |
| 1441 | cagagaaggt tttctcctac atggaccgac agccaaatct gccttcacct ggcacgcttg |
| 1501 | cccccaccac tctgcagggg gttgtgaaat tccaagacgt ctcctttgca tatcccaatc |
| 1561 | gccctgacag gcctgtgctc aagggctga cgtttaccct acgtcctggt gaggtgacgg |
| 1621 | cgctggtggg acccaatggg tctgggaaga gcacagtggc tgccctgctg cagaatctgt |
| 1681 | accagcccac aggggacag gtgctgctgg atgaaaagcc catctcacag tatgaacact |
| 1741 | gctacctgca cagccaggtg gtttcagttg gcaggagcc tgtgctgttc tccggttctg |
| 1801 | tgaggaacaa cattgcttat ggctgcaga gctgcgaaga tgataaggtg atggcggctg |
| 1861 | cccaggctgc ccacgcagat gacttcatcc aggaaatgga gcatggaata tacacagatg |
| 1921 | tagggagaa gggaagccag ctggctgcgg gacagaaaca acgtctggcc attgcccggg |
| 1981 | cccttgtacg agaccgcgg gtcctcatcc tggatgaggc tactagtgcc ctagatgtgc |
| 2041 | agtgcgagca ggccctgcag gactggaatt cccgtgggga tcgcacagtc tggtgattg |
| 2101 | ctcacaggct gcaggcagtt cagcgcgccc accagatcct ggtgctccag gagggcaagc |
| 2161 | tgcagaagct tgcccagctc caggaggac aggacctcta ttcccgcctg gttcagcagc |

TABLE 1-continued

```
2221  ggctgatgga ctgaggcccc agggatactg ggccctcttc tcaggggcgt ctccaggacc
2281  cagagctgtt cctgctttga gtttccctag agctgtgcgg ccagatagct gttcctgagt
2341  tgcaggcacg atggagattt ggacactgtg tgcttttggt ggggtagaga ggtggggtgg
2401  ggtggggtgg gggctgtctg tgtccaggaa acttaattcc ctggtgacta gagctttgcc
2461  tggtgatgag gagtattttg tggcataata catatatttt aaaatatttt ccttcttaca
2521  tgaactgtat acattcatat agaaaattta gacaatataa aaagtacaa agaagaaaag
2581  taaaagtacc cattgtttca cttcctggag ataaccatag ttgctatttt gctgcctgtc
2641  ccatcagtcg tttatctgtt gtttgagata gaaattaacc aaaaatgaca taaatattca
2701  tgagattgcc ttcctatatc cttccttgtt cctaccagtg tctgctattt tgaagaagct
2761  agggtctgga gggacagaga acagttccct gattaacagt attaatagca cattggtaa
2821  cagctaccat ttatagagtt ttaatgggag taggagctat gctaagtgtt tttcatgtat
2881  tatcgttttt aatcattatc cccaaccccta tgaggttggt tattatcccc attttacaga
2941  tgaggaaact gaagctcaaa gaggctcaat gactttccca aggtggtcgt agtggtggag
3001  ttggagtttg aacacaggcc tgaccctaga gtccacaccc tgacccaatc aattatattg
3061  catcttgggt ccataaaccc taatccataa tcccatcaag aaaagctctg ctgctcttag
3121  ctctaaataa ttcagaatct attctcttct ctccagtccc gttgttatag tcttcactca
3181  tagacttaag atgatcccat caccagagag gtttctctac cattagcttc cctcttccgg
3241  ccattcttca caaagtcatt tttctaaatt ctgtgtcaca tacgatgatg gcatttctgg
3301  aaattccttc aggtgctctc aagccctgct gcagagatcc ttttcagagc acacactgtt
3361  ccagcccatc tgtctcaccc tctcctgttg tatccagctc cacgacaaac ttctgccttc
3421  cccaacacct ttgtgccttt gcatatggtg ttttcttgcc cattttctgc tcgactcgcc
3481  cctgattttc aagttcaaga cttaactcag ggttcaggtc ttccaggagg ccttacttat
3541  gtcgtcagtc tggggaactc tccatgtgct tctatcactg tgcggttacc tctttcacag
3601  cccttttaaa gttctatctt ccctttccca cctttttga ccttccacta gaccatgagc
3661  acctgggcgg aaagccatat atcttattaa gctttatatc tgctacctgg ccgagggcct
3721  aattcatagt ggagaataaa tagtcaattg ataaatgaa taaatatctc caccatcgta
3781  ctaatcttaa tcctccctgc ccactcccac cactgaaaat gcaacattgt acacatcact
3841  ggttgttggg agggacttac cttggaaagt tgctattcta ggaaagagaa accttcatat
3901  tcctggaaac agcaggtagt ttccagtgct ggcaatgaat tccccagaac tgctgttttg
3961  gattttttct tgcctggcag ctgttgggag cagggtgcag tgaggatggg gtgagagtgg
4021  gcagtttctt gtgcagattt gcctttcttt catcctgggg ctgacttgca gctccacacc
4081  catccatctc tcaaatttca cagagggtaa aataggcatt tggagagaaa gaactctggc
4141  ctgattcctt tctctcccac aaatgtcctt tattcataaa acaggaataa taattcctgt
4201  atctcccaac tacatggaag ctgcagccct cacagaagaa gatgatctga gaaattcttt
4261  gatttcctca gtacagttat acccatgcat cataatactt taagcctgga aggcatctta
4321  aaaataatgc aacagtcaaa cctaattta cagagaaact gacatgaaat cacgcagcta
4381  atcatgataa agctgggtgg aaaacttatc ttgatgggca gtacaggaag atgcagtaga
4441  ccttaagatg tcctgaaagt ttcttatctc aggggaaact cccaggtagg ctttatgtca
4501  gggacacaga aaaatgctcc ctgaaagtca aaatattcgg gctagacaga caaattcctg
4561  taagtgtggt ttgtctggga accacagatg tcactaatcc tggtttgctc cagagttctt
```

TABLE 1-continued

```
4621    tttgttcact cctacccccc atcaccattt gattgatctc cttaccctgt aatttcccct
4681    tcttgtcgct tacctgcagt atctttccca cccaggcatg ccttattctt tctaaaggaa
4741    agtatgaatg gagaggggaa agcttgggaa actgatagat ttccttggat gccaaaacac
4801    ctccatagcc tgtctgcccg gccctatgtg aaacagcat tgagtttcaa gtcctttatg
4861    cctccaccca gggatagcca cttgtaatcc acatggcaat gtgaaacaa gcaggaaatg
4921    cgtaattgtc agaattttgt ggggaaagga ctaggaata aggaaaacaa agatcttcct
4981    tgtgttttag agctgtcagc tagaggagca cctgcttgag tctgatgcca tctaatggtc
5041    ccagaagaaa ctgggttttg aacctagagt tccatggact cttaggaatt agactactac
5101    tactactaag cattcactgg tgcttactat gtgctattgc tgtgccaagt atctgaaacc
5161    tgtcttctta ccttattttt caagataatt ctatgtggca ggtattacta tctcaattct
5221    aagagtgaga aaatggagtt ttagaaacat ttactaactt gcctgggtca catagctaag
5281    gaagaggtgg acttgcccag ctttgcataa aactcctcaa aagagttgcc tatactccct
5341    gactccactt atcttcctac tatcctcttt ttaaaatata ttatttattt atttaaataa
5401    gcaatatatg aatgtggttt gaaattcaaa agacacaaag aagtatacag aggaaagcct
5461    cactctcaat ccttctcaag gtttgctaat tcctcttgca taggcaatcc gttcttccag
5521    ctttgtgttt atctttccag agaagtttac tgtgtattaa gcaaatatgt atatctttat
5581    tcttgctcag tattttcgca aacagcagct gtctaagttc actgttctga actttatttt
5641    ttaaattaaa aatatatggc tatgtagtat tctatttta
```

SEQ ID NO: 24 Human TAP2 Isoform 1 Amino Acid Sequence (NP_000535.3)

```
  1    mrlpdlrpwt slllvdaall wllqgplgtl lpqglpglwl egtlrlgglw gllklrgllg
 61    fvgtllllplc latpltvslr alvagasrap parvasapws wllvgygaag lswslwavls
121    ppgaqekeqd qvnnkvlmwr llklsrpdlp llvaafffv lavlgetlip hysgrvidil
181    ggdfdphafa saiffmclfs fgsslsagcr ggcftytmsr inlrireqlf ssllrqdlgf
241    fqetktgeln srlssdttlm snwlplnanv llrslvkvvg lygfmlsisp rltllsllhm
301    pftiaaekvy ntrhqevlre iqdavaragq vvreavgglq tvrsfgaeeh evcrykeale
361    qcrqlywrrd leralyllvr rvlhlgvqml mlscglqqmq dgeltqgsll sfmiyqesvg
421    syvqtlvyiy gdmlsnvgaa ekvfsymdrq pnlpspgtla pttlqgvvkf qdvsfaypnr
481    pdrpvlkglt ftlrpgevta lvgpngsgks tvaallqnly qptggqvlld ekpisqyehc
541    ylhsqvvsvg qepvlfsgsv rnniayglqs ceddkvmaaa qaahaddfiq emehgiytdv
601    gekgsqlaag qkgrlalara lvrdprvlil deatsaldvq ceqalqdwns rgdrtvlvia
661    hrlqavqrah qilvlqegkl qklaqlqegq dlysrlvqqr lmd
```

SEQ ID NO: 25 Human TAP2 cDNA Variant 1, A allele Sequence
(NM_001290043.1, CDS region from position 176-2236)

```
  1    agaatgaagg ccttggctgg ggaagcgaaa gcgaaagctg cccgagccct gacgcccgcc
 61    ctggccgagc gtagctggcg gaccagagcc ggtagcgagg ttgggagaga cggagcggac
121    ctcagcgctg aagcagaagt ccccggagct gcggtctccc cgccgcggct gagccatgcg
181    gctccctgac ctgagaccct ggacctcct gctgctggtg gacgcggctt tactgtggct
241    gcttcagggc cctctgggga ctttgcttcc tcaagggctg ccaggactat ggctggaggg
301    gaccctgcgg ctgggagggc tgtggggggct gctaaagcta agagggctgc tgggatttgt
361    ggggacactg ctgctcccgc tctgtctggc caccccctg actgtctccc tgagagccct
421    ggtcgcgggg gcctcacgtg ctcccccagc cagagtcgct tcagcccctt ggagctggct
481    gctggtgggg tacggggctg cggggctcag ctggtcactg tgggctgttc tgagccctcc
```

TABLE 1-continued

| | | | | | |
|---|---|---|---|---|---|
| 541 | tggagcccag | gagaaggagc | aggaccaggt | gaacaacaaa | gtcttgatgt | ggaggctgct |
| 601 | gaagctctcc | aggccggacc | tgcctctcct | cgttgccgcc | ttcttcttcc | ttgtccttgc |
| 661 | tgttttgggt | gagacattaa | tccctcacta | ttctggtcgt | gtgattgaca | tcctgggagg |
| 721 | tgattttgac | ccccatgcct | ttgccagtgc | catcttcttc | atgtgcctct | ctcctttgg |
| 781 | cagctcactg | tctgcaggct | gccgaggagg | ctgcttcacc | tacaccatgt | ctcgaatcaa |
| 841 | cttgcggatc | cgggagcagc | ttttctcctc | cctgctgcgc | caggacctcg | gtttcttcca |
| 901 | ggagactaag | acaggggagc | tgaactcacg | gctgagctcg | gataccaccc | tgatgagtaa |
| 961 | ctggcttcct | ttaaatgcca | atgtgctctt | gcgaagcctg | gtgaaagtgg | tggggctgta |
| 1021 | tggcttcatg | ctcagcatat | cgcctcgact | caccctcctt | tctctgctgc | acatgcccct |
| 1081 | cacaatagca | gcggagaagg | tgtacaacac | ccgccatcag | gaagtgcttc | gggagatcca |
| 1141 | ggatgcagtg | gccagggcgg | ggcaggtggt | gcgggaagcc | gttggagggc | tgcagaccgt |
| 1201 | tcgcagtttt | ggggccgagg | agcatgaagt | ctgtcgctat | aaagaggccc | ttgaacaatg |
| 1261 | tcggcagctg | tattggcgga | gagacctgga | acgcgccttg | tacctgctcg | taaggagggt |
| 1321 | gctgcacttg | ggggtgcaga | tgctgatgct | gagctgtggg | ctgcagcaga | tgcaggatgg |
| 1381 | ggagctcacc | cagggcagcc | tgctttcctt | tatgatctac | caggagagcg | tggggagcta |
| 1441 | tgtgcagacc | ctggtataca | tatatgggga | tatgctcagc | aacgtgggag | ctgcagagaa |
| 1501 | ggttttctcc | tacatggacc | gacagccaaa | tctgccttca | cctggcacgc | ttgccccac |
| 1561 | cactctgcag | ggggttgtga | aattccaaga | cgtctccttt | gcatatccca | atcgccctga |
| 1621 | caggcctgtg | ctcaagggc | tgacgtttac | cctacgtcct | ggtgaggtga | cggcgctggt |
| 1681 | gggacccaat | gggtctggga | agagcacagt | ggctgccctg | ctgcagaatc | tgtaccagcc |
| 1741 | cacaggggga | caggtgctgc | tggatgaaaa | gcccatctca | cagtatgaac | actgctacct |
| 1801 | gcacagccag | gtggtttcag | ttgggcagga | gcctgtgctg | ttctccggtt | ctgtgaggaa |
| 1861 | caacattgct | tatgggctgc | agagctgcga | agatgataag | gtgatggcgg | ctgcccaggc |
| 1921 | tgcccacgca | gatgacttca | tccaggaaat | ggagcatgga | atatacacag | atgtagggga |
| 1981 | gaagggaagc | cagctggctg | cgggacagaa | acaacgtctg | gccattgccc | gggcccttgt |
| 2041 | acgagacccg | cgggtcctca | tcctggatga | ggctactagt | gccctagatg | tgcagtgcga |
| 2101 | gcaggccctg | caggactgga | attcccgtgg | ggatcgcaca | gtgctggtga | ttgctcacag |
| 2161 | gctgcagaca | gttcagcgcg | cccaccagat | cctggtgctc | caggagggca | agctgcagaa |
| 2221 | gcttgcccag | ctctaggagg | acaggacct | ctattcccgc | ctggtgcagc | agcggctgat |
| 2281 | ggactgaggc | cccagggata | ctgggccctc | ttctcagggg | cgtctccagg | acccagagct |
| 2341 | gttcctgctt | tgagtttccc | tagagctgtg | cggccagata | gctgttcctg | agttgcaggc |
| 2401 | acgatggaga | tttggacact | gtgtgctttt | ggtggggtag | agaggtgggg | tggggtgggg |
| 2461 | tggggctgt | ctgtgtccag | gaaacttaat | tccctggtga | ctagagcttt | gcctggtgat |
| 2521 | gaggagtatt | ttgtggcata | atacatatat | tttaaaatat | tttccttctt | acatgaactg |
| 2581 | tatacattca | tatagaaaat | ttagacaata | taaaaaagta | caaagaagaa | aagtaaaagt |
| 2641 | acccattgtt | tcacttcctg | gagataacca | tagttgctat | tttgctgcct | gtcccatcag |
| 2701 | tcgtttatct | gttgtttgag | atagaaatta | accaaaaatg | acataaatat | tcatgagatt |
| 2761 | gccttcctat | atccttcctt | gttcctacca | gtgtctgcta | ttttgaagaa | gctagggtct |
| 2821 | ggagggacag | agaacagttc | cctgattaac | agtattaata | gcgacattgg | taacagctac |
| 2881 | catttataga | gttttaatgg | gagtaggagc | tatgctaagt | gttttcatg | tattatcgtt |

TABLE 1-continued

| | |
|---|---|
| 2941 | tttaatcatt atccccaacc ctatgaggtt ggttattatc cccattttac agatgaggaa |
| 3001 | actgaagctc aaagaggctc aatgactttc ccaaggtggt cgtagtggtg gagttggagt |
| 3061 | ttgaacacag gcctgaccct agagtccaca ccctgaccca atcaattata ttgcatcttg |
| 3121 | ggtccataaa ccctaatcca taatcccatc aagaaaagct ctgctgctct tagctctaaa |
| 3181 | taattcagaa tctattctct tctctccagt cccgttgtta tagtcttcac tcatagactt |
| 3241 | aagatgatcc catcaccaga gaggtttctc taccattagc ttccctcttc cggccattct |
| 3301 | tcacaaagtc attttttctaa attctgtgtc acatacgatg atggcatttc tggaaattcc |
| 3361 | ttcaggtgct ctcaagccct gctgcagaga tccttttcag agcacacact gttccagccc |
| 3421 | atctgtctca ccctctcctg ttgtatccag ctccacgaca aacttctgcc ttccccaaca |
| 3481 | ccttttgtgcc tttgcatatg gtgttttctt gcccattttc tgctcgactc gcccctgatt |
| 3541 | ttcaagttca agacttaact cagggttcag gtcttccagg aggccttact tatgtcgtca |
| 3601 | gtctggggaa ctctccatgt gcttctatca ctgtgcggtt acctctttca cagcccttt |
| 3661 | aaagttctat cttccctttc ccacttttt tgaccttcca ctagaccatg agcacctggg |
| 3721 | cggaaagcca tatatcttat taagctttat atctgctacc tggccgaggg cctaattcat |
| 3781 | agtggagaat aaatagtcaa ttgaataaat gaataaatat ctccaccatc gtactaatct |
| 3841 | taatcctccc tgcccactcc caccactgaa aatgcaacat tgtacacatc actggttgtt |
| 3901 | gggagggact taccttggaa agttgctatt ctaggaaaga gaaaccttca tattcctgga |
| 3961 | aacagcaggt agtttccagt gctggcaatg aattccccag aactgctgtt ttggattttt |
| 4021 | tcttgcctgg cagctgttgg gagcagggtg cagtgaggat ggggtgagag tgggcagttt |
| 4081 | cttgtgcaga tttgcctttc tttcatcctg gggctgactt gcagctccac acccatccat |
| 4141 | ctctcaaatt tcacagaggg taaaataggc atttggagag aaagaactct ggcctgattc |
| 4201 | ctttctctcc cacaaatgtc ctttattcat aaaacaggaa taataattcc tgtatctccc |
| 4261 | aactacatgg aagctgcagc cctcacagaa gaagatgatc tgagaaattc tttgatttcc |
| 4321 | tcagtacagt tatacccatg catcataata ctttaagcct ggaaggcatc ttaaaaataa |
| 4381 | tgcaacagtc aaacctaatt ttacagaaa actgacatga aatcacgcag ctaatcatga |
| 4441 | taaagctggg tggaaaactt atcttgatgg gcagtacagg aagatgcagt agaccttaag |
| 4501 | atgtcctgaa agtttcttat ctcaggggaa actcccaggt aggctttatg tcagggacac |
| 4561 | agaaaaatgc tccctgaaag tcaaatatt cgggctagac agacaaattc ctgtaagtgt |
| 4621 | ggtttgtctg ggaaccacag atgtcactaa tcctggtttg ctccagagtt ctttttgttc |
| 4681 | actcctaccc cccatcacca tttgattgat ctccttaccc tgtaatttcc ccttcttgtc |
| 4741 | gcttacctgc agtatctttc ccacccaggc atgccttatt ctttctaaag gaaagtatga |
| 4801 | atggagaggg gaaagcttgg gaaactgata gatttccttg gatgccaaaa cacctccata |
| 4861 | gcctgtctgc ccggccctat gtggaaacag cattgagttt caagtccttt atgcctccac |
| 4921 | ccagggatag ccacttgtaa tccacatggc aattgtgaaa caagcaggaa atgcgtaatt |
| 4981 | gtcagaattt tgtggggaaa ggactaggga ataaggaaaa caaagatctt ccttgtgttt |
| 5041 | tagagctgtc agctagagga gcacctgctt gagtctgatg ccatctaatg gtcccagaag |
| 5101 | aaactgggtt ttgaacctag agttccatgg actcttagga attagactac tactactact |
| 5161 | aagcattcac tggtgcttac tatgtgctat tgctgtgcca agtatctgaa acctgtcttc |
| 5221 | ttaccttatt tttcaagata attctatgtg gcaggtatta ctatctcaat tctaagagtg |
| 5281 | agaaaatgga gttttagaaa catttactaa cttgcctggg tcacatagct aaggaagagg |

TABLE 1-continued

```
5341  tggacttgcc cagctttgca taaaactcct caaaagagtt gcctatactc cctgactcca
5401  cttatcttcc tactatcctc ttttaaaat atattattta tttatttaaa taagcaatat
5461  atgaatgtgg tttgaaattc aaaagacaca agaagtata cagaggaaag cctcactctc
5521  aatccttctc aaggtttgct aattcctctt gcataggcaa tccgttcttc cagctttgtg
5581  tttatctttc cagagaagtt tactgtgtat taagcaaata tgtatatctt tattcttgct
5641  cagtattttc gcaaacagca gctgtctaag ttcactgttc tgaactttat tttttaaatt
5701  aaaaatatat ggctatgtag tattctattt ta
```

SEQ ID NO: 26 Human TAP2 Isoform 2 Amino Acid Sequence
(NP_001276972.1)
```
  1  mrlpdlrpwt slllvdaall wllqgplgtl lpqglpglwl egtlrlgglw gllklrgllg
 61  fvgtlllplc latpltvslr alvagasrap parvasapws wllvgygaag lswslwavls
121  ppgaqekeqd qvnnkvlmwr llklsrpdlp llvaaffflv lavlgetlip hysgrvidil
181  ggdfdphafa saiffmclfs fgsslsagcr ggcftytmsr inlrireqlf ssllrqdlgf
241  fqetktgeln srlssdttlm snwlplnanv llrslvkvvg lygfmlsisp rltllsllhm
301  pftiaaekvy ntrhqevlre iqdavaragq vvreavgglq tvrsfgaeeh evcrykeale
361  qcrqlywrrd leralyllvr rvlhlgvqml mlscglqqmq dgeltqgsll sfmiyqesvg
421  syvqtlvyiy gdmlsnvgaa ekvfsymdrq pnlpspgtla pttlqgvvkf qdvsfaypnr
481  pdrpvlkglt ftlrpgevta lvgpngsgks tvaallqnly qptggqvlld ekpisqyehc
541  ylhsqvvsvg qepvlfsgsv rnniayglqs ceddkvmaaa qaahaddfiq emehgiytdv
601  gekgsqlaag qkgrlaiara lvrdprvlil deatsaldvq ceqalqdwns rgdrtvlvia
661  hrlqtvqrah qilvlqegkl qklaql
```

SEQ ID NO: 27 Human TAP2 cDNA Variant 2 Sequence (NM_018833.2, CDS
region from position 123-2084)
```
   1  gcccgccctg gccgagcgta gctggcggac cagagccggt agcgaggttg ggagagacgg
  61  agcggacctc agcgctgaag cagaagtccc cggagctgcg gtctccccgc cgcggctgag
 121  ccatgcggct ccctgacctg agaccctgga cctccctgct gctggtggac gcggctttac
 181  tgtggctgct tcagggccct ctggggactt tgcttcctca agggctgcca ggactatggc
 241  tggaggggac cctgcggctg gagggctgt ggggctgct aaagctaaga gggctgctgg
 301  gatttgtggg gacactgctg ctcccgctct gtctggccac ccccctgact gtctccctga
 361  gagccctggt cgcggggggcc tcacgtgctc ccccagccag agtcgcttca gccccttgga
 421  gctggctgct ggtggggtac ggggctgcgg ggctcagctg gtcactgtgg gctgttctga
 481  gccctcctgg agcccaggag aaggagcagg accaggtgaa caacaaagtc ttgatgtgga
 541  ggctgctgaa gctctccagg ccggacctgc ctctcctcgt gccgccttc ttcttccttg
 601  tccttgctgt tttgggtgag acattaatcc ctcactattc tggtcgtgtg attgacatcc
 661  tgggaggtga ttttgacccc catgcctttg ccagtgccat cttcttcatg tgcctcttct
 721  cctttggcag ctcactgtct gcaggctgcc gaggaggctg cttcacctac accatgtctc
 781  gaatcaactt gcggatccgg agcagctttt ctcctcccct gctgcgccag gacctcggtt
 841  tcttccagga gactaagaca ggggagctga actcacggct gagctcggat accaccctga
 901  tgagtaactg gcttcccttta aatgccaatg tgctcttgcg aagcctggtg aaagtggtgg
 961  ggctgtatgg cttcatgctc agcatatcgc ctcgactcac cctcctttct ctgctgcaca
1021  tgcccttcac aatagcagcg gagaaggtgt acaacacccg ccatcaggaa gtgcttcggg
1081  agatccagga tgcagtggcc agggcggggc aggtggtgcg ggaagccgtt ggagggctgc
```

TABLE 1-continued

```
1141    agaccgttcg cagttttggg gccgaggagc atgaagtctg tcgctataaa gaggcccttg 1201    aacaatgtcg gcagctgtat tggcggagag acctggaacg cgccttgtac ctgctcgtaa 1261    ggagggtgct gcacttgggg gtgcagatgc tgatgctgag ctgtgggctg cagcagatgc 1321    aggatgggga gctcacccag ggcagcctgc tttcctttat gatctaccag gagagcgtgg 1381    ggagctatgt gcagaccctg gtatacatat atgggatat gctcagcaac gtgggagctg 1441    cagagaaggt tttctcctac atggaccgac agccaaatct gccttcacct ggcacgcttg 1501    cccccaccac tctgcagggg gttgtgaaat ccaagacgt ctcctttgca tatcccaatc 1561    gccctgacag gcctgtgctc aaggggctga cgtttaccct acgtcctggt gaggtgacgg 1621    cgctggtggg acccaatggg tctgggaaga gcacagtggc tgccctgctg cagaatctgt 1681    accagcccac aggggacag gtgctgctgg atgaaaagcc catctcacag tatgaacact 1741    gctacctgca cagccaggtg gtttcagttg ggcaggagcc tgtgctgttc tccggttctg 1801    tgaggaacaa cattgcttat ggctgcaga gctgcgaaga tgataaggtg atggcggctg 1861    cccaggctgc ccacgcagat gacttcatcc aggaaatgga gcatggaata tacacagatg 1921    taggggagaa gggaagccag ctggctgcgg gacagaaaca acgtctggcc attgcccggg 1981    cccttgtacg agacccgcgg gtcctcatcc tggatgaggc tactagtgcc ctagatgtgc 2041    agtgcgagca ggccaaaacc ctttggaagt tcatgatatt ttgaatttca atggatattt 2101    cctgggaata atgagttcaa atgaacgaat atgtggaaca aagcatcacc aacatttatt 2161    ttttcaggat gaggtgatgg acaaaaccat cacagggaaa ttgaggcaaa tagtacatgt 2221    aaaacaatac ttcgggtgag tccacctatc ccaaagtcgt atcaaagaag tggctgcaga 2281    ttggagccca aagcctttgg ttcctcagtt tccaaatgga ttctcactag gtgggatcat 2341    gagtttgctt tggacacccc aaattctaac tatttctttt gtttcttaca tcctttccct 2401    cttccccagc cccttcccct catgttacac ctcttgctgg tttgagacgt caatcaccac 2461    tgagaaagaa ttaaaccagt attttgagct ggcaaaattc ttagcctagt acaattcctt 2521    caattaaact gtagctcaac
```

SEQ ID NO: 28 Human TAP2 Isoform 3 Amino Acid Sequence (NP_061313.2)
```
  1     mrlpdlrpwt slllvdaall wllqgplgtl lpqglpglwl egtlrlgglw gllklrgllg 61     fvgtlllplc latpltvslr alvagasrap parvasapws wllvgygaag lswslwavls 121     ppgaqekeqd qvnnkvlmwr llklsrpdlp llvaaffflv lavlgetlip hysgrvidil 181     ggdfdphafa saiffmclfs fgsslsagcr ggcftytmsr inlrireqlf ssllrqdlgf 241     fqetktgeln srlssdttlm snwlplnanv llrslvkvvg lygfmlsisp rltllsllhm 301     pftlaaekvy ntrhqevlre iqdavaragq vvreavgglq tvrsfgaeeh evcrykeale 361     qcrqlywrrd leralyllvr rvlhlgvqml mlscglqqmq dgeltqgsll sfmiyqesvg 421     syvqtlvyiy gdmlsnvgaa ekvfsymdrq pnlpspgtla pttlqgvvkf qdvsfaypnr 481     pdrpvlkglt ftlrpgevta lvgpngsgks tvaallqnly qptggqvlld ekpisqyehc 541     ylhsqvvsvg qepvlfsgsv rnniayglqs ceddkvmaaa qaahaddfiq emehgiytdv 601     gekgsqlaag qkqrlaiara lvrdprvlil deatsaldvq ceqaktlwkf mif
```

SEQ ID NO: 29 Mouse TAP2 cDNA Sequence (NM_011530.3, CDS region from position 154-2262)
```
  1     accgcgacca cggcagtgaa gtgaaagcga aagccgcggg acccaggcgc gctcccgcg 61     agggcgtcgc tgcgcaccca ggagatccag tttgagaaga agcagattcc agaagctctc 121     ctgagctgcc gctccgcagc cgcagaaccc accatggcgc gtgtcctacct gaggccctgg
```

TABLE 1-continued

```
 181   gtctctctgc tgctggcgga catggcttta cttgggttgc tacaaggatc tctgggaaat
 241   ctgcttcccc aggggctgcc aggactctgg atagagggca ccctgcgact tggagtgctg
 301   tggggactgc taaaagtggg agagctgctg ggacttgtgg ggacccttct gcccttgctc
 361   tgccttgcca ctcccctgtt tttctcgcta agagctctgg tgggaggcac cgcgagcacc
 421   tcagtagtcc gagtggcttc tgcctcttgg ggctggctgc tggctggcta tggggctgtt
 481   gcgctgagct gggccgtgtg gctgtgctga agcccggctg gagtccagga aaggaaccag
 541   ggccaggaga acagaacact gatgaagcgg ttgctgaagc tgtccaggcc ggacctgcct
 601   ttcctcatag ctgccttctt cttccttgtg gtggctgtgt gggggagac attaatccct
 661   cgctattcgg gtcgtgtaat tgacatcctg ggaggtgatt tcgaccccga cgcctttgca
 721   agcgccatct ttttcatgtg cctgttctct gttgggagct ccttctctgc aggctgtaga
 781   ggaggctcct tcctcttcac catgtccagg atcaacctgc ggatacgaga gcagcttttc
 841   tcatctttgt tgcgccaaga ccttggattc ttccaggaga ccaagacagg ggagctgaac
 901   tcgaggctga gctctgacac ctctctgatg agccgctggc tccctttcaa tgccaatatc
 961   ctgctgcgga gcctggtgaa ggtggtgggg ctctacttct tcatgctcca ggtatcgccc
1021   cgactcacct tcctctccct gctggacctg cccctcacga tagcagctga aaggtgtac
1081   aacccccgcc atcaggcggt gctaaaggag atccaggatg cagtggccaa ggcggggcag
1141   gtggtgcgcg aggcggtagg agggctgcag actgtgcgaa gctttggggc cgaggagcag
1201   gaagtcagcc actacaagga ggccctggag cgatgtagac agctgtggtg gcgccgagac
1261   ctggaaaaag acgtgtatct agtcatacgg agggtgatgg ccttgggcat gcaggtgctg
1321   attctgaact gcggcgtgca gcagattctg gctggagagg tcacccgggg tggcctgctc
1381   tccttcctgc tgtaccagga ggaagtggga caatatgtcc ggaacctggt ttacatgtac
1441   ggggatatgc tgagcaacgt gggcgctgct gaaaaggtgt tttcctacct ggaccgaaag
1501   ccgaatctgc cccagcctgg gatcctggcc cctccctggc tggaggggcg cgtggaattc
1561   caagacgtct ccttttcgta tcccaggcgc cccgagaagc ctgtgctcca gggtctgacg
1621   ttcaccctgc atcctggaac ggtgacagcg ttggtgggac ccaatggatc agggaagagc
1681   accgtggccg ccctgctgca gaacctgtac cagcccactg ggggccagct gctgctggat
1741   ggcgagcccc tgaccgagta tgatcaccac tacctgcacc gccaggtggt tctggtgggg
1801   caggagcctg tgctgttctc gggttctgtc aaggacaata ttgcctatgg cctgagggac
1861   tgtgaggacg ctcaagtgat ggcagctgcc caggcggcct gtgcagacga cttcataggg
1921   gaaatgacta atggaataaa cacagaaatc ggggaaaaag ggggccagtt agctgtggga
1981   cagaagcaac gtctggccat tgcccgggcc cttgtgcgga cccacgggt cctcatcctg
2041   gatgaggcta ccagcgccct ggacgcccag tgtgaacagg ccctacagaa ctgagatcg
2101   caggggaca ggacgatgct ggtgattgcc cacaggctgc acacggttca gaatgctgac
2161   caagttctgg tgctcaagca gggacgtctg gtggagcatg accagctcag ggacggccag
2221   gatgtctacg cccacctggt acagcagcgg ctgaggcat gaggcctcca gaccctgagc
2281   ccctctcagg actgtggcca ggatcagacc cacagggacc gtgccggagg aggctagggt
2341   caggataaag attgggaccg ttttggactt tgtgtgtttt tgtggccttg atgggtgagg
2401   gttggggag tgggtggttt gtggttctag aaacattatt tttttgctga atataaaaat
2461   aataaatata tataaaatgc tttccttaa
```

TABLE 1-continued

```
SEQ ID NO: 30 Mouse TAP2 Amino Acid Sequence (NP_035660.3)
   1   malsylrpwv sllladmall gllqgslgnl lpqglpglwi egtlrlgvlw gllkvgellg
  61   lvgtllpllc latplffslr alvggtasts vvrvasaswg wllagygava lswavwavls
 121   pagvqekepg qenrtlmkrl lklsrpdlpf liaaffflvv avwgetlipr ysgrvidilg
 181   gdfdpdafas aiffmclfsv gssfsagcrg gsflftmsri nlrireqlfs sllrqdlgff
 241   qetktgelns rlssdtslms rwlpfnanil lrslvkvvgl yffmlqvspr ltflslldlp
 301   ltiaaekvyn prhqavlkei qdavakagqv vreavgglqt vrsfgaeeqe vshykealer
 361   crqlwwrrdl ekdvylvirr vmalgmqvli lncgvqqila gevtrgglls fllyqeevgq
 421   yvrnlvymyg dmlsnvgaae kvfsyldrkp nlpqpgilap pwlegrvefq dvsfsyprrp
 481   ekpvlqgltf tlhpgtvtal vgpngsgkst vaallqnlyq ptggqlllag eplteydhhy
 541   lhrqvvlvgq epvlfsgsvk dniayglrdc edaqvmaaaq aacaddfige mtnginteig
 601   ekggqlavgq kqrlaiaral vrnprvlild eatsaldaqc eqalqnwrsq gdrtmlviah
 661   rlhtvgnadq vlvlkqgrlv ehdqlrdgqd vyahlvqqrl ea SEQ ID NO: 31 Human TAPBP cDNA Variant 1 Sequence (NM_003190.4, CDS
region from position 347-1693)
    1   ggggacgcgg cacagatagg gggaagccgg agtaatggtt ttcgggcaag tggatgttgg
   61   agagcacaca caggagttgg ggggcggggg agggcctggg gttggggagg gctcgaactc
  121   ggggctgctg ggtagtccag gagggcgcgg taaggctggg gtgtcctggt gagaactgga
  181   gaggatctac ccgggtccct gcctggccag tggggaaaca ccggtccccc aggcaccttc
  241   acctaaccag agcggggatt tccaccgccc ctcatgccgc cctttggagg aaagtgaaag
  301   tgaaaggagg aagaggaggc ttcatggctg aggaggtcgc agcgccatga agtccctgtc
  361   tctgctcctc gctgtggctt tgggcctggc gaccgccgtc tcagcaggac ccgcggtgat
  421   cgagtgttgg ttcgtggagg atgcgagcgg aaagggcctg ccaagagac ccggtgcact
  481   gctgttgcgc cagggaccgg ggaaccgcc gccccggccg gacctcgacc ctgagctcta
  541   tctcagtgta cacgaccccg cgggcgccct ccaggctgcc ttcaggcggt atccccgggg
  601   cgcccccgca ccacactgcg agatgagccg cttcgtgcct ctccccgcct gcgcgaaatg
  661   ggccagcggc ctgaccccgg cgcagaactg cccgcgggcc ctggatgggg cttggctgat
  721   ggtcagcata tccagcccag tcctcagcct ctccagcctc ttgcgaccac agccagagcc
  781   tcagcaggag cctgttctca tcaccatggc aacagtggta ctgactgtcc tcacccacac
  841   ccctgcccct cgagtgagac tgggacaaga tgctctgctg gacttgagct ttgcctacat
  901   gcccccacc tccgaggccg cctcatctct ggctccgggt cccctccct ttgggctaga
  961   gtggcgacgc cagcacctgg taaggaca tctgctcctg gctgcaactc ctgggctgaa
 1021   tggccagatg ccagcagccc aagaagggc cgtggcattt gctgcttggg atgatgatga
 1081   gccatggggc ccatggaccg gaaatggac cttctggctg cctacagttc aacccttca
 1141   ggagggcacc tatctggcca ccatacacct gccataccctg caaggacagg tcacccctgga
 1201   gcttgctgtg tacaaacccc ccaaagtgtc cctgatgcca gcaaccctttg cacgggccgc
 1261   cccagggaag gcaccccgg aattgctctg ccttgtgtcc cacttctacc cttctggggg
 1321   cctggaggtg gagtgggaac tccggggtgg cccaggggc cgctctcaga aggccagggg
 1381   gcagaggtgg ctctcggccc tgcgccacca ttccgatggc tctgtcagcc tctctgggca
 1441   cttgcagccg cccccagtca ccactgagca gcatggggca cgctatgcct gtcgaattca
 1501   ccatcccagc ctgcctgcct cggggcgcag cgctgaggtc accctggagg tagcaggtct
 1561   ttcagggccc tccctgagg acagcgtagg ccttttcctg tctgcctttc ttctgcttgg
```

TABLE 1-continued

```
1621    gctcttcaag gcactgggct gggctgctgt ctacctgtcc acctgcaagg attcaaagaa
1681    gaaagcagag tgagggcact cactgccatc ctgtggaagc caccatcatc tctgcccaa
1741    gcttctgtag tagctcccta aaataatacc ctatcatctg ctcctaatcc ctccaatctc
1801    tctccactga gtggctggaa tgctttttt ttttttcttc acttatataa gggataattt
1861    ttcttttttt ttttttttg agacggagtc tcactcttcc gcccaggctg cagtgcagtg
1921    gcatgatctt ggcttactgc aacctccgcc tcctgggttc aagcaattct gtggcttcag
1981    cctccggagt agctgggatt acaggcacat gccaccacac ccagtgaatt tttgtatttt
2041    tagtagagac ggggtttcac catgttggcc aggctggtct tgaattcctg acctcaggtg
2101    atctgcccac ctcagcctcc caaagtgctg ggattacagg cgtgagccac cacaccaggc
2161    ccgagaaatg cttttttaaa aaacacacat cttatggcat tcaccttctt ggagctctag
2221    gacagtggtt ctcaaaattt ttttctctca ggacctctta aaaatcatca aggaccccaa
2281    aaagcttttg ggtatgtggg ttatagctat caatatttat ggtactagaa cttaaaagtg
2341    agaaaaattt aaaacacgag aatacatagg cacacattct attcatcgtg ggaaccatgg
2401    tgtcaataca tatcatgtag cttctgaaaa actccactgt acacttatag aatgaagaag
2461    gcaaaaaact tttttttttt ttttttgag acggagtctc gctctgtcgc ccaggctgga
2521    gtgcagtggc gcgatctcgg ctcactgcaa gctccgcctc cgggttcac gccattctcc
2581    tgcctcagcc tcccaagtag ctcggactac aggcgtcctc caccatgcct ggctaatatt
2641    ttgtatttt tagtagagac ggggtttcac cgtgttagcc aggatggtct cgatctccta
2701    acctggtgat ccgcccgcct cggcctccca aagtattggg attacccgcg tgagccaccg
2761    cgcccggctg caaataatct ttcttttttt ctgagacaga gtctcgctct gttgcccagg
2821    ctggagtgca gtggcacgat ctcggctcac ggcacgctcc gcctccggg ttcacgccat
2881    tctcctgcct cagcttcccg agtagctggg actacagggg cccgccacca cgcccggcta
2941    actttttgtg ttttagtag agacgggtt tcaccgtgtt agccaggatg gtctcgatct
3001    cctgaccttg tgatctgccc gcctcggcct cccaaagtgc tgggattaca ggcgtgagcc
3061    accgcgcccg gcggcgaaac acgatattgt actaacatct taattttgtt ataaaatctc
3121    acaaaccccc tgacatagtc tcagagatct gtagggccga ggttacattt ggagaacccg
3181    tactctaggg ccaaatccat tcttcttgcc ctggctcact tgtccccccc accgccccgc
3241    gctggagcca ctgcctagtt cttcagccct agatggtgct cgccagacct cctctcaatg
3301    ctcatcacac acagggctat tcctttcctc caatgaacca aacgcctccc gcccacctcc
3361    aggtcccagt cctctgttcc ctttgcctgg tccacccttg ccctccctgg gtcgcagacg
3421    aggtcggcct cgtcattccc cgcagaccgc cgcgcgtccc tcttgtgcgg ttcaccacag
3481    ttgtatttaa gtgatcgtgt gagtcgtcgt taaatgcctg tctccccgcg gatcatgggc
3541    tcctcgagga cagggactgg cctgtctgtc cactgctgta accccgcgcc ggcataggga
3601    cctaaggccc actggagggc gctcatcaag tagctgctgg atgttgacga aggaagcggc
3661    ggcgcagctc agggatctcc gagtcaggac ggtcggccag acccacgggg taacgggtct
3721    aatcgtgtag gaataaagct gtattccagt gcttccaaaa aaaaaaaaaa aaaaaaaa
```

SEQ ID NO: 32 Human TAPBP Isoform 1 Amino Acid Sequence (NP_003181.3)

```
  1    mkslslllav alglataysa gpaviecwfv edasgkglak rpgalllrqg pgepppprpdl
 61    dpelylsvhd pagalqaafr ryprgapaph cemsrfvplp asakwasglt pagncprald
121    gawlmvsiss pvlslssllr pqpepqqepv litmatvvlt vlthtpaprv rlgqdalldl
181    sfaympptse aasslapgpp pfglewrrqh lgkghlllaa tpglngqmpa aqegavafaa
```

TABLE 1-continued

| | |
|---|---|
| 241 | wdddepwgpw tgngtfwlpt vqpfqegtyl atihlpylqg qvtlelavyk ppkvslmpat |
| 301 | laraapgeap pellclvshf ypsgglevew elrggpggrs qkaeggrwls alrhhsdgsv |
| 361 | slsghlqppp vtteqhgary acrihhpslp asgrsaevtl evaglsgpsl edsvglflsa |
| 421 | flllglfkal gwaavylstc kdskkkae |

SEQ ID NO: 33 Human TAPBP cDNA Variant 2 Sequence (NM_172208.2, CDS region from position 347-1861)

| | |
|---|---|
| 1 | ggggacgcgg cacagatagg gggaagccgg agtaatggtt ttcgggcaag tggatgttgg |
| 61 | agagcacaca caggagttgg ggggcggggg agggcctggg gttggggagg gctcgaactc |
| 121 | ggggctgctg gtagtccag gagggcgcgg taaggctggg gtgtcctggt gagaactgga |
| 181 | gaggatctac ccgggtccct gcctggccag tggggaaaca ccggtccccc aggcaccttc |
| 241 | acctaaccag agcggggatt ccaccgccc ctcatgccgc cctttggagg aaagtgaaag |
| 301 | tgaaaggagg aagaggaggc ttcatggctg aggaggtcgc agcgccatga agtccctgtc |
| 361 | tctgctcctc gctgtggctt gggcctggc gaccgccgtc tcagcaggac ccgcggtgat |
| 421 | cgagtgttgg ttcgtggagg atgcgagcgg aaagggcctg gccaagagac ccggtgcact |
| 481 | gctgttgcgc cagggaccgg ggaaccgcc gccccggccg gacctcgacc ctgagctcta |
| 541 | tctcagtgta cacgaccccg cgggcgccct ccaggctgcc ttcaggcggt atccccgggg |
| 601 | cgccccgca ccacactgcg agatgagccg cttcgtgcct ctcccgcct ctgcgaaatg |
| 661 | ggccagcggc ctgacccccg cgcagaactg cccgcgggcc ctggatgggg cttggctgat |
| 721 | ggtcagcata tccagcccag tcctcagcct ctccagcctc ttgcgaccac agccagagcc |
| 781 | tcagcaggag cctgttctca tcaccatggc aacagtggta ctgactgtcc tcacccacac |
| 841 | ccctgcccct cgagtgagac tgggacaaga tgctctgctg gacttgagct tgcctacat |
| 901 | gccccccacc tccgaggccg cctcatctct ggctccgggt ccccctccct ttgggctaga |
| 961 | gtggcgacgc cagcacctgg gtaagggaca tctgctcctg gctgcaactc ctgggctgaa |
| 1021 | tggccagatg ccagcagccc aagaagggc cgtggcattt gctgcttggg atgatgatga |
| 1081 | gccatggggc ccatggaccg gaaatgggac cttctggctg cctacagttc aaccctttca |
| 1141 | ggagggcacc tatctggcca ccatacacct gccatacctg caaggacagg tcaccctgga |
| 1201 | gcttgctgtg tacaaacccc ccaaagtgtc cctgatgcca gcaacccttg cacgggccgc |
| 1261 | cccaggggag gcaccccgg aattgctctg ccttgtgtcc cacttctacc cttctggggg |
| 1321 | cctggaggtg gagtgggaac tccggggtgg cccaggggc cgctctcaga aggccgaggg |
| 1381 | gcagaggtgg ctctcggccc tgcgccacca ttccgatggc tctgtcagcc tctctgggca |
| 1441 | cttgcagccg ccccagtca ccactgagca gcatgggca cgctatgcct gtcgaattca |
| 1501 | ccatcccagc ctgcctgcct cggggcgcag cgctgaggtc accctggagg tagcaggtct |
| 1561 | ttcagggccc tcccttgagg acagcgtagg ccttttcctg tctgcctttc ttctgcttgg |
| 1621 | gctcttcaag gcactgggct gggctgctgt ctacctgtcc acctgcaagg attcaaagaa |
| 1681 | ggtacagtgc tccacctctc tgtatctttc ccttgtcact ttatctcctc atcctatctc |
| 1741 | aaaaccatg gagggaggct gctggtgtgg taggcagaac ctaggcttgg aattcacact |
| 1801 | gatctgggtt aaaacctggc actatatcct aactgtagga ctctttgagc atgctactta |
| 1861 | atctatatgt ttccttgggt gtagggattt taaaaagtta cttaggcagt gctgtccaat |
| 1921 | agaaagataa tgcaagccac atatgtaaat ttaaatactc tagtactcac attaaaaaaa |
| 1981 | taagcagaaa caggtaaaat taa |

TABLE 1-continued

SEQ ID NO: 34 Human TAPBP Isoform 2 Amino Acid Sequence (NP_757345.2)
```
  1  mkslslllav alglataysa gpaviecwfv edasgkglak rpgalllrqg pgeppprpdl
 61  dpelylsvhd pagalqaafr ryprgapaph cemsrfvplp asakwasglt pagncprald
121  gawlmvsiss pvlslssllr pqpepqqepv litmatvvlt vlthtpaprv rlgqdallddl
181  sfaympptse aasslapgpp pfglewrrqh lgkghlllaa tpglngqmpa aqegavafaa
241  wdddepwgpw tgngtfwlpt vqpfqegtyl atihlpylqg qvtlelavyk ppkvslmpat
301  laraapgeap pellclvshf ypsgglevew elrggpggrs qkaegqrwls alrhhsdgsv
361  slsghlqppp vtteqhgary acrihhpslp asgrsaevtl evaglsgpsl edsvglflsa
421  flllglfkal gwaavylstc kdskkvqcst slylslvtls phpiskpmeg gcwcgrqnlg
481  leftliwvkt whyiltvglf ehat
```

SEQ ID NO: 35 Human TAPBP cDNA Variant 3 Sequence (NM_172209.2, CDS region from position 347-1432)
```
   1  ggggacgcgg cacagatagg gggaagccgg agtaatggtt ttcgggcaag tgatgttgg
  61  agagcacaca caggagttgg ggggcggggg agggcctggg gttggggagg gctcgaactc
 121  ggggctgctg ggtagtccag gagggcgcgg taaggctggg gtgtcctggt gagaactgga
 181  gaggatctac ccgggtccct gcctggccag tggggaaaca ccgtccccc aggcaccttc
 241  acctaaccag agcggggatt ccaccgccc ctcatgccgc cctttggagg aaagtgaaag
 301  tgaaggagg aagaggaggc ttcatggctg aggaggtcgc agcgccatga agtccctgtc
 361  tctgctcctc gctgtggctt tgggcctggc gaccgccgtc tcagcaggac cgcggtgat
 421  cgagtgttgg ttcgtggagg atgcgagcgg aaagggcctg ccaagagac ccggtgcact
 481  gctgttgcgc cagggaccgg gggaaccgcc gccccggccg gacctcgacc ctgagctcta
 541  tctcagtgta cacgtggtac tgactgtcct cacccacacc cctgcccctc gagtgagact
 601  gggacaagat gctctgctgg acttgagctt tgcctacatg ccccccacct ccgaggccgc
 661  ctcatctctg gctccgggtc ccctcccctt gggctagag tggcgacgcc agcacctggg
 721  taagggacat ctgctcctgg ctgcaactcc tgggctgaat ggccagatgc cagcagccca
 781  agaaggggcc gtggcatttg ctgcttggga tgatgatgag ccatggggcc catggaccgg
 841  aaatgggacc ttctggctgc ctacagttca acccttcag gagggcacct atctggccac
 901  catacacctg ccataccctgc aaggacaggt caccctggag cttgctgtgt acaaaccccc
 961  caaagtgtcc ctgatgccag caacccttgc acgggccgcc ccaggggagg caccccgga
1021  attgctctgc cttgtgtccc acttctaccc ttctggggc ctggaggtgg agtgggaact
1081  ccggggtggc ccaggggggcc gctctcagaa ggccgagggg cagaggtggc tctcggccct
1141  gcgccaccat tccgatggct ctgtcagcct ctctgggcac ttgcagccgc ccccagtcac
1201  cactgagcag catggggcac gctatgcctg tcgaattcac catcccagcc tgcctgcctc
1261  ggggcgcagc gctgaggtca ccctggaggt agcaggtctt cagggccct ccccttgagga
1321  cagcgtaggc ctttcctgt ctgcctttct tctgcttggg ctcttcaagg cactgggctg
1381  ggctgctgtc tacctgtcca cctgcaagga ttcaaagaag aaagcagagt gagggcactc
1441  actgccatcc tgtggaagcc accatcatct ctggcccaag cttctgtagt agctccctaa
1501  aataatacc tatcatctgc tcctaatccc tccaatctct ctccactgag tggctggaat
1561  gcttttttt tttctttca cttatataag ggataatttt tcttttttt ttttttttga
1621  gacggagtct cactcttccg cccaggctgc agtgcagtgg catgatcttg gcttactgca
1681  acctccgcct cctgggttca agcaattctg tggcttcagc ctccggagta gctgggatta
1741  caggcacatg ccaccacacc cagtgaattt ttgtattttt agtagagacg gggtttcacc
```

TABLE 1-continued

```
1801    atgttggcca ggctggtctt gaattcctga cctcaggtga tctgcccacc tcagcctccc
1861    aaagtgctgg gattacaggc gtgagccacc acaccaggcc cgagaaatgc ttttttaaaa
1921    aacacacatc ttatggcatt caccttcttg gagctctagg acagtggttc tcaaaatttt
1981    tttctctcag gacctcttaa aaatcatcaa ggaccccaaa aagcttttgg tatgtgggt
2041    tatagctatc aatatttatg gtactagaac ttaaaagtga gaaaattta aaacacgaga
2101    atacataggc acacattcta ttcatcgtgg gaaccatggt gtcaatacat atcatgtagc
2161    ttctgaaaaa ctccactgta cacttataga atgaagaagg caaaaaactt ttttttttt
2221    tttttgaga cggagtctcg ctctgtcgcc caggctggag tgcagtggcg cgatctcggc
2281    tcactgcaag ctccgcctct cgggttcacg ccattctcct gcctcagcct cccaagtagc
2341    tcggactaca ggcgtcctcc accatgcctg gctaatattt tgtattttt agtagagacg
2401    gggtttcacc gtgttagcca ggatggtctc gatctcctaa cctggtgatc cgcccgcctc
2461    ggcctcccaa agtattggga ttacccgcgt gagccaccgc gcccggctgc aaataatctt
2521    tcttttttc tgagacagag tctcgctctg ttgcccaggc tggagtgcag tggcacgatc
2581    tcggctcacg gcacgctccg cctcccgggt tcacgccatt ctcctgcctc agcttcccga
2641    gtagctggga ctacaggggc ccgccaccac gcccggctaa cttttgtgt tttagtaga
2701    gacggggttt caccgtgtta gccaggatgg tctcgatctc ctgaccttgt gatctgcccg
2761    cctcggcctc ccaaagtgct gggattacag gcgtgagcca ccgcgcccgg cggcgaaaca
2821    cgatattgta ctaacatctt aattttgtta taaatctca caaacccct gacatagtct
2881    cagagatctg tagggccgag gttacatttg gagaacccgt actctagggc caaatccatt
2941    cttcttgccc tggctcactt gtcccccca ccgcccgcg ctggagccac tgcctagttc
3001    ttcagcccta gatggtgctc gccagacctc ctctcaatgc tcatcacaca cagggctatt
3061    ccttcctcc aatgaaccaa acgcctccg cccacctcca ggtcccagtc tctgttccc
3121    tttgcctggt ccacccttgc cctccctggg tcgcagacga ggtcggcctc gtcattcccc
3181    gcagaccgcc gcgcgtcct cttgtgcggt tcaccacagt tgtatttaag tgatcgtgtg
3241    agtcgtcgtt aaatgcctgt ctccccgcgg atcatgggct cctcgaggac agggactggc
3301    ctgtctgtcc actgctgtaa ccccgcgccg gcatagggac ctaaggccca ctggagggcg
3361    ctcatcaagt agctgctgga tgttgacgaa ggaagcggcg gcgcagctca gggatctccg
3421    agtcaggacg tcggccaga cccacggggt aacgggtcta atcgtgtagg aataaagctg
3481    tattccagtg cttccaaaaa aaaaaaaaa aaaaaaaa1
```

SEQ ID NO: 36 Human TAPBP Isoform 3 Amino Acid Sequence (NP_757346.2)
```
  1     mkslslllav alglataysa gpaviecwfv edasgkglak rpgalllrqg pgeppprpdl
 61     dpelylsvhv vltvlthtpa prvrlgqdal ldlsfaympp tseaasslap gpppfglewr
121     rqhlgkghll laatpglngq mpaaqegava faawdddepw gpwtgngtfw lptvqpfqeg
181     tylatihlpy lqgqvtlela vykppkvslm patlaraapg eappellclv shfypsggle
241     vewelrggpg grsqkaegqr wlsalrhhsd gsvslsghlq pppvtteqhg aryacrihhp
301     slpasgrsae vtlevaglsg psledsvglf lsaflllglf kalgwaavyl stckdskkka
361     e
```

SEQ ID NO: 37 Mouse TAPBP cDNA Variant 1 Sequence (NM_001025313.1,
CDS region from position 211-1611)
```
  1     caagggggtg ggtgcagggc gaggagtggc tggagagcta cagacagggt ttcggcaact
 61     ctgtttggcc cctgtgggcg gcgttcctcc aacgcgcagt cacgccctca cctgaccaga
121     tcggggaatt ccagttcct caccccagcc ttagaaggaa aatgaaagtg aaggggaag
```

TABLE 1-continued

```
 181    aaaagacttg gtaggagaga tcgtagcacc atgaagcctc tgctcctgct cgtcgctgtg
 241    gcactgggcc tagcgaccgt cgtctccgtc gtctcggctg accagaggc gatcgagtgc
 301    tggttcgtgg aggatgcagg tggggtggc ctgtctaaga aacctgccac actgctactg
 361    cgccatggac ccaggggacc gccgccccgg ccagatcttg acccaaagct atacttcaag
 421    gtggatgacc cggcgggaat gctcctggcc gccttcaggc ggtaccccgc aggcgcctcc
 481    gccccacact gcgagatgag ccgcttcatc ccgttccctg cctcggcgaa gtgggctaga
 541    agtctgagtc cggagcagaa ctgcccgcgg gccctggacg gggattggct gctggtcagc
 601    gtatccagca ctctcttcag cctctccagc ctgctgcgac acagccgga gcctctgcgg
 661    gagcctgtcg tcatcaccat ggcaacagtg gtgctgaccg tcctcaccca taaccctgcc
 721    cctcgagtcc agctgggaaa ggatgcagtg ctggacctgc gcttcgccta cgcaccctcc
 781    gccctggaag gttctccctc tctggacgca ggccctcctc cctttgggct ggagtggcga
 841    cgccagcaca ggggaaaggg tcacctgctg ttggctgcca cccccgggct ggccgggaga
 901    atgccaccag cccaggaaaa ggctacggca tttgcagctt gggatgacga tgagccctgg
 961    ggcccgtgga ctgggaatgg gaccttctgg cttccagccg tgaagccttc tcaggagggt
1021    gtctacctgg ctacggtaca cctgccctac ctgcaaggac aggtctccct ggagctgact
1081    gtgcacaagg cccccagagt gtctctaaca ccagcaccg ttgtgtgggc tgcccagga
1141    gaggcacccc cagaactgct ctgtcttgca tcccacttct ccctgcgga gggtctggag
1201    gtcaagtggg agctcagagg cggcccagga ggaagttcta gaaaggttga ggggaagacg
1261    tggctctcca ccatccgcca ccattccgat ggctctgtca gccagtctgg gcacctgcag
1321    ctacctccag tcactgccaa gcagcatgga gttcactatg tctgtcgggt gtaccactct
1381    agcctgccag catcggggcg cagtgctgac gtcaccctgg aggtggcagg cttctcaggg
1441    ccctccatcg aggacggcat cggcctgttc ctgtctgctt ttctcctcct cggactcctc
1501    aaggtgctag gctggctggt agctgcctac tggaccattc ctgaagtctc aaaggagaag
1561    gccacagctg ccagcctgac cattcccagg aactcaaaga gtcacagta aagaagttct
1621    cgtctgtgga agccaccctc atctctggcc cagatgactc cagtagcccc tgccccagaa
1681    caacagcctt cttctcttct tctccctcca ttgaatagct cggattttt tttttaaggt
1741    tttttgttt gtttcaatct ttcttgttt gttcttgttt ttagacaagg tctctctatg
1801    tagccttggc tggctgtcct gaaccctcac caagccaacc aggctggcct cgaagtccca
1861    gagatccacc tgtccctctg cctcggagtg acaaacggca ctggacacca tgcctagagg
1921    tctttttttt ttttggtttt tggagacagg atttctctgt atagtcccgg ctgtcctgga
1981    actcactctg tagaccaggc tggcctcgaa ctcagaaatc cgcctgcctc tgcctcccag
2041    gtgctgggat taaaggcgtg cgccaccacc gctggactcg aactaaactt ttaagatgag
2101    aaaaaagcga gacttagcgc cacactcatt tgatgcccac agtcgggagg cagaggcagt
2161    ggatctctga catttccatg ccagcctgat ctacaaatag ggagtttcag gtcagtcggg
2221    gttacttggc ggggctttgt tgagagaact aaatataaga acacacatgc gtagagtccc
2281    agggttgaga agaaccagtg tatgcgccag agaggcgggt tcataacctg tggctcacaa
2341    ccccctttaa gtccatcgga ataccagac attaggattc acaacagtag taaaggcagt
2401    tacgaagtag caaagaaaat aattttacaa cttgaactgc gttaatgtta agaaggttga
2461    gaaccactgg ccaggggatt aggacgaaag gtcttcatag catcttaaga ttctagagac
2521    ctcagggaca gcccacagca gtagtctaga gacggaaagg tccatgtgtc tccctcgcgg
```

TABLE 1-continued

```
2581    actaaagcct  acctctccag  ctctccattc  ctaccacagc  ttttcttttg  cctggtccac 2641    ctttaccatc  tccgggcctg  gtgggtctcg  gcccttttacg aatgtccccg  tgtggttcgt 2701    cctctcctgt  tcgccggtcc  tcgtgagcta  ataaagtctt  tccgagtttc
```

SEQ ID NO: 38 Mouse TAPBP Isoform 1 Amino Acid Sequence
(NP_001020484.1)

```
  1    mkplllllvav  alglatvvsv  vsagpealec  wfvedagggg  lskkpatlll  rhgprgpppr 61    pdldpklyfk   vddpagmlla  afrrypagas  aphcemsrfl  pfpasakwar  slspeqncpr 121    aldgdwllvs   vsstlfslss  llrpqpeplr  epvvitmatv  vltvlthnpa  prvqlgkdav 181    ldlrfayaps   alegspslda  gpppfglewr  rqhrgkghll  laatpglagr  mppaqekata 241    faawdddepw   gpwtgngtfw  lpavkpsgeg  vylatvhlpy  lqgqvslelt  vhkaprvslt 301    papvvwaapg   eappellcla  shffpaegle  vkwelrggpg  gssrkvegkt  wlstirhhsd 361    gsvsgsghlq   lppvtakqhg  vhyvcrvyhs  slpasgrsad  vtlevagfsg  psiedgiglf 421    lsaflllgll   kvlgwlvaay  wtipevskek  ataasltipr  nskksq
```

SEQ ID NO: 39 Mouse TAPBP cDNA Variant 2 Sequence (NM_009318.2, CDS region from position 211-1608)

```
  1    caaggggggtg ggtgcagggc  gaggagtggc  tggagagcta  cagacagggt  ttcggcaact 61    ctgtttggcc  cctgtgggcg  gcgttcctcc  aacgcgcagt  cacgccctca  cctgaccaga 121    tcggggaatt  tccagttcct  cacccccagcc ttagaaggaa  aatgaaagtg  aaaggggaag 181    aaaagacttg  gtaggagaga  tcgtagcacc  atgaagcctc  tgctcctgct  cgtcgctgtg 241    gcactgggcc  tagcgaccgt  cgtctccgtc  gtctcggctg  gaccagaggc  gatcgagtgc 301    tggttcgtgg  aggatgcagg  tgggggtggc  ctgtctaaga  aacctgccac  actgctactg 361    cgccatggac  ccaggggacc  gccgccccgg  ccagatcttg  acccaaaagc  atacttcaag 421    gtggatgacc  cggcgggaat  gctcctggcc  gccttcaggc  ggtaccccgc  aggcgcctcc 481    gccccacact  gcgagatgag  ccgcttcatc  ccgttccctg  cctcggcgaa  gtgggctaga 541    agtctgagtc  cggagcagaa  ctgcccgcgg  gccctggacg  gggattggct  gctggtcagc 601    gtatccagca  ctctcttcag  cctctccagc  ctgctgcgac  acagccggga  gcctctgcgg 661    gagcctgtcg  tcatcaccat  ggcaacagtg  gtgctgaccg  tcctcaccca  taaccctgcc 721    cctcgagtcc  agctgggaaa  ggatgcagtg  ctggacctgc  gcttcgccta  cgcaccctcc 781    gccctggaag  ttctccctc   tctggacgca  ggccctcctc  cctttgggct  ggagtggcga 841    cgccagcaca  ggggaaaggg  tcacctgctg  ttggctgcca  ccccgggct   ggccgggaga 901    atgccaccag  cccaggaaaa  ggctacggca  tttgcagctt  gggatgacga  tgagccctgg 961    ggcccgtgga  ctgggaatgg  gaccttctgg  cttccagccg  tgaagccttc  tcaggagggt 1021   gtctacctgg  ctacggtaca  cctgccctac  ctgcaaggac  aggtctccct  ggagctgact 1081   gtgcacaagg  cccccagagt  gtctctaaca  ccagcacccg  ttgtgtgggc  tgccccagga 1141   gaggcacccc  cagaactgct  ctgtcttgca  tcccacttct  tccctgcgga  gggtctggag 1201   gtcaagtggg  agctcagagg  cggcccagga  ggaagttcta  gaaaggttga  ggggaagacg 1261   tggctctcca  ccatccgcca  ccattccgat  ggctctgtca  gccagtctgg  gcacctgcag 1321   ctacctccag  tcactgccaa  gcagcatgga  gttcactatg  tctgtcgggt  gtaccactct 1381   agcctgccag  catcggggcg  cagtgctgac  gtcaccctgg  aggtggcagg  cttctcaggg 1441   ccctccatcg  aggacggcat  cggcctgttc  ctgtctgctt  ttctcctcct  cggactcctc 1501   aaggtgctag  gctggctggc  tgcctactgg  accattcctg  aagtctcaaa  ggagaaggcc 1561   acagctgcca  gcctgaccat  tcccaggaac  tcaaagaagt  cacagtaaag  aagttctcgt
```

TABLE 1-continued

```
1621  ctgtggaagc caccctcatc tctggcccag atgactccag tagccctgc cccagaacaa
1681  cagccttctt ctcttcttct ccctccattg aatagctcgg attttttttt ttaaggtttt
1741  tttgtttgtt tcaatctttc ttgttttgtt cttgttttta gacaaggtct ctctatgtag
1801  ccttggctgg ctgtcctgaa ccctcaccaa gccaaccagg ctggcctcga agtcccagag
1861  atccacctgt ccctctgcct cggagtgaca aacggcactg gacaccatgc ctagaggtct
1921  ttttttttt tggttttgg agacaggatt tctctgtata gtcccggctg tcctggaact
1981  cactctgtag accaggctgg cctcgaactc agaaatccgc ctgcctctgc ctcccaggtg
2041  ctgggattaa aggcgtgcgc caccaccgct ggactcgaac taaacttta agatgagaaa
2101  aaagcgagac ttagcgccac actcatttga tgcccacagt cgggaggcag aggcagtgga
2161  tctctgacat ttccatgcca gcctgatcta caaatagggaa gtttcaggtc agtcggggtt
2221  acttggcggg gctttgttga gagaactaaa tataagaaca cacatgcgta gagtcccagg
2281  gttgagaaga accagtgtat gcgccagaga ggcgggttca taacctgtgg ctcacaaccc
2341  cctttaagtc catcggaaat accagacatt aggattcaca acagtagtaa aggcagttac
2401  gaagtagcaa agaaaataat tttacaactt gaactgcgtt aatgttaaga aggttgagaa
2461  ccactggcca ggggattagg acgaaaggtc ttcatagcat cttaagattc tagagacctc
2521  agggacagcc cacagcagta gtctagagac ggaaaggtcc atgtgtctcc ctcgcggact
2581  aaagcctacc tctccagctc tccattccta ccacagcttt tcttttgcct ggtccacctt
2641  taccatctcc gggcctggtg ggtctcggcc ctttacgaat gtccccgtgt ggttcgtcct
2701  ctcctgttcg ccggtcctcg tgagctaata aagtctttcc gagtttc
```

SEQ ID NO: 40 Mouse TAPBP Isoform 2 Amino Acid Sequence (NP_033344.1)
```
  1  mkpllllvav alglatvvsv vsagpeaiec wfvedagggg lskkpatlll rhgprgpppr
 61  pdldpklyfk vddpagmlla afrrypagas aphcemsrfl pfpasakwar slspeqncpr
121  aldgdwllvs vsstlfslss llrpqpeplr epvvitmatv vltvlthnpa prvqlgkdav
181  ldlrfayaps alegspslda gpppfglewr rqhrgkghll laatpglagr mppaqekata
241  faawdddepw gpwtgngtfw lpavkpsqeg vylatvhlpy lqgqvslelt vhkaprvslt
301  papvvwaapg eappellcla shffpaegle vkwelrggpg gssrkvegkt wlstirhhsd
361  gsvsqsghlq lppvtakqhg vhyvcrvyhs slpasgrsad vtlevagfsg psiedgiglf
421  lsaflllgll kvlgwlaayw tipevskeka taasltiprn skksq
```

SEQ ID NO: 41 Human ERAP1 cDNA Variant 1 Sequence (NM_016442.4, CDS region from position 348-3194)
```
  1  acggatccgc gttcagaaag gcgtgcactt cctacgcctg atccccgca tcgcaacctc
 61  gcagcttccc cggcgtgcag cgctcattta ccaattccct tcctgggagt tgcggcttcc
121  ctcgctcggc cccactcccg tttacccttt cccagctcc cgccttagcc aggggcttcc
181  ccgcctgccg ctagggctcg ggccgaagcg ccgctcagcg ccagcctgcc gctccccggg
241  ctccactttc actttcggtc ctggggagc taggccggcg gcagtggtgg tgcggcggc
301  gcaagggtga gggcggcccc agaaccccag gtaggtagag caagaagatg tgtttctgc
361  ccctcaaatg gtcccttgca accatgtcat ttctactttc ctcactgttg gctctcttaa
421  ctgtgtccac tccttcatgg tgtcagagca ctgaagcatc tccaaaacgt agtgatggga
481  caccatttcc ttgaataaaa atacgacttc ctgagtacgt catcccagtt cattatgatc
541  tcttgatcca tgcaaacctt accacgctga ccttctgggg aaccacgaaa gtagaaatca
601  cagccagtca gcccaccagc accatcatcc tgcatagtca ccactgcag atatctaggg
661  ccaccctcag gaagggagct ggagagaggc tatcggaaga accctgcag gtcctggaac
```

TABLE 1-continued

```
 721  acccccgtca ggagcaaatt gcactgctgg ctcccgagcc cctccttgtc gggctcccgt
 781  acacagttgt cattcactat gctggcaatc tttcggagac tttccacgga ttttacaaaa
 841  gcacctacag aaccaaggaa ggggaactga ggatactagc atcaacacaa tttgaaccca
 901  ctgcagctag aatggccttt ccctgctttg atgaacctgc cttcaaagca agtttctcaa
 961  tcaaaattag aagagagcca aggcacctag ccatctccaa tatgccattg gtgaaatctg
1021  tgactgttgc tgaaggactc atagaagacc attttgatgt cactgtgaag atgagcacct
1081  atctggtggc cttcatcatt tcagattttg agtctgtcag caagataacc aagagtggag
1141  tcaaggtttc tgtttatgct gtgccagaca agataaatca agcagattat gcactggatg
1201  ctgcggtgac tcttctagaa ttttatgagg attatttcag cataccgtat cccctaccca
1261  aacaagatct tgctgctatt cccgactttc agtctggtgc tatggaaaac tggggactga
1321  caacatatag agaatctgct ctgttgtttg atgcagaaaa gtcttctgca tcaagtaagc
1381  ttggcatcac aatgactgtg gcccatgaac tggctcacca gtggtttggg aacctggtca
1441  ctatggaatg gtggaatgat ctttggctaa atgaaggatt tgccaaattt atggagtttg
1501  tgtctgtcag tgtgacccat cctgaactga agttggaga ttatttcttt ggcaaatgtt
1561  ttgacgcaat ggaggtagat gctttaaatt cctcacaccc tgtgtctaca cctgtggaaa
1621  atcctgctca gatccgggag atgtttgatg atgtttctta tgataaggga gcttgtattc
1681  tgaatatgct aagggagtat cttagtgctg acgcatttaa aagtggtatt gtacagtatc
1741  tccagaagca tagctataaa aatacaaaaa acgaggacct gtgggatagt atggcaagta
1801  tttgccctac agatggtgta aaagggatgg atggcttttg ctctagaagt caacattcat
1861  cttcatcctc acattggcat caggaagggg tggatgtgaa aaccatgatg aacacttgga
1921  cactgcagaa gggttttccc ctaataacca tcacagtgag ggggaggaat gtacacatga
1981  agcaagagca ctacatgaag ggctctgacg gcgccccgga cactgggtac ctgtggcatg
2041  ttccattgac attcatcacc agcaaatccg acatggtcca tcgattttg ctaaaaacaa
2101  aaacagatgt gctcatcctc ccagaagagg tggaatggat caaatttaat gtgggcatga
2161  atggctatta cattgtgcat tacgaggatg atggatggga ctctttgact ggccttttaa
2221  aaggaacaca cacagcagtc agcagtaatg atcgggcgag tctcattaac aatgcatttc
2281  agctcgtcag cattgggaag ctgtccattg aaaaggcctt ggattatccc ctgtacttga
2341  aacatgaaac tgaaattatg cccgtgtttc aaggtttgaa tgagctgatt cctatgtata
2401  agttaatgga gaaaagagat atgaatgaag tggaaactca attcaaggcc ttcctcatca
2461  ggctgctaag ggacctcatt gataagcaga catggacaga cgagggctca gtctcagagc
2521  gaatgctgcg gagtcaacta ctactcctcg cctgtgtgca caactatcag ccgtgcgtac
2581  agagggcaga aggctatttc agaaagtgga aggaatccaa tggaaacttg agcctgcctg
2641  tcgacgtgac cttggcagtg tttgctgtgg gggcccagag cacagaaggc tgggattttc
2701  tttatagtaa atatcagttt tctttgtcca gtactgagaa aagccaaatt gaatttgccc
2761  tctgcagaac ccaaaataag gaaaagcttc aatggctact agatgaaagc tttaagggag
2821  ataaaataaa aactcaggag tttccacaaa ttcttacact cattggcagg aacccagtag
2881  gatacccact ggcctggcaa tttctgagga aaaactggaa caaacttgta caaaagtttg
2941  aacttggctc atcttccata gcccacatgg taatgggtac aacaaatcaa ttctccacaa
3001  gaacacggct tgaagaggta aaaggattct tcagctcttt gaagaaaaat ggttctcagc
3061  tccgttgtgt ccaacagaca attgaaacca ttgaagaaaa catcggttgg atggataaga
```

TABLE 1-continued

```
3121  attttgataa aatcagagtg tggctgcaaa gtgaaaagct tgaacatgat cctgaagctg
3181  acgcaacagg atgaaaatcc atcagaatct cagactacag cactaaatat gctttgatgc
3241  tacatcaaac ggaatggaag catagctgac ttcgctaaag ttacttcatc tccatctagc
3301  aaatgaggca ctgttctcaa ccaaaggaga tggggatctg gtttagggca atccctttat
3361  aatttgatgt gctgtggtct ccttggtaat gtataatttg gtattgcaca ggtgattagt
3421  caaggaagtc tggaaaagct ttggtcccac agccttgcct cacagcatgt aaataattaa
3481  aacaatattg atgctgaggt tcttctactg ctagtatgaa agtgacaaat ttttactggt
3541  gtgaattggg aagaaaacaa tgctattcca tgacgtttgt aaaatgtttg taaaagctca
3601  aacatgacga ttccataaaa taaacttgag gttaaataat gggtagtaaa ttatagaatg
3661  tataagaaaa aatataaagg agaaaatcaa ttatcaggaa agctaaagaa cttttcaaat
3721  ctagtaattt gaatatagac acaatgcact ttattgcact ttcaattctt ataaagcaac
3781  aataatatta aggtccttga ctatgtgtac aatgttttca catatatagt ttcatttaat
3841  catttcaaag ttaatctctg ccatctcgct aaatcatcag tctcggctct tctgaaatag
3901  aaggtgcctg atcttcctaa taattctgcc tattttcatt tgctttaaac aggcgcccta
3961  ttttctttct agttgtggct gcgcaaaaac atttatctcc caaataagat gtgctgctta
4021  ccgaggtatc acggggtggg gctccagctt gggtcgttga agctggggtt tgggaaacca
4081  cttcagagat ggcagcagca agtttagcat cttcaaattt cttttattga aaaaaatttt
4141  attagtaaca tgttgtatat aaaattatga gcacaatgcc atcacttaac tataactctt
4201  aaagatagct taatgactgt ttattctctt gaccaaatag actcataata acatataatt
4261  ttaaaagaaa tttaaattct ttcttctcta ttgtattatt ttatacaatt gctatttct
4321  atttccttct catattgatt attctaaata ctatgcaata atataactta gagttccacg
4381  gtttgtttac acatttcctg ttgtacattt aggttattca aagttttcag ctctttttaaa
4441  attgctctga ataagttcta gtgagtgagt tatggtgctg gctatatttt gctaaactgc
4501  cctctcaaat gttgctagga attcatactg cgaaaagcaa tgaataagca tgcctgtttt
4561  cccatggcct tgcttgccag aatttgactt ttattatgat aatcagtgta aaatgatata
4621  ctactattgc ttgtatattg tggtatacgg tgtcaggttt cagggttttt tttcaacgtt
4681  aaatattcta gaactttct gaaataattt ctgtttaaaa atattgaata tttgcttcat
4741  ttcaaatact cccttttgac aaaaaaactt aggtataact gttgatgaaa aaccagaaaa
4801  aagtccagaa ctcttggtg actccaacta tggatagctt attttgaaaa aggagaattg
4861  caaattttac caaagatgg agaaaagcac attaaaaaga taccaacatt cagaaattca
4921  tttcagcatg ttattattgg aaattattta aactaattta gataactata agatacttat
4981  tgtccattta taccctgtaa agccgtttta gaatgtaata ttttaggtaa tccaaaatgt
5041  actaaattaa attcattttt agttatgaga aatctttgct tatatgacaa atgaaaagaa
5101  taacaagttg tcaaatgaaa agaatgacat tgaaacattt gtattgtctc ttcttaaact
5161  atcttattga cttattattt aagcctttta atactaagta tgaaacaacc tatggtctgg
5221  aaatttgtat cgcaaagcta tatgtgcata tgttatttaa ttcatctaat gctacacaaa
5281  agcataaaat aatgattttt cactctcttt aaaaatacta aatcatttat gtccatttct
5341  caattttttc attgatctat gctttgagtt tgcttctca acattattgt attttccact
5401  tattattact gtataacata tgctagtgtt tagttggatt aatcttacct aaaagtactg
5461  aaaaatgctt tttagtactt tttcatattt tatacattta ttttccgaat gtatcattga
```

| | | | | |
|---|---|---|---|---|
| 5521 | ataattttat | tgagttataa | aagtatctta | ttgctattta | ataaaaaatt aacacataaa |
| 5581 | atgaaaaaaa | aaa | | | |

SEQ ID NO: 42 Human ERAP1 Isoform a Amino Acid Sequence (NP_057526.3)

| | | | | | |
|---|---|---|---|---|---|
| 1 | mvflplkwsl | atmsfllssl | lalltvstps | wcqsteaspk | rsdgtpfpwn kirlpeyvip |
| 61 | vhydllihan | ltttltfwgtt | kveitasqpt | stiilhshhl | qisratlrkg agerlseepl |
| 121 | qvlehprqeq | iallapepll | vglpytvvih | yagnlsetfh | gfykstyrtk egelrilast |
| 181 | qfeptaarma | fpcfdepafk | asfsikirre | prhlaisnmp | lvksvtvaeg liedhfdvtv |
| 241 | kmstylvafi | isdfesvski | tksgvkvsvy | avpdkinqad | yaldaavtll efyedyfsip |
| 301 | yplpkqdlaa | ipdfqsgame | nwglttyres | allfdaekss | assklgitmt vahelahqwf |
| 361 | gnlvtmewwn | dlwlnegfak | fmefvsvsvt | hpelkvgdyf | fgkcfdamev dalnsshpvs |
| 421 | tpvenpaqir | emfddvsydk | gacilnmlre | ylsadafksg | ivqylqkhsy kntknedlwd |
| 481 | smasicptdg | vkgmdgfcsr | sqhsssshw | hqegvdvktm | mntwtlqkgf plititvrgr |
| 541 | nvhmkqehym | kgsdgapdtg | ylwhvpltfi | tsksdmvhrf | llktktdvli lpeevewikf |
| 601 | nvgmngyyiv | hyeddgwdsl | tgllkgthta | vssndrasli | nnafqlvsig klsiekaldl |
| 661 | slylkhetei | mpvfqglnel | ipmyklmekr | dmnevetqfk | aflirllrdl idkqtwtdeg |
| 721 | svsermlrsq | llllacvhny | qpcvqraegy | frkwkesngn | lslpvdvtla vfavgaqste |
| 781 | gwdflyskyq | fslssteksq | iefalcrtqn | keklqwllde | sfkgdkiktq efpqiltlig |
| 841 | rnpvgyplaw | qflrknwnkl | vqkfelgsss | iahmvmgttn | qfstrtrlee vkgffsslke |
| 901 | ngsqlrcvqq | tietieenig | wmdknfdkir | vwlqsekleh | dpeadatg |

SEQ ID NO: 43 Human ERAP1 cDNA Variant 4 Sequence (NM_001349244.1, CDS region from position 344-3190)

| | | | | | |
|---|---|---|---|---|---|
| 1 | acggatccgc | gttcagaaag | gcgtgcactt | cctacgcctg | atcccccgca tcgcaacctc |
| 61 | gcagcttccc | cggcgtgcag | cgctcattta | ccaattccct | tcctgggagt tgcggcttcc |
| 121 | ctcgctcggc | cccactcccg | tttacccttt | cccagctcc | cgccttagcc aggggcttcc |
| 181 | ccgcctgccg | ctagggctcg | ggccgaagcg | ccgctcagcg | ccagcctgcc gctcccggg |
| 241 | ctccactttc | actttcggtc | ctggggagc | taggccggcg | gcagtggtgg tggcggcggc |
| 301 | gcaagggtga | gggcggcccc | agaacccag | gtagagcaag | aagatggtgt ttctgcccct |
| 361 | caaatggtcc | cttgcaacca | tgtcatttct | actttcctca | ctgttggctc tcttaactgt |
| 421 | gtccactcct | tcatggtgtc | agagcactga | agcatctcca | aaacgtagtg atgggacacc |
| 481 | atttccttgg | aataaaatac | gacttcctga | gtacgtcatc | ccagttcatt atgatctctt |
| 541 | gatccatgca | aaccttacca | cgctgacctt | ctggggaacc | acgaaagtag aaatcacagc |
| 601 | cagtcagccc | accagcacca | tcatcctgca | tagtcaccac | ctgcagatat ctagggccac |
| 661 | cctcaggaag | ggagctggag | agaggctatc | ggaagaaccc | ctgcaggtcc tggaacaccc |
| 721 | ccgtcaggag | caaattgcac | tgctggctcc | cgagccctc | cttgtcgggc tcccgtacac |
| 781 | agttgtcatt | cactatgctg | gcaatctttc | ggagactttc | cacggatttt acaaaagcac |
| 841 | ctacagaacc | aaggaagggg | aactgaggat | actagcatca | acacaatttg aacccactgc |
| 901 | agctagaatg | gcctttccct | gctttgatga | acctgcctc | aaagcaagtt tctcaatcaa |
| 961 | aattagaaga | gagccaaggc | acctagccat | ctccaatatg | ccattggtga atctgtgac |
| 1021 | tgttgctgaa | ggactcatag | aagaccattt | tgatgtcact | gtgaagatga gcacctatct |
| 1081 | ggtggccttc | atcatttcag | attttgagtc | tgtcagcaag | ataaccaaga gtggagtcaa |
| 1141 | ggtttctgtt | tatgctgtgc | cagacaagat | aaatcaagca | gattatgcac tggatgctgc |
| 1201 | ggtgactctt | ctagaatttt | atgaggatta | tttcagcata | ccgtatcccc tacccaaaca |

TABLE 1-continued

```
1261  agatcttgct gctattcccg actttcagtc tggtgctatg gaaaactggg gactgacaac
1321  atatagagaa tctgctctgt tgtttgatgc agaaaagtct tctgcatcaa gtaagcttgg
1381  catcacaatg actgtggccc atgaactggc tcaccagtgg tttgggaacc tggtcactat
1441  ggaatggtgg aatgatcttt ggctaaatga aggatttgcc aaatttatgg agtttgtgtc
1501  tgtcagtgtg acccatcctg aactgaaagt tggagattat ttctttggca aatgttttga
1561  cgcaatggag gtagatgctt taaattcctc acaccctgtg tctacacctg tggaaaatcc
1621  tgctcagatc cgggagatgt tgatgatgt ttcttatgat aagggagctt gtattctgaa
1681  tatgctaagg gagtatctta gtgctgacga atttaaaagt ggtattgtac agtatctcca
1741  gaagcatagc tataaaaata caaaaaacga ggacctgtgg gatagtatgg caagtatttg
1801  ccctacagat ggtgtaaaag ggatggatgg cttttgctct agaagtcaac attcatcttc
1861  atcctcacat tggcatcagg aagggtgga tgtgaaaacc atgatgaaca cttggacact
1921  gcagaagggt tttccctaa taaccatcac agtgagggg aggaatgtac acatgaagca
1981  agagcactac atgaagggct ctgacggcgc cccggacact gggtacctgt ggcatgttcc
2041  attgacattc atcaccagca aatccgacat ggtccatcga ttttgctaa aaacaaaaac
2101  agatgtgctc atcctcccag aagaggtgga atggatcaaa tttaatgtgg gcatgaatgg
2161  ctattacatt gtgcattacg aggatgatgg atgggactct ttgactggcc ttttaaaagg
2221  aacacacaca gcagtcagca gtaatgatcg ggcgagtctc attaacaatg catttcagct
2281  cgtcagcatt gggaagctgt ccattgaaaa ggccttggat ttatccctgt acttgaaaca
2341  tgaaactgaa attatgcccg tgtttcaagg tttgaatgag ctgattccta tgtataagtt
2401  aatggagaaa agagatatga atgaagtgga aactcaattc aaggccttcc tcatcaggct
2461  gctaagggac ctcattgata agcagacatg gacagacgag ggctcagtct cagagcgaat
2521  gctgcggagt caactactac tcctcgcctg tgtgcacaac tatcagccgt gcgtacagag
2581  ggcagaaggc tatttcagaa agtggaagga atccaatgga aacttgagcc tgcctgtcga
2641  cgtgacccttg gcagtgtttg ctgtggggc ccagagcaca gaaggctggg attttcttta
2701  tagtaaatat cagttttctt tgtccagtac tgagaaaagc caaattgaat ttgccctctg
2761  cagaacccaa aataaggaaa agcttcaatg gctactagat gaaagcttta agggagataa
2821  aataaaaact caggagtttc cacaaattct tacactcatt ggcaggaacc cagtaggata
2881  cccactggcc tggcaatttc tgaggaaaaa ctggaacaaa cttgtacaaa gtttgaact
2941  tggctcatct tccatagccc acatggtaat gggtacaaca atcaattct ccacaagaac
3001  acggcttgaa gaggtaaaag gattcttcag ctcttgaaa gaaaatggtt ctcagctccg
3061  ttgtgtccaa cagacaattg aaaccattga agaaacatc ggttggatgg ataagaattt
3121  tgataaaatc agagtgtggc tgcaaagtga aaagcttgaa catgatcctg aagctgacgc
3181  aacaggatga aaatccatca gaatctcaga ctacagcact aaatatgctt tgatgctaca
3241  tcaaacggaa tggaagcata gctgacttcg ctaaagttac ttcatctcca tctagcaaat
3301  gaggcactgt tctcaaccaa aggagatggg gatctggttt agggcaatcc ctttataatt
3361  tgatgtgctg tggtctcctt ggtaatgtat aatttggtat tgcacaggtg attagtcaag
3421  gaagtctgga aaagctttgg tcccacagcc ttgcctcaca gcatgtaaat aattaaaaca
3481  atattgatgc tgaggttctt ctactgctag tatgaaagtg acaaattttt actggtgtga
3541  attgggaaga aaacaatgct attccatgac gtttgtaaaa tgtttgtaaa agctcaaaca
3601  tgacgattcc ataaaataaa cttgaggtta ataatgggt agtaaattat agaatgtata
```

TABLE 1-continued

```
3661  agaaaaaata taaaggagaa aatcaattat caggaaagct aaagaacttt tcaaatctag
3721  taatttgaat atagacacaa tgcactttat tgcactttca attcttataa agcaacaata
3781  atattaaggt ccttgactat gtgtacaatg ttttcacata tatagtttca tttaatcatt
3841  tcaaagttaa tctctgccat ctcgctaaat catcagtctc ggctcttctg aaatagaagg
3901  tgcctgatct tcctaataat tctgcctatt ttcatttgct ttaaacaggc gccctatttt
3961  ctttctagtt gtggctgcgc aaaaacattt atctcccaaa taagatgtgc tgcttaccga
4021  ggtatcacgg ggtggggctc cagcttgggt cgttgaagct ggggtttggg aaaccacttc
4081  agagatggca gcagcaagtt tagcatcttc aaatttcttt tattgaaaaa aattttatta
4141  gtaacatgtt gtatataaaa ttatgagcac aatgccatca cttaactata actcttaaag
4201  atagcttaat gactgtttat tctcttgacc aaatagactc ataataacat ataattttaa
4261  aagaaattta aattctttct tctctattgt attattttat acaatttgct atttctattt
4321  ccttctcata ttgattattc taaatactat gcaataatat aacttagagt tccacggttt
4381  gtttacacat ttcctgttgt acatttaggt tattcaaagt tttcagctct tttaaaattg
4441  ctctgaataa gttctagtga gtgagttatg gtgctggcta tattttgcta aactgccctc
4501  tcaaatgttg ctaggaattc atactgcgaa aagcaatgaa taagcatgcc tgttttccca
4561  tggccttgct tgccagaatt tgacttttat tatgataatc agtgtaaaat gatatactac
4621  tattgcttgt atattgtggt atacggtgtc aggtttcagg gttttttttc aacgttaaat
4681  attctagaaa ctttctgaaa taatttctgt ttaaaaatat tgaatatttg cttcatttca
4741  aatactccct tttgacaaaa aaacttaggt ataactgttg atgaaaaacc agaaaaaagt
4801  ccagaactct ttggtgactc caactatgga tagcttattt tgaaaaagga gaattgcaaa
4861  ttttaccaaa agatggagaa aagcacatta aaaagatacc aacattcaga aattcatttc
4921  agcatgttat tattggaaat tatttaaact aatttagata actataagat acttattgtc
4981  catttatacc ctgtaaagcc gttttagaat gtaatatttt aggtaatcca aaatgtacta
5041  aattaaattc attttttagtt atgagaaatc tttgcttata tgacaaatga aagaataac
5101  aagttgtcaa atgaaaagaa tgacattgaa acatttgtat tgtctcttct taaactatct
5161  tattgactta ttatttaagc cttttaatac taagtatgaa acaacctatg gtctggaaat
5221  ttgtatcgca aagctatatg tgcatatgtt atttaattca tctaatgcta cacaaaagca
5281  taaaataatg atttttcact ctctttaaaa atactaaatc atttatgtcc atttctcaat
5341  tttttcattg atctatgctt tgagtttgct ttctcaacat tattgtattt tccacttatt
5401  attactgtat aacatatgct agtgtttagt tggattaatc ttacctaaaa gtactgaaaa
5461  atgcttttta gtacttttc atatttata catttatttt ccgaatgtat cattgaataa
5521  ttttattgag ttataaaagt atcttattgc tatttaataa aaaattaaca cataaaatga
5581  aaaaaaaaa
```

SEQ ID NO: 44 Human ERAP1 cDNA Variant 2 Sequence (NM_001040458.2,
CDS region from position 348-3173)

```
  1  acggatccgc gttcagaaag gcgtgcactt cctacgcctg atccccgca tcgcaacctc
 61  gcagcttccc cggcgtgcag cgctcattta ccaattccct tcctgggagt tgcggcttcc
121  ctcgctcggc cccactcccg tttacccttt cccagctcc cgccttagcc aggggcttcc
181  ccgcctgccg ctagggctcg ggccgaagcg ccgctcagcg ccagcctgcc gctccccggg
241  ctccactttc actttcggtc ctggggagc taggccggcg gcagtggtgg tggcggcgc
301  gcaagggtga gggcggcccc agaaccccag gtaggtagag caagaagatg gtgtttctgc
```

TABLE 1-continued

| | | | | |
|---|---|---|---|---|
| 361 | ccctcaaatg | gtcccttgca | accatgtcat | ttctactttc ctcactgttg gctctcttaa |
| 421 | ctgtgtccac | tccttcatgg | tgtcagagca | ctgaagcatc tccaaaacgt agtgatggga |
| 481 | caccatttcc | ttggaataaa | atacgacttc | ctgagtacgt catcccagtt cattatgatc |
| 541 | tcttgatcca | tgcaaacctt | accacgctga | ccttctgggg aaccacgaaa gtagaaatca |
| 601 | cagccagtca | gcccaccagc | accatcatcc | tgcatagtca ccacctgcag atatctaggg |
| 661 | ccaccctcag | gaagggagct | ggagagaggc | tatcggaaga acccctgcag gtcctggaac |
| 721 | accccgtca | ggagcaaatt | gcactgctgg | ctcccgagcc cctccttgtc gggctcccgt |
| 781 | acacagttgt | cattcactat | gctggcaatc | tttcggagac tttccacgga ttttacaaaa |
| 841 | gcacctacag | aaccaaggaa | ggggaactga | ggatactagc atcaacacaa tttgaaccca |
| 901 | ctgcagctag | aatggccttt | ccctgctttg | atgaacctgc cttcaaagca gtttctcaa |
| 961 | tcaaaattag | aagagagcca | aggcacctag | ccatctccaa tatgccattg gtgaaatctg |
| 1021 | tgactgttgc | tgaaggactc | atagaagacc | attttgatgt cactgtgaag atgagcacct |
| 1081 | atctggtggc | cttcatcatt | tcagattttg | agtctgtcag caagataacc aagagtggag |
| 1141 | tcaaggtttc | tgtttatgct | gtgccagaca | agataaatca agcagattat gcactggatg |
| 1201 | ctgcggtgac | tcttctagaa | ttttatgagg | attatttcag cataccgtat cccctaccca |
| 1261 | aacaagatct | tgctgctatt | cccgactttc | agtctggtgc tatggaaaac tggggactga |
| 1321 | caacatatag | agaatctgct | ctgttgtttg | atgcagaaaa gtcttctgca tcaagtaagc |
| 1381 | ttggcatcac | aatgactgtg | gcccatgaac | tggctcacca gtggtttggg aacctggtca |
| 1441 | ctatggaatg | gtggaatgat | ctttggctaa | atgaaggatt tgccaaattt atggagtttg |
| 1501 | tgtctgtcag | tgtgacccat | cctgaactga | agttggaga ttatttcttt ggcaaatgtt |
| 1561 | ttgacgcaat | ggaggtagat | gctttaaatt | cctcacaccc tgtgtctaca cctgtggaaa |
| 1621 | atcctgctca | gatccgggag | atgtttgatg | atgtttctta tgataaggga gcttgtattc |
| 1681 | tgaatatgct | aagggagtat | cttagtgctg | acgcatttaa aagtggtatt gtacagtatc |
| 1741 | tccagaagca | tagctataaa | aatacaaaaa | acgaggacct gtgggatagt atggcaagta |
| 1801 | tttgccctac | agatggtgta | aaagggatgg | atggcttttg ctctagaagt caacattcat |
| 1861 | cttcatcctc | acattggcat | caggaagggg | tggatgtgaa accatgatg aacacttgga |
| 1921 | cactgcagaa | gggttttccc | ctaataacca | tcacagtgag ggggaggaat gtacacatga |
| 1981 | agcaagagca | ctacatgaag | ggctctgacg | gcgccccgga cactgggtac ctgtggcatg |
| 2041 | ttccattgac | attcatcacc | agcaaatccg | acatggtcca tcgatttttg ctaaaaacaa |
| 2101 | aaacagatgt | gctcatcctc | ccagaagagg | tggaatggat caaatttaat gtgggcatga |
| 2161 | atggctatta | cattgtgcat | tacgaggatg | atgatgggga ctctttgact ggcctttaa |
| 2221 | aaggaacaca | cacagcagtc | agcagtaatg | atcgggcgag tctcattaac aatgcatttc |
| 2281 | agctcgtcag | cattgggaag | ctgtccattg | aaaaggcctt ggatttatcc ctgtacttga |
| 2341 | aacatgaaac | tgaaattatg | cccgtgtttc | aaggtttgaa tgagctgatt cctatgtata |
| 2401 | agttaatgga | gaaagagat | atgaatgaag | tggaaactca attcaaggcc ttcctcatca |
| 2461 | ggctgctaag | ggacctcatt | gataagcaga | catggacaga cgagggctca gtctcagagc |
| 2521 | gaatgctgcg | gagtcaacta | ctactcctcg | cctgtgtgca caactatcag ccgtgcgtac |
| 2581 | agagggcaga | aggctatttc | agaaagtgga | aggaatccaa tggaaacttg agcctgcctg |
| 2641 | tcgacgtgac | cttggcagtg | tttgctgtgg | gggcccagag cacagaaggc tgggatttc |
| 2701 | tttatagtaa | atatcagttt | tctttgtcca | gtactgagaa aagccaaatt gaatttgccc |

TABLE 1-continued

| | | | | | |
|---|---|---|---|---|---|
| 2761 | tctgcagaac | ccaaaataag | gaaaagcttc | aatggctact | agatgaaagc tttaagggag |
| 2821 | ataaaataaa | aactcaggag | tttccacaaa | ttcttacact | cattggcagg aacccagtag |
| 2881 | gatacccact | ggcctggcaa | tttctgagga | aaaactggaa | caaacttgta caaaagtttg |
| 2941 | aacttggctc | atcttccata | gcccacatgg | taatgggtac | aacaaatcaa ttctccacaa |
| 3001 | gaacacggct | tgaagaggta | aaaggattct | tcagctcttt | gaaagaaaat ggttctcagc |
| 3061 | tccgttgtgt | ccaacagaca | attgaaacca | ttgaagaaaa | catcggttgg atggataaga |
| 3121 | attttgataa | aatcagagtg | tggctgcaaa | gtgaaaagct | tgaacgtatg taaaaattcc |
| 3181 | tcccttgcca | ggttcctgtt | atctctaatc | accaacattt | tgttgagtgt attttcaaac |
| 3241 | tagagatggc | tgttttggct | ccaactggag | atacttttt  | cccttcaact catttttga  |
| 3301 | ctatccctgt | gaaaagaata | gctgttagtt | tttcatgaat | gggctatcgc taccatgtgt |
| 3361 | tttgttcatc | acaggtgttg | ccctgcaacg | taaacccaag | tgttgggttc cctgccacag |
| 3421 | aagaataaag | taccttattc | ttctcatttt | atagtttatg | cttaagcacc cgtgtccaaa |
| 3481 | accctgtacc | ccatgtttat | cattcataaa | ctgtttcatc | agtctcctcg aaagactctg |
| 3541 | aatagtcgac | tactgaacaa | tgaacacctg | gatctgagac | taagccggac gatgactggg |
| 3601 | ttaaagctct | cccggctcac | ccctccagac | ccgctgccca | tccctcttcc ttgctccatg |
| 3661 | cccagggget | gacttgtaaa | ggccaagtca | tcaagctttc | ttgccctttg gatgttggtc |
| 3721 | agtggggagc | cggagagctg | gagctggggt | cggaggaggt | agtaggtgga ggtgttcttc |
| 3781 | cctgattccc | ttgcgggatg | cctcgggctg | gcctcccctg | agggtcttag ctccgagagg |
| 3841 | ggaccctctt | ttccacacag | ccttctccac | ctctggattt | tggtaactgc tccctcctca |
| 3901 | tcccttcagg | attagtggcc | tcagtgggag | tctggctttt | actagtcctg gcggacttgt |
| 3961 | ggtttctaca | taatgtgctc | gcacttttgc | aaaaaatctt | tttatagaac cctcctcaga |
| 4021 | taattctgag | tgagtgtcat | ctatttccct | gactggtaca | gtatctcttc tgaaaaagca |
| 4081 | gagtgcattc | aagtctgtag | gaaaacccctt | ttcttaggga | ggtgattttt tttctctctc |
| 4141 | tgcttcttat | ttggcctact | ttacaatttc | taactaacta | gttattggca tttactgaca |
| 4201 | gtaaattatt | gcagtcacca | ataaatgata | gtacattgtg | aaacaaaata tttgctcata |
| 4261 | ttagcaaata | ggacattctt | tggctttgaa | gtcttctttt | cttttgtgaa gacttcacac |
| 4321 | acggttgctt | cagcacacag | ttgctgctca | ggttttatgt | atagatgata ataatagaaa |
| 4381 | gcacagttta | ctaacatggt | aaaccaacgg | agttcaagtc | aagtcagtta atacccctaag |
| 4441 | aattagattt | tatttcttat | tctgaaaact | tgctacacag | ggacttatct aacccatagt |
| 4501 | gtgctctgtt | gctgacttga | ttcaagttgc | agcgtgtttt | gcgctgactc taaggtgcgg |
| 4561 | aaatcctcac | acctggcaaa | ggagaattca | aactgaactt | tttgaatata aggcaaaaac |
| 4621 | ttcaagataa | gggaatatga | ttgatgattg | gtacgaaaaa | tgtcaaaatg tgttcccta  |
| 4681 | atacacgaca | aaatagagtg | acttctggac | ataaatctgc | catttattaa accattcact |
| 4741 | acaacaaata | aataggtata | aaagtggaat | tggaatttt  | atacttattt gttgtagtga |
| 4801 | atggtttaat | aaaaatagaa | atcactggta | atttccaccc | caaactaaac tatttccctt |
| 4861 | cttttaaaaa | aatacacaac | caagattta  | atgtaaaata | ttttgcttta attgtatttt |
| 4921 | atgccttgat | taatgaaaca | tggaaatatt | gattttcagt | tttggtcacc tgaggaacct |
| 4981 | atctttgttt | gcttttggaa | aagcccattt | tctaaacaga | tacaatattg ccacaacaat |
| 5041 | gtgcagaaac | cttttgata  | ataaaaaatt | gttctttgcc | tctaaaaaaa aaaaaaaaa  |
| 5101 | aaaaaaaaaa | | | | |

TABLE 1-continued

SEQ ID NO: 45 Human ERAP1 Isoform b Amino Acid Sequence
(NP_001035548.1)

```
  1   mvflplkwsl atmsfllssl lalltvstps wcqsteaspk rsdgtpfpwn kirlpeyvip
 61   vhydllihan ltttltfwgtt kveltasqpt stillhshhl qisratlrkg agerlseepl
121   qvlehprqeq iallapepll vglpytvvih yagnlsetfh gfykstyrtk egelrilast
181   qfeptaarma fpcfdepafk asfsikirre prhlaisnmp lvksvtvaeg liedhfdvtv
241   kmstylvafi isdfesvski tksgvkvsvy avpdkinqad yaldaavtll efyedyfsip
301   yplpkqdlaa ipdfqsgame nwglttyres allfdaekss assklgitmt vahelahqwf
361   gnlvtmewwn dlwlnegfak fmefvsvsvt hpelkvgdyf fgkcfdamev dalnsshpvs
421   tpvenpaqir emfddvsydk gacilnmlre ylsadafksg ivqylqkhsy kntknedlwd
481   smasicptdg vkgmdgfcsr sqhssssshw hqegvdvktm mntwtlqkgf plititvrgr
541   nvhmkqehym kgsdgapdtg ylwhvpltfi tsksdmvhrf llktktdvli lpeevewikf
601   nvgmngyyiv hyeddgwdsl tgllkgthta vssndrasli nnafqlvsig klsiekaldl
661   slylkhetei mpvfqglnel ipmyklmekr dmnevetqfk aflirllrdl idkqtwtdeg
721   svsermlrsq llllacvhny qpcvqraegy frkwkesngn lslpvdvtla vfavgaqste
781   gwdflyskyq fslssteksq iefalcrtqn keklqwllde sfkgdkiktq efpqiltlig
841   rnpvgyplaw qflrknwnkl vqkfelgsss lahmvmgttn qfstrtrlee vkgffsslke
901   ngsqlrcvqg tietieenig wmdknfdkir vwlgsekler m
```

SEQ ID NO: 46 Human ERAP1 cDNA Variant 3 Sequence (NM_001198541.2,
CDS region from position 106-2931)

```
   1   ccttcccttc tgctgggcct caggtgagac tgcagctcca gtcatcatct tgattgcagc
  61   ccacagaaac taccaaccca cagaaactgt aggtagagca agaagatggt gtttctgccc
 121   ctcaaatggt cccttgcaac catgtcattt ctactttcct cactgttggc tctcttaact
 181   gtgtccactc cttcatggtg tcagagcact gaagcatctc caaaacgtag tgatgggaca
 241   ccatttcctt ggaataaaat acgacttcct gagtacgtca tcccagttca ttatgatctc
 301   ttgatccatg caaaccttac cacgctgacc ttctggggaa ccacgaaagt agaaatcaca
 361   gccagtcagc ccaccagcac catcatcctg catagtcacc acctgcagat atctagggcc
 421   accctcagga agggagctgg agagaggcta tcggaagaac ccctgcaggt cctggaacac
 481   ccccgtcagg agcaaattgc actgctggct cccgagcccc tccttgtcgg gctcccgtac
 541   acagttgtca ttcactatgc tggcaatctt cggagacttc cacggatt ttacaaaagc
 601   acctacagaa ccaaggaagg ggaactgagg atactagcat caacacaatt gaacccact
 661   gcagctagaa tggcctttcc ctgctttgat gaacctgcct tcaaagcaag tttctcaatc
 721   aaaattagaa gagagccaag gcacctagcc atctccaata tgccattggt gaaatctgtg
 781   actgttgctg aaggactcat agaagaccat tttgatgtca ctgtgaagat gagcacctat
 841   ctggtggcct tcatcatttc agattttgag tctgtcagca agataaccaa gagtggagtc
 901   aaggtttctg tttatgctgt gccagacaag ataaatcaag cagattatgc actggatgct
 961   gcggtgactc ttctagaatt ttatgaggat tatttcagca taccgtatcc cctacccaaa
1021   caagatcttg ctgctattcc cgactttcag tctggtgcta tggaaaactg gggactgaca
1081   acatatagag aatctgctct gttgtttgat gcagaaaagt cttctgcatc aagtaagctt
1141   ggcatcacaa tgactgtggc ccatgaactg gctcaccagt ggtttgggaa cctggtcact
1201   atggaatggt ggaatgatct ttggctaaat gaaggatttg ccaaatttat ggagtttgtg
1261   tctgtcagtg tgacccatcc tgaactgaaa gttggagatt atttctttgg caaatgtttt
```

TABLE 1-continued

```
1321  gacgcaatgg aggtagatgc tttaaattcc tcacaccctg tgtctacacc tgtggaaaat
1381  cctgctcaga tccgggagat gtttgatgat gtttcttatg ataagggagc ttgtattctg
1441  aatatgctaa gggagtatct tagtgctgac gcatttaaaa gtggtattgt acagtatctc
1501  cagaagcata gctataaaaa tacaaaaaac gaggacctgt gggatagtat ggcaagtatt
1561  tgccctacag atggtgtaaa agggatggat ggcttttgct ctagaagtca acattcatct
1621  tcatcctcac attggcatca ggaaggggtg gatgtgaaaa ccatgatgaa cacttggaca
1681  ctgcagaagg gttttcccct aataaccatc acagtgaggg ggaggaatgt acacatgaag
1741  caagagcact acatgaaggg ctctgacggc gccccggaca ctgggtacct gtggcatgtt
1801  ccattgacat tcatcaccag caaatccgac atggtccatc gattttttgct aaaaacaaaa
1861  acagatgtgc tcatcctccc agaagaggtg gaatggatca aatttaatgt gggcatgaat
1921  ggctattaca ttgtgcatta cgaggatgat ggatgggact ctttgactgg ccttttaaaa
1981  ggaacacaca cagcagtcag cagtaatgat cgggcgagtc tcattaacaa tgcatttcag
2041  ctcgtcagca ttgggaagct gtccattgaa aaggccttgg atttatccct gtacttgaaa
2101  catgaaactg aaattatgcc cgtgtttcaa ggtttgaatg agctgattcc tatgtataag
2161  ttaatggaga aaagagatat gaatgaagtg gaaactcaat tcaaggcctt cctcatcagg
2221  ctgctaaggg acctcattga taagcagaca tggacagacg agggctcagt ctcagagcga
2281  atgctgcgga gtcaactact actcctcgcc tgtgtgcaca actatcagcc gtgcgtacag
2341  agggcagaag gctatttcag aaagtggaag gaatccaatg gaaacttgag cctgcctgtc
2401  gacgtgacct tggcagtgtt tgctgtgggg gcccagagca cagaaggctg ggatttttctt
2461  tatagtaaat atcagttttc tttgtccagt actgagaaaa gccaaattga atttgccctc
2521  tgcagaaccc aaaataagga aaagcttcaa tggctactag atgaaagctt taagggagat
2581  aaaataaaaa ctcaggagtt ccacaaaatt cttacactca ttggcaggaa cccagtagga
2641  tacccactgg cctggcaatt tctgaggaaa aactggaaca aacttgtaca aaagtttgaa
2701  cttggctcat cttccatagc ccacatggta atgggtacaa caatcaatt ctccacaaga
2761  acacggcttg aagaggtaaa aggattcttc agctcttttga aagaaaatgg ttctcagctc
2821  cgttgtgtcc aacagacaat tgaaaccatt gaagaaaaca tcggttggat ggataagaat
2881  tttgataaaa tcagagtgtg gctgcaaagt gaaaagcttg aacgtatgta aaaattcctc
2941  ccttgccagg ttcctgttat ctctaatcac caacattttg ttgagtgtat tttcaaacta
3001  gagatggctg ttttggctcc aactggagat actttttttcc cttcaactca ttttttttgact
3061  atccctgtga aaagaatagc tgttagtttt tcatgaatgg ctatcgcta ccatgtgttt
3121  tgttcatcac aggtgttgcc ctgcaacgta aacccaagtg ttgggttccc tgccacagaa
3181  gaataaagta ccttattctt ctcattttat agtttatgct taagcacccg tgtccaaaac
3241  cctgtacccc atgtttatca ttcataaact gtttcatcag tctcctcgaa agactctgaa
3301  tagtcgacta ctgaacaatg aacacctgga tctgagacta agccggacga tgactgggtt
3361  aaagctctcc cggctcaccc ctccagaccc gctgcccatc cctcttcctt gctccatgcc
3421  caggggctga cttgtaaagg ccaagtcatc aagcttttctt gcccttttgga tgttggtcag
3481  tggggagccg gagagctgga gctggggtcg gaggaggtag taggtggagg tgttcttccc
3541  tgattccctt gcgggatgcc tcggctggc ctcccctgag gtcttagct ccgagagggg
3601  accctctttt ccacacagcc ttctccacct ctggatttg gtaactgtc cctcctcatc
3661  ccttcaggat tagtggcctc agtgggagtc tggcttttac tagtcctggc ggacttgtgg
```

TABLE 1-continued

```
3721  tttctacata atgtgctcgc acttttgcaa aaaatctttt tatagaaccc tcctcagata
3781  attctgagtg agtgtcatct atttccctga ctggtacagt atctcttctg aaaaagcaga
3841  gtgcattcaa gtctgtagga aaacccttttt cttagggagg tgatttttttt tctctctctg
3901  cttcttatttt ggcctacttt acaatttcta actaactagt tattggcatt tactgacagt
3961  aaattattgc agtcaccaat aaatgatagt acattgtgaa acaaaatatt tgctcatatt
4021  agcaaatagg acattctttg gctttgaagt ctttctttct tttgtgaaga cttcacacac
4081  ggttgcttca gcacacagtt gctgctcagg ttttatgtat agatgataat aatagaaagc
4141  acagtttact aacatggtaa accaacggag ttcaagtcaa gtcagttaat accctaagaa
4201  ttagatttta tttcttattc tgaaaacttg ctacacaggg acttatctaa cccatagtgt
4261  gctctgttgc tgacttgatt caagttgcag cgtgttttgc gctgactcta aggtgcggaa
4321  atcctcacac ctggcaaagg agaattcaaa ctgacttttt tgaatataag gcaaaaactt
4381  caagataagg gaatatgatt gatgattggt acgaaaaatg tcaaaatgtg ttcccctaat
4441  acacgacaaa atagagtgac ttctggacat aaatctgcca tttattaaac cattcactac
4501  aacaaataaa taggtataaa agtggaattg gatttttttat acttatttgt tgtagtgaat
4561  ggtttaataa aaatagaaat cactggtaat ttccacccca aactaaacta tttcccttct
4621  tttaaaaaaa tacacaacca agatttttaat gtaaatatt ttgctttaat tgtattttat
4681  gccttgatta atgaaacatg gaaatattga tttttcagttt tggtcacctg aggaacctat
4741  ctttgtttgc ttttggaaaa gcccatttttc taaacagata caatattgcc acaacaatgt
4801  gcagaaacct ttttgataat aaaaaattgt tctttgcctc taaaaaaaaa aaaaaaaaa
4861  aaaaaaaa
```

SEQ ID NO: 47 Mouse ERAP1 cDNA Sequence (NM_030711.4, CDS region from position 76-2868)

```
   1  cagactggcg gctgtgatga aggtaatttg agcaagaaga tagtgtctct gctcctcaaa
  61  tagccacttg caagcatgcc ctctcttctt ccctagtat tgacatttt atctgtgtca
 121  tctccttctt ggtgtcagaa cagtgatata gaatctctaa aagctagtaa tggagactca
 181  ttcccttgga ataatatgcg acttcctgag tatatgaccc cgattcatta tgatctcatg
 241  atccatgcaa acctcagcac tctgactttc tggggaaaaa cagaagtaga aatcatagct
 301  agccggccca ccagcaccat tattatgcat agtcaccacc tgcaaatatc taaggccacc
 361  ctcagaagag gagctggaga gatgctgtct gaagaaccac tgaaggtcct ggaatatcct
 421  gctcatgagc aagttgcact gctggctgcc cagccgcttc ttgctgggtc cctgtacaca
 481  gttatcatcg actatgctgc caacctgtct gagagtttcc atggattcta taagagcacc
 541  tacagaacac aggaaggtga atgagaata cttgcagcaa cacagtttga acccacagct
 601  gctagaatgg cttttccctg ctttgatgaa cctgccctca aggcaagttt ttccatcaag
 661  ataaagaggg atccaaggca cctggccatc tccaacatgc ccctggtgaa atctgtgaat
 721  gttgctgaag gactcataga agaccatttt gacatcactg tgaagatgag tacctaccta
 781  gtggccttca tcatttctga ttttaagtct gtgagcaaga tgactaagag tggagtcaag
 841  gtttctgtgt atgctgtgcc agacaagata aatcaagccg attatgctct ggatgctgca
 901  gtgactcttc tagagtttta tgaggattat ttcaacattc catatccttt acccaagcaa
 961  gatcttgctg caatcccaga ctttcagtct ggtgctatgg aaaactgggg actgaccaca
1021  tacagagagt cctctctgtt atacgataaa gaaagtgtctt ctgcatctag taagcttggc
1081  atcacaatga ttgtgtccca tgaactggct caccagtggt tcgggaacct ggtcaccatg
```

TABLE 1-continued

```
1141   gaatggtgga atgacctttg gctcaatgaa ggatttgcca aatttatgga gtttgtgtct
1201   gtcactgtga cccatcctga actaaaagtt gaagactatt tctttggcaa gtgttttaat
1261   gcaatggaag ttgatgcatt aaactcctct caccctgtat ccacacctgt ggagaatcct
1321   gcgcagattc gggagatgtt tgatgatgtt tcttatgaaa agggagcttg tattctgaat
1381   atgctaagag attatctgag tgcagataca tttaaaagag gaattgtaca gtatctccaa
1441   aagtatagtt ataaaaacac aaaaaacgag gacctgtgga atagcatgat gcatatttgc
1501   cctacagatg gcacacaaac aatggatggc ttctgctcta gaagccaaca ctcatcatca
1561   acctcacact ggcgtcagga ggttgtagat gtaaagacca tgatgaacac atggacactg
1621   cagaagggct ttcctctgat aaccatcact gtgagtgggc ggaatgtgca catgaagcaa
1681   gaacactaca tgaagggttc agaacgcttc ccagagactg gtatttgtg gcatgttcca
1741   ctgacattca ttaccagcaa atcagactca gtccagagat ttttgctgaa gacaaagaca
1801   gatgtgctca tcctcccaga agcagtgcag tggatcaaat ttaacgtggg aatgaatggc
1861   tattacattg tgcattacgc ggatgatgga tgggcttctc tgagtggcct tttaaaagaa
1921   gcgcacacaa caatcagcag taatgatcgg gcaagtctca tcaacaatgc atttcagctg
1981   gtcagcattg aaaagttatc aatagaaaaa gccctggatt taaccctgta cttgaaaaat
2041   gaaactgaaa ttatgcccat attccaagct ttgaatgaac tcatacctat gtataagtta
2101   atggagaaaa gagatatgat tgaggtggaa actcaattta aggacttcct tctcaagttg
2161   ctgaaggacc ttattgataa gcagacttgg acagatgaag gctctgtctc agagaggatg
2221   ctcaggagcc agctcctcct cctcgcatgt gtgcgcaatt atcagccctg tgtgcagagg
2281   gcagagcgct atttcagaga gtggaagtca tctaatggaa acatgagcat ccctattgat
2341   gtgaccttgg ctgtgtttgc tgtcggggcc caaaacacag aaggctggga ttttctttat
2401   agtaaatatc agtcttcttt gtctagtact gagaaaagcc aaattgaatt ttccctctgt
2461   acaagcaaag atccagaaaa acttcagtgg cttctagatc aaagttttaa gggagagata
2521   ataaaaactc aggaatttcc acatattctc acactcattg gcagaaaccc agtgggttat
2581   ccattggcct ggaagtttct gagggaaaat tggaataagc ttgtacagaa atttgaactt
2641   ggctcatcgt ccatagctca catggtaatg ggaacaacag accagttttc caccagagca
2701   cgtcttgaag aggtaaaagg attcttcagt tccttgaaag aaaacggttc tcagctccgt
2761   tgtgttcaac aaaccattga gaccattgaa gaaaacatac gatggatgga taagaatttt
2821   gataaaataa gactgtggct gcaaaaagaa aagccagagt tgctgtgaca atatgtttct
2881   tgccaagttc cagaatttat gatgagcaaa attttgttca atttgagtat ttttaaacta
2941   aagatagttg ttttggctac tactgaagat atttctttat ttcatttcac ttgattatgt
3001   ctgagaaaag cttcaatgac tgtgattgac aggtttaaac ccaagtgccc agctccttgc
3061   cacagaaaaa cccaggggc ttcttctcag tttatacttc agcttctgtg tcggccattc
3121   atcagtattt ttgtaagact gaatagtgag gcataactgt gcagtgaatg cttggctcct
3181   tagccatgct gggaagtggc tgtgcagcag ccctcctgtt gacctctctg gctctacagt
3241   cctgcagtct ctcttcctgg gttcacttat gggtgctgcc ttgcaggatc cacttaatca
3301   gacactttg ccctctggat tttgttaata gtgtttggta gttgttatcc atgagggatt
3361   gcatagaggt gtttatttc ttgtacttgc ctctggctgg ctttcaacca ccgtaagtct
3421   tactcctaag aggtggcctt tcccccccc ccccccccgc actctgataa ctacttcctt
3481   ttcatccttt ggggcatggg gcaacagtgg aaacctgctg ataccagtca tggtagtact
```

TABLE 1-continued

```
3541    tgtcattttc actgaaccta cgtgcacatt tgtttttaaa aatattgtat atctataacc 3601    ctcgttggat aagtcaaata tgagagccac ttactttctt tggaaggtta ttttaaaaa 3661    tgcagagtgc attcagatct gtatcagaaa tatctcgttt taagatatac ttgtgagtca 3721    ctgatcccct aagtagggag tagggttgta aattcctaaa taactcataa tagcacttac 3781    tgaaaataaa tcattgagga ctcactaaca aaggacaata ttaataatat gtttatatta 3841    gtataaggaa agattcttta aatcttaaaa agattttttt gatgtatggc ataaatgata 3901    ggaaaaatat caacatatgg tgctgtaata tactatgaaa taaagcgatt ttaggggttc 3961    aattatattt tcactggcct accaaaatac ttgagattaa atgaggaaag attt SEQ ID NO: 48 Mouse ERAP1 Amino Acid Sequence (NP_109636.1)
    1   mpsllplvlt flsysspswc qnsdieslka sngdsfpwnn mrlpeymtpi hydlmihanl 61   stltfwgkte veiiasrpts tiimhshhlq iskatlrrga gemlseeplk vleypaheqv 121   allaaqplla gslytviidy aanlsesfhg fykstyrtqe gemrilaatq feptaarmaf 181   pcfdepalka sfsikikrdp rhlaisnmpl vksvnvaegl iedhfditvk mstylvafii 241   sdfksvskmt ksgvkvsvya vpdkinqady aldaavtlle fyedyfnipy plpkqdlaai 301   pdfqsgamen wglttyress llydkekssa ssklgitmiv shelahqwfg nlvtmewwnd 361   lwlnegfakf mefvsvtvth pelkvedyff gkcfnamevd alnsshpvst pvenpaqire 421   mfddvsyekg acilnmlrdy lsadtfkrgi vqylqkysyk ntknedlwns mmhicptdgt 481   qtmdgfcsrs qhssstshwr qevvdvktmm ntwtlqkgfp lititvsgrn vhmkqehymk 541   gserfpetgy lwhvpltfit sksdsvqrfl lktktdvlil peavqwikfn vgmngyyivh 601   yaddgwasls gllkeahtti ssndraslin nafqlvsiek lsiekaldlt lylkneteim 661   pifqalneli pmyklmekrd mievetqfkd fllkllkdli dkqtwtdegs vsermlrsql 721   lllacvrnyq pcvqraeryf rewkssngnm sipidvtlav favgaqnteg wdflyskyqs 781   slssteksqi efslctskdp eklqwlldqs fkgeiiktqe fphiltligr npvgyplawk 841   flrenwnklv qkfelgsssi ahmvmgttdq fstrarleev kgffsslken gsqlrcvqqt 901   ietieenirw mdknfdkirl wlqkekpell
```

* Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof Such nucleic acid molecules can have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

II. Subjects

In one embodiment, the subject for whom predicted likelihood of efficacy of an inhibitor of one or more biomarkers listed in Table 1, such as one or more regulators of antigen processing and presentation as described herein (e.g., HLA-E, Pdia3, Calr, Tap1, Tap2, Tapbp, Erap1, etc.), and an immunotherapy combination treatment is determined, is a mammal (e.g., mouse, rat, primate, non-human mammal, domestic animal, such as a dog, cat, cow, horse, and the like), and is preferably a human. In another embodiment, the subject is an animal model of cancer. For example, the animal model can be an orthotopic xenograft animal model of a human-derived cancer.

In another embodiment of the methods of the present invention, the subject has not undergone treatment, such as chemotherapy, radiation therapy, targeted therapy, and/or immunotherapies. In still another embodiment, the subject has undergone treatment, such as chemotherapy, radiation therapy, targeted therapy, and/or immunotherapies.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to inhibitor(s) of one or more biomarkers listed in Table 1, such as one or more regulators of antigen processing and presentation as described herein and immunotherapy combination treatment of many different cancers in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to an inhibitor of one or more biomarkers listed in Table 1, such as one or more regulators of antigen processing and presentation as described herein (e.g., HLA-E, Pdia3, Calr, Tap1, Tap2, Tapbp, Erap1, etc.), and an immunotherapy combination treatment, and/or evaluate a response to an inhibitor of one or more biomarkers listed in Table 1, such as one or more regulators of antigen processing and presentation as described herein, and an immunotherapy combination treatment with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more inhibitors of one or more biomarkers listed in Table 1, such as one or more regulators of antigen processing and presentation as described herein, and immunotherapy combination treatment alone or in combination with other anti-cancer agents, such as with immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $1/100$ or $1/1000$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. USA* 89:7811-7815; Delgrave et al., 1993, *Protein Engineering* 6(3):327-331).

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In some embodiments, the immunotherapy utilizes an inhibitor of at least one immune checkpoint, such as an antibody binds substantially specifically to an immune checkpoint, such as PD-1, and inhibits or blocks its immunoinhibitory function, such as by interrupting its interaction with a binding partner of the immune checkpoint, such as PD-L1 and/or PD-L2 binding partners of PD-1. In one embodiment, an antibody, especially an intrbody, binds substantially specifically to one or more biomarkers listed in Table 1, such as one or more regulators of antigen processing and presentation as described herein (e.g., HLA-E, Pdia3, Calr, Tap1, Tap2, Tapbp, Erap1, etc.) and inhibits or blocks its biological function, such as by interrupting its interaction with a substrate like STAT or JAK proteins. In another embodiment, an antibody, especially an intrbody, binds substantially specifically to the binding partner(s) of one or more biomarkers listed in Table 1, such as one or more proteins modulating antigen processing and presentation (e.g., HLA-E, Pdia3, Calr, Tap1, Tap2, Tapbp, Erap1, etc.), such as substrates of such one or more biomarkers described herein, and inhibits or blocks its biological function, such as by interrupting its interaction to one or more biomarkers listed in Table 1.

For example, a polypeptide immunogen typically is used to prepare antibodies by immunizing a suitable subject (e.g., rabbit, goat, mouse or other mammal) with the immunogen. A preferred animal is a mouse deficient in the desired target antigen. For example, a PD-1 knockout mouse if the desired antibody is an anti-PD-1 antibody, may be used. This results in a wider spectrum of antibody recognition possibilities as antibodies reactive to common mouse and human epitopes are not removed by tolerance mechanisms. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically. In some embodiments, the immunization is performed in a cell or animal host that has a knockout of a target antigen of interest (e.g., does not produce the antigen prior to immunization).

Any of the many well-known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Since it is well-known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the antibodies described herein and well-known in the art. Similarly, the antibodies can further comprise the CDR2s of variable regions of said antibodies. The antibodies can further comprise the CDR1s of variable regions of said antibodies. In other embodiments, the antibodies can comprise any combinations of the CDRs.

The CDR1, 2, and/or 3 regions of the engineered antibodies described above can comprise the exact amino acid sequence(s) as those of variable regions of the present invention described herein. However, the ordinarily skilled artisan will appreciate that some deviation from the exact CDR sequences may be possible while still retaining the ability of the antibody, especially an introbody, to bind a desired target, such as one or more biomarkers listed in Table 1, such as one or more regulators of antigen processing and presentation as described herein (e.g., HLA-E, Pdia3, Calr, Tap1, Tap2, Tapbp, Erap1, etc.) and/or a binding partner thereof, either alone or in combination with an immunotherapy, such as the one or more biomarkers, the binding partners/substrates of such biomarkers, or an immunotherapy effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention described herein or otherwise publicly available.

For example, the structural features of non-human or human antibodies (e.g., a rat anti-mouse/anti-human antibody) can be used to create structurally related human antibodies, especially introbodies, that retain at least one functional property of the antibodies of the present invention, such as binding to one or more biomarkers listed in Table 1, such as one or more regulators of antigen processing and presentation as described herein, the binding partners/substrates of such one or more biomarkers, and/or an immune checkpoint. Another functional property includes inhibiting binding of the original known, non-human or human antibodies in a competition ELISA assay.

Antibodies, immunoglobulins, and polypeptides of the invention can be used in an isolated (e.g., purified) form or contained in a vector, such as a membrane or lipid vesicle (e.g. a liposome). Moreover, amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Similarly, modifications and changes may be made in the structure of the antibodies described herein, and in the DNA sequences encoding them, and still obtain a functional molecule that encodes an antibody and polypeptide with desirable characteristics. For example, antibody glycosylation patterns can be modulated to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies, in addition to therapeutic utility, can be useful for diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}I$, $^{131}I$, $^{135}S$, or $^{3}H$.

[0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, Pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

Techniques for modulating antibodies, such as humanization, conjugation, recombinant techniques, and the like are well-known in the art.

In another aspect of this invention, peptides or peptide mimetics can be used to antagonize the activity of one or more biomarkers of the invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences described herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides described herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH$_2$S—, —CH2-CH2-, —CH=CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci*. pp. 463-468 (general review); Hudson, D. et al. (1979) *Int. J. Pept. Prot. Res*. 14:177-185 (—CH2NH—, CH2CH2-); Spatola, A. F. et al. (1986) *Life Sci*. 38:1243-1249 (—CH2-S); Hann, M. M. (1982) *J. Chem. Soc. Perkin Trans. I*. 307-314 (—CH—CH—, cis and trans); Almquist, R. G. et al. (190) *J. Med. Chem*. 23:1392-1398 (—COCH2-); Jennings-White, C. et al. (1982) *Tetrahedron Lett*. 23:2533 (—COCH2-); Szelke, M. et al. European Appln. EP 45665 (1982) CA: 97:39405 (1982)(—CH(OH)CH2-); Holladay, M. W. et al. (1983) *Tetrahedron Lett*. (1983) 24:4401-4404 (—C(OH)CH2-); and Hruby, V. J. (1982) *Life Sci*. (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des*. 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem*. 37:2678; Cho et al. (1993) *Science* 261:1303; Carrell et al. (1994) *Angew. Chem. Int. Ed. Engl*. 33:2059; Carell et al. (1994) *Angew. Chem. Int. Ed. Engl*. 33:2061; and in Gallop et al. (1994) *J. Med. Chem*. 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol*. 222:301-310); (Ladner supra.). Compounds can be screened in cell based or non-cell based assays. Compounds can be screened in pools (e.g. multiple compounds in each testing sample) or as individual compounds.

Chimeric or fusion proteins can be prepared for the inhibitor(s) of one or more biomarkers listed in Table 1, such as one or more regulators of antigen processing and presentation as described herein (e.g., HLA-E, Pdia3, Calr, Tap1, Tap2, Tapbp, Erap1, etc.) and/or agents for the immunotherapies described herein, such as inhibitors to the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cy4 domain (e.g., the hinge, CH2 and CH3 regions of human IgCγ 1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002) *Mol. Cell* 9:1327-1333; Tuschl (2002), *Nat. Biotechnol.* 20:446-448; Brummelkamp et al. (2002) *Science* 296:550-553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner (1994) *Nature* 372: 333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) *Proc. Natl. Acad. Sci. U.S.A.* 86:6553-6556; Lemaitre et al. (1987) *Proc. Natl. Acad. Sci. U.S.A.* 84:648-652; PCT Publication No. WO88/09810) or the blood-brain barrier (see, e.g., PCT Publication No. WO89/10134), hybridization-triggered cleavage agents. (See, e.g., Krol et al. (1988) *BioTech.* 6:958-976) or intercalating agents. (See, e.g., Zon (1988) *Pharm. Res.* 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxyti-ethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells, or piwiRNAs. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) *Nature* 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) *RNA* 8:842; Xia et al. (2002) *Nat. Biotechnol.* 20:1006; and Brummelkamp et al. (2002) *Science* 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) *Science* 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug et al. (1984) Science 224:574-578; Zaug et al. (1986) *Science* 231:470-475; Zaug et al. (1986) *Nature* 324:429-433; WO 88/04300; and Been et al. (1986) *Cell* 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein.

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of inhibitor(s) of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) Meth. Enzymol 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *Proc. Natl. Acad. Sci. U.S.A.* 86: 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}$P and $^{35}$S. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to inhibitor(s) of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I) carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify the one or more biomarkers listed in Table 1, such as one or more regulators of antigen processing and presentation as described herein (e.g., HLA-E, Pdia3, Calr, Tap1, Tap2, Tapbp, Erap1, etc.), or other biomarkers used in the immunotherapies described herein that are overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397 and Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatment is predicted according to biomarker amount and/or activity associated with a cancer in a subject according to the methods described herein. In one embodiment, such inhibitor and immunotherapy combination treatments (e.g., one or more inhibitor and immunotherapy combination treatment in combination with one or more additional anti-cancer therapies, such as another immune checkpoint inhibitor) can be administered, particularly if a subject has first been indicated as being a likely responder to inhibitor and immunotherapy combination treatment. In another embodiment, such inhibitor and immunotherapy combination treatment can be avoided once a subject is indicated as not being a likely responder to inhibitor and immunotherapy combination treatment and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy. In addition, any representative embodiment of an agent to modulate a particular target can be adapted to any other target described herein by the ordinarily skilled artisn (e.g., direct and indirect PD-1 inhibitors described herein can be applied to other immune checkpoint inhibitors and/or one or more biomarkers listed in Table 1, such as one or more regulators of antigen processing and presentation as described herein, such as monospecific antibodies, bispecific antibodies, non-activating forms, small molecules, peptides, interfering nucleic acids, and the like).

The term "targeted therapy" refers to administration of agents that selectively interact with a chosen biomolecule to thereby treat cancer. One example includes immunotherapies such as immune checkpoint inhibitors, which are well-known in the art. For example, anti-PD-1 pathway agents, such as therapeutic monoclonal blocking antibodies, which are well-known in the art and described above, can be used to target tumor microenvironments and cells expressing unwanted components of the PD-1 pathway, such as PD-1, PD-L1, and/or PD-L2.

For example, the term "PD-1 pathway" refers to the PD-1 receptor and its ligands, PD-L1 and PD-L2. "PD-1 pathway inhibitors" block or otherwise reduce the interaction between PD-1 and one or both of its ligands such that the immunoinhibitory signaling otherwise generated by the interaction is blocked or otherwise reduced. Anti-immune checkpoint inhibitors can be direct or indirect. Direct anti-immune checkpoint inhibitors block or otherwise reduce the interaction between an immune checkpoint and at least one of its ligands. For example, PD-1 inhibitors can block PD-1 binding with one or both of its ligands. Direct PD-1 combination inhibitors are well-known in the art, especially since the natural binding partners of PD-1 (e.g., PD-L1 and PD-L2), PD-L1 (e.g., PD-1 and B7-1), and PD-L2 (e.g., PD-1 and RGMb) are known.

For example, agents which directly block the interaction between PD-1 and PD-L1, PD-1 and PD-L2, PD-1 and both PD-L1 and PD-L2, such as a bispecific antibody, can prevent inhibitory signaling and upregulate an immune response (i.e., as a PD-1 pathway inhibitor). Alternatively, agents that indirectly block the interaction between PD-1 and one or both of its ligands can prevent inhibitory signaling and upregulate an immune response. For example, B7-1 or a soluble form thereof, by binding to a PD-L1 polypeptide indirectly reduces the effective concentration of PD-L1 polypeptide available to bind to PD-1. Exemplary agents include monospecific or bispecific blocking antibodies against PD-1, PD-L1, and/or PD-L2 that block the interaction between the receptor and ligand(s); a non-activating form of PD-1, PD-L1, and/or PD-L2 (e.g., a dominant negative or soluble polypeptide), small molecules or peptides that block the interaction between PD-1, PD-L1, and/or PD-L2; fusion proteins (e.g. the extracellular portion of PD-1, PD-L1, and/or PD-L2, fused to the Fc portion of an antibody or immunoglobulin) that bind to PD-1, PD-L1, and/or PD-L2 and inhibit the interaction between the receptor and ligand(s); a non-activating form of a natural PD-1, PD-L2, and/or PD-L2 ligand, and a soluble form of a natural PD-1, PD-L2, and/or PD-L2 ligand.

Indirect anti-immune checkpoint inhibitors block or otherwise reduce the immunoinhibitory signaling generated by the interaction between the immune checkpoint and at least one of its ligands. For example, an inhibitor can block the interaction between PD-1 and one or both of its ligands without necessarily directly blocking the interaction between PD-1 and one or both of its ligands. For example, indirect inhibitors include intrabodies that bind the intracellular portion of PD-1 and/or PD-L1 required to signal to block or otherwise reduce the immunoinhibitory signaling. Similarly, nucleic acids that reduce the expression of PD-1, PD-L1, and/or PD-L2 can indirectly inhibit the interaction between PD-1 and one or both of its ligands by removing the availability of components for interaction. Such nucleic acid molecules can block PD-L1, PD-L2, and/or PD-L2 transcription or translation.

Similarly, agents which directly block the interaction between one or more biomarkers listed in Table 1, such as one or more regulators of antigen processing and presentation as described herein (e.g., HLA-E, Pdia3, Calr, Tap1, Tap2, Tapbp, Erap1, etc.), and the binding partners and/or substrates of such one or more biomarkers, and the like, can remove the inhibition to such one or more biomarkers-regulated signaling and its downstream immune responses, such as increasing sensitivity to interferon signaling. Alternatively, agents that indirectly block the interaction between such one or more biomarkers and its binding partners/substrates can remove the inhibition to such one or more biomarkers-regulated signaling and its downstream immune responses. For example, a truncated or dominant negative form of such one or more biomarkers, such as biomarker fragments without functional activity, by binding to a substrate of such one or more biomarkers and indirectly reducing the effective concentration of such substrate available to bind to the one or more biomarkers in cell. Exemplary agents include monospecific or bispecific blocking antibodies, especially intrabodies, against the one or more biomarkers and/or their substrate(s) that block the interaction between the one or more biomarkers and their substrate(s); a non-active form of such one or more biomarkers and/or their substrate(s) (e.g., a dominant negative polypeptide), small molecules or peptides that block the interaction between such one or more biomarkers and their substrate(s) or the activity of such one or more biomarkers; and a non-activating form of a natural biomarker and/or its substrate(s).

Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment, immunotherapy comprises adoptive cell-based immunotherapies. Well-known adoptive cell-based immunotherapeutic modalities, including, without limitation, Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (MET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Pro1, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa.-super repressor overexpression, NFKB decoy oligodeoxynucleotide (ODN), or a derivative or analog of any thereto, are used. In yet another embodiment, immunomodulatory antibodies or protein are used. For example, antibodies that bind to CD40, Toll-like receptor (TLR), OX40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11 a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, ganteneumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, and the like.

Nutritional supplements that enhance immune responses, such as vitamin A, vitamin E, vitamin C, and the like, are well-known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used with in combination with inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), with or without immunotherapies to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well-known in the art.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antiestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter— less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatment, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to immunotherapies, such as anti-immune checkpoint therapies, are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any immunotherapy, such as anti-immune checkpoint therapy. The outcome measurement may be pathologic response to therapy given in the neoadjuvant setting. Alternatively, outcome measures, such as overall survival and disease-free survival can be monitored over a period of time for subjects following immunotherapies for whom biomarker measurement values are known. In certain embodiments, the same doses of immunotherapy agents, if any, are administered to each subject. In related embodiments, the doses administered are standard doses known in the art for those agents used in immunotherapies. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an immunotherapy can be determined using methods such as those described in the Examples section.

5. Further Uses and Methods of the Present Invention

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays and xenograft animal model assays. In one embodiment, the assays provide a method for identifying whether a cancer is likely to respond to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments, such as in a human by using a xenograft animal model assay, and/or whether an agent can inhibit the growth of or kill a cancer cell that is unlikely to respond to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments.

In one embodiment, the present invention relates to assays for screening test agents which bind to, or modulate the biological activity of, at least one biomarker described herein (e.g., in the tables, figures, examples, or otherwise in the specification). In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^3H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further pertains to novel agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker described herein in the context of a biological sample (e.g., blood, serum, cells, or tissue) to thereby determine whether an individual afflicted with a cancer is likely to respond to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments, such as in a cancer. Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

Another aspect of the present invention pertains to monitoring the influence of agents (e.g., drugs, compounds, and small nucleic acid-based molecules) on the expression or activity of a biomarker described herein. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments. In some embodiments, the present invention is useful for classifying a sample (e.g., from a subject) as associated with or at risk for responding to or not responding to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immunotherapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments), a biological sample from the subject during remission, or a biological sample from the subject during treatment for developing a cancer progressing despite inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments.

d. Prognostic Assays

The diagnostic methods described herein can furthermore be utilized to identify subjects having or at risk of developing a cancer that is likely or unlikely to be responsive to inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy combination treatments. The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The therapeutic compositions described herein, such as the combination of inhibitors of one or more biomarkers listed in Table 1, such as one or more regulators of antigen processing and presentation as described herein (e.g., HLA-E, Pdia3, Calr, Tap1, Tap2, Tapbp, Erap1, etc.), and immunotherapy, can be used in a variety of in vitro and in vivo therapeutic applications using the formulations and/or combinations described herein. In one embodiment, the therapeutic agents can be used to treat cancers determined to be responsive thereto. For example, single or multiple agents that inhibit or block both an inhibitor of one or more biomarkers listed in Table 1, such as one or more regulators of antigen processing and presentation as described herein (e.g., HLA-E, Pdia3, Calr, Tap1, Tap2, Tapbp, Erap1, etc.), and a immunotherapy can be used to treat cancers in subjects identified as likely responders thereto.

Modulatory methods of the present invention involve contacting a cell, such as an immune cell with an agent that inhibits or blocks the expression and/or activity of such one or more biomarkers and an immunotherapy, such as an immune checkpoint inhibitor (e.g., PD-1). Exemplary agents useful in such methods are described above. Such agents can be administered in vitro or ex vivo (e.g., by contacting the cell with the agent) or, alternatively, in vivo (e.g., by administering the agent to a subject). As such, the present invention provides methods useful for treating an individual afflicted with a condition that would benefit from an increased immune response, such as an infection or a cancer like colorectal cancer.

Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, or parasites), a parasitic infection, and an immunosuppressive disease.

Exemplary infectious disorders include viral skin diseases, such as Herpes or shingles, in which case such an agent can be delivered topically to the skin. In addition, systemic viral diseases, such as influenza, the common cold, and encephalitis might be alleviated by systemic administration of such agents. In one preferred embodiment, agents that upregulate the immune response described herein are useful for modulating the arginase/iNOS balance during *Trypanosoma cruzi* infection in order to facilitate a protective immune response against the parasite.

Immune responses can also be enhanced in an infected patient through an ex vivo approach, for instance, by removing immune cells from the patient, contacting immune cells in vitro with an agent described herein and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response. Such additional agents and therapies are described further below.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that preexisting tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

6. Administration of Agents

The immune modulating agents of the invention are administered to subjects in a biologically compatible form suitable for pharmaceutical administration in vivo, to enhance immune cell mediated immune responses. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

Inhibiting or blocking expression and/or activity of one or more biomarkers listed in Table 1, such as one or more regulators of antigen processing and presentation as described herein (e.g., HLA-E, Pdia3, Calr, Tap1, Tap2, Tapbp, Erap1, etc.), alone or in combination with an immunotherapy, can be accomplished by combination therapy with the modulatory agents described herein. Combination therapy describes a therapy in which such one or more biomarkers is inhibited or blocked with an immunotherapy simultaneously. This may be achieved by administration of the modulatory agent described herein with the immunotherapy simultaneously (e.g., in a combination dosage form or by simultaneous administration of single agents) or by administration of single inhibitory agent for such one or more biomarkers and the immunotherapy, according to a schedule that results in effective amounts of each modulatory agent present in the patient at the same time.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

7. Kits

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXAMPLES

Example 1: Materials and Methods for Examples 2-5 a. In Vivo CRISPR Screening in B16 Tumor Cells

A Cas9-expressing version of the B16 melanoma cell line was created and confirmed that it could edit DNA efficiently with CRISPR using sgRNAs targeting the PD-L1 gene. For screening the B16-Cas9 cell line, a library of 9,992 optimized sgRNAs was created to target 2,398 genes, selected from the GO term categories: kinase, phosphatase, cell surface, plasma membrane, antigen processing and presentation, immune system process, and chromatin remodeling. The transcript abundance of the genes in these categories were then filtered to include only those that were expressed>RPKM ($log_2$)=0.9. These genes were then ranked for expression in the B16 cell line using RNAseq to select for the top 2,398 expressed genes. The library was divided into 4 sub-pools, each containing one sgRNA per gene and 100 non-targeting control sgRNAs. The 4 sub-pools were screened individually and sgRNAs were delivered to B16-Cas9 cells via lentiviral infection at an infection rate of 30%. Transduced B16 cells were purified using a hCD19 reporter by positive magnetic selection (Miltenyi Biotech, Cambridge, Mass.) and then expanded in vitro before being implanted into animals. For each sub-pool, B16 cells were implanted into 10 $TCR\alpha^{-/-}$ mice, 10 WT mice treated with GVAX, and 10 WT mice treated with GVAX and PD-1 blockade (see below for treatment protocols). B16 cells transduced with libraries were also grown in vitro at approximately 2000× library coverage for the same time period as the animal experiment. Mice were sacrificed 12-14 days after tumor implantation tumor genomic DNA was prepared from whole tumor tissue using the Qiagen DNA Blood Midi kit (Qiagen, Hilden, Germany). PCR was used to amplify the sgRNA region and sequencing to determine sgRNA abundance was performed on an Illumina HiSeq system (Illumina, San Diego, Calif.). Significantly enriched or depleted sgRNAs from any comparison of conditions were identified using the STARS algorithm (Doench et al. (2014) *Nat. Biotechnol.* 32:1262-1267).

b. Animal Treatment and Tumor Challenges

The designs of these animal studies and procedures were approved by the Dana Farber Cancer Institute IACUC committee. Dana Farber's specific-pathogen free facility was used for the storage and care of all mice. Seven-week old wild-type female C57BL/6J mice were obtained from Jackson laboratories (Bar Harbor, Me.). A colony of B6.12952-Tcra$^{tm1Mom}$/J (Tcra) T cell-deficient mice were bred on site. Mice were aged matched to be 7-12 weeks old at the time of tumor inoculation. For screening, $2.0\times10^6$ library-transduced B16-Cas9 cells resuspended in Hanks Balanced Salt Solution (Gibco, Thermo Fisher Scientific, Waltham, Mass.) were mixed 1:1 by volume with Matrigel® (Corning, Corning, N.Y.) and subcutaneously injected into the right flank on day 0. Mice were vaccinated with $1.0\times10^6$ GM-CSF-secreting B16 (GVAX) cells that had been irradiated with 3500 Gy on days 1 and 4 to elicit an anti-tumor immune response. Subsequently, mice were treated with 100 µg of rat monoclonal anti-PD1 antibody (clone: 29F.1A12) on days 9 and 12 via intraperitoneal injection. For validation assays, $1.0\times10^6$ tumor cells were subcutaneously injected into the right flank without matrigel. Tumors were measured every 3 days beginning on day 6 after challenge until time of death. Measurements were taken manually by collecting the longest dimension (length) and the longest perpendicular dimension (width). Tumor volume was estimated with the formula: $(L\times W^2)/2$. $CO_2$ inhalation was used to euthanize mice on the day of sacrifice.

c. Creation of CRISPR Edited Tumor Cell Lines

Transient transfection of Cas9-sgRNA plasmid (pX459, Addgene, Cambridge, Mass.) was used to edit B16 and Braf/Pten melanoma cell lines. pX459 was digested with the enzyme BpiI (Thermo Fisher Scientific) as per the manufacturer's instructions and sgRNA oligos were cloned in using standard molecular cloning. For B16 cells, $5\times10^5$ cells were plated in a well of a 6-well plate and were transfected the following day using 2 µg of pX459 plasmid DNA and Turbofect™ (3:1 ratio, Thermo Fisher Scientific). Twenty-four hours after transfection, transfectants were selected in puromycin (6 µg/mL, Thermo Fisher Scientific). For Braf/Pten melanoma cells, $5\times10^5$ cells were plated in a well of a 6-well plate and were transfected the following day using 4 µg of pX459 plasmid DNA and Turbofect™ (3:1 ratio). After selection, cells were grown for 14 days in vitro before being implanted into mice.

d. In Vivo Competition Assays

B16 cells were engineered to express GFP or TdTomato by lentiviral transduction to differentiate populations. Cas9-target sgRNA-transfected cells and Cas9-control sgRNA-transfected cells were mixed and then grown for at least two passages in vitro before implantation into mice. Mixes were analyzed by flow cytometry on the day of tumor inoculation. Mice were euthanized 15-21 days after tumor inoculation for tumor harvest. Tumors were macerated on ice and incubated in collagenase P (2 mg/mL, Sigma, St. Louis, Mo.) and DNase I (50 µg/mL, Sigma) supplemented DMEM for 10 minutes at 37° C. After incubation, tumor cells were passed through 70 µm filters to remove undigested tumor. Tumor cells were washed with ice-cold MACS media and stained with Near-IR LIVE/DEAD® (1:1000, BD Biosciences, Franklin Lakes, N.J.) for 10 minutes on ice. Tumor cells were then washed and resuspended in ice-cold PBS with 2% FBS. An Accuri™ C6 flow cytometry system (BD Biosiences) was used to analyze final GFP/TdTomato tumor cell ratios.

e. In Vitro Cytokine Stimulations

Differentially labeled B16 cells were plated in 12-well plates in DMEM+10% FBS containing the indicated combinations of cytokines: TNFα (10 ng/mL, PeproTech, Rocky Hill, N.J.), IFNγ (100 ng/mL, Cell Signaling Technology, Danvers, Mass.), and IFNβ (1000 U/mL, Pb1 Assay Science, Piscataway Township, N.J.). Cells were passaged every 3 or 4 days. On day 14, tumor cells were analyzed by flow cytometry for changes in the ratio of $GFP^+/TdTomato^+$ cells.

f. In Vitro T Cell Killing Assays

Differentially labeled, ovalbumin-expressing B16 cells were plated onto 12 well plates in DMEM+10% FBS containing IFNβ at 50 U/mL. The following day, media was removed and RPMI+10% FBS was added containing pre-activated OT-1 T cells at the indicated ratio. Tumor cells were passaged and fresh OT-1 T cells were added every 2 days until day 6. On day 6, tumor cells were analyzed by flow cytometry for changes in the ratio of GFP$^+$/TdTomato$^+$ cells.

g. Analysis Tumor-Infiltrating Lymphocytes by Flow Cytometry

Mice were injected subcutaneously (s.c.) with $1.0 \times 10^6$ CRISPR/Cas9 modified B16 cells and treated with GVAX+ anti-PD-1 mAb as described above. Tumors were harvested on day 12-13, weighed, mechanically diced, incubated with collagenase P (2 mg/mL, Sigma Aldrich) and DNAse I (50 µg/mL, Sigma Aldrich) for 10 minutes, and pipetted into a single-cell suspension. After filtering through a 70 µm filter, cells were blocked with anti-mouse CD16/32 antibody (BioLegend, San Diego, Calif.) and stained with indicated antibodies for 30 minutes on ice. Dead cells were excluded using Aqua Live/Dead® (1:1000, ThermoFisher Scientific) added concurrently with surface antibodies. After washing, cells were fixed with Foxp3/transcription factor staining buffer set (eBiosciences, San Diego, Calif.) as per manufacturer's instructions, blocked with mouse and rat serum, then stained with intracellular antibodies. AccuCount Fluorescent particles (Spherotech, Lake Forest, Ill.) were added for cell quantification prior to analysis on an LSR Fortessa™ cell analyzer (BD Biosciences) using single-color compensation controls and fluorescence-minus-one thresholds to set gate margins. Comparisons between groups performed using Student's t test.

h. Flow Cytometry Analysis of B16 Tumor Cells

B16 cells were trypsinized and washed in PBS+2% FBS, stained with antibodies for cell surface proteins as per the manufacturer's instructions and then analyzed on an Accuri™ C6 flow cytometry system (BD Biosciences).

i. RNAseq Analysis of Tumor Cells

Null or control sgRNA-transfected B16 cells were stimulated with IFNγ (100 ng/mL, Cell Signaling Technology), TNFα (10 ng/mL, Peprotech) or both for 48 hours. RNA was extracted from cell pellets using the Qiagen RNeasy Mini kit according to manufacturer's instructions. First-strand Illumina-barcoded libraries were generated using the NEB RNA Ultra™ Directional kit according to manufacturer's instructions, including a 12-cycle PCR enrichment. Libraries were sequenced on an Illumina NextSeg™ 500 instrument using paired-end 37 bp reads. Data were trimmed for quality using the Trimmomatic pipeline with the following parameters: LEADING:15 TRAILING:15 SLIDINGWINDOW:4:15 MINLEN:16. Data were aligned to mouse reference genome mm10 using the Bowtie 2 aligning sequencing tool (available at the World Wide Web website of Johns Hopkins University). HTSeq was used to map aligned reads to genes and to generate a gene count matrix and it is available at the World Wide Web address of www-huber.embl.de/users/anders/HTSeq/doc/overview.html. Normalized counts and differential expression analysis was performed using the DESeq2 R package. The gene set enrichment analysis was performed as described previously in Subramanian et al. (2005) *Proc. Natl Acad Sci USA* 102:15545-15550. Principle Components Analysis (PCA) was performed on the normalized gene counts including all genes that passed a minimal expression filter. Signature scores for the individual samples were generated using FastProject (available at the World Wide Web address of bmcbioinformatics.biomedcentral.com/articles/10.1186/s12859-016-1176-5) and the Hallmark gene signature collection (Liberzon et al. (2015) *Cell Sys.* 1:417-425). Pearson correlation coefficients were calculated between the Hallmark gene signatures and PC1 and PC2. Selected signatures were plotted on a normalized PCA projection of the dataset.

j. Western Blotting

Whole cell lysates were prepared in lysis buffer (60 mM Tris HCl, 2% SDS, 10% glycerol, complete EDTA-free protease-inhibitor (Roche, Basel, Switzerland), and 500 U/mL benzonase nuclease (Novagen, Merck, Darmstadt, Germany)). Samples were boiled at 100° C. and clarified by centrifugation. Protein concentration was measured with a BCA protein assay kit (Pierce, Dallas, Tex.). Fifty to one hundred and fifty micrograms of protein was loaded on 4-12% Bolt® Bis-Tris Plus gels (Life Technologies, Carlsbad, Calif.) in MES buffer (Life Technologies). Protein was transferred to 0.45 µm nitrocellulose membranes (Bio-Rad, Hercules, Calif.). Membranes were blocked in Tris-buffered saline plus 0.1% Tween 20 (TBS-T) containing 5% non-fat dry milk for 1 hour at room temperature followed by overnight incubation with primary antibody at 4° C. Membranes were washed with TBS-T and incubated with HRP-conjugated secondary antibodies for 1 hour at room temperature. HRP was activated with Supersignal® West Dura Extended Duration Substrate (Pierce) and visualized with a chemiluminscent detection system using Fuji ImageQuant™ LAS4000 (GE Healthcare Life Sciences, Pittsburgh, Pa.). Blots were then analyzed using ImageJ and Adobe® Photoshop® software.

k. Immunohistochemistry

Whole B16 tumors were fixed for 24 hours in 10% neutral buffered formalin and then permeabilized in 70% ethanol overnight. Fixed tissue was then embedded into paraffin, sectioned and then mounted onto slides for staining with mouse CD8a (eBiosciences Cat. #14-0808-82). Slides were imaged on a Leica Scanscope XT and analyzed using Aperio software (Leica Biosystems, Buffalo Grove, Ill.).

l. Antibodies

For Western blotting, primary antibodies against 0-ACTIN (Abcam, Cambridge, UK, Cat. #8227), and FLAG (clone M2, Sigma Aldrich) were used. Peroxidase-conjugated secondaries against Rabbit-IgG (Cat. #111-035-046) and Mouse-IgG (Cat. #115-035-174) were purchased from Jackson Laboratories (Bar Harbor, Me.).

For flow cytometry, the following anti-mouse (m) fluorochrome-conjugated antibodies were used: H2K(b)/H2D (b) (clone 28-8-6, BioLegend), CD47 (clone miap301, BioLegend), SIINFEKL-H2K(b) (clone 25-D1.16, BioLegend), Granzyme B (clone GB11, BioLegend), TNF (clone MP6-XT22, BioLegend), IFNγ (clone XMG1.2, BioLegend), CD8α (clone 53-6.7, BioLegend), CD4 (clone RM4-5 or GK15, BioLegend), TCR-β (clone H57-597, BioLegend), PD-1 (clone RPMI-30, BioLegend), Tim-3 (clone TMR3-2.3, BioLegend), CD45 (clone 104 or 30-F11, BioLegend), Ly6C (clone HK1.4, BioLegend), I-A/I-E (clone M5/114.15.2, BioLegend), F4/80 (clone BM8, BioLegend), CD11c (clone N418, BioLegend), CD24 (clone M1/69, BioLegend), CD11b (clone M1/70, BioLegend), CD103 (clone 2E7, BioLegend), CD3ε (clone 145-2C11, BioLegend), TCRγ/δ (clone GL3, BioLegend), NK1.1 (clone PK136, BioLegend), CD44 (clone IM7, BioLegend), Ki-67 (clone B56, BD Biosciences), CD274 (clone MIH5, BD Biosciences), and Foxp3 (clone JFK-16s, eBioscience).

n. CRISPR sgRNA Sequences.

CRISPR sgRNA sequences uses are described in Table 2 below.

TABLE 2

| Gene Name/sg# | sgRNA Sequence | |
|---|---|---|
| Cd274 sgRNA 1 | GCCTGCTGTCACTTGCTACG | (SEQ ID NO: 49) |
| Cd274 sgRNA 2 | AATCAACCAGAGAATTTCCG | (SEQ ID NO: 50) |
| Cd274 sgRNA 3 | GGTCCAGCTCCCGTTCTACA | (SEQ ID NO: 51) |
| Cd274 sgRNA 4 | GTATGGCAGCAACGTCACGA | (SEQ ID NO: 52) |
| Cd47 sgRNA 1 | TATAGAGCTGAAAAACCGCA | (SEQ ID NO: 53) |
| Cd47 sgRNA 2 | CCACATTACGGACGATGCAA | (SEQ ID NO: 54) |
| Cd47 sgRNA 3 | TCTTACGAGGAGGAGAAAGG | (SEQ ID NO: 55) |
| Cd47 sgRNA 4 | GCAAGTGTAGTTTCCCACCA | (SEQ ID NO: 56) |
| control sgRNA 1 | GCGAGGTATTCGGCTCCGCG | (SEQ ID NO: 57) |
| control sgRNA 2 | GCTTTCACGGAGGTTCGACG | (SEQ ID NO: 58) |
| control sgRNA 3 | ATGTTGCAGTTCGGCTCGAT | (SEQ ID NO: 59) |
| control sgRNA 4 | ACGTGTAAGGCGAACGCCTT | (SEQ ID NO: 60) |
| control sgRNA 5 | ATTGTTCGACCGTCTACGGG | (SEQ ID NO: 61) |
| H2-T23 sgRNA 1 | TAGCCGACAATGATGAACCG | (SEQ ID NO: 62) |
| H2-T23 sgRNA 2 | AGGCCTCCTGACAATACCCG | (SEQ ID NO: 63) |
| H2-T23 sgRNA 3 | GGAACTTCAGAGTAAACCTG | (SEQ ID NO: 64) |

Examples 2-5 disclose the development of a pooled loss-of-function in vivo genetic screening approach that uses CRISPR-Cas9 genome editing to discover genes that increase sensitivity or cause resistance to immunotherapy in a mouse transplantable tumor model. About 2,400 genes expressed by tumor cells were screened in the B16 murine melanoma model to identify those that increase or decrease sensitivity to immunotherapy with tumor vaccination and PD-1 checkpoint blockade. The screen identified known immune evasion molecules PD-L1 and CD47, as tumor cells bearing sgRNAs for these targets were significantly depleted in animals treated with immunotherapy. In contrast, loss of function of any of the genes that sense or signal in response to interferon-γ (IFNγ) rendered cells resistant to immunotherapy with PD-1 checkpoint blockade and vaccination, recapitulating resistance mutations identified in melanoma patients (Zaretsky et al. (2016) N. Engl. J. Med. 375:819-829; Gao et al. (2016) Cell 167:397-404.e9). It was discovered and further validated that deletion of multiple new genes, such as those involved in antigen presentation (e.g., HLA-E/H2-T23, Pdia3, Calr, Tap2, Tap1, Erap1, Tapbp, etc.), sensitizes tumor cells to immunotherapy. These findings reveal that therapeutic strategies, such as HLA-E inhibition, that sensitize tumor cells to the effects of IFNγ are capable of increasing the efficacy of cancer immunotherapy. Moreover, this screening approach can discover new immunotherapy targets and prioritize their combination with existing immunotherapies.

Figure 2:
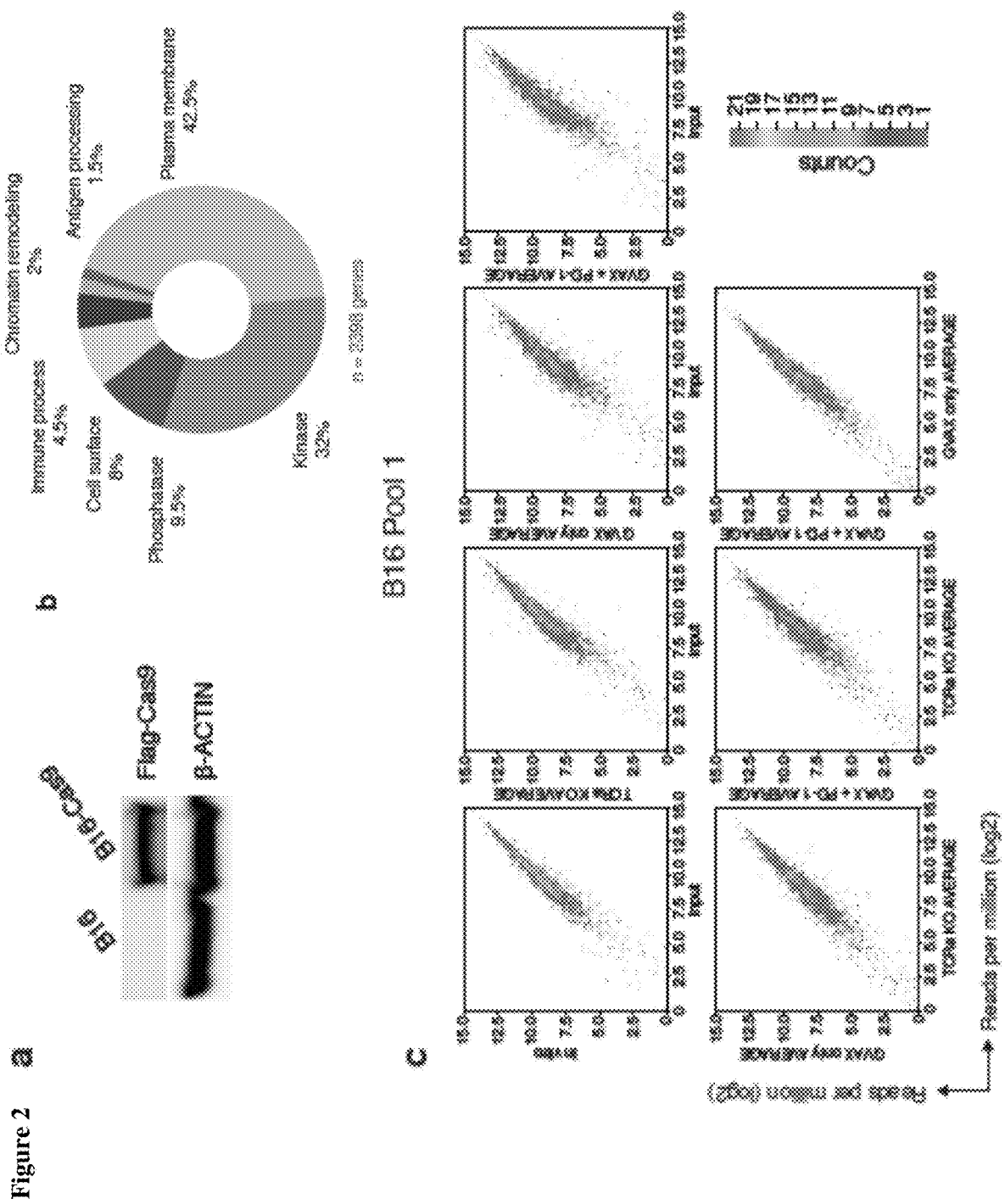
FIG. 2 includes 6 panels, identified as panels A, B, C, D, E, and F, which show the performance analysis of the screening in FIG. 1. Panel A shows Western blot of B16 cell lysate for Cas9 and β-ACTIN with or without transduction with a lentiviral vector encoding Cas9. A pie chart shows the fraction of genes targeted in the screening in each of the GO term categories indicated (Panel B). Two-dimensional histograms show the pair-wise distribution of sgRNAs abundance (averaged for each condition) (Panel C). Saturation analysis of animal replicates from the three in vivo screening conditions is shown in Panel D. Pearson correlations are calculated for the library distribution in one animal vs. any other animal, then for two animals averaged versus any other two averaged, and so on. Saturation approaches $r=0.95$. A matrix of the Pearson correlations of the library distribution from one animal compared to any other animal for B16 Pool 1 is shown (Panel E). Expression of CD47 by B16 cells transfected with either CD47-targeting (red) or control (grey) sgRNA is compared (Panel F).
Figure 2:
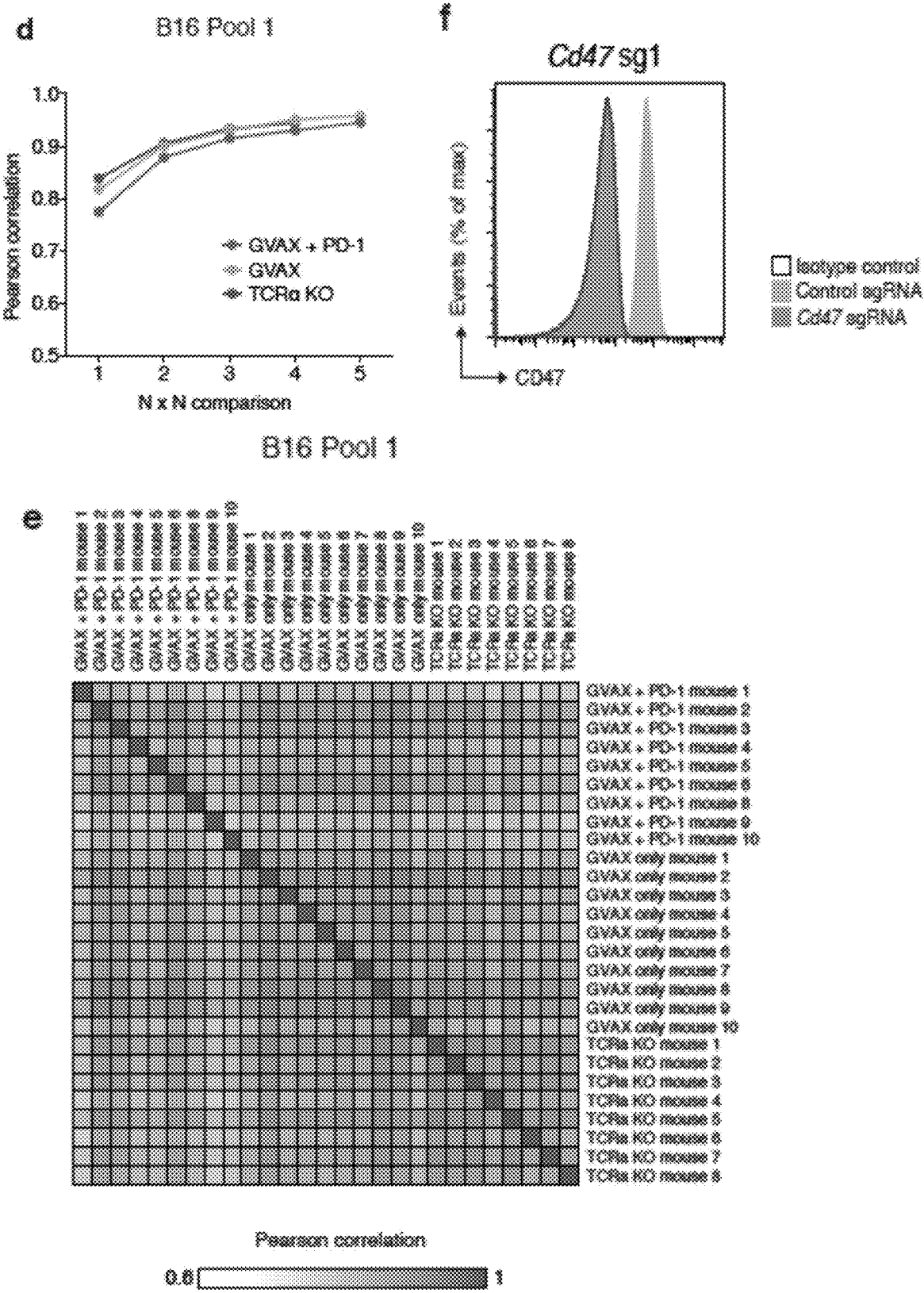

Example 2: A Pooled Loss-of-Function In Vivo Genetic Screen Recovers Known Immune Evasion Molecules Expressed by Tumors In order to systematically identify new cancer immunotherapy targets and resistance mechanisms, a pooled genetic screening approach was developed to identify genes that increase or decrease the fitness of tumor cells growing in vivo in animals treated with immunotherapy (FIG. 1A). First, a B16 melanoma cell line was engineered to express Cas9 (FIG. 2A), confirmed of efficient DNA editing using sgRNAs targeting PD-L1 (FIG. 1D, bottom). Next, a library of lentiviral vectors was created to encode 9,992 sgRNAs targeting 2,398 genes from relevant functional classes that were expressed at detectable levels in the tumor cell line (FIG. 2B). After transduction and in vitro passage to allow gene editing to take place, the tumor cells were transplanted into animals that were then treated with either a GM-CSF-secreting, irradiated tumor cell vaccine (GVAX) or GVAX plus PD-1 blockade using a monoclonal antibody for PD-1, in order to apply immune selective pressure on the tumor cells (FIG. 1B) (see Dranoff (2003) Oncogene 22:3188-3192; Dranoff et al. (1993) Proc. Natl. Acad. Sci. U.S.A. 90:3539-3543; and Duraiswamy et al. (2013) Cancer Res. 73:3591-3603; Curran & Allison (2009) Cancer Res 69:7747-7755; Curran et al. (2010) Proc. Natl. Acad. Sci. U.S.A. 107:4275-4280). In parallel, the library-transduced tumor cells were transplanted into TCRα$^{-/-}$ mice, which lack CD4$^+$ and CD8$^+$ T cells and were therefore unable to apply adaptive immune selective pressure on the tumors. This allowed to distinguish the effect of immune selective pressure on library representation from nonspecific effects on tumor cell viability. After 12-14 days, tumors were harvested (FIG. 1B), with all sgRNAs recovered from each animal with good inter-animal reproducibility (FIGS. 2C-2E).

The library representation in tumors from immunotherapy-treated wild-type (WT) animals were compared with that found in tumors growing in TCRα$^{-/-}$ mice, in which deletion of genes that result in resistance to immunotherapy would be expected to increase tumor sgRNA representation in WT animals, while deletion of genes that result in increased sensitivity of tumors to immunotherapy would decrease sgRNA representation. Analysis of sgRNAs enriched by immune selective pressure revealed those targeting genes involved in cytokine-mediating signaling and immune-system processes (FIG. 1C). sgRNAs depleted by immunotherapy included those targeting genes involved in antigen processing, necroptosis, and regulation of immune responses (FIG. 1C). These results indicate that the genetic screening approach used here identified genes expressed by tumors cells that play a role in interaction with the immune system.

Inspection of the list of genes targeted by sgRNAs depleted from tumors treated with immunotherapy revealed the known immune evasion molecule PD-L1, indicating that loss of PD-L1 increased the sensitivity of tumor cells to immune attack. sgRNAs targeting PD-L1 were not depleted from tumors in TCRα$^{-/-}$ mice relative to cells growing in vitro, presumably due to the absence of T cell-mediated selective pressure (FIG. 1D), but were significantly depleted in WT mice treated with GVAX relative to TCRα$^{-/-}$ mice (FDR=0.004). However, the depletion of PD-L1-targeting sgRNAs seen in GVAX-treated tumors was not observed in tumors treated with GVAX and anti-PD-1, indicating that loss of PD-L1 does not confer a selective disadvantage to tumors when PD-L1:PD-1 interactions are blocked (FIG. 1D).

It was also found that sgRNAs targeting CD47, which enables immune evasion by impairing engulfment of tumors cells by phagocytes (as in Liu et al. (2015) Nat. Med. 21:1209-1215; Weiskopf et al. (2016) J. Clin. Invest. 126: 2610-2620; and Tseng et al. (2013) Proc. Natl. Acad. Sci. U.S.A. 110: 11103-11108), were markedly depleted in tumors treated with either GVAX or with GVAX plus PD-1 blockade (FDR=0.005, 0.002 respectively) (FIG. 1E). To confirm that CD47 null tumors were more susceptible to GVAX and PD-1 blockade, CD47 null B16 melanoma cells were generated using transient transfection of a Cas9-sgRNA plasmid (as in Ran et al. (2013) Nat. Protoc. 8:2281-2308) (FIG. 2F). It was found that loss of CD47 significantly improved control of tumor growth mediated by GVAX plus anti-PD-1 immunotherapy (FIG. 1F, p<0.01).

Using the pooled loss-of-function in vivo genetic screen for identifying immune evasion molecules expressed by tumors described above, genes that increase or decrease the fitness of MC38 colon cancer cells growing in vivo in animal treated with immunotherapy. Thus, in vivo genetic screening recovered genes known to confer tumor evasion properties on cancer cells.

Example 3: Discovery of Novel Gene Targets to Increase the Efficacy of Immunotherapy Deletion of novel candidate immunotherapy targets was found to increase sensitivity of tumor cells to immunotherapy. sgRNAs targeting genes involved in antigen processing and presentation (e.g., HLA-E/H2-T23, Pdia3, Calr, Tap2, Tap1, Erap1, Tapbp, etc.) were markedly depleted in mice treated with GVAX and PD-1 blockade (FIG. 3A) relative to growth in TCRα$^{-/-}$ mice. In many cases, multiple members of the same pathway (e.g., Erap1, Tap2, Calr) or even the same multi-protein complex were depleted under immune selective pressure, underscoring the importance of these diverse biological pathways.

Figure 3:
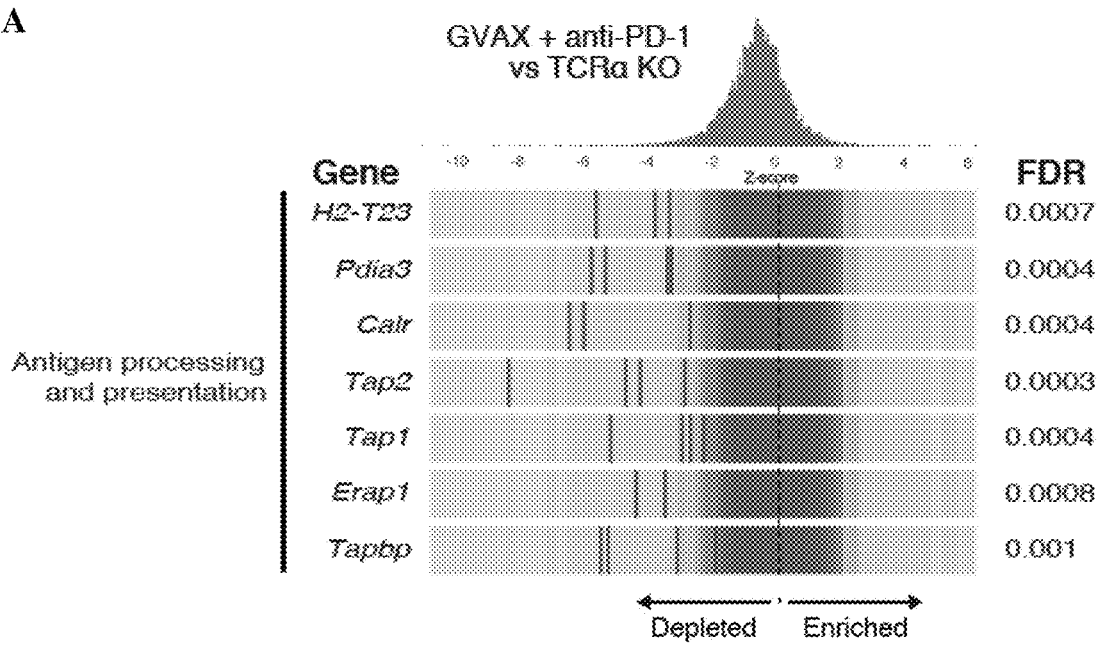
FIG. 3 includes 6 panels, identified as panels A, B, C, D, E, and F, which show that deletion of H2-T23 or its related genes sensitizes tumor cells to immunotherapy. Panel A shows frequency histogram (top) and collapsed histogram (below) of enrichment or depletion (normalized as Z scores) for sgRNAs in GVAX+PD-1 blockade-treated mice relative to TCRα$^{-/-}$ mice. sgRNAs targeting H2-T23, Pdia3, Calr, Tap2, Tap1, Erap1, and Tapbp are indicated in red. Panel B compares the expression of H2-T23 by B16 cells transfected with the indicated H2-T23-targeting (red) or control (grey) sgRNA and Cas9. Representative flow plots show frequencies of H2-T23 null and control B16 tumor cells in mixture in vitro or in vivo (Panel C). The cell number of either H2-T23 null or control B16 cells grown in GVAX+PD-1 blockade-treated wild-type mice, relative to the cell number of those cells grown in TCRα$^{-/-}$ mice, is shown in change in the ratios (log$_2$ normalized fold change) (mean and standard deviation; n=5 animals per group) (Panel D). Panel E compares tumor volume averaged for each group at each time point for H2-T23 null (red) or control (grey) B16 cells growing in mice treated with GVAX and PD-1 blockade (mean and standard error of the mean; n=10 animals per group). Panel F shows the survival analysis for the groups shown in panel D. * $p<0.05$;  $p<0.01$; * $p<0.001$; **** $p<0.0001$.
Figure 3:
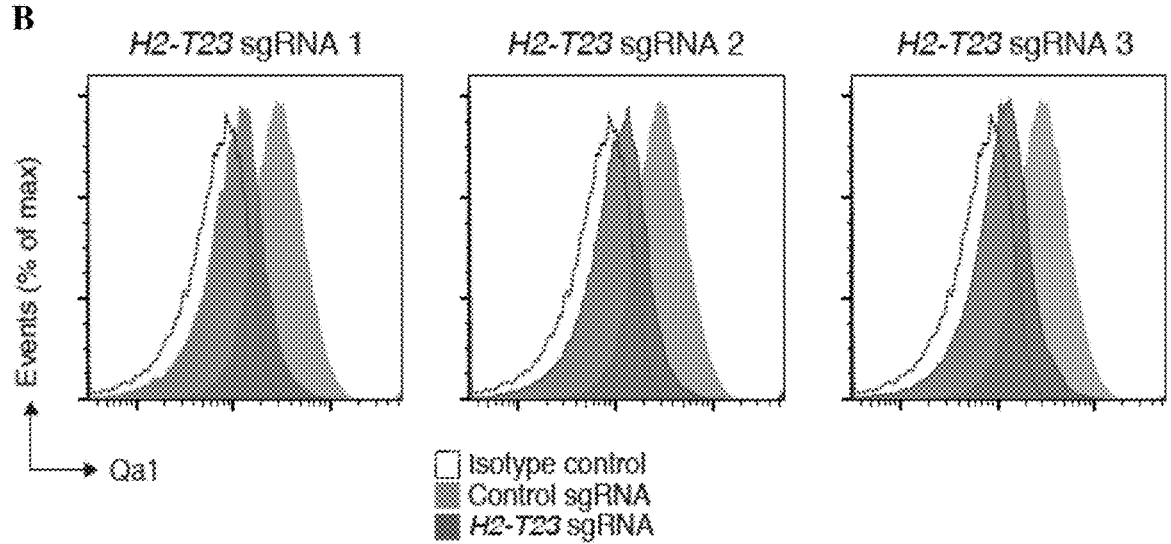
Figure 3:
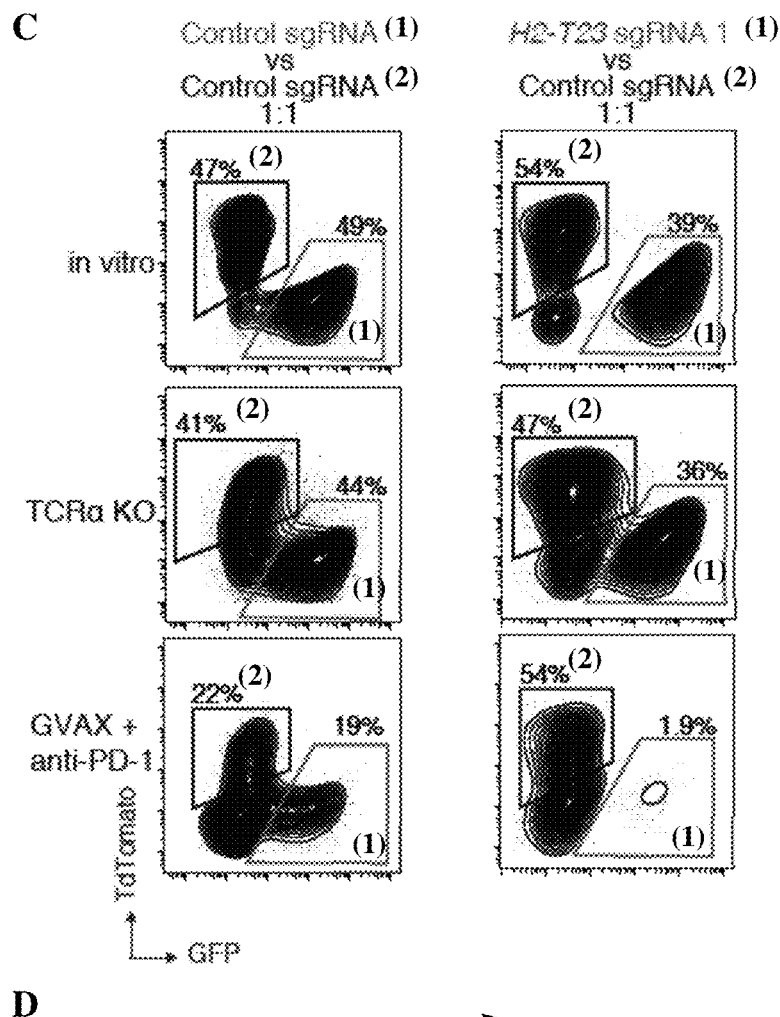
Figure 3:
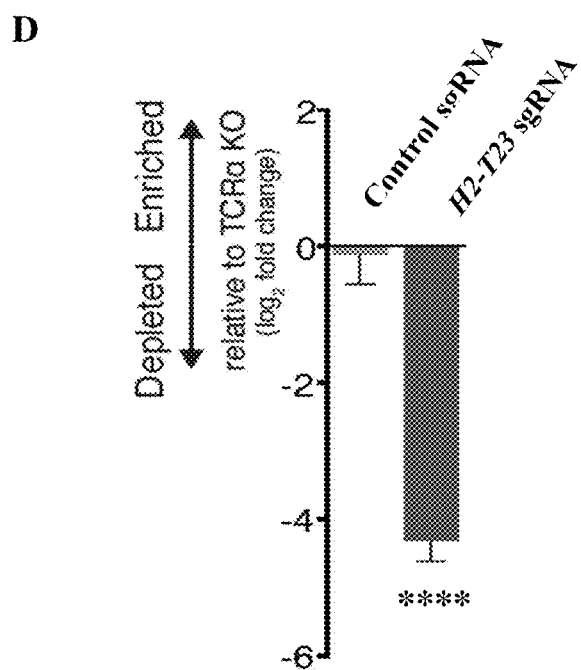
Figure 3:
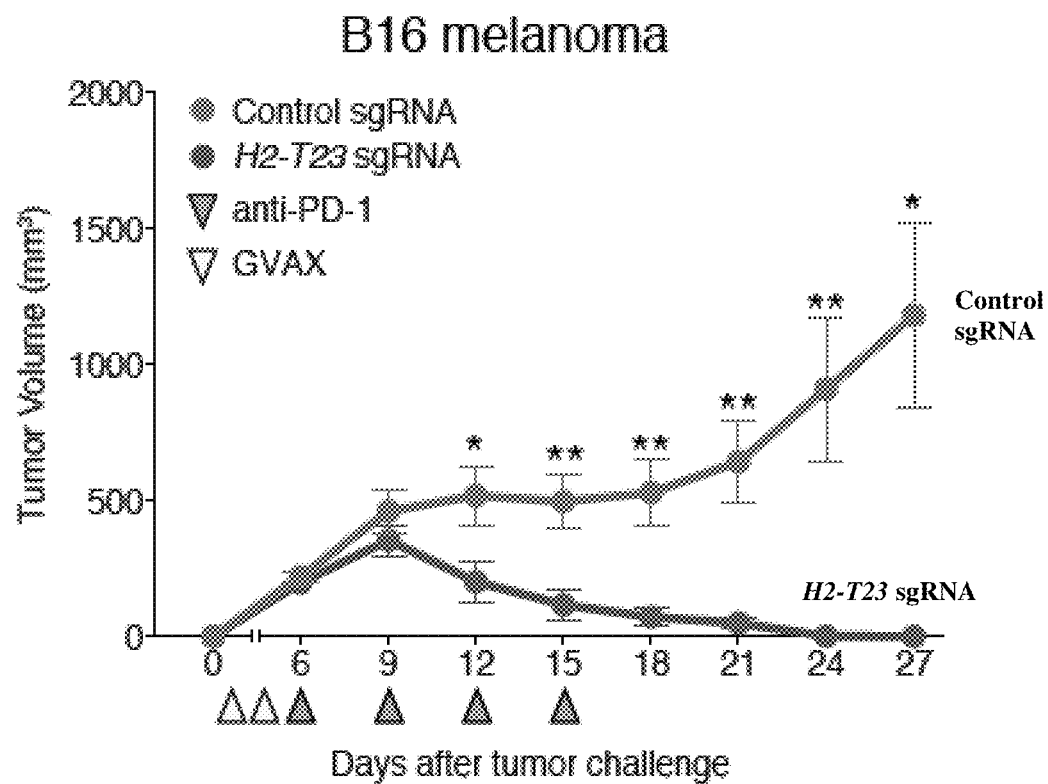
Figure 3:
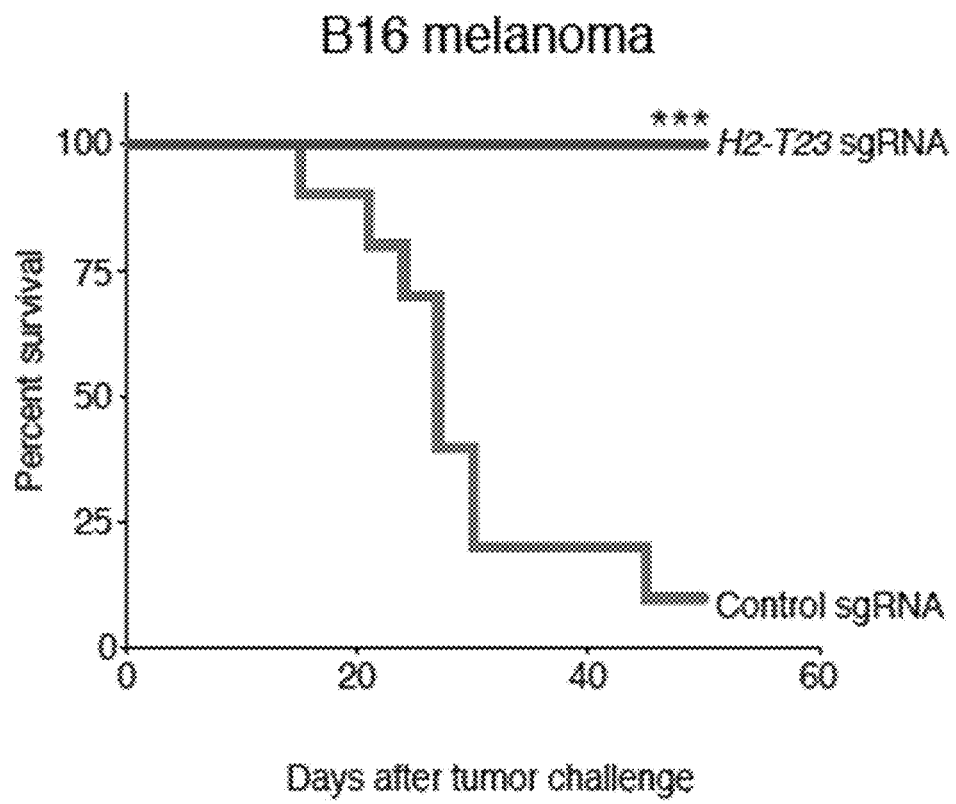
Figure 4:
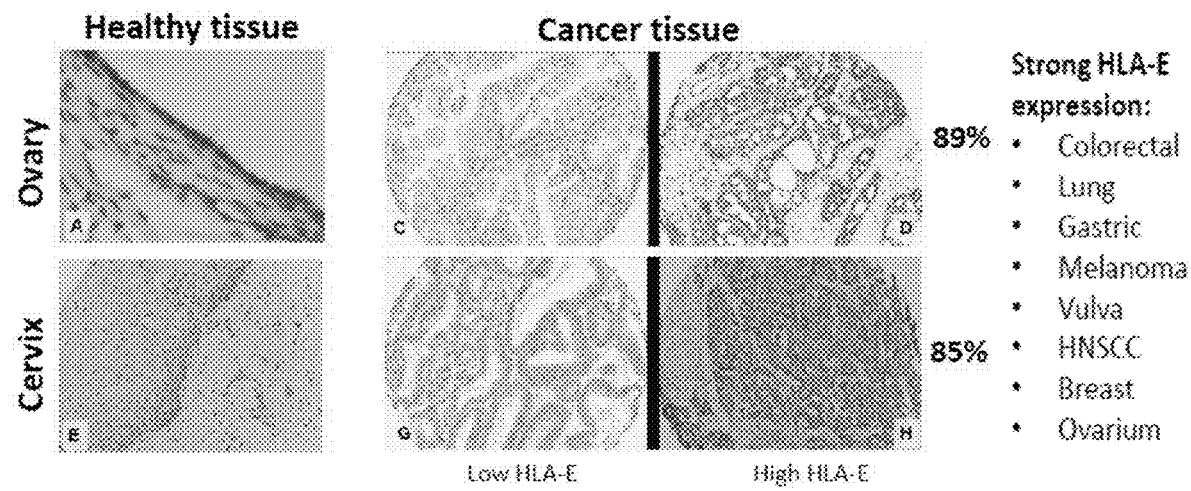
FIG. 4 shows the staining of HLA-E in different cancer and healthy tissues. HLA-E is generally overexpressed in cancer and the tissues having strong HLA-E expression include colorectal, lung, gastric, melanoma, vulva, HNSCC, breast, ovarium, etc. The figure and information is adapted from Gooden et al. (2011) *Proc. Natl. Acad. Sci. USA* 108:10656-10661;
van Esch et al. (2014) *Int. J. Cancer.* 135:830-842; Yazdi et al. (2016) *Oncotarget* 7:3477-3488.
Figure 5:
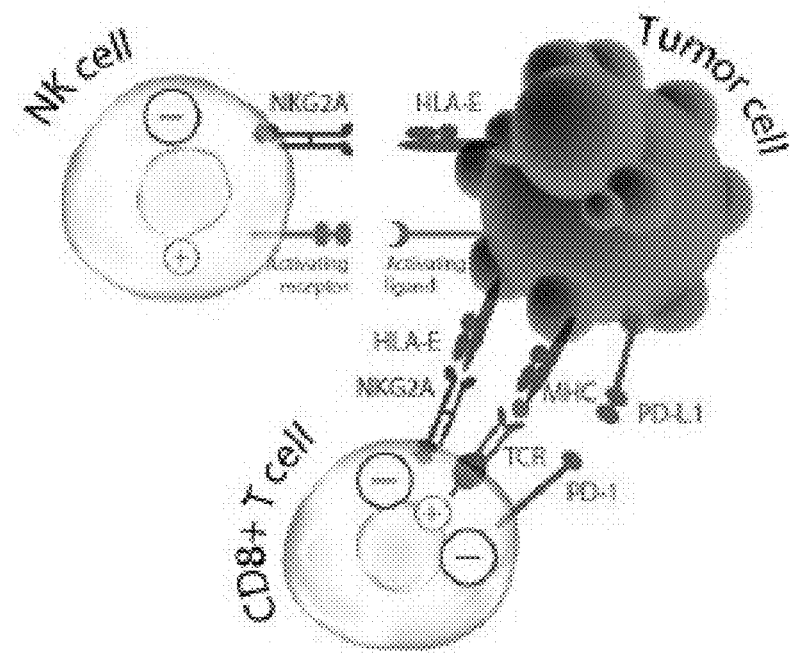
FIG. 5 shows the interaction between tumor cells, NK cells, and CD8+ T cells through the ligand-receptor recogniztion between HLA-E and NKG2A.
Figure 6:
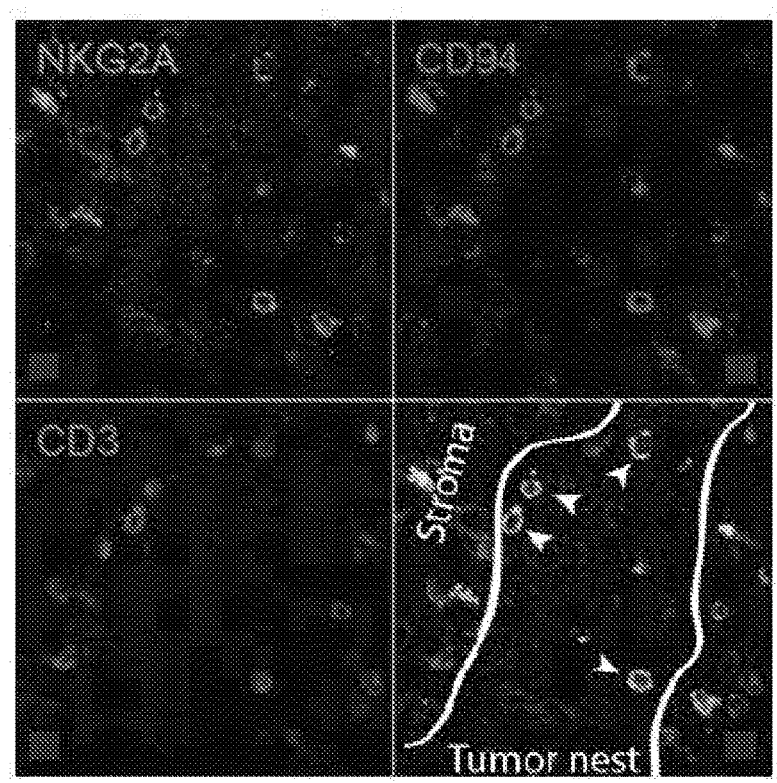
FIG. 6 shows the NKG2A expression on human tumor-infiltrating lymphocytes (TILs).
Figure 6:
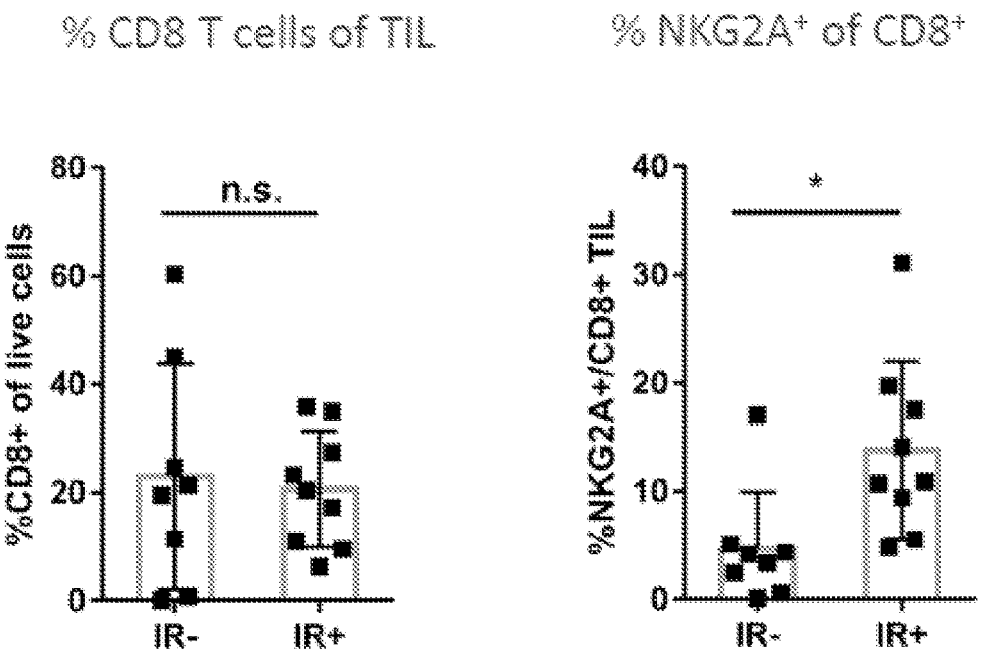
Figure 7A:
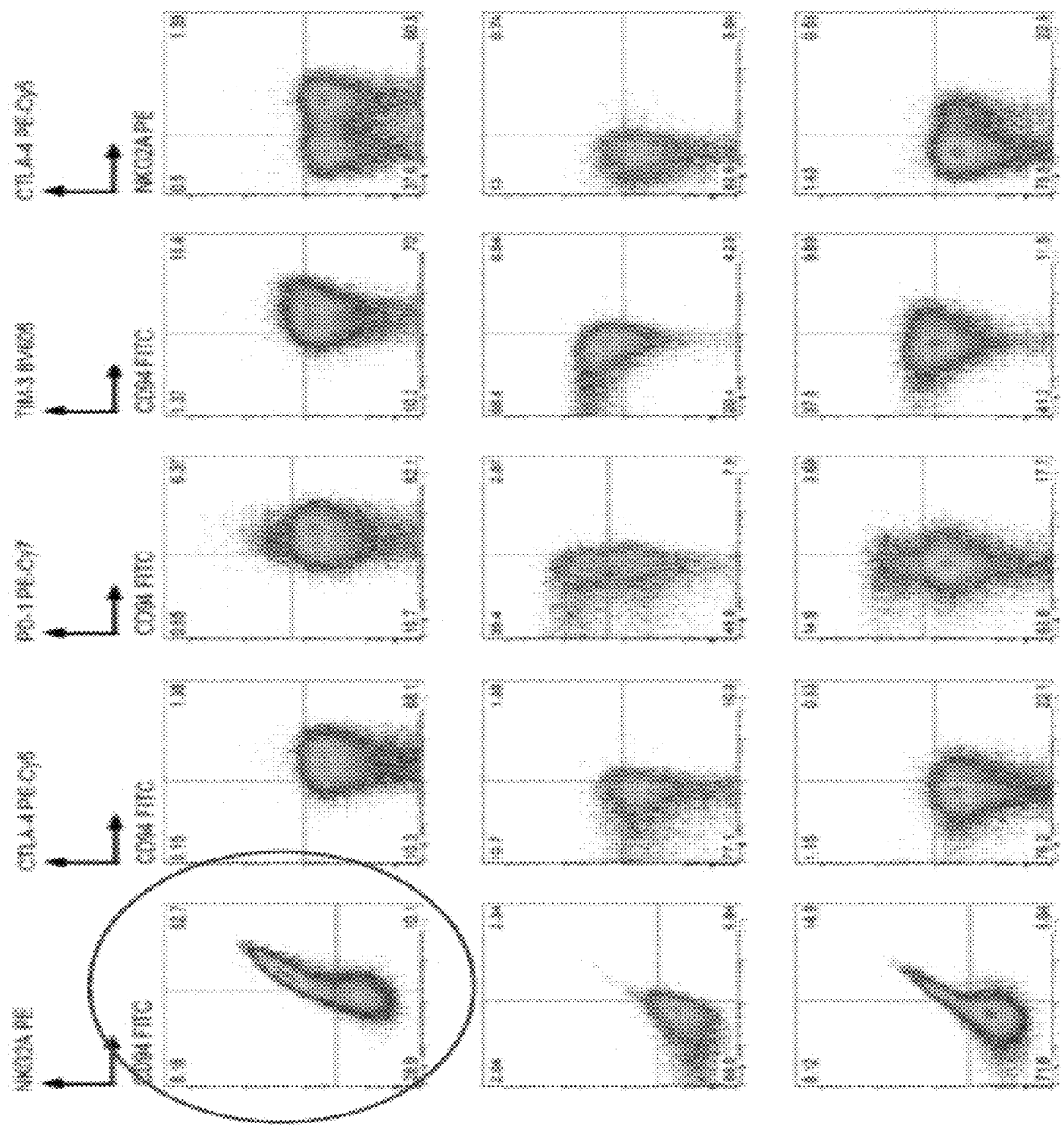
FIG. 7 includes 2 panels, identified as panels A and B, which show the co-expression of PD-1 and NKG2A on human TILs. Panel A shows the flow cytometry analysis of TILs (in head and neck squamous cell carcinoma (HN-SCC)). Panel B shows the Mass cytometry analysis of TILs.
Figure 7A:
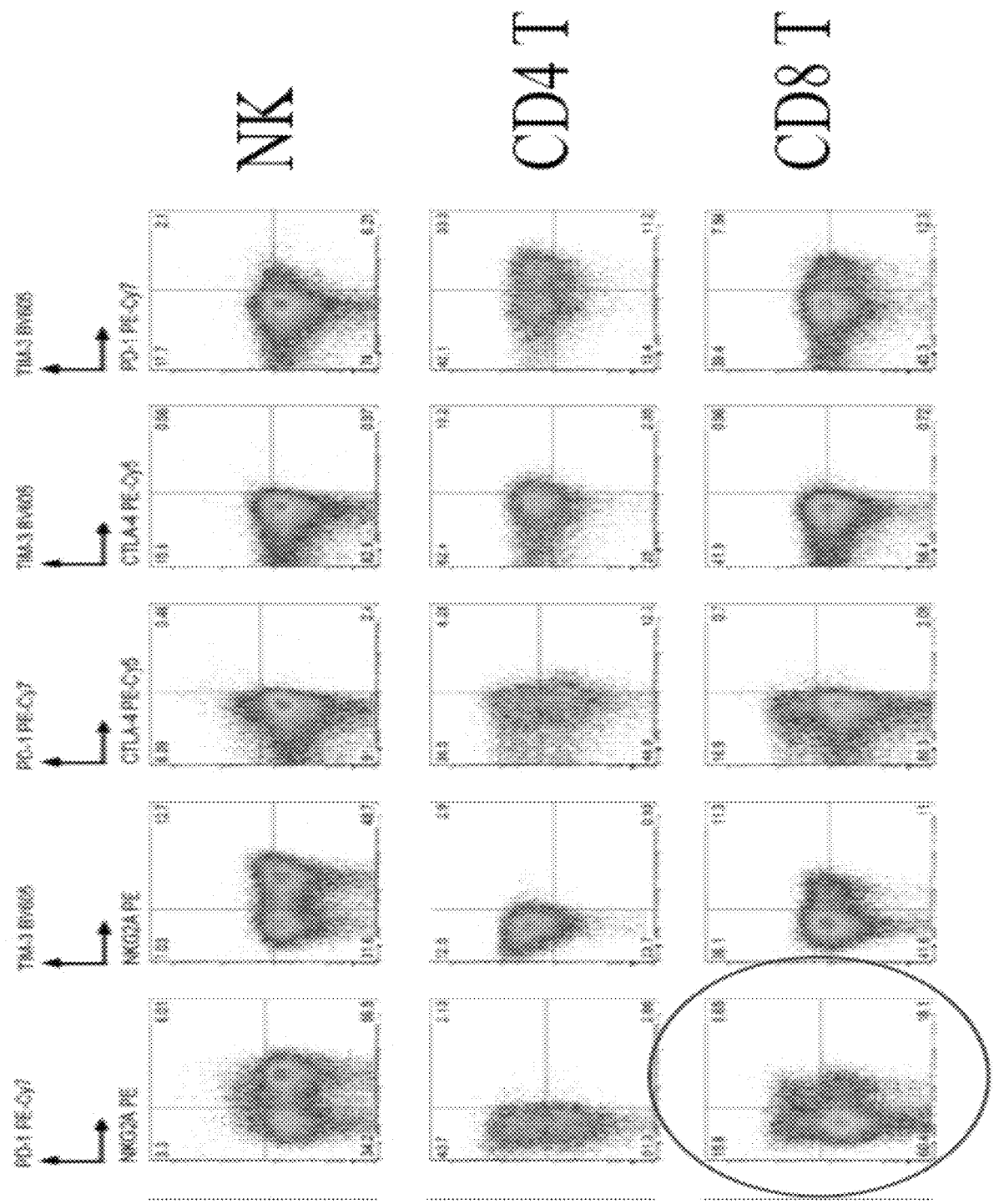
Figure 7:
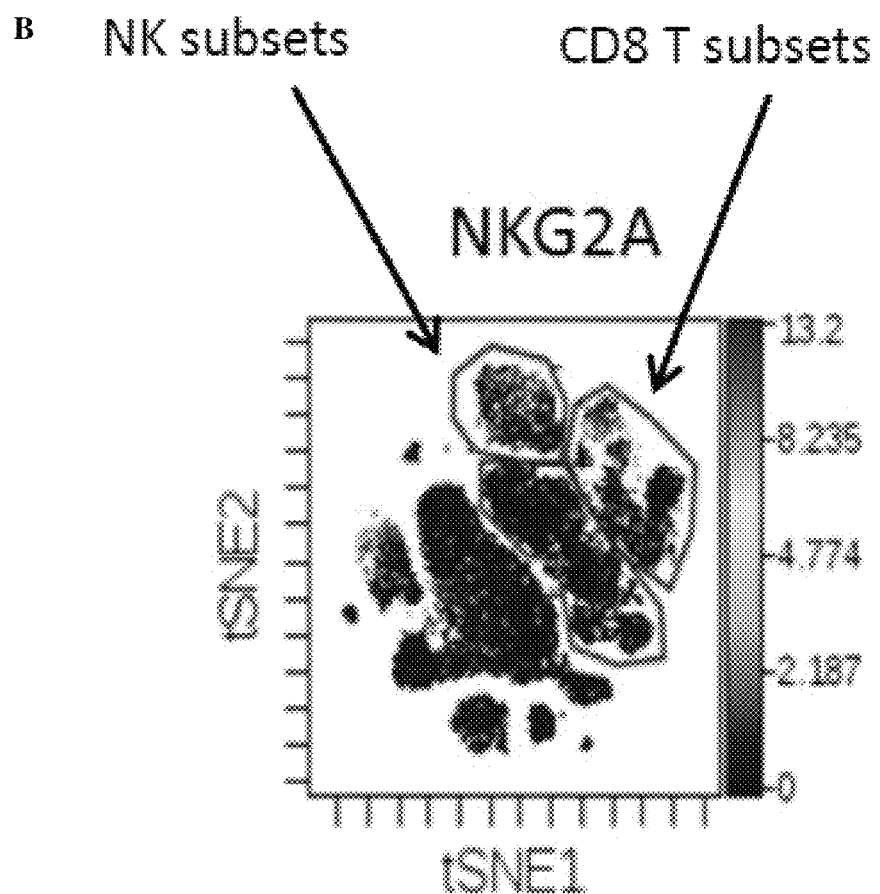
Figure 8:
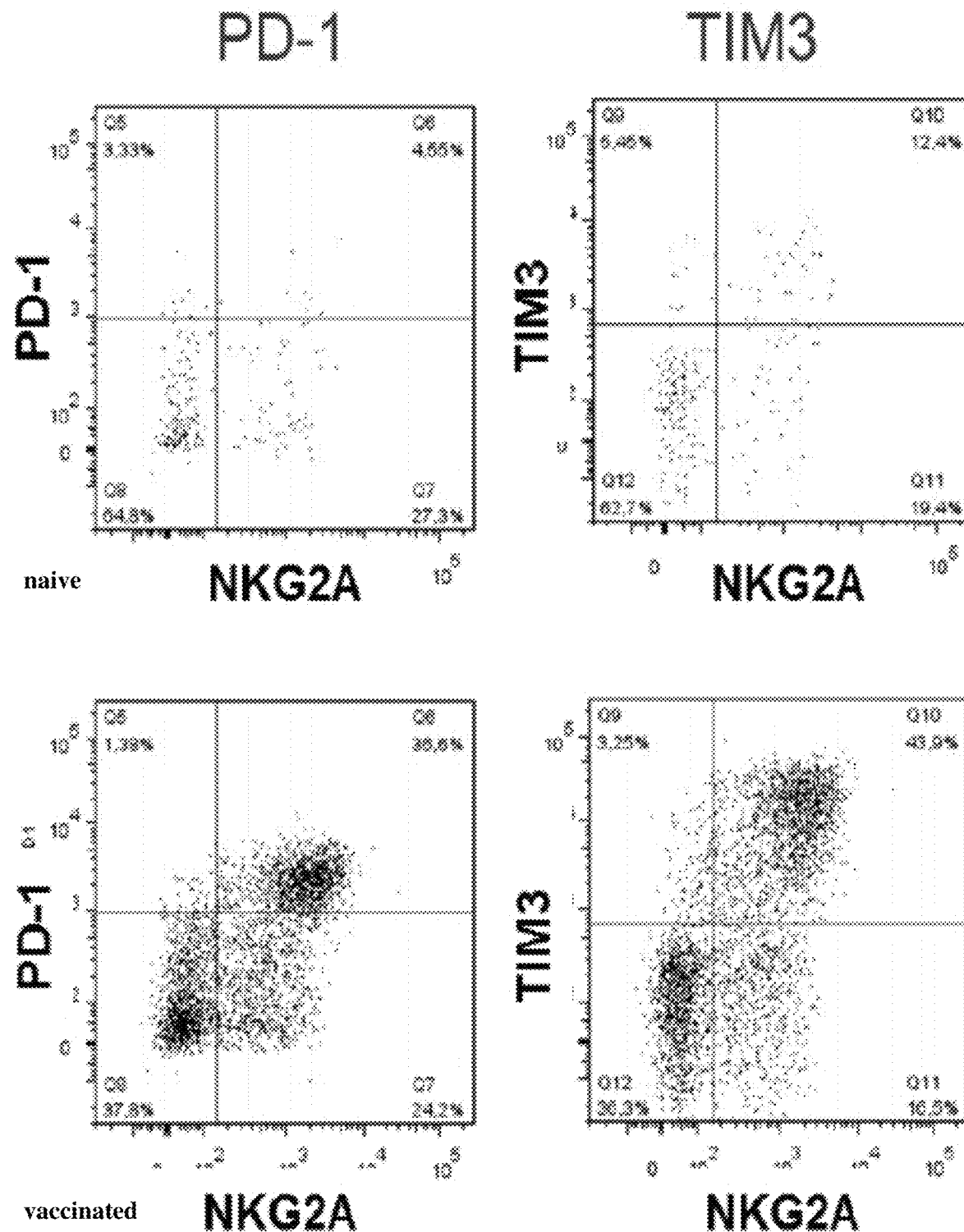
FIG. 8 shows the co-expression of multiple inhibitory receptors on mouse CD8 T cells. The mice model used here is TC-1 in C57BL/6 mice.
Figure 8:
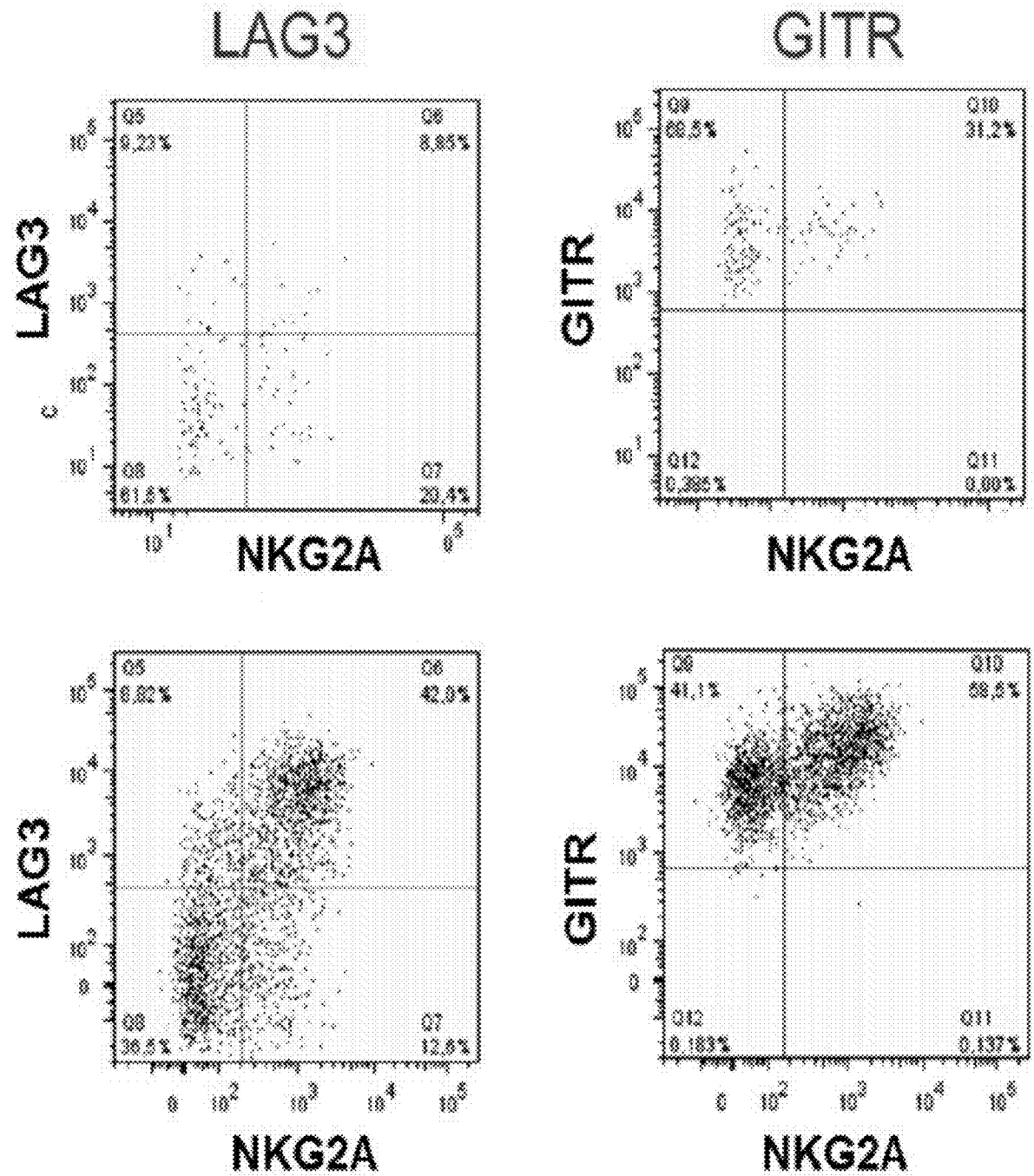
Figure 9:
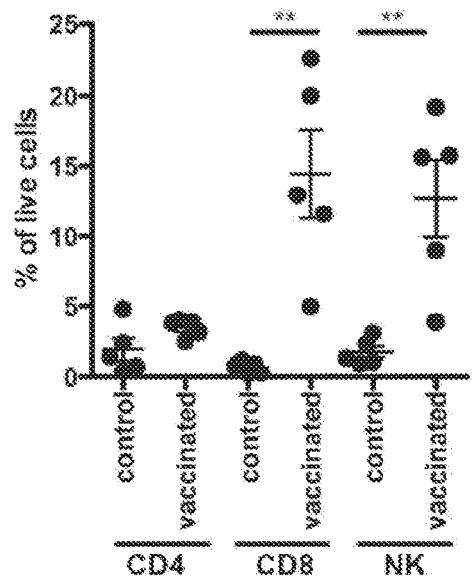
FIG. 9 includes 3 panels, identified as panels A, B, and C, which show that therapeutic vaccination increases NKG2A and H2-T23 (Qa-1) expression in TC-1 C57BL/6 mice. H2-T23 (Qa-1) expression was also seen in B16 mice model.
Figure 9:
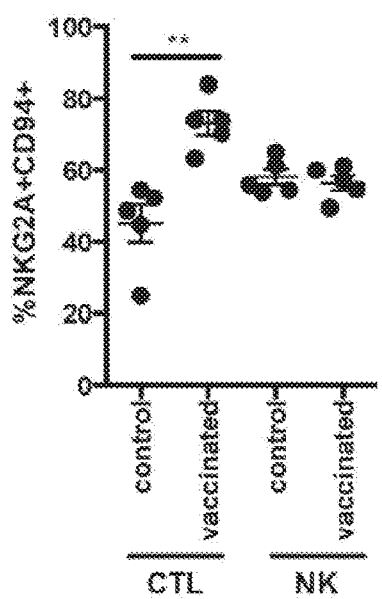
Figure 9:
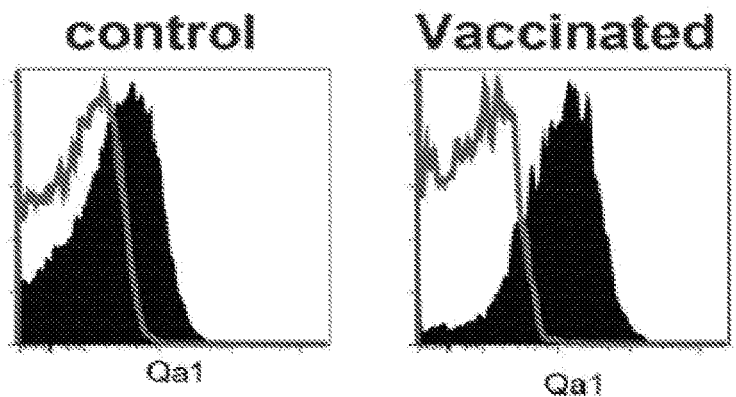
Figure 10:
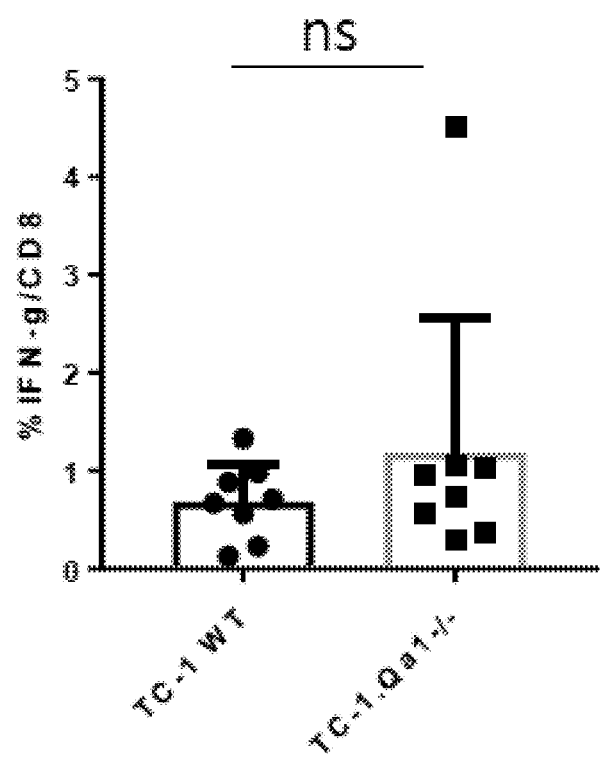
FIG. 10 includes 2 panels, identified as panels A and B, which show enhanced efficacy of vaccination in absence of H2-T23 (Qa-1).
Figure 10:
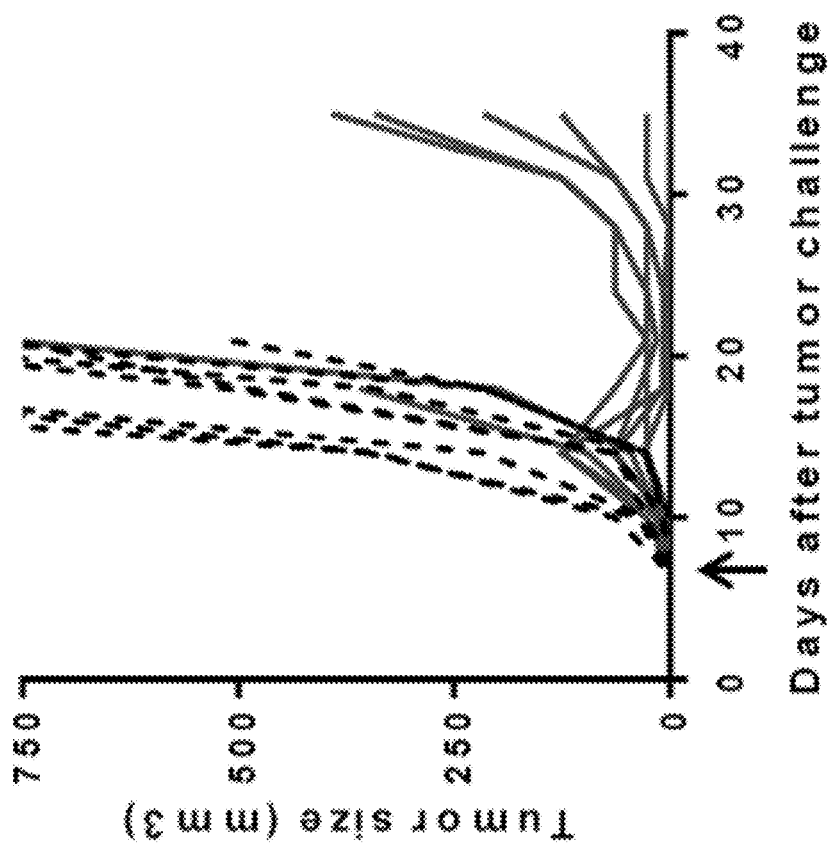
Figure 10:
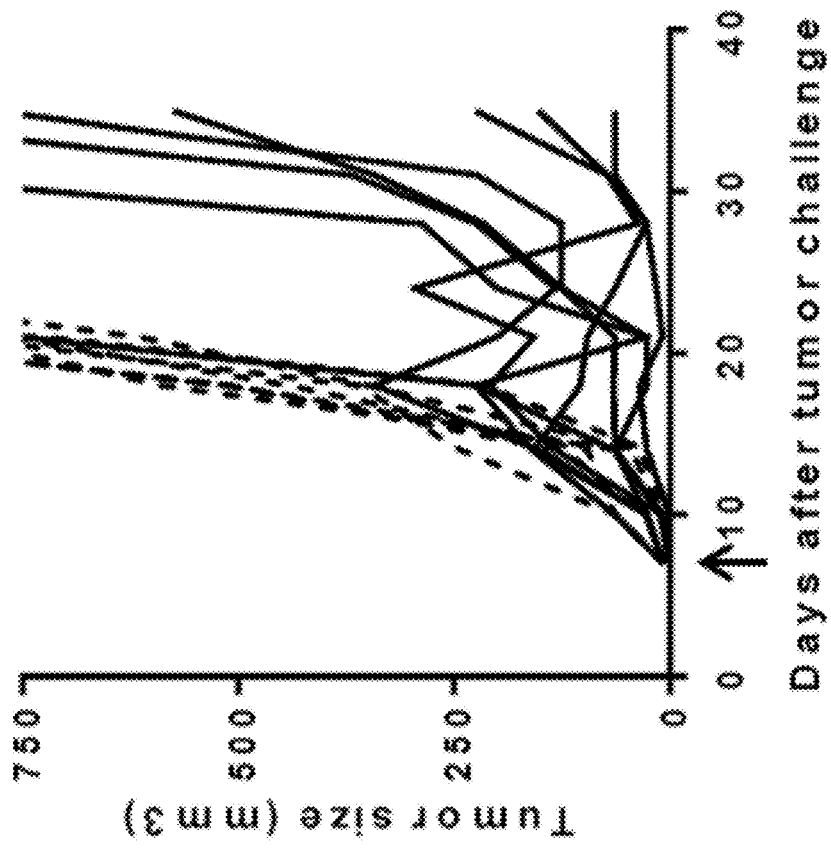
Figure 11:
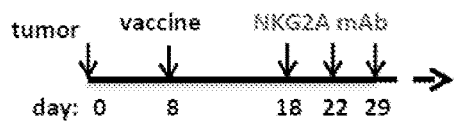
FIG. 11 includes 5 panels, identified as panels A, B, C, D, and E, which show that NKG2A-blocking monoclonal antibody recapitulates genetic model. Panel A shows the timeline of vaccination and administration of NKG2A mAb. Panel B compares mice survival rates after different treatments. Panel C summarizes the tumor size through time for each mouse without treatment. Panel D summarizes the tumor size through time for each mouse treated with vaccination and control mAb. Panel E summarizes the tumor size through time for each mouse treated with vaccination and anti-NKG2A mAb.
Figure 11:
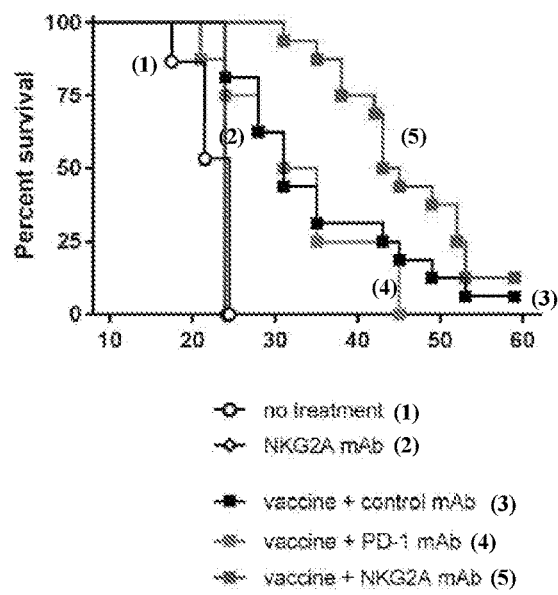
Figure 11:
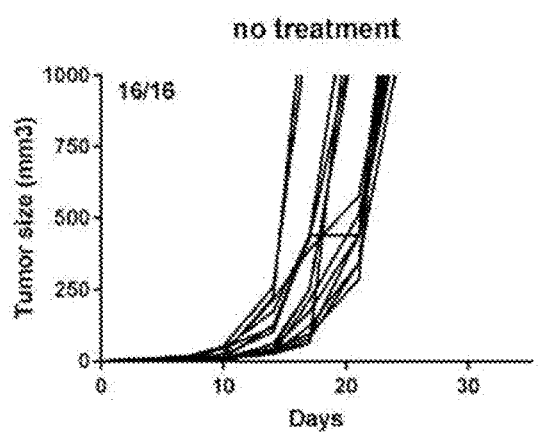
Figure 11:
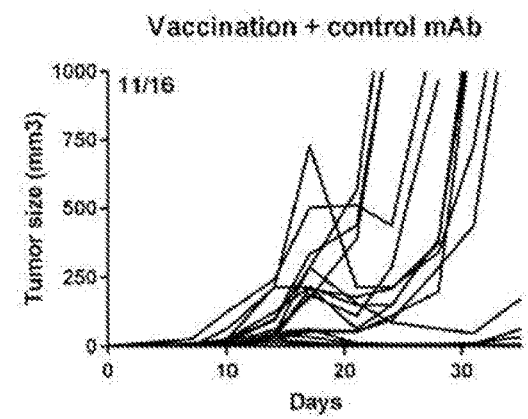
Figure 11:
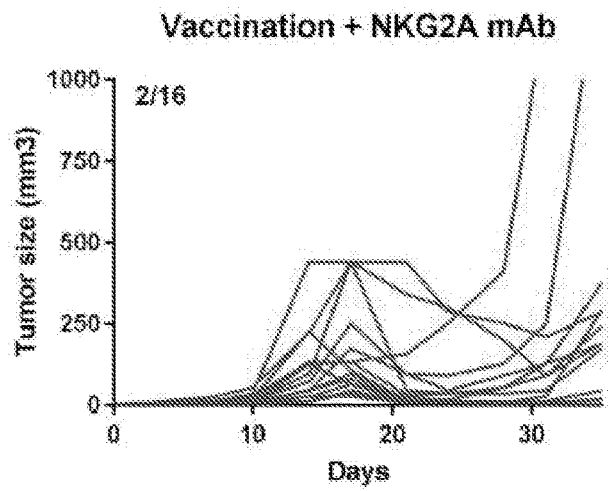
Figure 12:
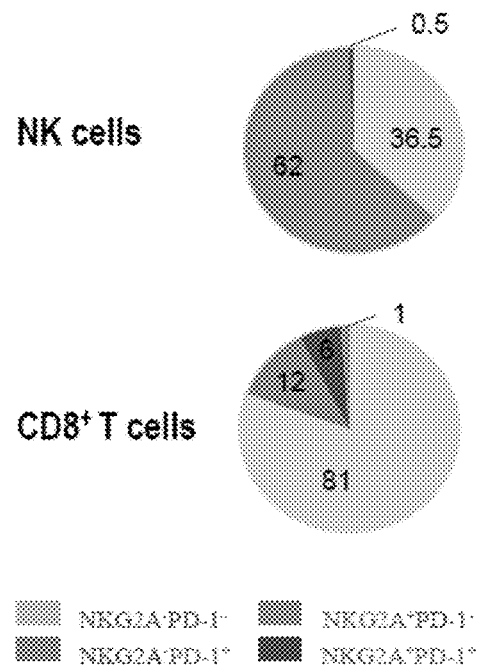
FIG. 12 includes 3 panels, identified as panels A, B, and C, which summarize NKG2A expression on TILs (panel A) or CD8 T cells after PD-1 treatment (panel B) and compare the mice survival rates with different treatments.
Figure 12:
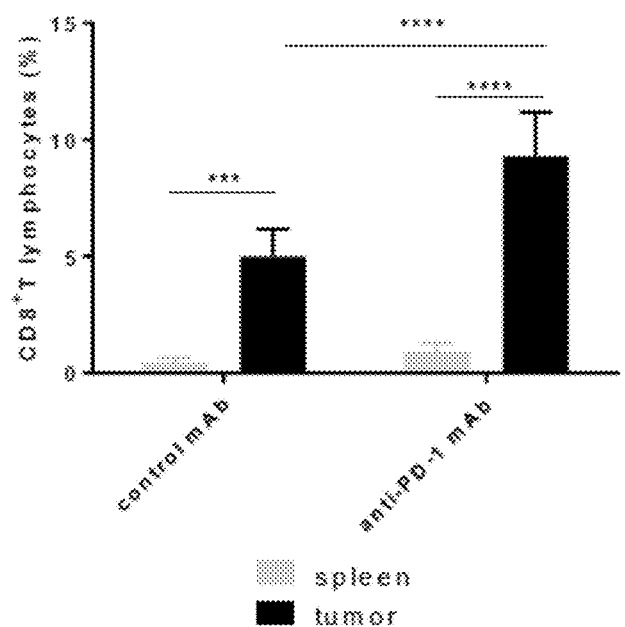
Figure 12:
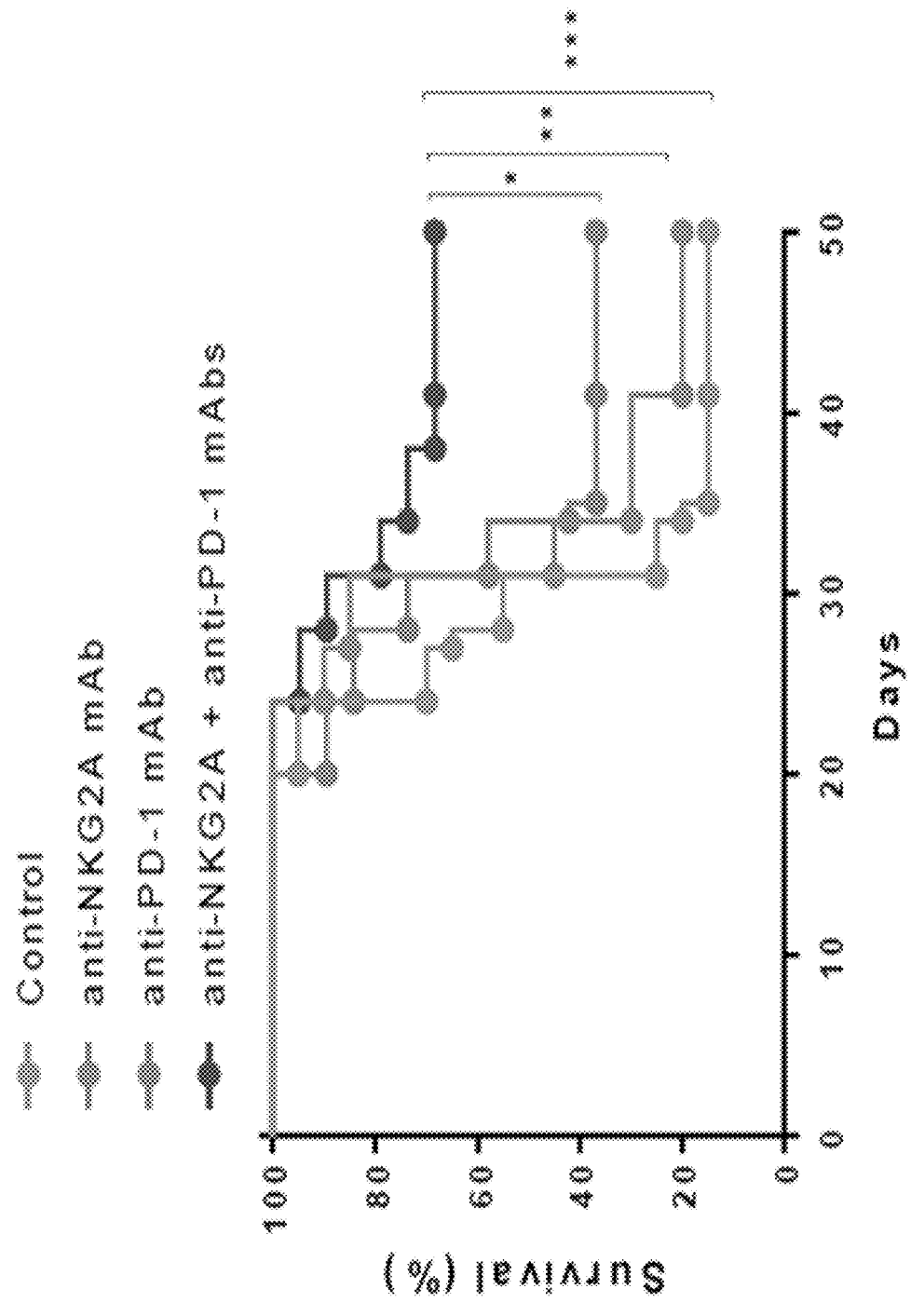

Example 4: In Vivo Validation of HLA-E as a Target for Combination with Immunotherapy Representative genes affecting antigen processing and presentation, e.g., HLA-E/H2-T23 (a non-classical MHC-I gene), were selected to validate based on their highest cumulative score as ranked by the STARS algorithm (Doench et al. (2014) Nat. Biotechnol. 32:1262-1267). In vivo competition assays showed that tumor cells deleted for H2-T23 were strongly selected against in WT animals treated with immunotherapy but grew at equivalent rates to control tumor cells in vitro and in TCR α$^{-/-}$ mice (FIGS. 3C and 3D; p<0.01, Student's t test). This indicates that these genes are synthetically lethal with an anti-tumor immune response, rendering tumor cells more sensitive to immunotherapy but not altering their cell growth or survival in the absence of T cells.

H2-T23 encodes Qa-1b (HLA-E in humans), a non-classical MHC molecule that binds the inhibitory receptor NKG2A on T cells and NK cells (Wada et al. (2004) Eur J Immunol. 34:81-90). It was confirmed that loss of function of Qa-1b in tumor cells enhances tumor immunity, by comparing the growth of H2-T23 null B16 melanoma cells (FIG. 3B) to control B16 tumors in mice treated with GVAX and PD-1 blockade. Immunotherapy in control tumors eradicated only 1 out of 10 tumors. In contrast, immunotherapy of H2-T23 null tumors was curative in all 10 animals (FIGS. 3E-3F; p<0.05, Student's t test). These results indicate that Qa-1b functions as an immune evasion molecule in tumors and that its loss of function improves tumor immunity.

Example 5: Mechanism Studies of HLA-E-Induced Sensitivity to Checkpoint Blockade HLA-E is a non-classical MHC-I gene expressed on the surface of both hematopoietic and non-hematopoietic cells. HLA-E can present antigen (Hansen et al. (2016) Science 351:714-720), but in addition is also thought to have tolerogenic properties (Morandi & Pistoia (2014) Front. Immunol. 5:394). In vivo screening using mouse transplantable tumor models treated with anti-PD-1 immunotherapy showed that H2-T23, the mouse ortholog of HLA-E, increased the sensitivity of tumor cells to immunotherapy and synergized with PD-1 pathway blockade.

HLA-E expression on tumors has been variably associated with good and bad prognosis (Benevolo et al. (2011) J. Transl. Med. 9:184; Seliger et al. (2016) Oncotarget 7:67360-67372; Yazdi et al. (2016) Oncotarget 7:3477-3488) and therefore its role as an immune evasion molecule has previously been open to question. Recent reports suggest that the molecule restrains the positive prognostic impact of having tumor infiltrating CD8+ T cells (Yazdi et al. (2016) Oncotarget 7:3477-3488). Like other HLA molecules, expression of HLA-E on tumor cells is induced by interferons. Additionally, polymorphisms that encode single amino acid changes in the invariant peptide that normally occupies the HLA-E binding groove (derived from a leader sequence in HLA-B) can substantially alter the stability of HLA-E complex and impact its expression level on the cell surface (Horowitz et al. (2016) Sci. Immunol. 1: eaag1672).

HLA-E has been shown to interact with both NKG2C and NKG2A. NKG2C is a cell-surface receptor expressed on NK cells and ligation of this receptor has been shown to have a stimulatory effect on NK cells (Wada et al. (2004) Eur. J. Immunol. 34:81-90). NKG2A is an inhibitory cell-surface receptor expressed on both NK cells and T cells. Due to fact that NKG2A has a greater affinity for HLA-E, this interaction is thought to be the dominant one and HLA-E is thus considered to have a tolerogenic role in immunity (Wada et al. (2004), supra). Blockade of the interaction between HLA-E and NKG2A has been shown to increase NK-cell mediated lysis in vitro (Levy et al. (2009) Innate Immun. 15:91-100) and NKG2A expression on antigen-specific T cells during viral infection limits their cytolytic abilities (Moser et al. (2002) Nat. Immunol. 3:189-195).

It has been demonstrated herein that H2-T23 expression on murine tumor cells is an important mechanism for immune evasion. H2-T23 deficient B16 melanoma tumor cells were completely rejected when implanted into mice that are treated with GVAX and PD-1 blocking antibodies, whereas control B16 tumors respond to treatment transiently and then continue to grow. The data indicate that, like PD-L1, H2-T23 is a major inhibitory ligand that protects B16 tumor cells from destruction by the immune system. Overexpression of HLA-E/H2-T23 correlates with worse prognosis, at least partly due to its neutralization of beneficial effects of T cell infiltration into the tumor. The data are consistent with another discovery that H2-T23 deficient tumor cells had a selective disadvantage compared to control tumor cells when the two populations were injected into mice as a mixture. Thus, the data indicate that depletion of H2-T23 deficient tumor cells is carried out by cytotoxic T cells, as the effect of depletion was not observed in TCRα KO mice that lack conventional T cells. Finally, when a monoclonal antibody (anti-NK1.1 mAb) was used to deplete NK cells, H2-T23 deficient tumor cells were still depleted from mice treated with immunotherapy, further indicating that the effect is mediated by cytotoxic T cells.

The data provided herein indicate that blocking the interaction between NKG2A and HLA-E using a monoclonal antibody would increase the efficacy of existing immunotherapies such as blockade of the PD-1 pathway. The checkpoint receptor, NKG2A, is expressed on intratumoral NK cells (~60%) and CD8 T cells (~15%) and its expression is found on nearly all activated cytotoxic T cell populations, analogous to the expression of PD-1. The frequencies of NKG2A is also enhanced after PD-1 blockade therapy and after vaccination. Similarly, the ligand HLA-E (Qa-1 in mice) is generally overexpressed in cancer and is upregulated after vaccination. Thus, blocking the NKG2A-HLA-E interaction would be expected to synergize with a broad array of immunotherapy strategies for most human cancers. In addition to increasing the efficacy of cancer immunotherapy or vaccination, blocking the interaction between HLA-E and NKG2A would be expected to improve the outcome of any therapy in which antigen specific T cells are being inhibited from eliminating target cells, such as in chronic viral infections including HIV and HCV. Because of its potent inhibitory role, recombinant HLA-E that could be administered systemically could also be used to control the progression of autoimmune diseases in which activated, self-reactive T cells are the cause of pathogenesis, such as multiple sclerosis.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with a cancer comprising administering to the subject a therapeutically effective amount of a nucleic acid agent that inhibits the copy number or the expression level or of HLA-E, in combination with an immunotherapy, wherein the immunotherapy inhibits a PD-1 pathway immune checkpoint; or
a method of killing cancer cells comprising contacting the cancer cells with the nucleic acid agent that inhibits the copy number or the expression level of of HLA-E, in combination with the immunotherapy, wherein the immunotherapy inhibits a PD-1 pathway immune checkpoint.

2. The method of claim 1, wherein
(1) the agent is a CRISPR single-guide RNA (sgRNA), RNA interfering agent, or antisense oligonucleotide;
(2) the agent increases the sensitivity of the cancer cells to the immunotherapy;
(3) the immunotherapy and/or a cancer therapy is (a) administered to the subject or (b) contacted with the cancer cells before, after, or concurrently with the agent;
(4) the HLA-E is a human HLA-E, a mouse H2-T23, a chimeric HLA-E, or a fusion HLA-E;
(5) the HLA-E comprises an amino acid sequence selected from the group consisting of SEQ ID Nos: 2, 4, 6, 8, 10, 12, and 14;
(6) the HLA-E is encoded by a nucleic acid sequence selected from the group consisting of SEQ ID Nos: 1, 3, 5, 7, 9, 11, and 13;
(7) the agent reduces the number of proliferating cells in the cancer and/or reduces the volume or size of a tumor comprising the cancer cells;
(8) the agent increases the sensitivity of the cancer to the immunotherapy, optionally wherein the immunotherapy is T-cell-mediated;
(9) the agent increases the amount of CD8+ T cells in a tumor comprising the cancer cells;
(10) the cancer is selected from the group consisting of melanoma and colorectal cancer, optionally wherein the cancer is melanoma;
(11) the subject is an animal model of the cancer, optionally wherein the animal model is a mouse model;
(12) the subject is a mammal, optionally wherein the mammal is a mouse or a human, optionally wherein the mammal is a human; and/or
(13) the agent is administered in a pharmaceutically acceptable formulation.

3. The method of claim 2, wherein
the RNA interfering agent is a small interfering RNA (siRNA), CRISPR RNA (crRNA), a small hairpin RNA (shRNA), a microRNA (miRNA), or a piwi-interacting RNA (piRNA), optionally wherein the RNA interfering agent is a CRISPR single-guide RNA (sgRNA), optionally wherein the sgRNA comprises a nucleic acid sequence selected from the group consisting of SEQ ID NOs: 49-64.

4. The method of claim 2, wherein
(1) the immunotherapy comprises an anti-cancer vaccine and/or virus;
(2) the immunotherapy is cell-based;
(3) the immune checkpoint is selected from the group consisting of PD-1 and PD-L2; or
(4) the cancer therapy is selected from the group consisting of radiation, a radiosensitizer, an immunogenic chemotherapy that induce interferon production by the cancer cells or at the site of a tumor, interferon, an interferon-inducing agent, a topical inflammatory agent, and a topical TLR agonist.

* * * * *

SEQUENCE LISTING

<160> NUMBER OF SEQ ID NOS: 65

<210> SEQ ID NO 1
<211> LENGTH: 2679
<212> TYPE: DNA
<213> ORGANISM: Homo sapiens

<400> SEQUENCE: 1

```
gcagactcag ttctcattcc caatgggtgt cgggtttcta gagaagccaa tcagcgtcgc      60
cacgactccc gactataaag tccccatccg gactcaagaa gttctcagga ctcagaggct     120
gggatcatgg tagatggaac cctccttta ctcctctcgg aggccctggc ccttacccag     180
acctgggcgg gctcccactc cttgaagtat ttccacactt ccgtgtcccg gcccggccgc     240
ggggagcccc gcttcatctc tgtgggctac gtggacgaca cccagttcgt gcgcttcgac     300
aacgacgccg cgagtccgag gatggtgccg cgggcgccgt ggatggagca ggagggtca     360 gagtattggg accgggagac acggagcgcc agggacaccg cacagatttt ccgagtgaat     420
ctgcggacgc tgcgcggcta ctacaatcag agcgaggccg ggtctcacac cctgcagtgg     480
atgcatggct gcgagctggg gcccgacggg cgcttcctcc gcgggtatga acagttcgcc     540
tacgacggca aggattatct caccctgaat gaggacctgc gctcctggac cgcggtggac     600
acggcggctc agatctccga gcaaaagtca aatgatgcct ctgaggcgga gcaccagaga     660
gcctacctgg aagacacatg cgtggagtgg ctccacaaat acctggagaa ggggaaggag     720
acgctgcttc acctggagcc cccaaagaca cacgtgactc accacccat ctctgaccat     780 gaggccaccc tgaggtgctg ggccctgggc ttctaccctg cggagatcac actgacctgg     840
cagcaggatg gggagggcca tacccaggac acggagctcg tggagaccag gcctgcaggg     900
gatggaacct tccagaagtg ggcagctgtg gtggtgcctt ctggagagga gcagagatac     960
```

```
acgtgccatg tgcagcatga ggggctaccc gagcccgtca ccctgagatg gaagccggct    1020
tcccagccca ccatccccat cgtgggcatc attgctggcc tggttctcct tggatctgtg    1080
gtctctggag ctgtggttgc tgctgtgata tggaggaaga agagctcagg tggaaaagga    1140
gggagctact ctaaggctga gtggagcgac agtgccaggg gtctgagtc tcacagcttg    1200 taaagcctga gacagctgcc ttgtgtgcga ctgagatgca cagctgcctt gtgtgcgact    1260
gagatgcagg atttcctcac gcctccccta tgtgtcttag gggactctgg cttctctttt    1320
tgcaagggcc tctgaatctg tctgtgtccc tgttagcaca atgtgaggag gtagagaaac    1380
agtccacctc tgtgtctacc atgaccccct cctcacact gacctgtgtt ccttccctgt    1440
tctcttttct attaaaaata gaacctgggc agagtgcgg cagctcatgc ctgtaatccc    1500
agcacttagg gaggccgagg agggcagatc acgaggtcag gagatcgaaa ccatcctggc    1560
taacacggtg aaaccccgtc tctactaaaa aatacaaaaa attagctggg cgcagaggca    1620
cgggcctgta gtcccagcta ctcaggaggc ggaggcagga gaatggcgtc aacccgggag    1680
gcggaggttg cagtgagcca ggattgtgcg actgcactcc agcctgggtg acagggtgaa    1740
acgccatctc aaaaaataaa aattgaaaaa taaaaaaaga acctggatct caatttaatt    1800
tttcatattc ttgcaatgaa atggacttga ggaagctaag atcatagcta gaaatacaga    1860
taattccaca gcacatctct agcaaattta gcctattcct attctctagc ctattcctta    1920
ccacctgtaa tcttgaccat ataccttgga gttaatatt gttttcatac tgctgtggtt    1980
tgaatgttcc ctccaacact catgttgaga cttaatccct aatgtggcaa tactgaaagg    2040
tggggccttt gagatgtgat tggatcgtaa ggctgtgcct tcattcatgg gttaatggat    2100
taatgggtta tcacaggaat gggactggtg gctttataag aagaggaaaa gagaactgag    2160
ctagcatgcc cagcccacag agagcctcca ctagagtgat gctaagtgga aatgtgaggt    2220
gcagctgcca cagagggccc ccaccaggga aatgtctagt gtctagtgga tccaggccac    2280
aggagagagt gccttgtgga gcgctgggag caggacctga ccaccaccag gaccccagaa    2340
ctgtggagtc agtggcagca tgcagcgccc ccttgggaaa gctttaggca ccagcctgca    2400
acccattcga gcagccacgt aggctgcacc cagcaaagcc acaggcacgg ggctacctga    2460
ggccttgggg gcccaatccc tgctccagtg tgtccgtgag gcagcacacg aagtcaaaag    2520
agattattct cttcccacag ataccttttc tctcccatga ccctttaaca gcatctgctt    2580
cattcccctc accttcccag gctgatctga ggtaaacttt gaagtaaaat aaaagctgtg    2640
tttgagcatc atttgtattt caaaaaaaaa aaaaaaaa                           2679
```

<210> SEQ ID NO 2
<211> LENGTH: 358
<212> TYPE: PRT
<213> ORGANISM: Homo sapiens

<400> SEQUENCE: 2

Met Val Asp Gly Thr Leu Leu Leu Leu Ser Glu Ala Leu Ala Leu
1               5                   10                  15

Thr Gln Thr Trp Ala Gly Ser His Ser Leu Lys Tyr Phe His Thr Ser
            20                  25                  30

Val Ser Arg Pro Gly Arg Gly Glu Pro Arg Phe Ile Ser Val Gly Tyr
        35                  40                  45

Val Asp Asp Thr Gln Phe Val Arg Phe Asp Asn Asp Ala Ala Ser Pro
    50                  55                  60

Arg Met Val Pro Arg Ala Pro Trp Met Glu Gln Glu Gly Ser Glu Tyr

```
                65                  70                  75                  80
Trp Asp Arg Glu Thr Arg Ser Ala Arg Asp Thr Ala Gln Ile Phe Arg
                        85                  90                  95

Val Asn Leu Arg Thr Leu Arg Gly Tyr Tyr Asn Gln Ser Glu Ala Gly
                    100                 105                 110

Ser His Thr Leu Gln Trp Met His Gly Cys Glu Leu Gly Pro Asp Gly
                115                 120                 125

Arg Phe Leu Arg Gly Tyr Glu Gln Phe Ala Tyr Asp Gly Lys Asp Tyr
            130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
        275                 280                 285

Glu Pro Val Thr Leu Arg Trp Lys Pro Ala Ser Gln Pro Thr Ile Pro
    290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
        355

<210> SEQ ID NO 3
<211> LENGTH: 1317
<212> TYPE: DNA
<213> ORGANISM: Mus musculus

<400> SEQUENCE: 3
attcaggttc ctcacagacc caggggggtga ggatgttgct ttttgcccac ttgcttcagc      60
tgctggtcag cgccacagtc ccgacccaga gtagcccaca ctcgctgcgg tatttcacca     120
ccgccgtgtc ccggcccggc ctcggggagc cccggttcat cattgtcggc tacgtggacg     180
acacgcagtt cgtgcgcttc gacagcgacg cggaaaatcc gaggatggag cctcgggcgc     240
ggtggattga gcaggagggg ccggagtatt gggagcggga gacttggaaa gccagggaca     300 tgggaggaa cttcagagta aacctgagga ccctgctcgg ctactacaat cagagtaacg     360
acgaatctca cacgctgcag tggatgtacg gctgcgacgt ggggcccgat gggcgcctgc     420
tccgcgggta ttgtcaggag gcctacgatg gccaggatta catctccctg aacgaggacc     480
```

```
tgcgttcctg gaccgcgaat gacatagcct cacagatctc taagcacaag tcagaggcag    540
tcgatgaggc ccaccaacag agggcatacc tgcaaggtcc ttgcgtggag tggctccata    600
gatacctacg gctgggaaat gagacactgc agcgctcaga ccctccaaag gcacatgtga    660
cccatcaccc tagatctgaa gatgaagtca ccctgaggtg ctgggccctg gcttctacc     720 ctgctgacat caccctgacc tggcagttga atggggagga gctgacccag gacatggagc    780
ttgtggagac caggcctgca ggggatggaa ccttccagaa gtgggcagct gtcgtggtgc    840
ctcttgggaa ggagcagtat tacacatgcc atgtgtacca tgaggggctg cctgagcccc    900
tcaccctgag atgggagcct cctccatcca ctgtctccaa catggtaatc atagctgttc    960
tggttgtcct tggagctgtg atcatccttg agctgtggt ggcttttgtg atgaagagga    1020
ggagacacat aggtgtaaaa ggatgctatg ctcatgttct aggcagcaag agcttccaga    1080
cctctgactg gcctcagaag gcatgaaaat ccctgggggg gctggtgaga tggctcagtg    1140
ggtaagagca ctgactgctc ttctgaaggt ccagagttca aatcccagca accacatggt    1200
ggctcacaac catccgtaac gagatctgac tccctcttct ggagtgtctg aagacagcta    1260
caatgtactt acatataata aataaataaa taaataaata aataaataaa taaataa       1317
```

<210> SEQ ID NO 4
<211> LENGTH: 357
<212> TYPE: PRT
<213> ORGANISM: Mus musculus

<400> SEQUENCE: 4

```
Met Leu Leu Phe Ala His Leu Leu Gln Leu Leu Val Ser Ala Thr Val
1               5                   10                  15

Pro Thr Gln Ser Ser Pro His Ser Leu Arg Tyr Phe Thr Thr Ala Val
            20                  25                  30

Ser Arg Pro Gly Leu Gly Glu Pro Arg Phe Ile Ile Val Gly Tyr Val
        35                  40                  45

Asp Asp Thr Gln Phe Val Arg Phe Asp Ser Asp Ala Glu Asn Pro Arg
    50                  55                  60

Met Glu Pro Arg Ala Arg Trp Ile Glu Gln Gly Pro Glu Tyr Trp
65                  70                  75                  80

Glu Arg Glu Thr Trp Lys Ala Arg Asp Met Gly Arg Asn Phe Arg Val
                85                  90                  95

Asn Leu Arg Thr Leu Leu Gly Tyr Tyr Asn Gln Ser Asn Asp Glu Ser
            100                 105                 110

His Thr Leu Gln Trp Met Tyr Gly Cys Asp Val Gly Pro Asp Gly Arg
        115                 120                 125

Leu Leu Arg Gly Tyr Cys Gln Glu Ala Tyr Asp Gly Gln Asp Tyr Ile
    130                 135                 140

Ser Leu Asn Glu Asp Leu Arg Ser Trp Thr Ala Asn Asp Ile Ala Ser
145                 150                 155                 160

Gln Ile Ser Lys His Lys Ser Glu Ala Val Asp Glu Ala His Gln Gln
                165                 170                 175

Arg Ala Tyr Leu Gln Gly Pro Cys Val Glu Trp Leu His Arg Tyr Leu
            180                 185                 190

Arg Leu Gly Asn Glu Thr Leu Gln Arg Ser Asp Pro Pro Lys Ala His
        195                 200                 205

Val Thr His His Pro Arg Ser Glu Asp Glu Val Thr Leu Arg Cys Trp
    210                 215                 220
```

```
Ala Leu Gly Phe Tyr Pro Ala Asp Ile Thr Leu Thr Trp Gln Leu Asn
225                 230                 235                 240
Gly Glu Glu Leu Thr Gln Asp Met Glu Leu Val Glu Thr Arg Pro Ala
            245                 250                 255
Gly Asp Gly Thr Phe Gln Lys Trp Ala Ala Val Val Pro Leu Gly
            260                 265                 270
Lys Glu Gln Tyr Tyr Thr Cys His Val Tyr His Glu Gly Leu Pro Glu
        275                 280                 285
Pro Leu Thr Leu Arg Trp Glu Pro Pro Ser Thr Val Ser Asn Met
    290                 295                 300
Val Ile Ile Ala Val Leu Val Val Leu Gly Ala Val Ile Ile Leu Gly
305                 310                 315                 320
Ala Val Val Ala Phe Val Met Lys Arg Arg Arg His Ile Gly Val Lys
                325                 330                 335
Gly Cys Tyr Ala His Val Leu Gly Ser Lys Ser Phe Gln Thr Ser Asp
            340                 345                 350
Trp Pro Gln Lys Ala
        355

<210> SEQ ID NO 5
<211> LENGTH: 1289
<212> TYPE: DNA
<213> ORGANISM: Mus musculus

<400> SEQUENCE: 5
```

| | | | | | |
|---|---|---|---|---|---|
| acagacccag | ggagtgagga | tgttgctttt | tgcccacttg | ctccagctgc | tggtcagcgc | 60 |
| cacagtcccg | acccagagta | gctcacactc | gctgcggtat | ttccacaccg | tcgtatcccg | 120 |
| gcccggcctc | ggagagcccc | ggttcatcat | tgtcggctac | gtggacgaca | cgcagttcgt | 180 |
| gcgcttcgac | agcgactcgg | agaatccgag | gatggagcct | cgggcgcggt | ggattgagca | 240 |
| ggaggggccg | gagtattggg | agcgggagac | tcggaaagcc | agggacatgg | ggaggaactt | 300 |
| cagagtaaac | ctgaggaccc | tgctcggcta | ctacaatcag | agtaaggacg | aatctcacac | 360 |
| gctgcagtgg | atgtacggct | gcgacgtggg | gcccgatggg | cgcctgctcc | gcggtattg | 420 |
| tcaggaggcc | tatgatggcc | aggattacat | ctccctgaac | gaagacctgc | gctcctggac | 480 |
| cgcgaccaac | ttagcctcgc | atatctctaa | gtgcaagtca | gaggcggtcg | atgaggccca | 540 |
| ccaacagagg | gcatacctgc | aaggtccttg | cgtggagtgg | ctccatacat | acctacagct | 600 |
| gggaagtgag | acactgctgc | gctcagaccc | tccaaaggca | catgtgaccc | gtcaccccag | 660 |
| acctgaaggt | gatgtcaccc | tgaggtgctg | ggccctgggc | ttctatcctg | ctgacatcac | 720 |
| cctgacctgg | cagttgaatg | ggaggagct | gacccaggac | atggagtttg | tggagaccag | 780 |
| gcctgcaggg | gatggaacct | tccagaagtg | gcatctgtg | gtggtgcctc | ttgggaagga | 840 |
| gcagaattac | acatgccatg | tgtaccatga | ggggctgcct | gagcccctca | ccctgagatg | 900 |
| ggagcctcct | ccatccactg | tctccaacat | ggtaatcatt | gctgttctgg | ttgtccttgg | 960 |
| agctgtgata | gtcattgttg | ctgtggtggc | ttttgtaatg | aagaggagga | aaacacaggt | 1020 |
| gtaaaaggat | gctatgctca | tgttctaggc | agcaagagct | tccagacctc | tgactggcct | 1080 |
| cagaaggcat | gacaatccct | gggggcctgg | gactggacct | gaggcacaag | ggagaccggg | 1140 |
| gttcaattcc | tagcactgac | atggcaggtg | tctgttacta | gtaacaaaca | gttcatgtct | 1200 |
| catgaatgta | gacatgaatg | cagctaaagc | accaacatac | ataatattaa | acctttaaaa | 1260 |
| aaataaaagg | tgtatgagct | ggacaaaca | | | | 1289 |

```
<210> SEQ ID NO 6
<211> LENGTH: 334
<212> TYPE: PRT
<213> ORGANISM: Mus musculus

<400> SEQUENCE: 6

Met Leu Leu Phe Ala His Leu Leu Gln Leu Val Ser Ala Thr Val
1               5                   10                  15

Pro Thr Gln Ser Ser Ser His Ser Leu Arg Tyr Phe His Thr Val Val
            20                  25                  30

Ser Arg Pro Gly Leu Gly Glu Pro Arg Phe Ile Ile Val Gly Tyr Val
            35                  40                  45

Asp Asp Thr Gln Phe Val Arg Phe Asp Ser Asp Ser Glu Asn Pro Arg
        50                  55                  60

Met Glu Pro Arg Ala Arg Trp Ile Glu Gln Gly Pro Glu Tyr Trp
65                  70                  75                  80

Glu Arg Glu Thr Arg Lys Ala Arg Asp Met Gly Arg Asn Phe Arg Val
                85                  90                  95

Asn Leu Arg Thr Leu Leu Gly Tyr Tyr Asn Gln Ser Lys Asp Glu Ser
            100                 105                 110

His Thr Leu Gln Trp Met Tyr Gly Cys Asp Val Gly Pro Asp Gly Arg
        115                 120                 125

Leu Leu Arg Gly Tyr Cys Gln Glu Ala Tyr Asp Gly Gln Asp Tyr Ile
    130                 135                 140

Ser Leu Asn Glu Asp Leu Arg Ser Trp Thr Ala Thr Asn Leu Ala Ser
145                 150                 155                 160

His Ile Ser Lys Cys Lys Ser Glu Ala Val Asp Glu Ala His Gln Gln
                165                 170                 175

Arg Ala Tyr Leu Gln Gly Pro Cys Val Glu Trp Leu His Thr Tyr Leu
            180                 185                 190

Gln Leu Gly Ser Glu Thr Leu Leu Arg Ser Asp Pro Pro Lys Ala His
        195                 200                 205

Val Thr Arg His Pro Arg Pro Glu Gly Asp Val Thr Leu Arg Cys Trp
    210                 215                 220

Ala Leu Gly Phe Tyr Pro Ala Asp Ile Thr Leu Thr Trp Gln Leu Asn
225                 230                 235                 240

Gly Glu Glu Leu Thr Gln Asp Met Glu Phe Val Glu Thr Arg Pro Ala
                245                 250                 255

Gly Asp Gly Thr Phe Gln Lys Trp Ala Ser Val Val Pro Leu Gly
            260                 265                 270

Lys Glu Gln Asn Tyr Thr Cys His Val Tyr His Glu Gly Leu Pro Glu
        275                 280                 285

Pro Leu Thr Leu Arg Trp Glu Pro Pro Ser Thr Val Ser Asn Met
    290                 295                 300

Val Ile Ile Ala Val Leu Val Val Leu Gly Ala Val Ile Val Ile Val
305                 310                 315                 320

Ala Val Val Ala Phe Val Met Lys Arg Arg Lys Thr Gln Val
                325                 330

<210> SEQ ID NO 7
<211> LENGTH: 3060
<212> TYPE: DNA
<213> ORGANISM: Homo sapiens

<400> SEQUENCE: 7
```

```
gccgggtttg ggggttggga cctccggctg caggtccgcc tgggccagac gcgcgagcgc    60
aagcagcggg ttagtggtcg cgcgcccgac ctccgcagtc ccagccgagc cgcgaccctt   120
ccggccgtcc ccaccccacc tcgccgccat gcgcctccgc cgcctagcgc tgttcccggg   180
tgtggcgctg cttcttgccg cggcccgcct cgccgctgcc tccgacgtgc tagaactcac   240
ggacgacaac ttcgagagtc gcatctccga cacgggctct gcgggcctca tgctcgtcga   300
gttcttcgcc ccctggtgtg gacactgcaa gagacttgca cctgagtatg aagctgcagc   360
taccagatta aaaggaatag tcccattagc aaaggttgat tgcactgcca acactaacac   420
ctgtaataaa tatggagtca gtggatatcc aaccctgaag atatttagag atggtgaaga   480
agcaggtgct tatgatggac ctaggactgc tgatggaatt gtcagccact gaagaagca    540
ggcaggacca gcttcagtgc ctctcaggac tgaggaagaa tttaagaaat tcattagtga   600
taaagatgcc tctatagtag gttttttcga tgattcattc agtgaggctc actccgagtt   660
cctaaaagca gccagcaact gagggataa ctaccgattt gcacatacga atgttgagtc    720
tctggtgaac gagtatgatg ataatggaga gggtatcatc ttatttcgtc cttcacatct   780
cactaacaag tttgaggaca agactgtggc atatacagag caaaaaatga ccagtggcaa   840
aattaaaaag tttatccagg aaaacatttt tggtatctgc cctcacatga cagaagacaa   900
taaagatttg atacagggca aggacttact tattgcttac tatgatgtgg actatgaaaa   960
gaacgctaaa ggttccaact actggagaaa cagggtaatg atggtggcaa agaaattcct  1020
ggatgctggg cacaaactca actttgctgt agctagccgc aaaaccttta gccatgaact  1080
ttctgatttt ggcttggaga gcactgctgg agagattcct gttgttgcta tcagaactgc  1140
taaaggagag aagtttgtca tgcaggagga gttctcgcgt gatgggaagg ctctggagag  1200
gttcctgcag gattactttg atggcaatct gaagagatac ctgaagtctg aacctatccc  1260
agagagcaat gatgggcctg tgaaggtagt ggtagcagag aattttgatg aaatagtgaa  1320
taatgaaaat aaagatgtgc tgattgaatt ttatgcccct tggtgtggtc actgtaagaa  1380
cctggagccc aagtataaag aacttggcga gaagctcagc aaagacccaa atatcgtcat  1440
agccaagatg gatgccacag ccaatgatgt gccttctcca tatgaagtca gaggttttcc  1500
taccatatac ttctctccag ccaacaagaa gctaaatcca agaaatatg aaggtggccg   1560
tgaattaagt gattttatta gctatctaca aagagaagct acaaaccccc ctgtaattca  1620
agaagaaaaa cccaagaaga agaagaaggc acaggaggat ctctaaagca gtagccaaac  1680
accactttgt aaaaggactc ttccatcaga gatgggaaaa ccattgggga ggactaggac  1740
ccatatggga attattacct ctcagggccg agaggacaga atggatataa tctgaatcct  1800
gttaaatttt ctctaaactg tttcttagct gcactgttta tggaaatacc aggaccagtt  1860
tatgtttgtg gttttgggaa aaattatttg tgttggggga atgttgtgg gggtggggtt  1920
gagttggggg tattttctaa ttttttttgt acatttggaa cagtgacaat aaatgagacc  1980
cctttaaact gtcttatttt ccaccagatt gagaaccaga tgttctctac acactatcac  2040
tgttcaatag agctttcttc agtgatggaa atgctctgta atctacactg ttcagtacag  2100
gtagctacgg agcatctgaa atatggctag aaactacatt tttgtttga ttaatttaaa   2160
tagccataca gttgctacca tactggtcac ggcagctgta gactgactgg gtccatagtt  2220
catcacctca aaattctttc aaaatttatt atctctttct ctccttacat gtttatttcc  2280
caggcctacc ctggtgatta gaacagctga agggcctttt tgttaggct gtccatgccc   2340
taaggatggg ttcctgttta tccttgccac gcagctgagc ttactgcatg tttatatctc  2400
```

```
ccaaggactg ttctctgctc agaaatgccc tgtcaagggt gtggcatcac gcagtttcat    2460
ccaagttgtt tcaggaattg ctgacactgc tgggtgcagt tctatcccct aaagcctagg    2520
gtgtggccct ttaacttccc cttcagtaga actgggaaag gcagtaccat tcctagttat    2580
gagtgaagca tccactttct tttgtaacaa tgaggaacag aaaggataag actgaagagt    2640
gatcttttgt ccaactaaac catttatctc cttttgtagg taaattcaaa tcctgcccag    2700
ttatagtttt cagtcactgg agaattccag gtaggagccc tactttaggt gatcctagga    2760
actcctatgt tcagaaaaga attttcttcc tactatataa ttacagtatt tagctgtcaa    2820
ttttaagatg aatttggtag agccttatag taaagtatgt atcttggtca cacacaaagc    2880
ttggaaaaag taaagatgt ctaaaccata atcttgtaac tcataacatc tgggctgggg    2940
cccggggatc taattgttta gagagcccca aaagtggctc agatgtaaag ccaggggttaa    3000 gaaccatctg ccttggaaga tttaagggaa acatataaac ttgtacaaag gacaaaaaaa    3060
```

<210> SEQ ID NO 8
<211> LENGTH: 505
<212> TYPE: PRT
<213> ORGANISM: Homo sapiens

<400> SEQUENCE: 8

```
Met Arg Leu Arg Arg Leu Ala Leu Phe Pro Gly Val Ala Leu Leu Leu
1               5                   10                  15

Ala Ala Ala Arg Leu Ala Ala Ala Ser Asp Val Leu Glu Leu Thr Asp
                20                  25                  30

Asp Asn Phe Glu Ser Arg Ile Ser Asp Thr Gly Ser Ala Gly Leu Met
            35                  40                  45

Leu Val Glu Phe Phe Ala Pro Trp Cys Gly His Cys Lys Arg Leu Ala
        50                  55                  60

Pro Glu Tyr Glu Ala Ala Ala Thr Arg Leu Lys Gly Ile Val Pro Leu
65                  70                  75                  80

Ala Lys Val Asp Cys Thr Ala Asn Thr Asn Thr Cys Asn Lys Tyr Gly
                85                  90                  95

Val Ser Gly Tyr Pro Thr Leu Lys Ile Phe Arg Asp Gly Glu Glu Ala
            100                 105                 110

Gly Ala Tyr Asp Gly Pro Arg Thr Ala Asp Gly Ile Val Ser His Leu
        115                 120                 125

Lys Lys Gln Ala Gly Pro Ala Ser Val Pro Leu Arg Thr Glu Glu Glu
    130                 135                 140

Phe Lys Lys Phe Ile Ser Asp Lys Asp Ala Ser Ile Val Gly Phe Phe
145                 150                 155                 160

Asp Asp Ser Phe Ser Glu Ala His Ser Glu Phe Leu Lys Ala Ala Ser
                165                 170                 175

Asn Leu Arg Asp Asn Tyr Arg Phe Ala His Thr Asn Val Glu Ser Leu
            180                 185                 190

Val Asn Glu Tyr Asp Asp Asn Gly Glu Gly Ile Ile Leu Phe Arg Pro
        195                 200                 205

Ser His Leu Thr Asn Lys Phe Glu Asp Lys Thr Val Ala Tyr Thr Glu
    210                 215                 220

Gln Lys Met Thr Ser Gly Lys Ile Lys Lys Phe Ile Gln Glu Asn Ile
225                 230                 235                 240

Phe Gly Ile Cys Pro His Met Thr Glu Asp Asn Lys Asp Leu Ile Gln
                245                 250                 255
```

Gly Lys Asp Leu Leu Ile Ala Tyr Tyr Asp Val Asp Tyr Glu Lys Asn
            260                 265                 270

Ala Lys Gly Ser Asn Tyr Trp Arg Asn Arg Val Met Met Val Ala Lys
        275                 280                 285

Lys Phe Leu Asp Ala Gly His Lys Leu Asn Phe Ala Val Ala Ser Arg
    290                 295                 300

Lys Thr Phe Ser His Glu Leu Ser Asp Phe Gly Leu Glu Ser Thr Ala
305                 310                 315                 320

Gly Glu Ile Pro Val Ala Ile Arg Thr Ala Lys Gly Glu Lys Phe
                325                 330                 335

Val Met Gln Glu Glu Phe Ser Arg Asp Gly Lys Ala Leu Glu Arg Phe
            340                 345                 350

Leu Gln Asp Tyr Phe Asp Gly Asn Leu Lys Arg Tyr Leu Lys Ser Glu
        355                 360                 365

Pro Ile Pro Glu Ser Asn Asp Gly Pro Val Lys Val Val Ala Glu
    370                 375                 380

Asn Phe Asp Glu Ile Val Asn Asn Glu Asn Lys Asp Val Leu Ile Glu
385                 390                 395                 400

Phe Tyr Ala Pro Trp Cys Gly His Cys Lys Asn Leu Glu Pro Lys Tyr
                405                 410                 415

Lys Glu Leu Gly Glu Lys Leu Ser Lys Asp Pro Asn Ile Val Ile Ala
            420                 425                 430

Lys Met Asp Ala Thr Ala Asn Asp Val Pro Ser Pro Tyr Glu Val Arg
        435                 440                 445

Gly Phe Pro Thr Ile Tyr Phe Ser Pro Ala Asn Lys Lys Leu Asn Pro
    450                 455                 460

Lys Lys Tyr Glu Gly Gly Arg Glu Leu Ser Asp Phe Ile Ser Tyr Leu
465                 470                 475                 480

Gln Arg Glu Ala Thr Asn Pro Pro Val Ile Gln Glu Glu Lys Pro Lys
                485                 490                 495

Lys Lys Lys Lys Ala Gln Glu Asp Leu
            500                 505

<210> SEQ ID NO 9
<211> LENGTH: 2658
<212> TYPE: DNA
<213> ORGANISM: Mus musculus

<400> SEQUENCE: 9
cgagcaggcc tagggggttg ggacctcggc agcgggtctg cccgggccag acgcgcgagc      60
gcaggcaagc ggctgcagat tgcgggctct cccatctcat ttctccggtc ccggccctcc     120
gaccgcgacc cgccgccatg cgcttcagct gcctagctct gctcccgggc gtggcgctgc     180
tgctcgcctc ggcccgtctc gccgccgcct ccgatgtgtt ggaactgacg gacgaaaact     240
tcgagagtcg cgtctccgac acgggctcgg cggggctcat gctagtcgag ttcttcgccc     300
cctggtgtgg acattgcaag aggcttgccc ctgagtatga agctgcagca accagattaa     360
aaggaatagt cccattagca aaggtggatt gcactgccaa cacaaacacc tgtaataagt     420
atggggtcag tggctacccca actcttaaga tctttagaga tggtgaagaa gcgggtgctt     480
atgatgggcc taggactgct gatggaattg tcagccactt gaagaaacaa gcaggaccag     540
cttcagttcc tctcaggact gaggaagaat ttaagaagtt cattagtgat aaagatgcct     600
cagtggtggg tttttcagg gattattca gtgatgggca ctctgaattc ctaaaagcag     660
ccagcaactt gagagataac taccgatttg cacacaccaa cattgagtct ctggtgaagg     720

```
agtacgatga taatggagag gggatcacta tattccgtcc attacatctt gctaacaagt      780
ttgaagacaa aactgtggca tatactgaaa agaaaatgac cagtggcaag atcaagaaat      840
ttattcagga tagcattttt ggtctctgtc ctcatatgac ggaagataat aaagatttga      900
tacaaggcaa ggacttactc accgcttact atgatgtgga ctatgaaaag aatgctaaag      960
gttctaacta ctggagaaac agggtcatga tggtggcaaa gaaattcctt gatgctggac     1020
acaaactcaa ctttgctgta gctagccgta aacctttag ccatgaactg tcagattttg      1080
gcttagaaag cactactgga gaggttcctg ttgtggctat cagaactgct aaaggagaga     1140
agtttgtcat gcaggaggag ttctcgcgag atggcaaggc tcttgaacag ttcctgcaag     1200
aatactttga tggcaacttg aagagatacc tgaagtctga acccatccca gagtccaacg     1260
aagggcctgt caaggttgtg gtagcagaga attttgatga catagtgaat gaagaagata     1320
aggacgtgct gattgaattt tacgcccctt ggtgtggcca ctgtaagaat ctggaaccca     1380
agtataaaga gctgggagaa aaactcagca agatccaaa tattgtcata gccaagatgg      1440
atgccacagc caatgatgtg ccttctccat atgaagtcaa gggttttcct accatctact     1500
tctcaccagc caacaagaag ctaactccaa agaagtatga aggtggccgt gaattaaatg     1560
attttattag ctatctacaa cgagaagcta caaaccccc tataattcaa gaagaaaaac      1620
ctaagaagaa gaagaaggca caagaggacc tctaaagcaa cagccaaatg caccacttta     1680
taaaaggact cttacaccag agaaggcaaa accagagagg acagaatgga tatactctga     1740
atcctgttaa atttctcta aactgtttct tagctgcact gtttgaaaat acaaggacca      1800
gtttatgttt gtggttttgg gagaaaatta tttgtgttgg gaagaatgtt gtggggtgg      1860 ggggaattga gttgggggt tattttctaa tttttttgt acatttggaa cagtgacaat       1920
aaatgtgccc cctttatact gtcgttttt tcccctcatg ggatggagaa tcagggtctc      1980
taaactgtaa tacagtaata gatagaagtg tttgagctat gctgttcaat gctgtagcta     2040
aaccagatat gttatctcct ataatcgcaa cacttgggag gtgcaggcaa gagatctcaa     2100
gttcaagatc ttccatggct acatagcagg ttttgaggct agcatcttaa acaggtttga     2160
tctttcaaaa acaaagaaaa ccagctatgc tgattcctgt aacttgagac tgaataggtc     2220
cagttaccat ctccaaattg tataattat tagtttcttt ctgtagctca agctgtcctt      2280
gaacttgtga tggtctccct ccctggccct gagatactga gatgacagtt gtttctagcc     2340
tcattcatgt cctaaaggtg aatgcttact cttgccacac agccaagctt tctgcatgtg     2400
catgcctcct gaggatggtt ctctgcccag aaatgccctg tgtgagtgac agcagtttgg     2460
ggttccatcc aattttagga attattgaaa ctgctgggtg cagctctccc caaatcattg     2520
ggtgtagcca tttacttccc tccagtgaac agggaaacag tatcaatcgc tggcaagaac     2580
aagaacccac agagatgttt tcttttgaat ggattaaagt attgccctcc ttttatagct     2640
aaaaaaaaaa aaaaaaaa                                                   2658
```

<210> SEQ ID NO 10  
<211> LENGTH: 505  
<212> TYPE: PRT  
<213> ORGANISM: Mus musculus

<400> SEQUENCE: 10

Met Arg Phe Ser Cys Leu Ala Leu Leu Pro Gly Val Ala Leu Leu Leu  
1               5                   10                  15

Ala Ser Ala Arg Leu Ala Ala Ala Ser Asp Val Leu Glu Leu Thr Asp

```
                    20                  25                  30
Glu Asn Phe Glu Ser Arg Val Ser Asp Thr Gly Ser Ala Gly Leu Met
                    35                  40                  45

Leu Val Glu Phe Phe Ala Pro Trp Cys Gly His Cys Lys Arg Leu Ala
         50                  55                  60

Pro Glu Tyr Glu Ala Ala Thr Arg Leu Lys Gly Ile Val Pro Leu
65                   70                  75                  80

Ala Lys Val Asp Cys Thr Ala Asn Thr Asn Cys Asn Lys Tyr Gly
                     85                  90                  95

Val Ser Gly Tyr Pro Thr Leu Lys Ile Phe Arg Asp Gly Glu Glu Ala
             100                 105                 110

Gly Ala Tyr Asp Gly Pro Arg Thr Ala Asp Gly Ile Val Ser His Leu
             115                 120                 125

Lys Lys Gln Ala Gly Pro Ala Ser Val Pro Leu Arg Thr Glu Glu
             130                 135                 140

Phe Lys Lys Phe Ile Ser Asp Lys Asp Ala Ser Val Val Gly Phe Phe
145                 150                 155                 160

Arg Asp Leu Phe Ser Asp Gly His Ser Glu Phe Leu Lys Ala Ala Ser
                 165                 170                 175

Asn Leu Arg Asp Asn Tyr Arg Phe Ala His Thr Asn Ile Glu Ser Leu
             180                 185                 190

Val Lys Glu Tyr Asp Asp Asn Gly Glu Gly Ile Thr Ile Phe Arg Pro
             195                 200                 205

Leu His Leu Ala Asn Lys Phe Glu Asp Lys Thr Val Ala Tyr Thr Glu
210                 215                 220

Lys Lys Met Thr Ser Gly Lys Ile Lys Lys Phe Ile Gln Asp Ser Ile
225                 230                 235                 240

Phe Gly Leu Cys Pro His Met Thr Glu Asp Asn Lys Asp Leu Ile Gln
                 245                 250                 255

Gly Lys Asp Leu Leu Thr Ala Tyr Tyr Asp Val Asp Tyr Glu Lys Asn
             260                 265                 270

Ala Lys Gly Ser Asn Tyr Trp Arg Asn Arg Val Met Met Val Ala Lys
             275                 280                 285

Lys Phe Leu Asp Ala Gly His Lys Leu Asn Phe Ala Val Ala Ser Arg
             290                 295                 300

Lys Thr Phe Ser His Glu Leu Ser Asp Phe Gly Leu Glu Ser Thr Thr
305                 310                 315                 320

Gly Glu Val Pro Val Val Ala Ile Arg Thr Ala Lys Gly Glu Lys Phe
                 325                 330                 335

Val Met Gln Glu Glu Phe Ser Arg Asp Gly Lys Ala Leu Glu Gln Phe
             340                 345                 350

Leu Gln Glu Tyr Phe Asp Gly Asn Leu Lys Arg Tyr Leu Lys Ser Glu
             355                 360                 365

Pro Ile Pro Glu Ser Asn Glu Gly Pro Val Lys Val Val Ala Glu
             370                 375                 380

Asn Phe Asp Asp Ile Val Asn Glu Glu Asp Lys Asp Val Leu Ile Glu
385                 390                 395                 400

Phe Tyr Ala Pro Trp Cys Gly His Cys Lys Asn Leu Glu Pro Lys Tyr
                 405                 410                 415

Lys Glu Leu Gly Glu Lys Leu Ser Lys Asp Pro Asn Ile Val Ile Ala
             420                 425                 430

Lys Met Asp Ala Thr Ala Asn Asp Val Pro Ser Pro Tyr Glu Val Lys
             435                 440                 445
```

```
Gly Phe Pro Thr Ile Tyr Phe Ser Pro Ala Asn Lys Leu Thr Pro
    450                 455                 460
Lys Lys Tyr Glu Gly Gly Arg Glu Leu Asn Asp Phe Ile Ser Tyr Leu
465                 470                 475                 480
Gln Arg Glu Ala Thr Asn Pro Pro Ile Ile Gln Glu Glu Lys Pro Lys
                485                 490                 495
Lys Lys Lys Lys Ala Gln Glu Asp Leu
            500                 505

<210> SEQ ID NO 11
<211> LENGTH: 1929
<212> TYPE: DNA
<213> ORGANISM: Homo sapiens

<400> SEQUENCE: 11
```

| | | | | | |
|---|---|---|---|---|---|
| gcggcgtccg | tccgtactgc | agagccgctg | ccggagggtc | gttttaaagg | gcccgcgcgt | 60 |
| tgccgccccc | tcggcccgcc | atgctgctat | ccgtgccgct | gctgctcggc | ctcctcggcc | 120 |
| tggccgtcgc | cgagcctgcc | gtctacttca | aggagcagtt | tctggacgga | gacgggtgga | 180 |
| cttcccgctg | gatcgaatcc | aaacacaagt | cagattttgg | caaattcgtt | ctcagttccg | 240 |
| gcaagttcta | cggtgacgag | gagaaagata | aaggtttgca | gacaagccag | gatgcacgct | 300 |
| tttatgctct | gtcggccagt | ttcgagcctt | tcagcaacaa | aggccagacg | ctggtggtgc | 360 |
| agttcacggt | gaaacatgag | cagaacatcg | actgtggggg | cggctatgtg | aagctgtttc | 420 |
| ctaatagttt | ggaccagaca | gacatgcacg | gagactcaga | atacaacatc | atgtttggtc | 480 |
| ccgacatctg | tggccctggc | accaagaagg | ttcatgtcat | cttcaactac | aagggcaaga | 540 |
| acgtgctgat | caacaaggac | atccgttgca | aggatgatga | gtttacacac | ctgtacacac | 600 |
| tgattgtgcg | gccagacaac | acctatgagg | tgaagattga | caacagccag | gtggagtccg | 660 |
| gctccttgga | agacgattgg | gacttcctgc | cacccaagaa | gataaaggat | cctgatgctt | 720 |
| caaaaccgga | agactgggat | gagcgggcca | agatcgatga | tcccacagac | tccaagcctg | 780 |
| aggactggga | caagcccgag | catatccctg | accctgatgc | taagaagccc | gaggactggg | 840 |
| atgaagagat | ggacggagag | tgggaacccc | cagtgattca | gaaccctgag | tacaagggtg | 900 |
| agtggaagcc | ccggcagatc | gacaacccag | attacaaggg | cacttggatc | cacccagaaa | 960 |
| ttgacaaccc | cgagtattct | cccgatccca | gtatctatgc | ctatgataac | tttggcgtgc | 1020 |
| tgggcctgga | cctctggcag | gtcaagtctg | gcaccatctt | tgacaacttc | ctcatcacca | 1080 |
| acgatgaggc | atacgctgag | gagtttggca | acgagacgtg | gggcgtaaca | aaggcagcag | 1140 |
| agaaacaaat | gaaggacaaa | caggacgagg | agcagaggct | taaggaggag | gaagaagaca | 1200 |
| agaaacgcaa | agaggaggag | gaggcagagg | acaaggagga | tgatgaggac | aaagatgagg | 1260 |
| atgaggagga | tgaggaggac | aaggaggaag | atgaggagga | agatgtcccc | ggccaggcca | 1320 |
| aggacgagct | gtagagaggc | ctgcctccag | ggctggactg | aggcctgagc | gctcctgccg | 1380 |
| cagagctggc | cgcgccaaat | aatgtctctg | tgagactcga | gaactttcat | tttttttcag | 1440 |
| gctggttcgg | atttggggtg | gattttggtt | ttgttcccct | cctccactct | ccccacccc | 1500 |
| ctccccgccc | tttttttttt | tttttttaa | actggtattt | tatctttgat | tctccttcag | 1560 |
| ccctcacccc | tggttctcat | ctttcttgat | caacatcttt | tcttgcctct | gtccccttct | 1620 |
| ctcatctctt | agctccccctc | caacctgggg | ggcagtggtg | tggagaagcc | acaggcctga | 1680 |
| gatttcatct | gctctccttc | ctggagccca | gaggagggca | gcagaagggg | gtggtgtctc | 1740 |

```
caaccccca gcactgagga agaacggggc tcttctcatt tcacccctcc ctttctcccc    1800 tgccccagg actgggccac ttctgggtgg ggcagtgggt cccagattgg ctcacactga    1860
gaatgtaaga actacaaaca aaatttctat taaattaaat tttgtgtctc caaaaaaaa    1920 aaaaaaaaa                                                           1929
```

<210> SEQ ID NO 12
<211> LENGTH: 417
<212> TYPE: PRT
<213> ORGANISM: Homo sapiens

<400> SEQUENCE: 12

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335
```

```
Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
    370                 375                 380

Lys Glu Asp Asp Glu Asp Lys Asp Glu Asp Glu Asp Glu Asp
385                 390                 395                 400

Lys Glu Glu Asp Glu Glu Asp Val Pro Gly Gln Ala Lys Asp Glu
                405                 410                 415

Leu

<210> SEQ ID NO 13
<211> LENGTH: 1943
<212> TYPE: DNA
<213> ORGANISM: Mus musculus

<400> SEQUENCE: 13
ggctgtgtca ggttcgggtg agaggtaggt gaatataaat tgaagcggcg gtggccgcgt      60
ccgtcaatac cgcagagccg ctgcctgaag atcgtcttaa aaggcctgtg tgccgccgcc     120
ccctcggccc gccatgctcc tttcggtgcc gctcctgctt ggcctcctcg gcctggccgc     180
cgcagaccct gccatctatt tcaaagagca gttcttggac ggagatgcct ggaccaaccg     240
ctgggtcgaa tccaaacata gtccgatttt ggcaaatttt gtcctcagtt ctggcaaatt     300
ttacggggac ctggagaagg ataaagggct gcagacaagc caagatgccc gattttacgc     360
actgtccgcc aaattcgaac ccttcagcaa taagggccag acactggtgg tacagttcac     420
ggtgaagcat gagcagaata tcgactgtgg ggcggctac gtgaagctgt tccgagtgg     480 tttggaccag aaggacatgc atggagactc agaatataac atcatgtttg gtccggacat     540
ctgcggtcct ggcaccaaga aggttcatgt catctttaac tacaagggca agaatgtgct     600
gatcaacaag gatatccggt gtaaggatga tgaattcaca cacctataca cactgattgt     660
gcggccagac aacaccctat ggagtgaaaat tgacaacagc caggtggagt caggctcctt     720
ggaggatgat tgggactttc tgccacccaa gaagataaag gaccctgatg ctgccaagcc     780
ggaagactgg gatgaacgag ccaagatcga tgaccccaca gattccaagc tgaggactg     840 ggacaagcca gagcacatcc tgaccctga tgctaagaag cctgaggact gggatgaaga     900
gatggatgga gagtgggaac caccagtgat tcaaaatcct gaatacaagg gcgagtggaa     960
accacgtcaa attgacaacc cagattacaa gggtacctgg atacacccag aaattgacaa    1020
ccctgaatac tcccccgatg caaatatcta tgcctatgat agttttgctg tactgggcct    1080
agatctctgg caggtcaagt ccgggacaat ctttgacaat tcctcatca ccaatgatga    1140 ggcctatgca gaggagtttg gcaatgagac gtggggtgtt accaaggctg cagagaagca    1200
gatgaaggac aagcaggatg aggagcagag gcttaaggaa gagaagagg acaagaagcg    1260 taaagaggaa gaagaagctg aggataaaga ggatgatgat gacagagatg aagatgagga    1320
cgaagaagat gagaaggagg aagatgagga agaatcccct ggccaagcca aggatgagct    1380
gtagaggcca caccacctgc cttcagggct ggactgaggc ctgaacaccc tgccgcagag    1440
ctggctgctc ccaataatgt ctctatgaga ctcaagaact tttcattttt tccaggcagg    1500
ttcagatctg gggtagattc tgatttttgtt ccctgcctc cccattacc ccccccctt     1560 tttttttta ctggtgtttg tctttaattc tccttcagcc ctcatctggt ttctcatttt    1620
```

```
tgaatcaaca tcttttcctt ctgtccctcc ctttctccat cttttggtca ctaccctcca    1680
actctaggaa cagggtgta gaggagaagc cctaggcttg agatttcatc tgctctcctt    1740
cctgcatctc agaggagggc aggagaaggg ggtggtgttt ccctccccc cgcactgagg    1800 aagaatgggg ctcttctcat ccccttctc ccttgcccc aggactgggc acttgtggg     1860 gcagccagtt ctagcacagc tcacactgag agtgtaagaa ctacaaacaa aatttctatt   1920
aaattaagtt ttgtgtcttc cct                                            1943
```

```
<210> SEQ ID NO 14
<211> LENGTH: 416
<212> TYPE: PRT
<213> ORGANISM: Mus musculus

<400> SEQUENCE: 14
```

```
Met Leu Leu Ser Val Pro Leu Leu Gly Leu Leu Gly Leu Ala Ala
1               5                   10                  15

Ala Asp Pro Ala Ile Tyr Phe Lys Glu Gln Phe Leu Asp Gly Asp Ala
                20                  25                  30

Trp Thr Asn Arg Trp Val Glu Ser Lys His Lys Ser Asp Phe Gly Lys
            35                  40                  45

Phe Val Leu Ser Ser Gly Lys Phe Tyr Gly Asp Leu Glu Lys Asp Lys
    50                  55                  60

Gly Leu Gln Thr Ser Gln Asp Ala Arg Phe Tyr Ala Leu Ser Ala Lys
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Ser Gly Leu Asp Gln Lys Asp Met His Gly Asp Ser Glu Tyr
    115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
    195                 200                 205

Lys Asp Pro Asp Ala Ala Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
    275                 280                 285

Trp Ile His Pro Glu Ile Asp Asn Pro Glu Tyr Ser Pro Asp Ala Asn
290                 295                 300

Ile Tyr Ala Tyr Asp Ser Phe Ala Val Leu Gly Leu Asp Leu Trp Gln
305                 310                 315                 320
```

```
Val Lys Ser Gly Thr Ile Phe Asp Asn Phe Leu Ile Thr Asn Asp Glu
            325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
            355                 360                 365

Glu Glu Glu Glu Asp Lys Lys Arg Lys Glu Glu Glu Ala Glu Asp
        370                 375                 380

Lys Glu Asp Asp Asp Arg Asp Glu Asp Glu Glu Asp Glu
385                 390                 395                 400

Lys Glu Glu Asp Glu Glu Glu Ser Pro Gly Gln Ala Lys Asp Glu Leu
            405                 410                 415

<210> SEQ ID NO 15
<211> LENGTH: 2974
<212> TYPE: DNA
<213> ORGANISM: Homo sapiens

<400> SEQUENCE: 15
gtgtgcgtga tggagaaaat tgggcaccag ggctgctccc gagattctca gatctgattt      60
ccacgcttgc taccaaaata gtctgggcag gccacttttg gaagtaggcg ttatctagtg     120
agcaggcggc cgctttcgat ttcgctttcc cctaaatggc tgagcttctc gccagcgcag     180
gatcagcctg ttcctgggac tttccgagag ccccgccctc gttcctcccc cagccgcca     240 gtaggggagg actcggcggt acccggagct tcaggcccca ccggggcgcg gagagtccca     300
ggcccggccg ggaccgggac ggcgtccgag tgccaatggc tagctctagg tgtcccgctc     360
cccgcgggtg ccgctgcctc cccggagctt ctctcgcatg gctggggaca gtactgctac     420
ttctcgccga ctgggtgctg ctccggaccg cgctgccccg catattctcc ctgctggtgc     480
ccaccgcgct gccactgctc cgggtctggg cggtgggcct gagccgctgg gccgtgctct     540
ggctgggggc ctgcggggtc ctcagggcaa cggttggctc aagagcgaa aacgcaggtg     600 cccagggctg gctggctgct ttgaagccat tagctgcggc actgggcttg gccctgccgg     660
gacttgcctt gttccgagag ctgatctcat ggggagcccc cgggtccgcg gatagcacca     720
ggctactgca ctggggaagt caccctaccg ccttcgttgt cagttatgca gcggcactgc     780
ccgcagcagc cctgtggcac aaactcggga gcctctgggt gcccggcggt cagggcggct     840
ctggaaaccc tgtgcgtcgg cttctaggct gcctgggctc ggagacgcgc cgcctctcgc     900
tgttcctggt cctggtggtc ctctcctctc ttggggagat ggccattcca ttctttacgg     960
gccgcctcac tgactggatt ctacaagatg gctcagccga taccttcact cgaaacttaa    1020
ctctcatgtc cattctcacc atagccagtg cagtgctgga gttcgtgggt gacgggatct    1080
ataacaacac catgggccac gtgcacagcc acttgcaggg agaggtgttt ggggctgtcc    1140
tgcgccagga gacggagttt ttccaacaga ccagacagg taacatcatg tctcgggtaa    1200
cagaggacac gtccacccctg agtgattctc tgagtgagaa tctgagctta tttctgtggt    1260
acctggtgcg aggcctatgt ctcttgggga tcatgctctg gggatcagtg tccctcacca    1320
tggtcaccct gatcaccctg cctctgcttt tccttctgcc caagaaggtg ggaaaatggt    1380
accagttgct ggaagtgcag gtgcgggaat ctctggcaaa gtccagccag gtggccattg    1440
aggctctgtc ggccatgcct acagttcgaa gctttgccaa cgaggagggc gaagcccaga    1500
agtttaggga aaagctgcaa gaaataaaga cactcaacca gaaggaggct gtggcctatg    1560
```

```
cagtcaactc ctggaccact agtatttcag gtatgctgct gaaagtggga atcctctaca    1620
ttggtgggca gctggtgacc agtggggctg taagcagtgg gaaccttgtc acatttgttc    1680
tctaccagat gcagttcacc caggctgtgg aggtactgct ctccatctac cccagagtac    1740
agaaggctgt gggctcctca gagaaaatat ttgagtacct ggaccgcacc cctcgctgcc    1800
cacccagtgg tctgttgact cccttacact tggagggcct tgtccagttc aagatgtct    1860 cctttgccta cccaaaccgc ccagatgtct tagtgctaca ggggctgaca ttcaccctac    1920
gccctggcga ggtgacggcg ctggtgggac ccaatgggtc tgggaagagc acagtggctg    1980
ccctgctgca gaatctgtac cagcccaccg ggggacagct gctgttggat gggaagcccc    2040
ttccccaata tgagcaccgc tacctgcaca ggcaggtggc tgcagtggga caagagccac    2100
aggtatttgg aagaagtctt caagaaaata ttgcctatgg cctgacccag aagccaacta    2160
tggaggaaat cacagctgct gcagtaaagt ctggggccca tagtttcatc tctggactcc    2220
ctcagggcta tgacacagag gtagacgagg ctgggagcca gctgtcaggg ggtcagcgac    2280
aggcagtggc gttggcccga gcattgatcc ggaaaccgtg tgtacttatc ctggatgatg    2340
ccaccagtgc cctggatgca aacagccagt tacaggtgga gcagctcctg tacgaaagcc    2400
ctgagcggta ctcccgctca gtgcttctca tcacccagca cctcagcctg gtggagcagg    2460
ctgaccacat cctctttctg gaaggaggcg ctatccggga gggggaacc caccagcagc    2520 tcatggagaa aaagggggtgc tactgggcca tggtgcaggc cctgcagat gctccagaat    2580 gaaagccttc tcagacctgc gcactccatc tccctccctt ttcttctctc tgtggtggag    2640
aaccacagct gcagagtagg cagctgcctc caggatgagt tacttgaaat ttgccttgag    2700
tgtgttacct cctttccaag ctcctcgtga taatgcagac ttcctggagt acaaacacag    2760
gatttgtaat tccttactgt aacggagttt agagccaggg ctgatgcttt ggtgtggcca    2820
gcactctgaa actgagaaat gttcagaatg tacggaaaga tgatcagcta ttttcaacat    2880
aactgaaggc atatgctggc ccataaacac cctgtaggtt cttgatattt ataataaaat    2940
tggtgttttg taaaaaaaaa aaaaaaaaaa aaaa                                2974
```

<210> SEQ ID NO 16
<211> LENGTH: 808
<212> TYPE: PRT
<213> ORGANISM: Homo sapiens

<400> SEQUENCE: 16

```
Met Ala Glu Leu Leu Ala Ser Ala Gly Ser Ala Cys Ser Trp Asp Phe
1               5                   10                  15

Pro Arg Ala Pro Pro Ser Phe Pro Pro Ala Ala Ser Arg Gly Gly
            20                  25                  30

Leu Gly Gly Thr Arg Ser Phe Arg Pro His Arg Gly Ala Glu Ser Pro
        35                  40                  45

Arg Pro Gly Arg Asp Arg Asp Gly Val Arg Val Pro Met Ala Ser Ser
    50                  55                  60

Arg Cys Pro Ala Pro Arg Gly Cys Arg Cys Leu Pro Gly Ala Ser Leu
65                  70                  75                  80

Ala Trp Leu Gly Thr Val Leu Leu Leu Ala Asp Trp Val Leu Leu
                85                  90                  95

Arg Thr Ala Leu Pro Arg Ile Phe Ser Leu Leu Val Pro Thr Ala Leu
            100                 105                 110

Pro Leu Leu Arg Val Trp Ala Val Gly Leu Ser Arg Trp Ala Val Leu
        115                 120                 125
```

```
Trp Leu Gly Ala Cys Gly Val Leu Arg Ala Thr Val Gly Ser Lys Ser
        130                 135                 140

Glu Asn Ala Gly Ala Gln Gly Trp Leu Ala Ala Leu Lys Pro Leu Ala
145                 150                 155                 160

Ala Ala Leu Gly Leu Ala Leu Pro Gly Leu Ala Leu Phe Arg Glu Leu
                165                 170                 175

Ile Ser Trp Gly Ala Pro Gly Ser Ala Asp Ser Thr Arg Leu Leu His
                180                 185                 190

Trp Gly Ser His Pro Thr Ala Phe Val Val Ser Tyr Ala Ala Ala Leu
            195                 200                 205

Pro Ala Ala Ala Leu Trp His Lys Leu Gly Ser Leu Trp Val Pro Gly
        210                 215                 220

Gly Gln Gly Gly Ser Gly Asn Pro Val Arg Arg Leu Leu Gly Cys Leu
225                 230                 235                 240

Gly Ser Glu Thr Arg Arg Leu Ser Leu Phe Leu Val Leu Val Leu
                245                 250                 255

Ser Ser Leu Gly Glu Met Ala Ile Pro Phe Phe Thr Gly Arg Leu Thr
                260                 265                 270

Asp Trp Ile Leu Gln Asp Gly Ser Ala Asp Thr Phe Thr Arg Asn Leu
        275                 280                 285

Thr Leu Met Ser Ile Leu Thr Ile Ala Ser Ala Val Leu Glu Phe Val
        290                 295                 300

Gly Asp Gly Ile Tyr Asn Asn Thr Met Gly His Val His Ser His Leu
305                 310                 315                 320

Gln Gly Glu Val Phe Gly Ala Val Leu Arg Gln Glu Thr Glu Phe Phe
                325                 330                 335

Gln Gln Asn Gln Thr Gly Asn Ile Met Ser Arg Val Thr Glu Asp Thr
                340                 345                 350

Ser Thr Leu Ser Asp Ser Leu Ser Glu Asn Leu Ser Leu Phe Leu Trp
            355                 360                 365

Tyr Leu Val Arg Gly Leu Cys Leu Leu Gly Ile Met Leu Trp Gly Ser
        370                 375                 380

Val Ser Leu Thr Met Val Thr Leu Ile Thr Leu Pro Leu Leu Phe Leu
385                 390                 395                 400

Leu Pro Lys Lys Val Gly Lys Trp Tyr Gln Leu Leu Glu Val Gln Val
                405                 410                 415

Arg Glu Ser Leu Ala Lys Ser Ser Gln Val Ala Ile Glu Ala Leu Ser
                420                 425                 430

Ala Met Pro Thr Val Arg Ser Phe Ala Asn Glu Glu Gly Glu Ala Gln
        435                 440                 445

Lys Phe Arg Glu Lys Leu Gln Glu Ile Lys Thr Leu Asn Gln Lys Glu
450                 455                 460

Ala Val Ala Tyr Ala Val Asn Ser Trp Thr Thr Ser Ile Ser Gly Met
465                 470                 475                 480

Leu Leu Lys Val Gly Ile Leu Tyr Ile Gly Gly Gln Leu Val Thr Ser
                485                 490                 495

Gly Ala Val Ser Ser Gly Asn Leu Val Thr Phe Val Leu Tyr Gln Met
            500                 505                 510

Gln Phe Thr Gln Ala Val Glu Val Leu Leu Ser Ile Tyr Pro Arg Val
        515                 520                 525

Gln Lys Ala Val Gly Ser Ser Glu Lys Ile Phe Glu Tyr Leu Asp Arg
530                 535                 540
```

-continued

| | | | | | | | | | | | | |
|---|---|---|---|---|---|---|---|---|---|---|---|---|
| Thr | Pro | Arg | Cys | Pro | Pro | Ser | Gly | Leu | Leu | Thr | Pro | Leu | His | Leu | Glu |
| 545 | | | | 550 | | | | | 555 | | | | | 560 | |

Gly Leu Val Gln Phe Gln Asp Val Ser Phe Ala Tyr Pro Asn Arg Pro
               565                      570                     575

Asp Val Leu Val Leu Gln Gly Leu Thr Phe Thr Leu Arg Pro Gly Glu
        580                         585                       590

Val Thr Ala Leu Val Gly Pro Asn Gly Ser Gly Lys Ser Thr Val Ala
     595                       600                    605

Ala Leu Leu Gln Asn Leu Tyr Gln Pro Thr Gly Gly Gln Leu Leu Leu
        610                     615                  620

Asp Gly Lys Pro Leu Pro Gln Tyr Glu His Arg Tyr Leu His Arg Gln
625                  630                    635                640

Val Ala Ala Val Gly Gln Glu Pro Gln Val Phe Gly Arg Ser Leu Gln
             645                    650                  655

Glu Asn Ile Ala Tyr Gly Leu Thr Gln Lys Pro Thr Met Glu Glu Ile
            660                  665                670

Thr Ala Ala Val Lys Ser Gly Ala His Ser Phe Ile Ser Gly Leu
     675                      680                  685

Pro Gln Gly Tyr Asp Thr Glu Val Asp Glu Ala Gly Ser Gln Leu Ser
   690                     695                  700

Gly Gly Gln Arg Gln Ala Val Ala Leu Ala Arg Ala Leu Ile Arg Lys
705                  710                  715          720

Pro Cys Val Leu Ile Leu Asp Asp Ala Thr Ser Ala Leu Asp Ala Asn
                 725                  730              735

Ser Gln Leu Gln Val Glu Gln Leu Leu Tyr Glu Ser Pro Glu Arg Tyr
          740                    745                750

Ser Arg Ser Val Leu Leu Ile Thr Gln His Leu Ser Leu Val Glu Gln
             755                  760              765

Ala Asp His Ile Leu Phe Leu Glu Gly Gly Ala Ile Arg Glu Gly Gly
        770                     775                  780

Thr His Gln Gln Leu Met Glu Lys Lys Gly Cys Tyr Trp Ala Met Val
785                  790                  795          800

Gln Ala Pro Ala Asp Ala Pro Glu
          805

<210> SEQ ID NO 17
<211> LENGTH: 2234
<212> TYPE: DNA
<213> ORGANISM: Homo sapiens

<400> SEQUENCE: 17

```
gctctggggc cgaagggcgg ggcatcctca tctctaacag gaggcttttc tacttcatga      60
tctccagcct tcctaataaa atcctgaaag ttctggtaga gcaaccacag ggtagtgagt     120
tccagggcag cctatttagg ttcgggattg agacgtcagt gtttcctttc tgctgatgcc     180
ctccaggata atgggagat ggccattcca ttctttacgg ccgcctcac tgactggatt      240 ctacaagatg gctcagccga taccttcact cgaaacttaa ctctcatgtc cattctcacc     300
atagccagtg cagtgctgga gttcgtgggt gacgggatct ataacaacac catgggccac     360
gtgcacagcc acttgcaggg agaggtgttt ggggctgtcc tgcgccagga gacggagttt     420
ttccaacaga accagacagg taacatcatg tctcgggtaa cagaggacac gtccacactg     480
agtgattctc tgagtgagaa tctgagctta tttctgtggt acctggtgcg aggcctatgt     540
ctcttgggga tcatgctctg gggatcagtg tccctcacca tggtcaccct gatcaccctg     600
```

```
cctctgctttt tccttctgcc caagaaggtg ggaaaatggt accagttgct ggaagtgcag      660
gtgcgggaat ctctggcaaa gtccagccag gtggccattg aggctctgtc ggccatgcct      720
acagttcgaa gctttgccaa cgaggagggc gaagcccaga agtttaggga aaagctgcaa      780
gaaataaaga cactcaacca gaaggaggct gtggcctatg cagtcaactc ctggaccact      840
agtatttcag gtatgctgct gaaagtggga atcctctaca ttggtgggca gctggtgacc      900 agtgggctg taagcagtgg gaaccttgtc acatttgttc tctaccagat gcagttcacc      960
caggctgtgg aggtactgct ctccatctac cccagagtac agaaggctgt gggctcctca     1020
gagaaaatat ttgagtacct ggaccgcacc cctcgctgcc cacccagtgg tctgttgact     1080
cccttacact tggagggcct tgtccagttc aagatgtct cctttgccta cccaaaccgc      1140
ccagatgtct tagtgctaca ggggctgaca ttcaccctac gccctggcga ggtgacggcg     1200
ctggtgggac ccaatgggtc tgggaagagc acagtggctg ccctgctgca gaatctgtac     1260
cagcccaccg ggggacagct gctgttggat gggaagcccc ttccccaata tgagcaccgc     1320
tacctgcaca ggcaggtggc tgcagtggga caagagccac aggtatttgg aagaagtctt     1380
caagaaaata ttgcctatgg cctgacccag aagccaacta tggaggaaat cacagctgct     1440
gcagtaaagt ctggggccca tagtttcatc tctggactcc ctcagggcta tgacacagag     1500
gtagacgagg ctgggagcca gctgtcaggg ggtcagcgac aggcagtggc gttggcccga     1560
gcattgatcc ggaaaccgtg tgtacttatc ctggatgatg ccaccagtgc cctggatgca     1620
aacagccagt tacaggtgga gcagctcctg tacgaaagcc ctgagcggta ctcccgctca     1680
gtgcttctca tcacccagca cctcagcctg gtggagcagg ctgaccacat cctctttctg     1740
gaaggaggcg ctatccggga gggggaacc caccagcagc tcatggagaa aaggggtgc      1800 tactgggcca tggtgcaggc tcctgcagat gctccagaat gaaagccttc tcagacctgc     1860
gcactccatc tccctccctt ttcttctctc tgtggtggag aaccacagct gcagagtagg     1920
cagctgcctc caggatgagt tacttgaaat ttgccttgag tgtgttacct cctttccaag     1980
ctcctcgtga taatgcagac ttcctggagt acaaacacag gatttgtaat tccttactgt     2040
aacggagttt agagccaggg ctgatgcttt ggtgtggcca gcactctgaa actgagaaat     2100
gttcagaatg tacggaaaga tgatcagcta ttttcaacat aactgaaggc atatgctggc     2160
ccataaacac cctgtaggtt cttgatattt ataataaaat tggtgttttg taaaaaaaaa     2220
aaaaaaaaaa aaaa                                                      2234
```

<210> SEQ ID NO 18
<211> LENGTH: 547
<212> TYPE: PRT
<213> ORGANISM: Homo sapiens

<400> SEQUENCE: 18

```
Met Ala Ile Pro Phe Phe Thr Gly Arg Leu Thr Asp Trp Ile Leu Gln
1               5                   10                  15

Asp Gly Ser Ala Asp Thr Phe Thr Arg Asn Leu Thr Leu Met Ser Ile
            20                  25                  30

Leu Thr Ile Ala Ser Ala Val Leu Glu Phe Val Gly Asp Gly Ile Tyr
        35                  40                  45

Asn Asn Thr Met Gly His Val His Ser His Leu Gln Gly Glu Val Phe
    50                  55                  60

Gly Ala Val Leu Arg Gln Glu Thr Glu Phe Phe Gln Gln Asn Gln Thr
65                  70                  75                  80
```

-continued

Gly Asn Ile Met Ser Arg Val Thr Glu Asp Thr Ser Thr Leu Ser Asp
                 85                  90                  95

Ser Leu Ser Glu Asn Leu Ser Leu Phe Leu Trp Tyr Leu Val Arg Gly
            100                 105                 110

Leu Cys Leu Leu Gly Ile Met Leu Trp Gly Ser Val Ser Leu Thr Met
            115                 120                 125

Val Thr Leu Ile Thr Leu Pro Leu Leu Phe Leu Pro Lys Lys Val
        130                 135                 140

Gly Lys Trp Tyr Gln Leu Glu Val Gln Arg Glu Ser Leu Ala
145                 150                 155                 160

Lys Ser Ser Gln Val Ala Ile Glu Ala Leu Ser Ala Met Pro Thr Val
            165                 170                 175

Arg Ser Phe Ala Asn Glu Glu Gly Glu Ala Gln Lys Phe Arg Glu Lys
            180                 185                 190

Leu Gln Glu Ile Lys Thr Leu Asn Gln Lys Glu Ala Val Ala Tyr Ala
            195                 200                 205

Val Asn Ser Trp Thr Thr Ser Ile Ser Gly Met Leu Leu Lys Val Gly
        210                 215                 220

Ile Leu Tyr Ile Gly Gly Gln Leu Val Thr Ser Gly Ala Val Ser Ser
225                 230                 235                 240

Gly Asn Leu Val Thr Phe Val Leu Tyr Gln Met Gln Phe Thr Gln Ala
            245                 250                 255

Val Glu Val Leu Leu Ser Ile Tyr Pro Arg Val Gln Lys Ala Val Gly
            260                 265                 270

Ser Ser Glu Lys Ile Phe Glu Tyr Leu Asp Arg Thr Pro Arg Cys Pro
        275                 280                 285

Pro Ser Gly Leu Leu Thr Pro Leu His Leu Glu Gly Leu Val Gln Phe
        290                 295                 300

Gln Asp Val Ser Phe Ala Tyr Pro Asn Arg Pro Asp Val Leu Val Leu
305                 310                 315                 320

Gln Gly Leu Thr Phe Thr Leu Arg Pro Gly Glu Val Thr Ala Leu Val
            325                 330                 335

Gly Pro Asn Gly Ser Gly Lys Ser Thr Val Ala Ala Leu Leu Gln Asn
        340                 345                 350

Leu Tyr Gln Pro Thr Gly Gly Gln Leu Leu Leu Asp Gly Lys Pro Leu
        355                 360                 365

Pro Gln Tyr Glu His Arg Tyr Leu His Arg Gln Val Ala Ala Val Gly
        370                 375                 380

Gln Glu Pro Gln Val Phe Gly Arg Ser Leu Gln Glu Asn Ile Ala Tyr
385                 390                 395                 400

Gly Leu Thr Gln Lys Pro Thr Met Glu Glu Ile Thr Ala Ala Ala Val
            405                 410                 415

Lys Ser Gly Ala His Ser Phe Ile Ser Gly Leu Pro Gln Gly Tyr Asp
            420                 425                 430

Thr Glu Val Asp Glu Ala Gly Ser Gln Leu Ser Gly Gly Gln Arg Gln
            435                 440                 445

Ala Val Ala Leu Ala Arg Ala Leu Ile Arg Lys Pro Cys Val Leu Ile
        450                 455                 460

Leu Asp Asp Ala Thr Ser Ala Leu Asp Ala Asn Ser Gln Leu Gln Val
465                 470                 475                 480

Glu Gln Leu Leu Tyr Glu Ser Pro Glu Arg Tyr Ser Arg Ser Val Leu
            485                 490                 495

Leu Ile Thr Gln His Leu Ser Leu Val Glu Gln Ala Asp His Ile Leu

```
                500              505              510
Phe Leu Glu Gly Gly Ala Ile Arg Glu Gly Gly Thr His Gln Gln Leu
            515              520              525

Met Glu Lys Lys Gly Cys Tyr Trp Ala Met Val Gln Ala Pro Ala Asp
    530              535              540

Ala Pro Glu
545

<210> SEQ ID NO 19
<211> LENGTH: 2950
<212> TYPE: DNA
<213> ORGANISM: Mus musculus

<400> SEQUENCE: 19
gaggagaatg agattcatgg agaagaacac gacaggccag ggctgctagg cagaactcca      60
actacagctt cagcggcagc ttccagaaca gcctgagcaa gccagtctca gaaggaggcg     120
tgtctagtga ttcgaggtcg gctttcggtt tcttcttcct ctaaacgcca gcacttctag     180
tcagctccac cagctcgagc gggttcccgg gactttacgc gcacgccctc ggacccgccc     240
ttcttccttc cccacggaga ctcctgtgca gcgcggacgt cgagagtccc aggctaggac     300
cagactctgg acagctcacg ctcgatggct gcgcacgtct ggctggcggc cgccctgctc     360
cttctggtgg actggctgct gctgcggccc atgctcccgg gaatcttctc cctgttggtt     420
cccgaggtgc cgctgctccg ggtctgggtg gtgggcctga gtcgctgggc catcctagga     480
ctaggggtcc gcggggtcct cggggtcacc gcaggagccc atggctggct ggctgctttg     540
cagccgctgg tggccgcact gagtttggcc ctgcctggac ttgccttgtt ccgagagctg     600
gccgcctggg gaacactccg ggagggtgac agcgctggat tactgtactg gaacagtcgt     660
ccagatgcct tcgctatcag ttatgtggca gcattgcccg cagccgccct gtggcacaag     720
ttggggagcc tctgggcgcc cagcggcaac agggacgctg agacatgct gtgtcggatg      780 ctgggcttcc tgggccctaa gagagacgt ctctacctgg ttctggttct cttgattctc      840
tcttgccttg gggaaatggc cattcccttc ttcacgggcc gcatcactga ctggattctt     900
caggataaga cagttcctag cttcacccgc aacatatggc tcatgtccat ctctcaccata     960 gccagcacag cgctggagtt tgcaagtgat ggaatctaca acatcaccat gggacacatg    1020
cacggccgtg tgcacagaga ggtgtttcgg gccgtccttc gccaggagac agggtttttc    1080
ctgaagaacc cagcaggttc catcacatct cgggtgactg aggacacagc caacgtgtgc    1140
gagtccatta gtggcacgct gagcctgctg ctgtggtacc tggggcgagc cctgtgtctc    1200
ttggtgttca tgttttgggg gtcaccgtac ctcactctgg tcaccctgat caacctgccc    1260 ctgcttttc ttttgcctaa gaagctggga aaagtgcatc agtcactggc agtgaaggtg     1320
caggagtctc tagcaaagtc cacgcaggtg gcccttgagg ccttatcggc gatgcctact    1380
gtgcggagct tgccaacga ggagggtgag gcccagaagt tcaggcagaa gttggaagaa     1440
atgaagactc taaacaagaa ggaggccttg gcttacgtgg ctgaagtctg gaccacgagt    1500
gtctcgggaa tgctgctgaa ggtgggaatt ctgtacctgg gcgggcagct ggtgatcaga    1560
ggggctgtca gcagcggcaa ccttgtctca ttcgttctct accagcttca gttcacccag    1620
gctgttcagg tcctgctctc cctctacccc tccatgcaga aggctgtggg ctcctcagag    1680
aaaatattcg aatacttgga ccggactcct tgctctccac tcagtggctc gttgcaccc     1740 tcaaacatga aaggccttgt ggagttccaa gatgtctctt ttgcctaccc aaaccagccc    1800
```

-continued

```
aaagtccagg tgcttcaggg gctgacgttc accctgcatc ctggaacggt gacagcgttg    1860
gtgggaccca atggatcagg gaagagcacc gtggctgccc tgctgcagaa cctgtaccag    1920
cccaccgggg gccagctgct gctggatggc cagtgcctgg tccagtatga tcaccattac    1980
ctgcacactc aggtggccgc agtgggacaa gagccgctgc tatttggaag aagctttcga    2040
gaaaatattg cgtatggcct gaaccggact ccaaccatgg aggaaatcac agctgtggcc    2100
gtggagtctg gagcccacga tttcatctct gggttccctc agggctatga cacagaggta    2160
ggtgagactg ggaaccagct gtcaggaggt cagcgacagg cagtggcctt ggcccgagcc    2220
ttgatccgga agccactcct gcttatcttg gatgatgcca ccagtgccct ggatgctggc    2280
aaccagctac gggtccagcg gctcctgtat gagagcccca gcgggcttc tcggacggtt     2340 cttcttatca cccagcagct cagcctggca gagcaggccc accacatcct ctttctcaga    2400
gaaggctctg tcggcgagca gggcacccac ctgcagctca tgaagagagg agggtgctac    2460
cgggccatgg tagaggctct tgcggctcct gcagactgac aaggcctctg gactgcacac    2520
tgcgtgctgt ccccctcctg tcctctactc tgtgtgacag agaacctggg agcaaagata    2580
ttaccacacc cacggagaca gttgaggagc ggaggtgctt gttacatgag aaaatgtaaa    2640
ctctaggaga tacccggaat ttaccacgaa tgtgtttccc cgacccgctc cctattagac    2700
ggggtttcag gtacctcaca ccaacactga gctgctaaat ctccggtctc caccctcccg    2760
gtgctgagct tgtatcacag catgcacaca caaacctggt ttatgtggcg ttgtgataga    2820
atgagaagaa acgcccaaag tgtacagaga gaaaggacaa gcagcttgca attaaccaaa    2880
ggcataggct ggcatttggg tgttctatgg gtgtttgata tttgtaataa aactggtgtt    2940
ttgtactgtg                                                          2950
```

<210> SEQ ID NO 20
<211> LENGTH: 724
<212> TYPE: PRT
<213> ORGANISM: Mus musculus

<400> SEQUENCE: 20

Met Ala Ala His Val Trp Leu Ala Ala Leu Leu Leu Leu Val Asp
1               5                   10                  15

Trp Leu Leu Leu Arg Pro Met Leu Pro Gly Ile Phe Ser Leu Val
            20                  25                  30

Pro Glu Val Pro Leu Leu Arg Val Trp Val Gly Leu Ser Arg Trp
        35                  40                  45

Ala Ile Leu Gly Leu Gly Val Arg Gly Val Leu Gly Val Thr Ala Gly
    50                  55                  60

Ala His Gly Trp Leu Ala Ala Leu Gln Pro Leu Val Ala Ala Leu Ser
65                  70                  75                  80

Leu Ala Leu Pro Gly Leu Ala Leu Phe Arg Glu Leu Ala Ala Trp Gly
                85                  90                  95

Thr Leu Arg Glu Gly Asp Ser Ala Gly Leu Leu Tyr Trp Asn Ser Arg
            100                 105                 110

Pro Asp Ala Phe Ala Ile Ser Tyr Val Ala Ala Leu Pro Ala Ala Ala
        115                 120                 125

Leu Trp His Lys Leu Gly Ser Leu Trp Ala Pro Ser Gly Asn Arg Asp
    130                 135                 140

Ala Gly Asp Met Leu Cys Arg Met Leu Gly Phe Leu Gly Pro Lys Lys
145                 150                 155                 160

Arg Arg Leu Tyr Leu Val Leu Val Leu Leu Ile Leu Ser Cys Leu Gly

```
                165                 170                 175
Glu Met Ala Ile Pro Phe Phe Thr Gly Arg Ile Thr Asp Trp Ile Leu
                180                 185                 190

Gln Asp Lys Thr Val Pro Ser Phe Thr Arg Asn Ile Trp Leu Met Ser
                195                 200                 205

Ile Leu Thr Ile Ala Ser Thr Ala Leu Glu Phe Ala Ser Asp Gly Ile
            210                 215                 220

Tyr Asn Ile Thr Met Gly His Met His Gly Arg Val His Arg Glu Val
225                 230                 235                 240

Phe Arg Ala Val Leu Arg Gln Glu Thr Gly Phe Phe Leu Lys Asn Pro
                245                 250                 255

Ala Gly Ser Ile Thr Ser Arg Val Thr Glu Asp Thr Ala Asn Val Cys
            260                 265                 270

Glu Ser Ile Ser Gly Thr Leu Ser Leu Leu Trp Tyr Leu Gly Arg
        275                 280                 285

Ala Leu Cys Leu Leu Val Phe Met Phe Trp Gly Ser Pro Tyr Leu Thr
        290                 295                 300

Leu Val Thr Leu Ile Asn Leu Pro Leu Leu Phe Leu Leu Pro Lys Lys
305                 310                 315                 320

Leu Gly Lys Val His Gln Ser Leu Ala Val Lys Val Gln Glu Ser Leu
                325                 330                 335

Ala Lys Ser Thr Gln Val Ala Leu Glu Ala Leu Ser Ala Met Pro Thr
            340                 345                 350

Val Arg Ser Phe Ala Asn Glu Glu Gly Glu Ala Gln Lys Phe Arg Gln
            355                 360                 365

Lys Leu Glu Glu Met Lys Thr Leu Asn Lys Lys Glu Ala Leu Ala Tyr
        370                 375                 380

Val Ala Glu Val Trp Thr Thr Ser Val Ser Gly Met Leu Leu Lys Val
385                 390                 395                 400

Gly Ile Leu Tyr Leu Gly Gly Gln Leu Val Ile Arg Gly Ala Val Ser
                405                 410                 415

Ser Gly Asn Leu Val Ser Phe Val Leu Tyr Gln Leu Gln Phe Thr Gln
            420                 425                 430

Ala Val Gln Val Leu Leu Ser Leu Tyr Pro Ser Met Gln Lys Ala Val
            435                 440                 445

Gly Ser Ser Glu Lys Ile Phe Glu Tyr Leu Asp Arg Thr Pro Cys Ser
        450                 455                 460

Pro Leu Ser Gly Ser Leu Ala Pro Ser Asn Met Lys Gly Leu Val Glu
465                 470                 475                 480

Phe Gln Asp Val Ser Phe Ala Tyr Pro Asn Gln Pro Lys Val Gln Val
                485                 490                 495

Leu Gln Gly Leu Thr Phe Thr Leu His Pro Gly Thr Val Thr Ala Leu
            500                 505                 510

Val Gly Pro Asn Gly Ser Gly Lys Ser Thr Val Ala Ala Leu Leu Gln
            515                 520                 525

Asn Leu Tyr Gln Pro Thr Gly Gly Gln Leu Leu Leu Asp Gly Gln Cys
        530                 535                 540

Leu Val Gln Tyr Asp His His Tyr Leu His Thr Gln Val Ala Ala Val
545                 550                 555                 560

Gly Gln Glu Pro Leu Leu Phe Gly Arg Ser Phe Arg Glu Asn Ile Ala
                565                 570                 575

Tyr Gly Leu Asn Arg Thr Pro Thr Met Glu Glu Ile Thr Ala Val Ala
            580                 585                 590
```

```
Val Glu Ser Gly Ala His Asp Phe Ile Ser Gly Phe Pro Gln Gly Tyr
            595                 600                 605

Asp Thr Glu Val Gly Glu Thr Gly Asn Gln Leu Ser Gly Gly Gln Arg
        610                 615                 620

Gln Ala Val Ala Leu Ala Arg Ala Leu Ile Arg Lys Pro Leu Leu Leu
625                 630                 635                 640

Ile Leu Asp Asp Ala Thr Ser Ala Leu Asp Ala Gly Asn Gln Leu Arg
                645                 650                 655

Val Gln Arg Leu Leu Tyr Glu Ser Pro Lys Arg Ala Ser Arg Thr Val
            660                 665                 670

Leu Leu Ile Thr Gln Gln Leu Ser Leu Ala Glu Gln Ala His His Ile
        675                 680                 685

Leu Phe Leu Arg Glu Gly Ser Val Gly Glu Gln Gly Thr His Leu Gln
690                 695                 700

Leu Met Lys Arg Gly Gly Cys Tyr Arg Ala Met Val Glu Ala Leu Ala
705                 710                 715                 720

Ala Pro Ala Asp

<210> SEQ ID NO 21
<211> LENGTH: 2866
<212> TYPE: DNA
<213> ORGANISM: Mus musculus

<400> SEQUENCE: 21
```

| | | | | |
|---|---|---|---|---|
| gaggagaatg agattcatgg agaagaacac gacaggccag ggctgctagg cagaactcca | 60 |
| actacagctt cagcggcagc ttccagaaca gcctgagcaa gccagtctca gaaggaggcg | 120 |
| tgtctagtga ttcgaggtcg gctttcggtt tcttcttcct ctaaacgcca gcacttctag | 180 |
| tcagctccac cagctcgagc gggttcccgg gactttacgc gcacgccctc ggacccgccc | 240 |
| ttcttccttc cccacggaga ctcctgtgca gcgcggacgt cgagagtccc aggctaggac | 300 |
| cagactctgg acagctcacg ctcgatggct gcgcacgtct ggctggcggc cgccctgctc | 360 |
| cttctggtgg actggctgct gctgcggccc atgctcccgg gaatcttctc cctgttggtt | 420 |
| cccgaggtgc cgctgctccg ggtctgggtg gtgggcctga gtcgctgggc catcctagga | 480 |
| ctagggtgtcc gcggggtcct cggggtcacc gcaggagccc atggctggct ggctgctttg | 540 |
| cagccgctgg tggccgcact gagtttggcc ctgcctggac ttgccttgtt ccagagctg | 600 |
| gccgcctggg gaacactccg ggagggtgac agcgctggat tactgtactg aacagtcgt | 660 |
| ccagatgcct tcgctatcag ttatgtggca gcattgcccg cagccgccct gtggcacaag | 720 |
| ttggggagcc tctgggcgcc cagcggcaac agggacgctg agacatgct gtgtcggatg | 780 |
| ctgggcttcc tggcccctaa gaagagacgt ctctacctgg ttctggttct cttgattctc | 840 |
| tcttgccttg gggaaatggc cattcccttc ttcacgggcc gcatcactga ctggattctt | 900 |
| caggataaga cagttcctag cttcacccgc aacatatggc tcatgtccat ctctcaccata | 960 |
| gccagcacag cgctggagtt tgcaagtgat ggaatctaca acatcaccat gggacacatg | 1020 |
| cacggccgtg tgcacagaga ggtgtttcgg ccgtccttc gccaggagac agggtttttc | 1080 |
| ctgaagaacc cagcaggttc catcacatct cgggtgactg aggacacagc caacgtgtgc | 1140 |
| gagtccatta gtggcacgct gagcctgctg ctgtggtacc tggggcgagc cctgtgtctc | 1200 |
| ttggtgttca tgtttgggg gtcaccgtac ctcactctgg tcaccctgat caacctgccc | 1260 |
| ctgcttttc ttttgcctaa gaagctggga aaagtgcatc agtcactggc agtgaaggtg | 1320 |

```
caggagtctc tagcaaagtc cacgcaggtg cccttgagg ccttatcggc gatgcctact    1380
gtgcggagct ttgccaacga ggagggtgag cccagaagt tcaggcagaa gttggaagaa    1440
atgaagactc taaacaagaa ggaggccttg gcttacgtgg ctgaagtctg gaccacgagt    1500
gtctcgggaa tgctgctgaa gcttcagttc acccaggctg ttcaggtcct gctctccctc    1560
taccctcca tgcagaaggc tgtgggctcc tcagagaaaa tattcgaata cttggaccgg    1620
actccttgct ctccactcag tggctcgttg gcaccctcaa acatgaaagg ccttgtggag    1680
ttccaagatg tctcttttgc ctacccaaac cagcccaaag tccaggtgct tcagggctg    1740
acgttcaccc tgcatcctgg aacggtgaca gcgttggtgg gacccaatgg atcagggaag    1800
agcaccgtgg ctgccctgct gcagaacctg taccagccca ccggggggcca gctgctgctg    1860
gatggccagt gcctggtcca gtatgatcac cattacctgc acactcaggt ggccgcagtg    1920
ggacaagagc cgctgctatt tggaagaagc tttcgagaaa atattgcgta tggcctgaac    1980
cggactccaa ccatggagga aatcacagct gtggccgtgg agtctggagc ccacgatttc    2040
atctctgggt tccctcaggg ctatgacaca gaggtaggtg agactgggaa ccagctgtca    2100
ggaggtcagc gacaggcagt ggccttggcc cgagccttga tccggaagcc actcctgctt    2160
atcttggatg atgccaccag tgccctggat gctggcaacc agctacgggt ccagcggctc    2220
ctgtatgaga gccccaagcg ggcttctcgg acggttcttc ttatcaccca gcagctcagc    2280
ctggcagagc aggcccacca catcctcttt ctcagagaag gctctgtcgg cgagcagggc    2340
acccacctgc agctcatgaa gagaggaggg tgctaccggg ccatggtaga ggctcttgcg    2400
gctcctgcag actgacaagg cctctggact gcacactgcg tgctgtcccc ctcctgtcct    2460
ctactctgtg tgacagagaa cctgggagca agatattac cacacccacg agacagttg     2520
aggagcggag gtgcttgtta catgagaaaa tgtaaactct aggagatacc cggaatttac    2580
cacgaatgtg tttccccgac ccgctcccta ttagacgggg tttcaggtac ctcacaccaa    2640
cactgagctg ctaaatctcc ggtctccacc ctcccggtgc tgagcttgta tcacagcatg    2700
cacacacaaa cctggtttat gtggcgttgt gatagaatga aagaaacgc ccaaagtgta    2760
cagagagaaa ggacaagcag cttgcaatta accaaaggca taggctggca tttgggtgtt    2820
ctatgggtgt ttgatatttg taataaaact ggtgttttgt actgtg                   2866
```

<210> SEQ ID NO 22
<211> LENGTH: 696
<212> TYPE: PRT
<213> ORGANISM: Mus musculus

<400> SEQUENCE: 22

```
Met Ala Ala His Val Trp Leu Ala Ala Leu Leu Leu Leu Val Asp
1               5                   10                  15

Trp Leu Leu Leu Arg Pro Met Leu Pro Gly Ile Phe Ser Leu Val
                20                  25                  30

Pro Glu Val Pro Leu Leu Arg Val Trp Val Val Gly Leu Ser Arg Trp
            35                  40                  45

Ala Ile Leu Gly Leu Gly Val Arg Gly Val Leu Gly Val Thr Ala Gly
        50                  55                  60

Ala His Gly Trp Leu Ala Leu Gln Pro Leu Val Ala Ala Leu Ser
65                  70                  75                  80

Leu Ala Leu Pro Gly Leu Ala Leu Phe Arg Glu Leu Ala Ala Trp Gly
                85                  90                  95

Thr Leu Arg Glu Gly Asp Ser Ala Gly Leu Leu Tyr Trp Asn Ser Arg
```

```
                100                 105                 110
Pro Asp Ala Phe Ala Ile Ser Tyr Val Ala Ala Leu Pro Ala Ala Ala
                115                 120                 125
Leu Trp His Lys Leu Gly Ser Leu Trp Ala Pro Ser Gly Asn Arg Asp
                130                 135                 140
Ala Gly Asp Met Leu Cys Arg Met Leu Gly Phe Leu Gly Pro Lys Lys
145                 150                 155                 160
Arg Arg Leu Tyr Leu Val Leu Val Leu Ile Leu Ser Cys Leu Gly
                165                 170                 175
Glu Met Ala Ile Pro Phe Phe Thr Gly Arg Ile Thr Asp Trp Ile Leu
                180                 185                 190
Gln Asp Lys Thr Val Pro Ser Phe Thr Arg Asn Ile Trp Leu Met Ser
                195                 200                 205
Ile Leu Thr Ile Ala Ser Thr Ala Leu Glu Phe Ala Ser Asp Gly Ile
                210                 215                 220
Tyr Asn Ile Thr Met Gly His Met His Gly Arg Val His Arg Glu Val
225                 230                 235                 240
Phe Arg Ala Val Leu Arg Gln Glu Thr Gly Phe Phe Leu Lys Asn Pro
                245                 250                 255
Ala Gly Ser Ile Thr Ser Arg Val Thr Glu Asp Thr Ala Asn Val Cys
                260                 265                 270
Glu Ser Ile Ser Gly Thr Leu Ser Leu Leu Leu Trp Tyr Leu Gly Arg
                275                 280                 285
Ala Leu Cys Leu Leu Val Phe Met Phe Trp Gly Ser Pro Tyr Leu Thr
                290                 295                 300
Leu Val Thr Leu Ile Asn Leu Pro Leu Leu Phe Leu Leu Pro Lys Lys
305                 310                 315                 320
Leu Gly Lys Val His Gln Ser Leu Ala Val Lys Val Gln Glu Ser Leu
                325                 330                 335
Ala Lys Ser Thr Gln Val Ala Leu Glu Ala Leu Ser Ala Met Pro Thr
                340                 345                 350
Val Arg Ser Phe Ala Asn Glu Glu Gly Glu Ala Gln Lys Phe Arg Gln
                355                 360                 365
Lys Leu Glu Glu Met Lys Thr Leu Asn Lys Lys Glu Ala Leu Ala Tyr
                370                 375                 380
Val Ala Glu Val Trp Thr Thr Ser Val Ser Gly Met Leu Leu Lys Leu
385                 390                 395                 400
Gln Phe Thr Gln Ala Val Gln Val Leu Leu Ser Leu Tyr Pro Ser Met
                405                 410                 415
Gln Lys Ala Val Gly Ser Ser Glu Lys Ile Phe Glu Tyr Leu Asp Arg
                420                 425                 430
Thr Pro Cys Ser Pro Leu Ser Gly Ser Leu Ala Pro Ser Asn Met Lys
                435                 440                 445
Gly Leu Val Glu Phe Gln Asp Val Ser Phe Ala Tyr Pro Asn Gln Pro
                450                 455                 460
Lys Val Gln Val Leu Gln Gly Leu Thr Phe Thr Leu His Pro Gly Thr
465                 470                 475                 480
Val Thr Ala Leu Val Gly Pro Asn Gly Ser Gly Lys Ser Thr Val Ala
                485                 490                 495
Ala Leu Leu Gln Asn Leu Tyr Gln Pro Thr Gly Gly Gln Leu Leu Leu
                500                 505                 510
Asp Gly Gln Cys Leu Val Gln Tyr Asp His His Tyr Leu His Thr Gln
                515                 520                 525
```

```
Val Ala Ala Val Gly Gln Glu Pro Leu Leu Phe Gly Arg Ser Phe Arg
    530                 535                 540

Glu Asn Ile Ala Tyr Gly Leu Asn Arg Thr Pro Thr Met Glu Glu Ile
545                 550                 555                 560

Thr Ala Val Ala Val Glu Ser Gly Ala His Asp Phe Ile Ser Gly Phe
                565                 570                 575

Pro Gln Gly Tyr Asp Thr Glu Val Gly Glu Thr Gly Asn Gln Leu Ser
            580                 585                 590

Gly Gly Gln Arg Gln Ala Val Ala Leu Ala Arg Ala Leu Ile Arg Lys
        595                 600                 605

Pro Leu Leu Leu Ile Leu Asp Asp Ala Thr Ser Ala Leu Asp Ala Gly
    610                 615                 620

Asn Gln Leu Arg Val Gln Arg Leu Leu Tyr Glu Ser Pro Lys Arg Ala
625                 630                 635                 640

Ser Arg Thr Val Leu Leu Ile Thr Gln Gln Leu Ser Leu Ala Glu Gln
                645                 650                 655

Ala His His Ile Leu Phe Leu Arg Glu Gly Ser Val Gly Glu Gln Gly
            660                 665                 670

Thr His Leu Gln Leu Met Lys Arg Gly Gly Cys Tyr Arg Ala Met Val
        675                 680                 685

Glu Ala Leu Ala Ala Pro Ala Asp
    690                 695

<210> SEQ ID NO 23
<211> LENGTH: 5679
<212> TYPE: DNA
<213> ORGANISM: Homo sapiens

<400> SEQUENCE: 23
gcccgccctg ccgagcgta gctggcggac cagagccggt agcgaggttg ggagagacgg      60
agcggacctc agcgctgaag cagaagtccc cggagctgcg gtctccccgc cgcggctgag    120
ccatgcggct ccctgacctg agaccctgga cctccctgct gctggtggac gcggctttac    180
tgtggctgct tcagggccct ctggggactt tgcttcctca agggctgcca ggactatggc    240
tggaggggac cctgcggctg gagggctgtg ggggctgctg aaagctaaga gggctgctgg    300
gatttgtggg gacactgctg ctcccgctct gtctggccac cccctgact gtctccctga    360
gagccctggt cgcgggggcc tcacgtgctc ccccagccag agtcgcttca gccccttgga    420
gctggctgct ggtggggtac ggggctgcgg ggctcagctg gtcactgtgg gctgttctga    480
gccctcctgg agcccaggag aaggagcagg accaggtgaa caacaaagtc ttgatgtgga    540
ggctgctgaa gctctccagg ccggacctgc ctctcctcgt tgccgccttc ttcttccttg    600
tccttgctgt tttgggtgag acattaatcc ctcactattc tggtcgtgtg attgacatcc    660
tgggaggtga ttttgacccc catgcctttg ccagtgccat cttcttcatg tgcctcttct    720
cctttggcag ctcactgtct gcaggctgcc gaggaggctg cttcacctac accatgtctc    780
gaatcaactt gcggatccgg agcagctttt ctcctcccct gctgcgccag gacctcggtt    840
tcttccagga gactaagaca ggggagctga actcacggct gagctcggat caccacctga    900
tgagtaactg gcttccttta aatgccaatg tgctcttgcg aagcctggtg aaagtggtgg    960
ggctgtatgg cttcatgctc agcatatcgc ctcgactcac cctcctttct ctgctgcaca    1020
tgcccttcac aatagcagcg gagaaggtgt acaacacccg ccatcaggaa gtgcttcggg    1080
agatccagga tgcagtggcc agggcggggc aggtggtgcg ggaagccgtt ggagggctgc    1140
```

```
agaccgttcg cagttttggg gccgaggagc atgaagtctg tcgctataaa gaggcccttg    1200
aacaatgtcg gcagctgtat tggcggagag acctggaacg cgccttgtac ctgctcgtaa    1260
ggagggtgct gcacttgggg gtgcagatgc tgatgctgag ctgtgggctg cagcagatgc    1320
aggatgggga gctcacccag ggcagcctgc tttcctttat gatctaccag agagcgtgg     1380 ggagctatgt gcagaccctg gtatacatat atggggatat gctcagcaac gtgggagctg    1440
cagagaaggt tttctcctac atggaccgac agccaaatct gccttcacct ggcacgcttg    1500
cccccaccac tctgcagggg gttgtgaaat ccaagacgt ctcctttgca tatcccaatc     1560
gccctgacag gcctgtgctc aaggggctga cgtttaccct acgtcctggt gaggtgacgg    1620
cgctggtggg acccaatggg tctgggaaga gcacagtggc tgccctgctg cagaatctgt    1680
accagcccac aggggacag tgctgctgg atgaaaagcc catctcacag tatgaacact      1740
gctacctgca cagccaggtg gtttcagttg gcaggagcc tgtgctgttc tccggttctg     1800
tgaggaacaa cattgcttat gggctgcaga gctgcgaaga tgataaggtg atggcggctg    1860
cccaggctgc ccacgcagat gacttcatcc aggaaatgga gcatggaata tacacagatg    1920
taggggagaa gggaagccag ctggctgcgg gacagaaaca acgtctggcc attgcccggg    1980
cccttgtacg agacccgcgg gtcctcatcc tggatgaggc tactagtgcc ctagatgtgc    2040
agtgcgagca ggccctgcag gactggaatt cccgtgggga tcgcacagtg ctggtgattg    2100
ctcacaggct gcaggcagtt cagcgcgccc accagatcct ggtgctccag gagggcaagc    2160
tgcagaagct tgcccagctc caggagggac aggacctcta ttcccgcctg gttcagcagc    2220
ggctgatgga ctgaggcccc agggatactg ggccctcttc tcaggggcgt ctccaggacc    2280
cagagctgtt cctgctttga gtttccctag agctgtgcgg ccagatagct gttcctgagt    2340
tgcaggcacg atggagattt ggacactgtg tgcttttggt ggggtagaga ggtggggtgg    2400
ggtggggtgg gggctgtctg tgtccaggaa acttaattcc ctggtgacta gagctttgcc    2460
tggtgatgag gagtattttg tggcataata catatatttt aaaatatttt ccttcttaca    2520
tgaactgtat acattcatat agaaaattta gacaatataa aaaagtacaa agaagaaaag    2580
taaaagtacc cattgtttca cttcctggag ataaccatag ttgctatttt gctgcctgtc    2640
ccatcagtcg tttatctgtt gtttgagata gaaattaacc aaaaatgaca taaatattca    2700
tgagattgcc ttcctatatc cttccttgtt cctaccagtg tctgctattt tgaagaagct    2760
agggtctgga gggacagaga acagttccct gattaacagt attaatagcg acattggtaa    2820
cagctaccat ttatagagtt ttaatgggag taggagctat gctaagtgtt tttcatgtat    2880
tatcgttttt aatcattatc cccaaccta tgaggttggt tattatcccc attttacaga     2940
tgaggaaact gaagctcaaa gaggctcaat gactttccca aggtggtcgt agtggtggag    3000
ttggagtttg aacacaggcc tgaccctaga gtccacaccc tgacccaatc aattatattg    3060
catcttgggt ccataaaccc taatccataa tcccatcaag aaaagctctg ctgctcttag    3120
ctctaaataa ttcagaatct attctcttct ctccagtccc gttgttatag tcttcactca    3180
tagacttaag atgatcccat caccagagag gtttctctac cattagcttc cctcttccgg    3240
ccattcttca caaagtcatt tttctaaatt ctgtgtcaca tacgatgatg gcatttctgg    3300
aaattccttc aggtgctctc aagccctgct gcagagatcc ttttcagagc acacactgtt    3360
ccagcccatc tgtctcaccc tctcctgttg tatccagctc cacgacaaac ttctgccttc    3420
cccaacacct ttgtgccttt gcatatggtg ttttcttgcc cattttctgc tcgactcgcc    3480
```

```
cctgattttc aagttcaaga cttaactcag ggttcaggtc ttccaggagg ccttacttat    3540
gtcgtcagtc tggggaactc tccatgtgct tctatcactg tgcggttacc tctttcacag    3600
cccttttaaa gttctatctt cccttttccca ccttttttga ccttccacta gaccatgagc    3660
acctgggcgg aaagccatat atcttattaa gctttatatc tgctacctgg ccgagggcct    3720
aattcatagt ggagaataaa tagtcaattg aataaatgaa taaatatctc caccatcgta    3780
ctaatcttaa tcctccctgc ccactcccac cactgaaaat gcaacattgt acacatcact    3840
ggttgttggg agggacttac cttggaaagt tgctattcta ggaaagagaa accttcatat    3900
tcctggaaac agcaggtagt ttccagtgct ggcaatgaat tccccagaac tgctgttttg    3960
gattttttct tgcctggcag ctgttgggag cagggtgcag tgaggatggg gtgagagtgg    4020
gcagtttctt gtgcagattt gcctttcttt catcctgggg ctgacttgca gctccacacc    4080
catccatctc tcaaatttca cagagggtaa ataggcatt tggagagaaa gaactctggc    4140
ctgattcctt tctctcccac aaatgtcctt tattcataaa acaggaataa taattcctgt    4200
atctcccaac tacatggaag ctgcagccct cacagaagaa gatgatctga gaaattcttt    4260
gatttcctca gtacagttat acccatgcat cataatactt taagcctgga aggcatctta    4320
aaaataatgc aacagtcaaa cctaattta cagaaaact gacatgaaat cacgcagcta    4380
atcatgataa agctgggtgg aaaacttatc ttgatgggca gtacaggaag atgcagtaga    4440
ccttaagatg tcctgaaagt ttcttatctc agggaaact cccaggtagg ctttatgtca    4500
gggacacaga aaatgctcc ctgaaagtca aaatattcgg gctagacaga caaattcctg    4560
taagtgtggt ttgtctggga accacagatg tcactaatcc tggtttgctc cagagttctt    4620
tttgttcact cctaccccc atcaccattt gattgatctc cttaccctgt aatttcccct    4680
tcttgtcgct tacctgcagt atcttttccca cccaggcatg ccttattctt tctaaaggaa    4740
agtatgaatg gagaggggaa gcttgggaa actgatagat ttccttggat gccaaaacac    4800
ctccatagcc tgtctgcccg gccctatgtg gaaacagcat tgagtttcaa gtcctttatg    4860
cctccaccca gggatagcca cttgtaatcc acatggcaat tgtgaaacaa gcaggaaatg    4920
cgtaattgtc agaattttgt ggggaaagga ctagggaata aggaaaacaa agatcttcct    4980
tgtgttttag agctgtcagc tagaggagca cctgcttgag tctgatgcca tctaatggtc    5040
ccagaagaaa ctgggttttg aacctagagt tccatggact cttaggaatt agactactac    5100
tactactaag cattcactgg tgcttactat gtgctattgc tgtgccaagt atctgaaacc    5160
tgtcttctta ccttatttt caagataatt ctatgtggca ggtattacta tctcaattct    5220
aagagtgaga aatggagtt ttagaaacat ttactaactt gcctgggtca catagctaag    5280
gaagaggtgg acttgcccag cttgcataa aactcctcaa aagagttgcc tatactccct    5340
gactccactt atcttcctac tatcctcttt ttaaaatata ttatttattt atttaaataa    5400
gcaatatatg aatgtggttt gaaattcaaa agacacaaag aagtatacag aggaaagcct    5460
cactctcaat ccttctcaag gtttgctaat tcctcttgca taggcaatcc gttcttccag    5520
ctttgtgttt atcttttccag agaagtttac tgtgtattaa gcaaatatgt atatcttat    5580 tcttgctcag tattttcgca aacagcagct gtcaagttc actgttctga actttatttt    5640
ttaaattaaa aatatatggc tatgtagtat tctattttta    5679
```

<210> SEQ ID NO 24
<211> LENGTH: 703
<212> TYPE: PRT
<213> ORGANISM: Homo sapiens

<400> SEQUENCE: 24

Met Arg Leu Pro Asp Leu Arg Pro Trp Thr Ser Leu Leu Leu Val Asp
1               5                   10                  15

Ala Ala Leu Leu Trp Leu Leu Gln Gly Pro Leu Gly Thr Leu Leu Pro
            20                  25                  30

Gln Gly Leu Pro Gly Leu Trp Leu Glu Gly Thr Leu Arg Leu Gly Gly
        35                  40                  45

Leu Trp Gly Leu Leu Lys Leu Arg Gly Leu Leu Gly Phe Val Gly Thr
50                  55                  60

Leu Leu Leu Pro Leu Cys Leu Ala Thr Pro Leu Thr Val Ser Leu Arg
65                  70                  75                  80

Ala Leu Val Ala Gly Ala Ser Arg Ala Pro Pro Ala Arg Val Ala Ser
                85                  90                  95

Ala Pro Trp Ser Trp Leu Leu Val Gly Tyr Gly Ala Ala Gly Leu Ser
            100                 105                 110

Trp Ser Leu Trp Ala Val Leu Ser Pro Pro Gly Ala Gln Glu Lys Glu
        115                 120                 125

Gln Asp Gln Val Asn Asn Lys Val Leu Met Trp Arg Leu Leu Lys Leu
130                 135                 140

Ser Arg Pro Asp Leu Pro Leu Val Ala Ala Phe Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
        195                 200                 205

Cys Arg Gly Gly Cys Phe Thr Tyr Thr Met Ser Arg Ile Asn Leu Arg
210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile
        275                 280                 285

Ser Pro Arg Leu Thr Leu Leu Ser Leu Leu His Met Pro Phe Thr Ile
290                 295                 300

Ala Ala Glu Lys Val Tyr Asn Thr Arg His Gln Glu Val Leu Arg Glu
305                 310                 315                 320

Ile Gln Asp Ala Val Ala Arg Ala Gly Gln Val Val Arg Glu Ala Val
                325                 330                 335

Gly Gly Leu Gln Thr Val Arg Ser Phe Gly Ala Glu Glu His Glu Val
            340                 345                 350

Cys Arg Tyr Lys Glu Ala Leu Glu Gln Cys Arg Gln Leu Tyr Trp Arg
        355                 360                 365

Arg Asp Leu Glu Arg Ala Leu Tyr Leu Leu Val Arg Arg Val Leu His
370                 375                 380

Leu Gly Val Gln Met Leu Met Leu Ser Cys Gly Leu Gln Gln Met Gln
385                 390                 395                 400

Asp Gly Glu Leu Thr Gln Gly Ser Leu Leu Ser Phe Met Ile Tyr Gln

```
                    405                 410                 415
Glu Ser Val Gly Ser Tyr Val Gln Thr Leu Val Tyr Ile Tyr Gly Asp
                420                 425                 430

Met Leu Ser Asn Val Gly Ala Ala Glu Lys Val Phe Ser Tyr Met Asp
            435                 440                 445

Arg Gln Pro Asn Leu Pro Ser Pro Gly Thr Leu Ala Pro Thr Thr Leu
    450                 455                 460

Gln Gly Val Val Lys Phe Gln Asp Val Ser Phe Ala Tyr Pro Asn Arg
465                 470                 475                 480

Pro Asp Arg Pro Val Leu Lys Gly Leu Thr Phe Thr Leu Arg Pro Gly
                485                 490                 495

Glu Val Thr Ala Leu Val Gly Pro Asn Gly Ser Gly Lys Ser Thr Val
                500                 505                 510

Ala Ala Leu Leu Gln Asn Leu Tyr Gln Pro Thr Gly Gly Gln Val Leu
            515                 520                 525

Leu Asp Glu Lys Pro Ile Ser Gln Tyr Glu His Cys Tyr Leu His Ser
    530                 535                 540

Gln Val Val Ser Val Gly Gln Glu Pro Val Leu Phe Ser Gly Ser Val
545                 550                 555                 560

Arg Asn Asn Ile Ala Tyr Gly Leu Gln Ser Cys Glu Asp Asp Lys Val
                565                 570                 575

Met Ala Ala Ala Gln Ala Ala His Ala Asp Asp Phe Ile Gln Glu Met
                580                 585                 590

Glu His Gly Ile Tyr Thr Asp Val Gly Glu Lys Gly Ser Gln Leu Ala
            595                 600                 605

Ala Gly Gln Lys Gln Arg Leu Ala Ile Ala Arg Ala Leu Val Arg Asp
    610                 615                 620

Pro Arg Val Leu Ile Leu Asp Glu Ala Thr Ser Ala Leu Asp Val Gln
625                 630                 635                 640

Cys Glu Gln Ala Leu Gln Asp Trp Asn Ser Arg Gly Asp Arg Thr Val
                645                 650                 655

Leu Val Ile Ala His Arg Leu Gln Ala Val Gln Arg Ala His Gln Ile
                660                 665                 670

Leu Val Leu Gln Glu Gly Lys Leu Gln Lys Leu Ala Gln Leu Gln Glu
            675                 680                 685

Gly Gln Asp Leu Tyr Ser Arg Leu Val Gln Gln Arg Leu Met Asp
    690                 695                 700

<210> SEQ ID NO 25
<211> LENGTH: 5732
<212> TYPE: DNA
<213> ORGANISM: Homo sapiens

<400> SEQUENCE: 25
agaatgaagg ccttggctgg ggaagcgaaa gcgaaagctg cccgagccct gacgcccgcc      60
ctggccgagc gtagctggcg gaccagagcc ggtagcgagg ttgggagaga cggagcggac     120
ctcagcgctg aagcagaagt ccccggagct gcggtctccc cgccgcggct gagccatgcg     180
gctccctgac ctgagaccct ggacctccct gctgctggtg gacgcggctt tactgtggct     240
gcttcagggc cctctgggga ctttgcttcc tcaagggctg ccaggactat ggctggaggg     300
gaccctgcgg ctgggagggc tgtggggggct gctaaagcta agagggctgc tgggatttgt     360
ggggacactg ctgctcccgc tctgtctggc accccctg actgtctccc tgagagccct     420
ggtcgcgggg gcctcacgtg ctcccccagc cagagtcgct tcagcccctt ggagctggct     480
```

```
gctggtgggg tacggggctg cggggctcag ctggtcactg tgggctgttc tgagccctcc      540
tggagcccag gagaaggagc aggaccaggt gaacaacaaa gtcttgatgt ggaggctgct      600
gaagctctcc aggccggacc tgcctctcct cgttgccgcc ttcttcttcc ttgtccttgc      660
tgttttgggt gagacattaa tccctcacta ttctggtcgt gtgattgaca tcctgggagg      720
tgattttgac ccccatgcct ttgccagtgc catcttcttc atgtgcctct tctcctttgg      780
cagctcactg tctgcaggct gccgaggagg ctgcttcacc tacaccatgt ctcgaatcaa      840
cttgcggatc cgggagcagc ttttctcctc cctgctgcgc caggacctcg gtttcttcca      900
ggagactaag acaggggagc tgaactcacg gctgagctcg gataccaccc tgatgagtaa      960
ctggcttcct ttaaatgcca atgtgctctt gcgaagcctg gtgaaagtgg tgggctgta      1020 tggcttcatg ctcagcatat cgcctcgact caccctcctt tctctgctgc acatgccctt     1080
cacaatagca gcggagaagg tgtacaacac ccgccatcag gaagtgcttc gggagatcca     1140
ggatgcagtg gccagggcgg ggcaggtggt gcgggaagcc gttggagggc tgcagaccgt     1200
tcgcagtttt ggggccgagg agcatgaagt ctgtcgctat aaagaggccc ttgaacaatg     1260
tcggcagctg tattggcgga gagacctgga acgcgccttg tacctgctcg taaggagggt     1320
gctgcacttg ggggtgcaga tgctgatgct gagctgtggg ctgcagcaga tgcaggatgg     1380
ggagctcacc cagggcagcc tgctttcctt tatgatctac caggagagcg tggggagcta     1440
tgtgcagacc ctggtataca tatatgggga tatgctcagc aacgtgggag ctgcagagaa     1500
ggttttctcc tacatggacc gacagccaaa tctgccttca cctggcacgc ttgccccac     1560 cactctgcag ggggttgtga attccaaga cgtctccttt gcatatccca atcgccctga     1620
caggcctgtg ctcaagggc tgacgtttac cctacgtcct ggtgaggtga cggcgctggt     1680
gggacccaat gggtctggga gagcacagt ggctgccctg ctgcagaatc tgtaccagcc     1740
cacaggggga caggtgctgc tggatgaaaa gcccatctca cagtatgaac actgctacct     1800
gcacagccag gtggtttcag ttgggcagga gcctgtgctg ttctccggtt ctgtgaggaa     1860
caacattgct tatgggctgc agagctgcga agatgataag gtgatggcgg ctgcccaggc     1920
tgcccacgca gatgacttca tccaggaaat ggagcatgga atatacacag atgtaggga     1980 gaagggaagc cagctggctg cgggacagaa acaacgtctg gccattgccc gggcccttgt     2040
acgagacccg cgggtcctca tcctggatga ggctactagt gccctagatg tgcagtgcga     2100
gcaggccctg caggactgga attcccgtgg ggatcgcaca gtgctggtga ttgctcacag     2160
gctgcagaca gttcagcgcg cccaccagat cctggtgctc aggagggca agctgcagaa     2220 gcttgcccag ctctaggagg gacaggacct ctattcccgc ctggtgcagc agcggctgat     2280
ggactgaggc cccagggata ctgggccctc ttctcagggg cgtctccagg acccagagct     2340
gttcctgctt tgagtttccc tagagctgtg cggccagata gctgttcctg agttgcaggc     2400
acgatggaga tttggacact gtgtgctttt ggtggggtag agaggtgggg tggggtgggg     2460
tgggggctgt ctgtgtccag gaaacttaat tccctggtga ctagagcttt gcctggtgat     2520
gaggagtatt ttgtgcata atacatatat tttaaaatat tttccttctt acatgaactg     2580
tatacattca tatagaaaat ttagacaata taaaaagta caaagaagaa aagtaaagt     2640 acccattgtt tcacttcctg gagataacca tagttgctat tttgctgcct gtcccatcag     2700
tcgtttatct gttgtttgag atagaaatta accaaaaatg acataaatat tcatgagatt     2760
gccttcctat atccttcctt gttcctacca gtgtctgcta ttttgaagaa gctagggtct     2820
```

```
ggagggacag agaacagttc cctgattaac agtattaata gcgacattgg taacagctac    2880
catttataga gttttaatgg gagtaggagc tatgctaagt gttttccatg tattatcgtt    2940
tttaatcatt atccccaacc ctatgaggtt ggttattatc cccattttac agatgaggaa    3000
actgaagctc aaagaggctc aatgactttc ccaaggtggt cgtagtggtg gagttggagt    3060
ttgaacacag gcctgaccct agagtccaca ccctgaccca atcaattata ttgcatcttg    3120
ggtccataaa ccctaatcca taatcccatc aagaaaagct ctgctgctct tagctctaaa    3180
taattcagaa tctattctct tctctccagt cccgttgtta tagtcttcac tcatagactt    3240
aagatgatcc catcaccaga gaggtttctc taccattagc ttccctcttc cggccattct    3300
tcacaaagtc attttctaa attctgtgtc acatacgatg atggcatttc tggaaattcc     3360
ttcaggtgct ctcaagccct gctgcagaga tccttttcag agcacacact gttccagccc    3420
atctgtctca ccctctcctg ttgtatccag ctccacgaca aacttctgcc ttccccaaca    3480
cctttgtgcc tttgcatatg gtgttttctt gcccattttc tgctcgactc gcccctgatt    3540
ttcaagttca agacttaact cagggttcag gtcttccagg aggccttact tatgtcgtca    3600
gtctggggaa ctctccatgt gcttctatca ctgtgcggtt acctctttca cagcccttt     3660
aaagttctat cttcccttc ccacctttt tgaccttcca ctagaccatg agcacctggg      3720
cggaaagcca tatatcttat taagctttat atctgctacc tggccgaggg cctaattcat    3780
agtggagaat aaatagtcaa ttgaataaat gaataaatat ctccaccatc gtactaatct    3840
taatcctccc tgcccactcc caccactgaa aatgcaacat tgtacacatc actggttgtt    3900
gggagggact taccttggaa agttgctatt ctaggaaaga gaaaccttca tattcctgga    3960
aacagcaggt agtttccagt gctggcaatg aattccccag aactgctgtt ttggattttt    4020
tcttgcctgg cagctgttgg gagcagggtg cagtgaggat ggggtgagag tgggcagttt    4080
cttgtgcaga tttgcctttc tttcatcctg gggctgactt gcagctccac acccatccat    4140
ctctcaaatt tcacagaggg taaaataggc atttggagag aaagaactct ggcctgattc    4200
ctttctctcc cacaaatgtc ctttattcat aaaacaggaa taataattcc tgtatctccc    4260
aactacatgg aagctgcagc cctcacagaa gaagatgatc tgagaaattc tttgatttcc    4320
tcagtacagt tatacccatg catcataata ctttaagcct ggaaggcatc ttaaaaataa    4380
tgcaacagtc aaacctaatt ttacagagaa actgacatga aatcacgcag ctaatcatga    4440
taaagctggg tggaaaactt atcttgatgg gcagtacagg aagatgcagt agaccttaag    4500
atgtcctgaa agtttcttat ctcagggaa actcccaggt aggctttatg tcagggacac     4560
agaaaaatgc tccctgaaag tcaaaatatt cgggctagac agacaaattc ctgtaagtgt    4620
ggtttgtctg gaaccacag atgtcactaa tcctggtttg ctccagagtt cttttttgttc    4680
actcctaccc cccatcacca tttgattgat ctccttaccc tgtaatttcc ccttcttgtc    4740
gcttacctgc agtatctttc ccacccaggc atgccttatt cttctaaag gaaagtatga    4800
atggagaggg gaaagcttgg gaaactgata gatttccttg gatgccaaaa cacctccata    4860
gcctgtctgc ccggccctat gtggaaacag cattgagttt caagtccttt atgcctccac    4920
ccagggatag ccacttgtaa tccacatggc aattgtgaaa caagcaggaa atgcgtaatt    4980
gtcagaattt tgtggggaaa ggactaggga ataaggaaaa caaagatctt ccttgtgttt    5040
tagagctgtc agctagagga gcacctgctt gagtctgatg ccatctaatg gtcccagaag    5100
aaactggggtt ttgaacctag agttccatgg actcttagga attagactac tactactact    5160
aagcattcac tggtgcttac tatgtgctat tgctgtgcca agtatctgaa acctgtcttc    5220
```

-continued

```
ttaccttatt tttcaagata attctatgtg gcaggtatta ctatctcaat tctaagagtg    5280
agaaaatgga gttttagaaa catttactaa cttgcctggg tcacatagct aaggaagagg    5340
tggacttgcc cagctttgca taaaactcct caaaagagtt gcctatactc cctgactcca    5400
cttatcttcc tactatcctc ttttaaaat atattattta tttatttaaa taagcaatat    5460
atgaatgtgg tttgaaattc aaaagacaca aagaagtata cagaggaaag cctcactctc    5520
aatccttctc aaggtttgct aattcctctt gcataggcaa tccgttcttc cagctttgtg    5580
tttatctttc cagagaagtt tactgtgtat taagcaaata tgtatatctt tattcttgct    5640
cagtattttc gcaaacagca gctgtctaag ttcactgttc tgaactttat tttttaaatt    5700
aaaaatatat ggctatgtag tattctattt ta    5732
```

<210> SEQ ID NO 26
<211> LENGTH: 686
<212> TYPE: PRT
<213> ORGANISM: Homo sapiens

<400> SEQUENCE: 26

```
Met Arg Leu Pro Asp Leu Arg Pro Trp Thr Ser Leu Leu Val Asp
1               5                   10                  15

Ala Ala Leu Leu Trp Leu Leu Gln Gly Pro Leu Gly Thr Leu Leu Pro
                20                  25                  30

Gln Gly Leu Pro Gly Leu Trp Leu Glu Gly Thr Leu Arg Leu Gly Gly
            35                  40                  45

Leu Trp Gly Leu Leu Lys Leu Arg Gly Leu Leu Gly Phe Val Gly Thr
        50                  55                  60

Leu Leu Leu Pro Leu Cys Leu Ala Thr Pro Leu Thr Val Ser Leu Arg
65                  70                  75                  80

Ala Leu Val Ala Gly Ala Ser Arg Ala Pro Pro Ala Arg Val Ala Ser
                85                  90                  95

Ala Pro Trp Ser Trp Leu Leu Val Gly Tyr Gly Ala Ala Gly Leu Ser
            100                 105                 110

Trp Ser Leu Trp Ala Val Leu Ser Pro Pro Gly Ala Gln Glu Lys Glu
        115                 120                 125

Gln Asp Gln Val Asn Asn Lys Val Leu Met Trp Arg Leu Leu Lys Leu
    130                 135                 140

Ser Arg Pro Asp Leu Pro Leu Val Ala Ala Phe Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
        195                 200                 205

Cys Arg Gly Gly Cys Phe Thr Tyr Thr Met Ser Arg Ile Asn Leu Arg
    210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile
```

```
            275                 280                 285
Ser Pro Arg Leu Thr Leu Leu Ser Leu Leu His Met Pro Phe Thr Ile
290                 295                 300

Ala Ala Glu Lys Val Tyr Asn Thr Arg His Gln Glu Val Leu Arg Glu
305                 310                 315                 320

Ile Gln Asp Ala Val Arg Ala Gly Gln Val Val Arg Glu Ala Val
                325                 330                 335

Gly Gly Leu Gln Thr Val Arg Ser Phe Gly Ala Glu Glu His Glu Val
                340                 345                 350

Cys Arg Tyr Lys Glu Ala Leu Glu Gln Cys Arg Gln Leu Tyr Trp Arg
                355                 360                 365

Arg Asp Leu Glu Arg Ala Leu Tyr Leu Leu Val Arg Arg Val Leu His
                370                 375                 380

Leu Gly Val Gln Met Leu Met Leu Ser Cys Gly Leu Gln Gln Met Gln
385                 390                 395                 400

Asp Gly Glu Leu Thr Gln Gly Ser Leu Leu Ser Phe Met Ile Tyr Gln
                405                 410                 415

Glu Ser Val Gly Ser Tyr Val Gln Thr Leu Val Tyr Ile Tyr Gly Asp
                420                 425                 430

Met Leu Ser Asn Val Gly Ala Ala Glu Lys Val Phe Ser Tyr Met Asp
                435                 440                 445

Arg Gln Pro Asn Leu Pro Ser Pro Gly Thr Leu Ala Pro Thr Thr Leu
450                 455                 460

Gln Gly Val Val Lys Phe Gln Asp Val Ser Phe Ala Tyr Pro Asn Arg
465                 470                 475                 480

Pro Asp Arg Pro Val Leu Lys Gly Leu Thr Phe Thr Leu Arg Pro Gly
                485                 490                 495

Glu Val Thr Ala Leu Val Gly Pro Asn Gly Ser Gly Lys Ser Thr Val
                500                 505                 510

Ala Ala Leu Leu Gln Asn Leu Tyr Gln Pro Thr Gly Gly Gln Val Leu
                515                 520                 525

Leu Asp Glu Lys Pro Ile Ser Gln Tyr Glu His Cys Tyr Leu His Ser
530                 535                 540

Gln Val Val Ser Val Gly Gln Glu Pro Val Leu Phe Ser Gly Ser Val
545                 550                 555                 560

Arg Asn Asn Ile Ala Tyr Gly Leu Gln Ser Cys Glu Asp Asp Lys Val
                565                 570                 575

Met Ala Ala Ala Gln Ala Ala His Ala Asp Asp Phe Ile Gln Glu Met
                580                 585                 590

Glu His Gly Ile Tyr Thr Asp Val Gly Glu Lys Gly Ser Gln Leu Ala
                595                 600                 605

Ala Gly Gln Lys Gln Arg Leu Ala Ile Ala Arg Ala Leu Val Arg Asp
                610                 615                 620

Pro Arg Val Leu Ile Leu Asp Glu Ala Thr Ser Ala Leu Asp Val Gln
625                 630                 635                 640

Cys Glu Gln Ala Leu Gln Asp Trp Asn Ser Arg Gly Asp Arg Thr Val
                645                 650                 655

Leu Val Ile Ala His Arg Leu Gln Thr Val Gln Arg Ala His Gln Ile
                660                 665                 670

Leu Val Leu Gln Glu Gly Lys Leu Gln Lys Leu Ala Gln Leu
                675                 680                 685

<210> SEQ ID NO 27
```

<211> LENGTH: 2540
<212> TYPE: DNA
<213> ORGANISM: Homo sapiens

<400> SEQUENCE: 27

| | | | | | |
|---|---|---|---|---|---|
| gcccgccctg | gccgagcgta | gctggcggac | cagagccggt | agcgaggttg | ggagagacgg | 60 |
| agcggacctc | agcgctgaag | cagaagtccc | cggagctgcg | gtctcccgc | cgcggctgag | 120 |
| ccatgcggct | ccctgacctg | agaccctgga | cctccctgct | gctggtggac | gcggctttac | 180 |
| tgtggctgct | tcagggccct | ctggggactt | tgcttcctca | agggctgcca | ggactatggc | 240 |
| tggagggac | cctgcggctg | ggagggctgt | ggggctgct | aaagctaaga | gggctgctgg | 300 |
| gatttgtggg | gacactgctg | ctcccgctct | gtctggccac | cccctgact | gtctccctga | 360 |
| gagccctggt | cgcgggggcc | tcacgtgctc | ccccagccag | agtcgcttca | gcccttgga | 420 |
| gctggctgct | ggtggggtac | ggggctgcgg | ggctcagctg | gtcactgtgg | gctgttctga | 480 |
| gccctcctgg | agcccaggag | aaggagcagg | accaggtgaa | caacaaagtc | ttgatgtgga | 540 |
| ggctgctgaa | gctctccagg | ccggacctgc | ctctcctcgt | tgccgccttc | ttcttccttg | 600 |
| tccttgctgt | tttgggtgag | acattaatcc | ctcactattc | tggtcgtgtg | attgacatcc | 660 |
| tgggaggtga | ttttgacccc | catgcctttg | ccagtgccat | cttcttcatg | tgcctcttct | 720 |
| cctttggcag | ctcactgtct | gcaggctgcc | gaggaggctg | cttcacctac | accatgtctc | 780 |
| gaatcaactt | gcggatccgg | gagcagcttt | tctcctccct | gctgcgccag | gacctcggtt | 840 |
| tcttccagga | gactaagaca | ggggagctga | actcacggct | gagctcggat | accaccctga | 900 |
| tgagtaactg | gcttccttta | aatgccaatg | tgctcttgcg | aagcctggtg | aaagtggtgg | 960 |
| ggctgtatgg | cttcatgctc | agcatatcgc | ctcgactcac | cctccttttct | ctgctgcaca | 1020 |
| tgcccttcac | aatagcagcg | gagaaggtgt | acaacacccg | ccatcaggaa | gtgcttcggg | 1080 |
| agatccagga | tgcagtggcc | agggcgggc | aggtggtgcg | ggaagccgtt | ggagggctgc | 1140 |
| agaccgttcg | cagttttggg | gccgaggagc | atgaagtctg | tcgctataaa | gaggcccttg | 1200 |
| aacaatgtcg | gcagctgtat | tggcggagag | acctggaacg | cgccttgtac | ctgctcgtaa | 1260 |
| ggagggtgct | gcacttgggg | gtgcagatgc | tgatgctgag | ctgtgggctg | cagcagatgc | 1320 |
| aggatgggga | gctcacccag | ggcagcctgc | tttcctttat | gatctaccag | gagagcgtgg | 1380 |
| ggagctatgt | gcagaccctg | gtatacatat | atggggatat | gctcagcaac | gtgggagctg | 1440 |
| cagagaaggt | tttctcctac | atggaccgac | agccaaatct | gccttcacct | ggcacgcttg | 1500 |
| cccccaccac | tctgcagggg | gttgtgaaat | tccaagacgt | ctcctttgca | tatcccaatc | 1560 |
| gccctgacag | gcctgtgctc | aaggggctga | cgtttaccct | acgtcctggt | gaggtgacgg | 1620 |
| cgctggtggg | acccaatggg | tctgggaaga | gcacagtggc | tgccctgctg | cagaatctgt | 1680 |
| accagcccac | aggggacag | gtgctgctgg | atgaaaagcc | catctcacag | tatgaacact | 1740 |
| gctacctgca | cagccaggtg | gtttcagttg | gcaggagcc | tgtgctgttc | tccggttctg | 1800 |
| tgaggaacaa | cattgcttat | gggctgcaga | gctgcgaaga | tgataaggtg | atggcggctg | 1860 |
| cccaggctgc | ccacgcagat | gacttcatcc | aggaaatgga | gcatggaata | tacacagatg | 1920 |
| taggggagaa | gggaagccag | ctggctgcgg | gacagaaaca | acgtctggcc | attgcccggg | 1980 |
| cccttgtacg | agacccgcgg | gtcctcatcc | tggatgaggc | tactagtgcc | ctagatgtgc | 2040 |
| agtgcgagca | ggccaaaacc | ctttggaagt | tcatgatatt | ttgaatttca | atggatattt | 2100 |
| cctgggaata | atgagttcaa | atgaacgaat | atgtggaaca | aagcatcacc | aacatttatt | 2160 |
| ttttcaggat | gaggtgatgg | acaaaaccat | cacagggaaa | ttgaggcaaa | tagtacatgt | 2220 |

-continued

```
aaaacaatac ttcgggtgag tccacctatc ccaaagtcgt atcaaagaag tggctgcaga    2280
ttggagccca agcctttgg ttcctcagtt tccaaatgga ttctcactag gtgggatcat    2340
gagtttgctt tggacacccc aaattctaac tatttctttt gtttcttaca tcctttccct    2400
cttccccagc cccttcccct catgttacac ctcttgctgg tttgagacgt caatcaccac    2460
tgagaaagaa ttaaaccagt attttgagct ggcaaaattc ttagcctagt acaattcctt    2520
caattaaact gtagctcaac                                                 2540
```

<210> SEQ ID NO 28
<211> LENGTH: 653
<212> TYPE: PRT
<213> ORGANISM: Homo sapiens

<400> SEQUENCE: 28

```
Met Arg Leu Pro Asp Leu Arg Pro Trp Thr Ser Leu Leu Leu Val Asp
1               5                   10                  15

Ala Ala Leu Leu Trp Leu Leu Gln Gly Pro Leu Gly Thr Leu Leu Pro
            20                  25                  30

Gln Gly Leu Pro Gly Leu Trp Leu Glu Gly Thr Leu Arg Leu Gly Gly
        35                  40                  45

Leu Trp Gly Leu Leu Lys Leu Arg Gly Leu Leu Gly Phe Val Gly Thr
    50                  55                  60

Leu Leu Leu Pro Leu Cys Leu Ala Thr Pro Leu Thr Val Ser Leu Arg
65                  70                  75                  80

Ala Leu Val Ala Gly Ala Ser Arg Ala Pro Pro Ala Arg Val Ala Ser
                85                  90                  95

Ala Pro Trp Ser Trp Leu Leu Val Gly Tyr Gly Ala Ala Gly Leu Ser
            100                 105                 110

Trp Ser Leu Trp Ala Val Leu Ser Pro Pro Gly Ala Gln Glu Lys Glu
        115                 120                 125

Gln Asp Gln Val Asn Asn Lys Val Leu Met Trp Arg Leu Leu Lys Leu
    130                 135                 140

Ser Arg Pro Asp Leu Pro Leu Leu Val Ala Ala Phe Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
            180                 185                 190

Ile Phe Phe Met Cys Leu Phe Ser Phe Gly Ser Ser Leu Ser Ala Gly
        195                 200                 205

Cys Arg Gly Gly Cys Phe Thr Tyr Thr Met Ser Arg Ile Asn Leu Arg
    210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
                245                 250                 255

Thr Thr Leu Met Ser Asn Trp Leu Pro Leu Asn Ala Asn Val Leu Leu
            260                 265                 270

Arg Ser Leu Val Lys Val Gly Leu Tyr Gly Phe Met Leu Ser Ile
        275                 280                 285

Ser Pro Arg Leu Thr Leu Leu Ser Leu Leu His Met Pro Phe Thr Ile
    290                 295                 300

Ala Ala Glu Lys Val Tyr Asn Thr Arg His Gln Glu Val Leu Arg Glu
```

```
            305                 310                 315                 320
Ile Gln Asp Ala Val Ala Arg Ala Gly Gln Val Val Arg Glu Ala Val
                325                 330                 335
Gly Gly Leu Gln Thr Val Arg Ser Phe Gly Ala Glu Glu His Glu Val
                340                 345                 350
Cys Arg Tyr Lys Glu Ala Leu Glu Gln Cys Arg Gln Leu Tyr Trp Arg
                355                 360                 365
Arg Asp Leu Glu Arg Ala Leu Tyr Leu Leu Val Arg Arg Val Leu His
            370                 375                 380
Leu Gly Val Gln Met Leu Met Leu Ser Cys Gly Leu Gln Gln Met Gln
385                 390                 395                 400
Asp Gly Glu Leu Thr Gln Gly Ser Leu Leu Ser Phe Met Ile Tyr Gln
                405                 410                 415
Glu Ser Val Gly Ser Tyr Val Gln Thr Leu Val Tyr Ile Tyr Gly Asp
                420                 425                 430
Met Leu Ser Asn Val Gly Ala Ala Glu Lys Val Phe Ser Tyr Met Asp
            435                 440                 445
Arg Gln Pro Asn Leu Pro Ser Pro Gly Thr Leu Ala Pro Thr Thr Leu
450                 455                 460
Gln Gly Val Val Lys Phe Gln Asp Val Ser Phe Ala Tyr Pro Asn Arg
465                 470                 475                 480
Pro Asp Arg Pro Val Leu Lys Gly Leu Thr Phe Thr Leu Arg Pro Gly
                485                 490                 495
Glu Val Thr Ala Leu Val Gly Pro Asn Gly Ser Gly Lys Ser Thr Val
                500                 505                 510
Ala Ala Leu Leu Gln Asn Leu Tyr Gln Pro Thr Gly Gly Gln Val Leu
            515                 520                 525
Leu Asp Glu Lys Pro Ile Ser Gln Tyr Glu His Cys Tyr Leu His Ser
            530                 535                 540
Gln Val Val Ser Val Gly Gln Glu Pro Val Leu Phe Ser Gly Ser Val
545                 550                 555                 560
Arg Asn Asn Ile Ala Tyr Gly Leu Gln Ser Cys Glu Asp Asp Lys Val
                565                 570                 575
Met Ala Ala Gln Ala Ala His Ala Asp Asp Phe Ile Gln Glu Met
                580                 585                 590
Glu His Gly Ile Tyr Thr Asp Val Gly Glu Lys Gly Ser Gln Leu Ala
            595                 600                 605
Ala Gly Gln Lys Gln Arg Leu Ala Ile Ala Arg Ala Leu Val Arg Asp
            610                 615                 620
Pro Arg Val Leu Ile Leu Asp Glu Ala Thr Ser Ala Leu Asp Val Gln
625                 630                 635                 640
Cys Glu Gln Ala Lys Thr Leu Trp Lys Phe Met Ile Phe
                645                 650

<210> SEQ ID NO 29
<211> LENGTH: 2490
<212> TYPE: DNA
<213> ORGANISM: Mus musculus

<400> SEQUENCE: 29
accgcgacca cggcagtgaa gtgaaagcga aagccgcggg acccaggcgc gctccccgcg      60
agggcgtcgc tgcgcaccca ggagatccag tttgagaaga agcagattcc agaagctctc     120
ctgagctgcc gctccgcagc cgcagaaccc accatggcgc tgtcctacct gaggccctgg     180
```

-continued

```
gtctctctgc tgctggcgga catggccttta cttgggttgc tacaaggatc tctgggaaat    240
ctgcttcccc aggggctgcc aggactctgg atagagggca ccctgcgact tggagtgctg    300
tggggactgc taaaagtggg agagctgctg ggacttgtgg ggacccttct gcccttgctc    360
tgccttgcca ctcccctgtt tttctcgcta agagctctgg tgggaggcac cgcgagcacc    420
tcagtagtcc gagtggcttc tgcctcttgg ggctggctgc tggctggcta tggggctgtt    480
gcgctgagct gggccgtgtg ggctgtgctg agcccggctg gagtccagga gaaggaacca    540
ggccaggaga acagaacact gatgaagcgg ttgctgaagc tgtccaggcc ggacctgcct    600
ttcctcatag ctgccttctt cttccttgtg gtggctgtgt gggggagac attaatccct    660
cgctattcgg gtcgtgtaat tgacatcctg ggaggtgatt tcgaccccga cgcctttgca    720
agcgccatct tttcatgtg cctgttctct gttgggagct ccttctctgc aggctgtaga    780
ggaggctcct tcctcttcac catgtccagg atcaacctgc ggatacgaga gcagcttttc    840
tcatctttgt tgcgccaaga ccttggattc ttccaggaga ccaagacagg ggagctgaac    900
tcgaggctga gctctgacac ctctctgatg agccgctggc tccctttcaa tgccaatatc    960
ctgctgcgga gcctggtgaa ggtggtgggg ctctacttct tcatgctcca ggtatcgccc   1020
cgactcacct tcctctcccct gctggacctg cccctcacga tagcagctga aaggtgtac   1080
aaccccgcc atcaggcggt gctaaaggag atccaggatg cagtggccaa ggcggggcag   1140
gtggtgcgcg aggcggtagg agggctgcag actgtgcgaa gctttgggc cgaggagcag   1200
gaagtcagcc actacaagga ggccctggag cgatgtagac agctgtggtg gcgccgagac   1260
ctggaaaaag acgtgtatct agtcatacgg agggtgatgg ccttgggcat gcaggtgctg   1320
attctgaact gcggcgtgca gcagattctg gctggagagg tcacccgggg tggcctgctc   1380
tccttcctgc tgtaccagga ggaagtggga caatatgtcc ggaacctggt ttacatgtac   1440
ggggatatgc tgagcaacgt gggcgctgct gaaaaggtgt tttcctacct ggaccgaaag   1500
ccgaatctgc cccagcctgg gatcctggcc cctccctggc tggaggggcg cgtgaattc    1560
caagacgtct cctttttcgta tcccaggcgc cccgagaagc ctgtgctcca gggtctgacg   1620
ttcaccctgc atcctggaac ggtgacagcg ttggtgggac ccaatggatc agggaagagc   1680
accgtggccg ccctgctgca gaacctgtac cagcccactg ggggccagct gctgctggat   1740
ggcgagcccc tgaccgagta tgatcaccac tacctgcacc gccaggtggt tctggtgggg   1800
caggagcctg tgctgttctc gggttctgtc aaggacaata ttgccatatgg cctgagggac   1860
tgtgaggacg ctcaagtgat ggcagctgcc caggcggcct gtgcagacga cttcataggg   1920
gaaatgacta atggaataaa cacagaaatc ggggaaaaag ggggccagtt agctgtggga   1980
cagaagcaac gtctggccat tgcccgggcc cttgtgcgga acccacgggt cctcatcctg   2040
gatgaggcta ccagcgccct ggacgcccag tgtgaacagg cccctacagaa ctggagatcg   2100
caggggggaca ggacgatgct ggtgattgcc cacaggctgc acacggttca gaatgctgac   2160
caagttctgg tgctcaagca gggacgtctg gtggagcatg accagctcag ggacggccag   2220
gatgtctacg cccacctggt acagcagcgg ctggaggcat gaggcctcca gaccctgagc   2280
ccctctcagg actgtggcca ggatcagacc cacagggacc gtgccggagg aggctagggt   2340
caggataaag attgggaccg ttttggactt tgtgtgtttt tgtggccttg atgggtgagg   2400
gttgggggag tgggtggttt gtggttctag aaacattatt ttttgctga atataaaaat   2460
aataaatata tataaaatgc ttttccttaa                                    2490
```

```
<210> SEQ ID NO 30
<211> LENGTH: 702
<212> TYPE: PRT
<213> ORGANISM: Mus musculus

<400> SEQUENCE: 30

Met Ala Leu Ser Tyr Leu Arg Pro Trp Val Ser Leu Leu Ala Asp
1               5                   10                  15

Met Ala Leu Leu Gly Leu Leu Gln Gly Ser Leu Gly Asn Leu Leu Pro
            20                  25                  30

Gln Gly Leu Pro Gly Leu Trp Ile Glu Gly Thr Leu Arg Leu Gly Val
            35                  40                  45

Leu Trp Gly Leu Leu Lys Val Gly Glu Leu Leu Gly Leu Val Gly Thr
    50                  55                  60

Leu Leu Pro Leu Leu Cys Leu Ala Thr Pro Leu Phe Phe Ser Leu Arg
65                  70                  75                  80

Ala Leu Val Gly Gly Thr Ala Ser Thr Ser Val Val Arg Val Ala Ser
                85                  90                  95

Ala Ser Trp Gly Trp Leu Leu Ala Gly Tyr Gly Ala Val Ala Leu Ser
            100                 105                 110

Trp Ala Val Trp Ala Val Leu Ser Pro Ala Gly Val Gln Glu Lys Glu
        115                 120                 125

Pro Gly Gln Glu Asn Arg Thr Leu Met Lys Arg Leu Leu Lys Leu Ser
    130                 135                 140

Arg Pro Asp Leu Pro Phe Leu Ile Ala Ala Phe Phe Leu Val Val
145                 150                 155                 160

Ala Val Trp Gly Glu Thr Leu Ile Pro Arg Tyr Ser Gly Arg Val Ile
                165                 170                 175

Asp Ile Leu Gly Gly Asp Phe Asp Pro Asp Ala Phe Ala Ser Ala Ile
            180                 185                 190

Phe Phe Met Cys Leu Phe Ser Val Gly Ser Ser Phe Ser Ala Gly Cys
        195                 200                 205

Arg Gly Gly Ser Phe Leu Phe Thr Met Ser Arg Ile Asn Leu Arg Ile
    210                 215                 220

Arg Glu Gln Leu Phe Ser Ser Leu Leu Arg Gln Asp Leu Gly Phe Phe
225                 230                 235                 240

Gln Glu Thr Lys Thr Gly Glu Leu Asn Ser Arg Leu Ser Ser Asp Thr
                245                 250                 255

Ser Leu Met Ser Arg Trp Leu Pro Phe Asn Ala Asn Ile Leu Leu Arg
            260                 265                 270

Ser Leu Val Lys Val Val Gly Leu Tyr Phe Phe Met Leu Gln Val Ser
        275                 280                 285

Pro Arg Leu Thr Phe Leu Ser Leu Leu Asp Leu Pro Leu Thr Ile Ala
    290                 295                 300

Ala Glu Lys Val Tyr Asn Pro Arg His Gln Ala Val Leu Lys Glu Ile
305                 310                 315                 320

Gln Asp Ala Val Ala Lys Ala Gly Gln Val Arg Glu Ala Val Gly
                325                 330                 335

Gly Leu Gln Thr Val Arg Ser Phe Gly Ala Glu Glu Gln Glu Val Ser
            340                 345                 350

His Tyr Lys Glu Ala Leu Glu Arg Cys Arg Gln Leu Trp Trp Arg Arg
        355                 360                 365

Asp Leu Glu Lys Asp Val Tyr Leu Val Ile Arg Arg Val Met Ala Leu
    370                 375                 380
```

Gly Met Gln Val Leu Ile Leu Asn Cys Gly Val Gln Ile Leu Ala
385                 390                 395                 400

Gly Glu Val Thr Arg Gly Gly Leu Leu Ser Phe Leu Leu Tyr Gln Glu
            405                 410                 415

Glu Val Gly Gln Tyr Val Arg Asn Leu Val Tyr Met Tyr Gly Asp Met
            420                 425                 430

Leu Ser Asn Val Gly Ala Ala Glu Lys Val Phe Ser Tyr Leu Asp Arg
            435                 440                 445

Lys Pro Asn Leu Pro Gln Pro Gly Ile Leu Ala Pro Trp Leu Glu
    450                 455                 460

Gly Arg Val Glu Phe Gln Asp Val Ser Phe Ser Tyr Pro Arg Arg Pro
465                 470                 475                 480

Glu Lys Pro Val Leu Gln Gly Leu Thr Phe Thr Leu His Pro Gly Thr
            485                 490                 495

Val Thr Ala Leu Val Gly Pro Asn Gly Ser Gly Lys Ser Thr Val Ala
            500                 505                 510

Ala Leu Leu Gln Asn Leu Tyr Gln Pro Thr Gly Gln Leu Leu Leu
    515                 520                 525

Asp Gly Glu Pro Leu Thr Glu Tyr Asp His His Tyr Leu His Arg Gln
530                 535                 540

Val Val Leu Val Gly Gln Glu Pro Val Leu Phe Ser Gly Ser Val Lys
545                 550                 555                 560

Asp Asn Ile Ala Tyr Gly Leu Arg Asp Cys Glu Asp Ala Gln Val Met
            565                 570                 575

Ala Ala Ala Gln Ala Ala Cys Ala Asp Asp Phe Ile Gly Glu Met Thr
            580                 585                 590

Asn Gly Ile Asn Thr Glu Ile Gly Glu Lys Gly Gly Gln Leu Ala Val
            595                 600                 605

Gly Gln Lys Gln Arg Leu Ala Ile Ala Arg Ala Leu Val Arg Asn Pro
610                 615                 620

Arg Val Leu Ile Leu Asp Glu Ala Thr Ser Ala Leu Asp Ala Gln Cys
625                 630                 635                 640

Glu Gln Ala Leu Gln Asn Trp Arg Ser Gln Gly Asp Arg Thr Met Leu
            645                 650                 655

Val Ile Ala His Arg Leu His Thr Val Gln Asn Ala Asp Gln Val Leu
            660                 665                 670

Val Leu Lys Gln Gly Arg Leu Val Glu His Asp Gln Leu Arg Asp Gly
            675                 680                 685

Gln Asp Val Tyr Ala His Leu Val Gln Gln Arg Leu Glu Ala
690                 695                 700

<210> SEQ ID NO 31
<211> LENGTH: 3779
<212> TYPE: DNA
<213> ORGANISM: Homo sapiens

<400> SEQUENCE: 31
ggggacgcgg cacagatagg gggaagccgg agtaatggtt ttcgggcaag tggatgttgg    60
agagcacaca caggagttgg ggggcggggg agggcctggg gttggggagg gctcgaactc   120
ggggctgctg ggtagtccag gagggcgcgg taaggctggg gtgtcctggt gagaactgga   180
gaggatctac ccgggtccct gcctggccag tggggaaaca ccggtccccc aggcaccttc   240
acctaaccag agcggggatt tccaccgccc ctcatgccgc cctttggagg aaagtgaaag   300
tgaaaggagg aagaggaggc ttcatggctg aggaggtcgc agcgccatga agtccctgtc   360

```
tctgctcctc gctgtggctt tgggcctggc gaccgccgtc tcagcaggac ccgcggtgat    420
cgagtgttgg ttcgtggagg atgcgagcgg aaagggcctg gccaagagac ccggtgcact    480
gctgttgcgc cagggaccgg gggaaccgcc gccccggccg gacctcgacc ctgagctcta    540
tctcagtgta cacgaccccg cggggcgccct ccaggctgcc ttcaggcggt atccccgggg   600
cgcccccgca ccacactgcg agatgagccg cttcgtgcct ctccccgcct ctgcgaaatg    660
ggccagcggc ctgaccccg cgcagaactg cccgcgggcc ctggatgggg cttggctgat     720
ggtcagcata tccagcccag tcctcagcct ctccagcctc ttgcgaccac agccagagcc    780
tcagcaggag cctgttctca tcaccatggc aacagtggta ctgactgtcc tcacccacac    840
ccctgcccct cgagtgagac tgggacaaga tgctctgctg gacttgagct ttgcctacat    900
gccccccacc tccgaggccg cctcatctct ggctccgggt cccccctcct tgggctaga    960
gtggcgacgc cagcacctgg gtaagggaca tctgctcctg gctgcaactc ctgggctgaa   1020
tggccagatg ccagcagccc aagaaggggc cgtggcattt gctgcttggg atgatgatga   1080
gccatggggc ccatggaccg gaaatgggac cttctggctg cctacagttc aacccttca    1140
ggagggcacc tatctggcca ccatacacct gccataccctg caaggacagg tcaccctgga   1200
gcttgctgtg tacaaacccc ccaaagtgtc cctgatgcca gcaaccctttg cacgggccgc   1260
cccaggggag gcaccccgg aattgctctg ccttgtgtcc cacttctacc cttctggggg    1320
cctggaggtg gagtgggaac tccggggtgg cccaggggc cgctctcaga aggccgaggg    1380
gcagaggtgg ctctcggccc tgcgccacca ttccgatggc tctgtcagcc tctctgggca   1440
cttgcagccg cccccagtca ccactgagca gcatgggca cgctatgcct gtcgaattca    1500
ccatcccagc ctgcctgcct cggggcgcag cgctgaggtc accctggagg tagcaggtct   1560
ttcagggccc tcccttgagg acagcgtagg ccttttcctg tctgcctttc ttctgcttgg   1620
gctcttcaag gcactgggct gggctgctgt ctacctgtcc acctgcaagg attcaaagaa   1680
gaaagcagag tgagggcact cactgccatc ctgtggaagc caccatcatc tctggcccaa   1740
gcttctgtag tagctcccta aaataatacc ctatcatctg ctcctaatcc ctccaatctc   1800
tctccactga gtggctggaa tgcttttttt ttttctttc acttatataa gggataattt   1860
ttcttttttt tttttttttg agacggagtc tcactcttcc gcccaggctg cagtgcagtg   1920
gcatgatctt ggcttactgc aacctccgcc tcctgggttc aagcaattct gtggcttcag   1980
cctccggagt agctgggatt acaggcacat gccaccacac ccagtgaatt tttgtatttt   2040
tagtagagac ggggttcac catgttggcc aggctggtct tgaattcctg acctcaggtg   2100
atctgcccac ctcagcctcc caaagtgctg ggattacagg cgtgagccac cacaccaggc   2160
ccgagaaatg cttttttaaa aaacacacat cttatgcat tcaccttctt ggagctctag    2220
gacagtggtt ctcaaaattt ttttctctca ggacctctta aaaatcatca aggaccccaa   2280
aaagcttttg ggtatgtggg ttatagctat caatatttat ggtactagaa cttaaaagtg   2340
agaaaaattt aaaacacgag aatacatagg cacacattct attcatcgtg ggaaccatgg   2400
tgtcaataca tatcatgtag cttctgaaaa actccactgt acacttatag aatgaagaag   2460
gcaaaaaact tttttttttt tttttttgag acggagtctc gctctgtcgc ccaggctgga   2520
gtgcagtggc gcgatctcgg ctcactgcaa gctccgcctc tcgggttcac gccattctcc   2580
tgcctcagcc tcccaagtag ctcggactac aggcgtcctc caccatgcct ggctaatatt   2640
ttgtattttt tagtagagac ggggtttcac cgtgttagcc aggatggtct cgatctccta   2700
```

```
acctggtgat ccgcccgcct cggcctccca aagtattggg attacccgcg tgagccaccg    2760
cgcccggctg caaataatct ttcttttttt ctgagacaga gtctcgctct gttgcccagg    2820
ctggagtgca gtggcacgat ctcggctcac ggcacgctcc gcctcccggg ttcacgccat    2880
tctcctgcct cagcttcccg agtagctggg actacagggg cccgccacca cgcccggcta    2940 acttttgtg ttttagtag agacggggtt tcaccgtgtt agccaggatg gtctcgatct      3000
cctgaccttg tgatctgccc gcctcggcct cccaaagtgc tgggattaca ggcgtgagcc    3060
accgcgcccg gcggcgaaac acgatattgt actaacatct taattttgtt ataaaatctc    3120
acaaaccccc tgacatagtc tcagagatct gtagggccga ggttacattt ggagaacccg    3180
tactctaggg ccaaatccat tcttcttgcc ctggctcact tgtccccccc accgccccgc    3240
gctggagcca ctgcctagtt cttcagccct agatggtgct cgccagacct cctctcaatg    3300
ctcatcacac acagggctat tcctttcctc caatgaacca aacgcctccc gcccacctcc    3360
aggtcccagt cctctgttcc ctttgcctgg tccaccttg ccctccctgg gtcgcagacg     3420
aggtcggcct cgtcattccc cgcagaccgc cgcgcgtccc tcttgtgcgg ttcaccacag    3480
ttgtatttaa gtgatcgtgt gagtcgtcgt taaatgcctg tctccccgcg gatcatgggc    3540
tcctcgagga cagggactgg cctgtctgtc cactgctgta accccgcgcc ggcataggga    3600
cctaaggccc actggagggc gctcatcaag tagctgctgg atgttgacga aggaagcggc    3660
ggcgcagctc agggatctcc gagtcaggac ggtcggccag acccacgggg taacgggtct    3720
aatcgtgtag gaataaagct gtattccagt gcttccaaaa aaaaaaaaaa aaaaaaaaa    3779
```

<210> SEQ ID NO 32
<211> LENGTH: 448
<212> TYPE: PRT
<213> ORGANISM: Homo sapiens

<400> SEQUENCE: 32

```
Met Lys Ser Leu Ser Leu Leu Ala Val Ala Leu Gly Leu Ala Thr
1               5                   10                  15

Ala Val Ser Ala Gly Pro Ala Val Ile Glu Cys Trp Phe Val Glu Asp
            20                  25                  30

Ala Ser Gly Lys Gly Leu Ala Lys Arg Pro Gly Ala Leu Leu Leu Arg
        35                  40                  45

Gln Gly Pro Gly Glu Pro Pro Arg Pro Asp Leu Asp Pro Glu Leu
    50                  55                  60

Tyr Leu Ser Val His Asp Pro Ala Gly Ala Leu Gln Ala Ala Phe Arg
65                  70                  75                  80

Arg Tyr Pro Arg Gly Ala Pro Ala Pro His Cys Glu Met Ser Arg Phe
                85                  90                  95

Val Pro Leu Pro Ala Ser Ala Lys Trp Ala Ser Gly Leu Thr Pro Ala
            100                 105                 110

Gln Asn Cys Pro Arg Ala Leu Asp Gly Ala Trp Leu Met Val Ser Ile
        115                 120                 125

Ser Ser Pro Val Leu Ser Leu Ser Leu Leu Arg Pro Gln Pro Glu
    130                 135                 140

Pro Gln Gln Glu Pro Val Leu Ile Thr Met Ala Thr Val Val Leu Thr
145                 150                 155                 160

Val Leu Thr His Thr Pro Ala Pro Arg Val Arg Leu Gly Gln Asp Ala
                165                 170                 175

Leu Leu Asp Leu Ser Phe Ala Tyr Met Pro Pro Thr Ser Glu Ala Ala
            180                 185                 190
```

```
Ser Ser Leu Ala Pro Gly Pro Pro Phe Gly Leu Glu Trp Arg Arg
    195                 200                 205

Gln His Leu Gly Lys Gly His Leu Leu Leu Ala Ala Thr Pro Gly Leu
    210                 215                 220

Asn Gly Gln Met Pro Ala Ala Gln Glu Gly Ala Val Ala Phe Ala Ala
225                 230                 235                 240

Trp Asp Asp Glu Pro Trp Gly Pro Trp Thr Gly Asn Gly Thr Phe
                    245                 250                 255

Trp Leu Pro Thr Val Gln Pro Phe Gln Glu Gly Thr Tyr Leu Ala Thr
            260                 265                 270

Ile His Leu Pro Tyr Leu Gln Gly Gln Val Thr Leu Glu Leu Ala Val
            275                 280                 285

Tyr Lys Pro Pro Lys Val Ser Leu Met Pro Ala Thr Leu Ala Arg Ala
    290                 295                 300

Ala Pro Gly Glu Ala Pro Pro Glu Leu Leu Cys Leu Val Ser His Phe
305                 310                 315                 320

Tyr Pro Ser Gly Gly Leu Glu Val Glu Trp Glu Leu Arg Gly Gly Pro
                325                 330                 335

Gly Gly Arg Ser Gln Lys Ala Glu Gly Gln Arg Trp Leu Ser Ala Leu
            340                 345                 350

Arg His His Ser Asp Gly Ser Val Ser Leu Ser Gly His Leu Gln Pro
        355                 360                 365

Pro Pro Val Thr Thr Glu Gln His Gly Ala Arg Tyr Ala Cys Arg Ile
    370                 375                 380

His His Pro Ser Leu Pro Ala Ser Gly Arg Ser Ala Glu Val Thr Leu
385                 390                 395                 400

Glu Val Ala Gly Leu Ser Gly Pro Ser Leu Glu Asp Ser Val Gly Leu
                405                 410                 415

Phe Leu Ser Ala Phe Leu Leu Leu Gly Leu Phe Lys Ala Leu Gly Trp
            420                 425                 430

Ala Ala Val Tyr Leu Ser Thr Cys Lys Asp Ser Lys Lys Lys Ala Glu
        435                 440                 445

<210> SEQ ID NO 33
<211> LENGTH: 2003
<212> TYPE: DNA
<213> ORGANISM: Homo sapiens

<400> SEQUENCE: 33
ggggacgcgg cacagatagg gggaagccgg agtaatggtt tcgggcaag tggatgttgg      60 agagcacaca caggagttgg ggggcggggg agggcctggg gttggggagg gctcgaactc    120
ggggctgctg ggtagtccag gagggcgcgg taaggctggg gtgtcctggt gagaactgga    180
gaggatctac ccgggtccct gcctggccag tggggaaaca ccggtccccc aggcaccttc    240
acctaaccag agcggggatt ccaccgccc ctcatgccgc cctttggagg aaagtgaaag    300
tgaaaggagg aagaggaggc ttcatggctg aggaggtcgc agcgccatga agtccctgtc    360
tctgctcctc gctgtggctt tgggcctggc gaccgccgtc tcagcaggac ccgcggtgat    420
cgagtgttgg ttcgtggagg atgcgagcgg aaagggcctg ccaagagac ccggtgcact    480 gctgttgcgc cagggaccgg ggaaccgcc gccccggccg acctcgaccc tgagctcta    540 tctcagtgta cacgaccccg cgggcgccct ccaggctgcc ttcaggcggt atccccgggg    600
cgcccccgca ccacactgcg agatgagccg cttcgtgcct ctccccgcct ctgcgaaatg    660
```

```
ggccagcggc ctgacccccg cgcagaactg cccgcgggcc ctggatgggg cttggctgat    720
ggtcagcata tccagcccag tcctcagcct ctccagcctc ttgcgaccac agccagagcc    780
tcagcaggag cctgttctca tcaccatggc aacagtggta ctgactgtcc tcacccacac    840
ccctgcccct cgagtgagac tgggacaaga tgctctgctg gacttgagct ttgcctacat    900
gccccccacc tccgaggccg cctcatctct ggctccgggt cccctccct  ttgggctaga    960
gtggcgacgc cagcacctgg gtaagggaca tctgctcctg gctgcaactc ctgggctgaa    1020
tggccagatg ccagcagccc aagaaggggc cgtggcattt gctgcttggg atgatgatga    1080
gccatggggc ccatggaccg gaaatgggac cttctggctg cctacagttc aaccctttca    1140
ggagggcacc tatctggcca ccatacacct gccatacctg caaggacagg tcaccctgga    1200
gcttgctgtg tacaaacccc ccaaagtgtc cctgatgcca gcaacccttg cacgggccgc    1260
cccaggggag gcaccccgg  aattgctctg ccttgtgtcc cacttctacc cttctggggg    1320
cctggaggtg gagtgggaac tccggggtgg cccaggggc  cgctctcaga aggccgaggg    1380
gcagaggtgg ctctcggccc tgcgccacca ttccgatggc tctgtcagcc tctctgggca    1440
cttgcagccg ccccagtca  ccactgagca gcatgggca  cgctatgcct gtcgaattca    1500
ccatcccagc ctgcctgcct cggggcgcag cgctgaggtc accctggagg tagcaggtct    1560
ttcagggccc tcccttgagg acagcgtagg ccttttcctg tctgccttc  ttctgcttgg    1620
gctcttcaag gcactgggct gggctgctgt ctacctgtcc acctgcaagg attcaaagaa    1680
ggtacagtgc tccacctctc tgtatctttc ccttgtcact ttatctcctc atcctatctc    1740
aaaacccatg gagggaggct gctggtgtgg taggcagaac ctaggcttgg aattcacact    1800
gatctgggtt aaaacctggc actatatcct aactgtagga ctctttgagc atgctactta    1860
atctatatgt ttccttgggt gtagggattt taaaaagtta cttaggcagt gctgtccaat    1920
agaaagataa tgcaagccac atatgtaaat ttaaatactc tagtactcac attaaaaaaa    1980
taagcagaaa caggtaaaat taa                                            2003
```

<210> SEQ ID NO 34
<211> LENGTH: 504
<212> TYPE: PRT
<213> ORGANISM: Homo sapiens

<400> SEQUENCE: 34

```
Met Lys Ser Leu Ser Leu Leu Leu Ala Val Ala Leu Gly Leu Ala Thr
1               5                   10                  15

Ala Val Ser Ala Gly Pro Ala Val Ile Glu Cys Trp Phe Val Glu Asp
            20                  25                  30

Ala Ser Gly Lys Gly Leu Ala Lys Arg Pro Gly Ala Leu Leu Leu Arg
        35                  40                  45

Gln Gly Pro Gly Glu Pro Pro Arg Pro Asp Leu Asp Pro Glu Leu
    50                  55                  60

Tyr Leu Ser Val His Asp Pro Ala Gly Leu Gln Ala Ala Phe Arg
65                  70                  75                  80

Arg Tyr Pro Arg Gly Ala Pro Ala Pro His Cys Glu Met Ser Arg Phe
                85                  90                  95

Val Pro Leu Pro Ala Ser Ala Lys Trp Ala Ser Gly Leu Thr Pro Ala
            100                 105                 110

Gln Asn Cys Pro Arg Ala Leu Asp Gly Ala Trp Leu Met Val Ser Ile
        115                 120                 125

Ser Ser Pro Val Leu Ser Leu Ser Ser Leu Leu Arg Pro Gln Pro Glu
```

```
            130             135             140
Pro Gln Gln Glu Pro Val Leu Ile Thr Met Ala Thr Val Val Leu Thr
145                 150                 155                 160

Val Leu Thr His Thr Pro Ala Pro Arg Val Arg Leu Gly Gln Asp Ala
            165                 170                 175

Leu Leu Asp Leu Ser Phe Ala Tyr Met Pro Pro Thr Ser Glu Ala Ala
            180                 185                 190

Ser Ser Leu Ala Pro Gly Pro Pro Phe Gly Leu Glu Trp Arg Arg
            195                 200                 205

Gln His Leu Gly Lys Gly His Leu Leu Leu Ala Ala Thr Pro Gly Leu
            210                 215                 220

Asn Gly Gln Met Pro Ala Ala Gln Glu Gly Ala Val Ala Phe Ala Ala
225                 230                 235                 240

Trp Asp Asp Glu Pro Trp Gly Pro Trp Thr Gly Asn Gly Thr Phe
            245                 250                 255

Trp Leu Pro Thr Val Gln Pro Phe Gln Glu Gly Thr Tyr Leu Ala Thr
            260                 265                 270

Ile His Leu Pro Tyr Leu Gln Gly Gln Val Thr Leu Glu Leu Ala Val
            275                 280                 285

Tyr Lys Pro Pro Lys Val Ser Leu Met Pro Ala Thr Leu Ala Arg Ala
290                 295                 300

Ala Pro Gly Glu Ala Pro Pro Glu Leu Leu Cys Leu Val Ser His Phe
305                 310                 315                 320

Tyr Pro Ser Gly Gly Leu Glu Val Glu Trp Glu Leu Arg Gly Gly Pro
            325                 330                 335

Gly Gly Arg Ser Gln Lys Ala Glu Gly Gln Arg Trp Leu Ser Ala Leu
            340                 345                 350

Arg His His Ser Asp Gly Ser Val Ser Leu Ser Gly His Leu Gln Pro
            355                 360                 365

Pro Pro Val Thr Thr Glu Gln His Gly Ala Arg Tyr Ala Cys Arg Ile
            370                 375                 380

His His Pro Ser Leu Pro Ala Ser Gly Arg Ser Ala Glu Val Thr Leu
385                 390                 395                 400

Glu Val Ala Gly Leu Ser Gly Pro Ser Leu Glu Asp Ser Val Gly Leu
            405                 410                 415

Phe Leu Ser Ala Phe Leu Leu Leu Gly Leu Phe Lys Ala Leu Gly Trp
            420                 425                 430

Ala Ala Val Tyr Leu Ser Thr Cys Lys Asp Ser Lys Lys Val Gln Cys
            435                 440                 445

Ser Thr Ser Leu Tyr Leu Ser Leu Val Thr Leu Ser Pro His Pro Ile
450                 455                 460

Ser Lys Pro Met Glu Gly Gly Cys Trp Cys Gly Arg Gln Asn Leu Gly
465                 470                 475                 480

Leu Glu Phe Thr Leu Ile Trp Val Lys Thr Trp His Tyr Ile Leu Thr
            485                 490                 495

Val Gly Leu Phe Glu His Ala Thr
            500
```

<210> SEQ ID NO 35
<211> LENGTH: 3518
<212> TYPE: DNA
<213> ORGANISM: Homo sapiens

<400> SEQUENCE: 35

-continued

| | |
|---|---|
| ggggacgcgg cacagatagg gggaagccgg agtaatggtt ttcgggcaag tggatgttgg | 60 |
| agagcacaca caggagttgg ggggcggggg agggcctggg gttggggagg gctcgaactc | 120 |
| ggggctgctg ggtagtccag gagggcgcgg taaggctggg gtgtcctggt gagaactgga | 180 |
| gaggatctac ccgggtccct gcctggccag tggggaaaca ccggtccccc aggcaccttc | 240 |
| acctaaccag agcggggatt tccaccgccc ctcatgccgc cctttggagg aaagtgaaag | 300 |
| tgaaaggagg aagaggaggc ttcatggctg aggaggtcgc agcgccatga agtccctgtc | 360 |
| tctgctcctc gctgtggctt tgggcctggc gaccgccgtc tcagcaggac ccgcggtgat | 420 |
| cgagtgttgg ttcgtggagg atgcgagcgg aaagggcctg gccaagagac ccggtgcact | 480 |
| gctgttgcgc cagggaccgg gggaaccgcc gccccggccg gacctcgacc ctgagctcta | 540 |
| tctcagtgta cacgtggtac tgactgtcct cacccacacc cctgcccctc gagtgagact | 600 |
| gggacaagat gctctgctgg acttgagctt tgcctacatg ccccccacct ccgaggccgc | 660 |
| ctcatctctg gctccgggtc cccctccctt tgggctagag tggcgacgcc agcacctggg | 720 |
| taagggacat ctgctcctgg ctgcaactcc tgggctgaat ggccagatgc cagcagccca | 780 |
| agaaggggcc gtggcatttg ctgcttggga tgatgatgag ccatggggcc catggaccgg | 840 |
| aaatgggacc ttctggctgc ctacagttca acccttcag gagggcacct atctggccac | 900 |
| catacacctg ccatacctgc aaggacaggt caccctggag cttgctgtgt acaaaccccc | 960 |
| caaagtgtcc ctgatgccag caacccttgc acgggccgcc caggggagg cacccccgga | 1020 |
| attgctctgc cttgtgtccc acttctaccc ttctgggggc ctggaggtgg agtgggaact | 1080 |
| ccggggtggc ccaggggggcc gctctcagaa ggccgagggg cagaggtggc tctcggccct | 1140 |
| gcgccaccat tccgatggct ctgtcagcct ctctgggcac ttgcagccgc ccccagtcac | 1200 |
| cactgagcag catggggcac gctatgcctg tcgaattcac catcccagcc tgcctgcctc | 1260 |
| ggggcgcagc gctgaggtca ccctggaggt agcaggtctt tcagggccct cccttgagga | 1320 |
| cagcgtaggc cttttcctgt ctgcctttct tctgcttggg ctcttcaagg cactgggctg | 1380 |
| ggctgctgtc tacctgtcca cctgcaagga ttcaaagaag aaagcagagt gagggcactc | 1440 |
| actgccatcc tgtggaagcc accatcatct ctggcccaag cttctgtagt agctccctaa | 1500 |
| aataatacccc tatcatctgc tcctaatccc tccaatctct ctccactgag tggctggaat | 1560 |
| gcttttttttt tttctttca cttatataag ggataatttt tcttttttttt tttttttga | 1620 |
| gacggagtct cactcttccg cccaggctgc agtgcagtgg catgatcttg gcttactgca | 1680 |
| acctccgcct cctgggttca agcaattctg tggcttcagc ctccggagta gctgggatta | 1740 |
| caggcacatg ccaccacacc cagtgaattt ttgtattttt agtagagacg gggtttcacc | 1800 |
| atgttggcca ggctggtctt gaattcctga cctcaggtga tctgcccacc tcagcctccc | 1860 |
| aaagtgctgg gattacaggc gtgagccacc acaccaggcc cgagaaatgc ttttttaaaa | 1920 |
| aacacacatc ttatggcatt caccttcttg gagctctagg acagtggttc tcaaaatttt | 1980 |
| tttctctcag gacctcttaa aaatcatcaa ggaccccaaa aagcttttgg gtatgtgggt | 2040 |
| tatagctatc aatatttatg gtactagaac ttaaagtga gaaaaattta aaacacgaga | 2100 |
| atacataggc acacattcta ttcatcgtgg gaaccatggt gtcaatacat atcatgtagc | 2160 |
| ttctgaaaaa ctccactgta cacttataga atgaagaagg caaaaaactt ttttttttt | 2220 |
| ttttttgaga cggagtctcg ctctgtcgcc caggctggag tgcagtggcg cgatctcggc | 2280 |
| tcactgcaag ctccgcctct cgggttcacg ccattctcct gcctcagcct cccaagtagc | 2340 |
| tcggactaca ggcgtcctcc accatgcctg gctaatattt tgtattttt agtagagacg | 2400 |

-continued

```
gggtttcacc gtgttagcca ggatggtctc gatctcctaa cctggtgatc cgcccgcctc    2460
ggcctcccaa agtattggga ttacccgcgt gagccaccgc gcccggctgc aaataatctt    2520 tcttttttc tgagacagag tctcgctctg ttgcccaggc tggagtgcag tggcacgatc     2580
tcggctcacg gcacgctccg cctcccgggt tcacgccatt ctcctgcctc agcttcccga    2640
gtagctggga ctacagggc cgccaccac gcccggctaa cttttttgtgt ttttagtaga    2700 gacgggtttt caccgtgtta gccaggatgg tctcgatctc ctgaccttgt gatctgcccg    2760
cctcggcctc ccaaagtgct gggattacag gcgtgagcca ccgcgcccgg cggcgaaaca    2820
cgatattgta ctaacatctt aattttgtta taaaatctca caaaccccct gacatagtct    2880
cagagatctg tagggccgag gttacatttg gagaacccgt actctagggc caaatccatt    2940
cttcttgccc tggctcactt gtcccccca ccgcccgcg ctggagccac tgcctagttc     3000
ttcagcccta gatggtgctc gccagacctc ctctcaatgc tcatcacaca cagggctatt    3060
cctttcctcc aatgaaccaa acgcctcccg cccacctcca ggtcccagtc ctctgttccc    3120
tttgcctggt ccacccttgc cctccctggg tcgcagacga ggtcggcctc gtcattcccc    3180
gcagaccgcc gcgcgtccct cttgtgcggt tcaccacagt tgtatttaag tgatcgtgtg    3240
agtcgtcgtt aaatgcctgt ctccccgcgg atcatgggct cctcgaggac agggactggc    3300
ctgtctgtcc actgctgtaa ccccgcgccg gcatagggac ctaaggccca ctggagggcg    3360
ctcatcaagt agctgctgga tgttgacgaa ggaagcggcg gcgcagctca gggatctccg    3420
agtcaggacg gtcggccaga cccacggggt aacgggtcta atcgtgtagg aataaagctg    3480
tattccagtg cttccaaaaa aaaaaaaaaa aaaaaaaa                            3518
```

<210> SEQ ID NO 36
<211> LENGTH: 361
<212> TYPE: PRT
<213> ORGANISM: Homo sapiens

<400> SEQUENCE: 36

```
Met Lys Ser Leu Ser Leu Leu Ala Val Ala Leu Gly Leu Ala Thr
1               5                   10                  15

Ala Val Ser Ala Gly Pro Ala Val Ile Glu Cys Trp Phe Val Glu Asp
                20                  25                  30

Ala Ser Gly Lys Gly Leu Ala Lys Arg Pro Gly Ala Leu Leu Leu Arg
            35                  40                  45

Gln Gly Pro Gly Glu Pro Pro Arg Pro Asp Leu Asp Pro Glu Leu
        50                  55                  60

Tyr Leu Ser Val His Val Leu Thr Val Leu Thr His Thr Pro Ala
65                  70                  75                  80

Pro Arg Val Arg Leu Gly Gln Asp Ala Leu Leu Asp Leu Ser Phe Ala
                85                  90                  95

Tyr Met Pro Pro Thr Ser Glu Ala Ala Ser Ser Leu Ala Pro Gly Pro
                100                 105                 110

Pro Pro Phe Gly Leu Glu Trp Arg Arg Gln His Leu Gly Lys Gly His
            115                 120                 125

Leu Leu Leu Ala Ala Thr Pro Gly Leu Asn Gly Gln Met Pro Ala Ala
        130                 135                 140

Gln Glu Gly Ala Val Ala Phe Ala Ala Trp Asp Asp Glu Pro Trp
145                 150                 155                 160

Gly Pro Trp Thr Gly Asn Gly Thr Phe Trp Leu Pro Thr Val Gln Pro
                165                 170                 175
```

```
Phe Gln Glu Gly Thr Tyr Leu Ala Thr Ile His Leu Pro Tyr Leu Gln
                180                 185                 190
Gly Gln Val Thr Leu Glu Leu Ala Val Tyr Lys Pro Pro Lys Val Ser
            195                 200                 205
Leu Met Pro Ala Thr Leu Ala Arg Ala Ala Pro Gly Glu Ala Pro Pro
210                 215                 220
Glu Leu Leu Cys Leu Val Ser His Phe Tyr Pro Ser Gly Gly Leu Glu
225                 230                 235                 240
Val Glu Trp Glu Leu Arg Gly Pro Gly Gly Arg Ser Gln Lys Ala
                245                 250                 255
Glu Gly Gln Arg Trp Leu Ser Ala Leu Arg His Ser Asp Gly Ser
                260                 265                 270
Val Ser Leu Ser Gly His Leu Gln Pro Pro Val Thr Thr Glu Gln
            275                 280                 285
His Gly Ala Arg Tyr Ala Cys Arg Ile His Pro Ser Leu Pro Ala
                290                 295                 300
Ser Gly Arg Ser Ala Glu Val Thr Leu Glu Val Ala Gly Leu Ser Gly
305                 310                 315                 320
Pro Ser Leu Glu Asp Ser Val Gly Leu Phe Leu Ser Ala Phe Leu Leu
                325                 330                 335
Leu Gly Leu Phe Lys Ala Leu Gly Trp Ala Ala Val Tyr Leu Ser Thr
                340                 345                 350
Cys Lys Asp Ser Lys Lys Lys Ala Glu
                355                 360

<210> SEQ ID NO 37
<211> LENGTH: 2750
<212> TYPE: DNA
<213> ORGANISM: Mus musculus

<400> SEQUENCE: 37 caaggggtg  ggtgcagggc gaggagtggc tggagagcta cagacagggt ttcggcaact    60
ctgtttggcc cctgtgggcg gcgttcctcc aacgcgcagt cacgccctca cctgaccaga   120
tcggggaatt tccagttcct caccccagcc ttagaaggaa aatgaaagtg aaagggaag    180 aaaagacttg gtaggagaga tcgtagcacc atgaagcctc tgctcctgct cgtcgctgtg    240
gcactgggcc tagcgaccgt cgtctccgtc gtctcggctg accagaggc gatcgagtgc    300 tggttcgtgg aggatgcagg tgggggtggc ctgtctaaga aacctgccac actgctactg    360
cgccatggac ccaggggacc gccgccccgg ccagatcttg acccaaagct atacttcaag    420
gtggatgacc cggcgggaat gctcctggcc gccttcaggc ggtaccccgc aggcgcctcc    480
gccccacact gcgagatgag ccgcttcatc ccgttccctg cctcggcgaa gtgggctaga    540
agtctgagtc cggagcagaa ctgcccgcgg gccctggacg gggattggct gctggtcagc    600
gtatccagca ctctcttcag cctctccagc ctgctgcgac acagccgga gcctctgcgg    660 gagcctgtcg tcatcaccat ggcaacagtg gtgctgaccg tcctcaccca taaccctgcc    720
cctcgagtcc agctgggaaa ggatgcagtg ctggacctgc gcttcgccta cgcaccctcc    780
gccctggaag ttctcccctc tctgacgca ggccctcctc cctttgggct ggagtggcga    840
cgccagcaca ggggaaaggg tcacctgctg ttggctgcca ccccggggct ggccgggaga    900
atgccaccag cccaggaaaa ggctacggca tttgcagctt gggatgacga tgagccctgg    960
ggcccgtgga ctgggaatgg gaccttctgg cttccagccg tgaagccttc tcaggagggt   1020
```

| | | |
|---|---|---|
| gtctacctgg ctacggtaca cctgccctac ctgcaaggac aggtctccct ggagctgact | 1080 |
| gtgcacaagg cccccagagt gtctctaaca ccagcacccg ttgtgtgggc tgccccagga | 1140 |
| gaggcacccc cagaactgct ctgtcttgca tcccacttct tccctgcgga gggtctggag | 1200 |
| gtcaagtggg agctcagagg cggcccagga ggaagttcta gaaaggttga ggggaagacg | 1260 |
| tggctctcca ccatccgcca ccattccgat ggctctgtca gccagtctgg gcacctgcag | 1320 |
| ctacctccag tcactgccaa gcagcatgga gttcactatg tctgtcgggt gtaccactct | 1380 |
| agcctgccag catcggggcg cagtgctgac gtcaccctgg aggtggcagg cttctcaggg | 1440 |
| ccctccatcg aggacggcat cggcctgttc ctgtctgctt ttctcctcct cggactcctc | 1500 |
| aaggtgctag gctggctggt agctgcctac tggaccattc ctgaagtctc aaaggagaag | 1560 |
| gccacagctg ccagcctgac cattcccagg aactcaaaga agtcacagta agaagttct | 1620 |
| cgtctgtgga agccaccctc atctctggcc cagatgactc cagtagcccc tgccccagaa | 1680 |
| caacagcctt cttctcttct tctccctcca ttgaatagct cggatttttt tttttaaggt | 1740 |
| ttttttgttt gtttcaatct ttcttgtttt gttcttgttt ttagacaagg tctctctatg | 1800 |
| tagccttggc tggctgtcct gaaccctcac caagccaacc aggctggcct cgaagtccca | 1860 |
| gagatccacc tgtccctctg cctcggagtg acaaacggca ctggacacca tgcctagagg | 1920 |
| tcttttttt ttttggtttt tggagacagg atttctctgt atagtcccgg ctgtcctgga | 1980 |
| actcactctg tagaccaggc tggcctcgaa ctcagaaatc cgcctgcctc tgcctcccag | 2040 |
| gtgctgggat taaaggcgtg cgccaccacc gctggactcg aactaaactt ttaagatgag | 2100 |
| aaaaaagcga gacttagcgc cacactcatt tgatgcccac agtcgggagg cagaggcagt | 2160 |
| ggatctctga catttccatg ccagcctgat ctacaaatag ggagtttcag gtcagtcggg | 2220 |
| gttacttggc ggggctttgt tgagagaact aaatataaga acacacatgc gtagagtccc | 2280 |
| agggttgaga agaaccagtg tatgcgccag agaggcgggt tcataacctg tggctcacaa | 2340 |
| ccccctttaa gtccatcgga aataccgagac attaggattc acaacagtag taaaggcagt | 2400 |
| tacgaagtag caaagaaaat aatttttacaa cttgaactgc gttaatgtta agaaggttga | 2460 |
| gaaccactgg ccaggggatt aggacgaaag gtcttcatag catcttaaga ttctagagac | 2520 |
| ctcagggaca gcccacagca gtagtctaga gacggaaagg tccatgtgtc tccctcgcgg | 2580 |
| actaaagcct acctctccag ctctccattc ctaccacagc ttttcttttg cctggtccac | 2640 |
| ctttaccatc tccgggcctg gtgggtctcg gcccttacg aatgtccccg tgtggttcgt | 2700 |
| cctctcctgt tcgccggtcc tcgtgagcta ataaagtctt tccgagtttc | 2750 |

<210> SEQ ID NO 38
<211> LENGTH: 466
<212> TYPE: PRT
<213> ORGANISM: Mus musculus

<400> SEQUENCE: 38

Met Lys Pro Leu Leu Leu Val Ala Val Ala Leu Gly Leu Ala Thr
1               5                   10                  15

Val Val Ser Val Val Ser Ala Gly Pro Glu Ala Ile Glu Cys Trp Phe
                20                  25                  30

Val Glu Asp Ala Gly Gly Gly Gly Leu Ser Lys Lys Pro Ala Thr Leu
            35                  40                  45

Leu Leu Arg His Gly Pro Arg Gly Pro Pro Arg Pro Asp Leu Asp
        50                  55                  60

Pro Lys Leu Tyr Phe Lys Val Asp Asp Pro Ala Gly Met Leu Leu Ala

```
              65                  70                  75                  80
Ala Phe Arg Arg Tyr Pro Ala Gly Ala Ser Ala Pro His Cys Glu Met
                     85                  90                  95

Ser Arg Phe Ile Pro Phe Pro Ala Ser Ala Lys Trp Ala Arg Ser Leu
                100                 105                 110

Ser Pro Glu Gln Asn Cys Pro Arg Ala Leu Asp Gly Asp Trp Leu Leu
            115                 120                 125

Val Ser Val Ser Ser Thr Leu Phe Ser Leu Ser Ser Leu Leu Arg Pro
        130                 135                 140

Gln Pro Glu Pro Leu Arg Glu Pro Val Val Ile Thr Met Ala Thr Val
145                 150                 155                 160

Val Leu Thr Val Leu Thr His Asn Pro Ala Pro Arg Val Gln Leu Gly
                165                 170                 175

Lys Asp Ala Val Leu Asp Leu Arg Phe Ala Tyr Ala Pro Ser Ala Leu
                180                 185                 190

Glu Gly Ser Pro Ser Leu Asp Ala Gly Pro Pro Phe Gly Leu Glu
            195                 200                 205

Trp Arg Arg Gln His Arg Gly Lys Gly His Leu Leu Leu Ala Ala Thr
        210                 215                 220

Pro Gly Leu Ala Gly Arg Met Pro Pro Ala Gln Glu Lys Ala Thr Ala
225                 230                 235                 240

Phe Ala Ala Trp Asp Asp Asp Glu Pro Trp Gly Pro Trp Thr Gly Asn
                245                 250                 255

Gly Thr Phe Trp Leu Pro Ala Val Lys Pro Ser Gln Glu Gly Val Tyr
                260                 265                 270

Leu Ala Thr Val His Leu Pro Tyr Leu Gln Gly Gln Val Ser Leu Glu
            275                 280                 285

Leu Thr Val His Lys Ala Pro Arg Val Ser Leu Thr Pro Ala Pro Val
        290                 295                 300

Val Trp Ala Ala Pro Gly Glu Ala Pro Pro Glu Leu Leu Cys Leu Ala
305                 310                 315                 320

Ser His Phe Phe Pro Ala Glu Gly Leu Glu Val Lys Trp Glu Leu Arg
                325                 330                 335

Gly Gly Pro Gly Gly Ser Ser Arg Lys Val Glu Gly Lys Thr Trp Leu
                340                 345                 350

Ser Thr Ile Arg His His Ser Asp Gly Ser Val Ser Gln Ser Gly His
            355                 360                 365

Leu Gln Leu Pro Pro Val Thr Ala Lys Gln His Gly Val His Tyr Val
        370                 375                 380

Cys Arg Val Tyr His Ser Ser Leu Pro Ala Ser Gly Arg Ser Ala Asp
385                 390                 395                 400

Val Thr Leu Glu Val Ala Gly Phe Ser Gly Pro Ser Ile Glu Asp Gly
                405                 410                 415

Ile Gly Leu Phe Leu Ser Ala Phe Leu Leu Gly Leu Leu Lys Val
                420                 425                 430

Leu Gly Trp Leu Val Ala Ala Tyr Trp Thr Ile Pro Glu Val Ser Lys
        435                 440                 445

Glu Lys Ala Thr Ala Ala Ser Leu Thr Ile Pro Arg Asn Ser Lys Lys
450                 455                 460

Ser Gln
465

<210> SEQ ID NO 39
```

<211> LENGTH: 2747
<212> TYPE: DNA
<213> ORGANISM: Mus musculus

<400> SEQUENCE: 39

```
caagggggtg ggtgcagggc gaggagtggc tggagagcta cagacagggt ttcggcaact      60
ctgtttggcc cctgtgggcg gcgttcctcc aacgcgcagt cacgccctca cctgaccaga     120
tcggggaatt ccagttcct caccccagcc ttagaaggaa aatgaaagtg aaaggggaag      180
aaaagacttg gtaggagaga tcgtagcacc atgaagcctc tgctcctgct cgtcgctgtg     240
gcactgggcc tagcgaccgt cgtctccgtc gtctcggctg accagaggc gatcgagtgc      300
tggttcgtgg aggatgcagg tggggtggc ctgtctaaga aacctgccac actgctactg      360
cgccatggac ccaggggacc gccgccccgg ccagatcttg acccaaagct atacttcaag     420
gtggatgacc cggcgggaat gctcctggcc gccttcaggc ggtaccccgc aggcgcctcc     480
gccccacact gcgagatgag ccgcttcatc ccgttccctg cctcggcgaa gtgggctaga     540
agtctgagtc cggagcagaa ctgcccgcgg ccctggacg gggattggct gctggtcagc      600
gtatccagca ctctcttcag cctctccagc ctgctgcgac acagccgga gcctctgcgg      660
gagcctgtcg tcatcaccat ggcaacagtg gtgctgaccg tcctcaccca taaccctgcc     720
cctcgagtcc agctgggaaa ggatgcagtg ctggacctgc gcttcgccta cgcaccctcc     780
gccctggaag gttctcccctc tctggacgca ggccctcctc cctttgggct ggagtggcga     840
cgccagcaca ggggaaaggg tcacctgctg ttggctgcca ccccgggct ggccgggaga      900
atgccaccag cccaggaaaa ggctacggca tttgcagctt gggatgacga tgagccctgg     960
ggcccgtgga ctgggaatgg daccttctgg cttccagccg tgaagccttc tcaggagggt    1020
gtctacctgg ctacggtaca cctgccctac ctgcaaggac aggtctccct ggagctgact    1080
gtgcacaagg cccccagagt gtctctaaca ccagcacccg ttgtgtgggc tgccccagga    1140
gaggcacccc cagaactgct ctgtcttgca tcccacttct tccctgcgga gggtctggag    1200
gtcaagtggg agctcagagg cggcccagga ggaagttcta gaaaggttga ggggaagacg    1260
tggctctcca ccatccgcca ccattccgat ggctctgtca gccagtctgg gcacctgcag    1320
ctacctccag tcactgccaa gcagcatgga gttcactatg tctgtcgggt gtaccactct    1380
agcctgccag catcggggcg cagtgctgac gtcaccctgg aggtggcagg cttctcaggg    1440
ccctccatcg aggacggcat cggcctgttc ctgtctgctt ttctcctcct cggactcctc    1500
aaggtgctag gctggctggc tgcctactgg accattcctg aagtctcaaa ggagaaggcc    1560
acagctgcca gcctgaccat tcccaggaac tcaaagaagt cacagtaaag aagttctcgt    1620
ctgtggaagc caccctcatc tctggcccag atgactccag tagcccctgc cccagaacaa    1680
cagccttctt ctcttcttct ccctccattg aatagctcgg atttttttt ttaaggtttt    1740
tttgtttgtt tcaatctttc ttgttttgtt cttgttttta gacaaggtct ctctatgtag    1800
ccttggctgg ctgtcctgaa ccctcaccaa gccaaccagg ctggcctcga agtcccagag    1860
atccacctgt ccctctgcct cggagtgaca aacggcactg acaccatgc ctagaggtct     1920
ttttttttt tggttttgg agacaggatt tctctgtata gtcccggctg tcctggaact    1980
cactctgtag accaggctgg cctcgaactc agaaatccgc ctgcctctgc tcccaggtg     2040
ctgggattaa aggcgtgcgc caccaccgct ggactcgaac taaacttta agatgagaaa    2100
aaagcgagac ttagcgccac actcatttga tgcccacagt cggaggcag aggcagtgga     2160
tctctgacat ttccatgcca gcctgatcta caaatagggaa gtttcaggtc agtcggggtt    2220
```

-continued

```
acttggcggg gctttgttga gagaactaaa tataagaaca cacatgcgta gagtcccagg    2280
gttgagaaga accagtgtat gcgccagaga ggcgggttca taacctgtgg ctcacaaccc    2340
cctttaagtc catcggaaat accagacatt aggattcaca acagtagtaa aggcagttac    2400
gaagtagcaa agaaaataat tttacaactt gaactgcgtt aatgttaaga aggttgagaa    2460
ccactggcca ggggattagg acgaaaggtc ttcatagcat cttaagattc tagagacctc    2520
agggacagcc cacagcagta gtctagagac ggaaaggtcc atgtgtctcc ctcgcggact    2580
aaagcctacc tctccagctc tccattccta ccacagcttt tcttttgcct ggtccacctt    2640
taccatctcc gggcctggtg ggtctcggcc ctttacgaat gtccccgtgt ggttcgtcct    2700
ctcctgttcg ccggtcctcg tgagctaata aagtcttttcc gagtttc                 2747
```

<210> SEQ ID NO 40  
<211> LENGTH: 465  
<212> TYPE: PRT  
<213> ORGANISM: Mus musculus

<400> SEQUENCE: 40

```
Met Lys Pro Leu Leu Leu Val Ala Val Ala Leu Gly Leu Ala Thr
1               5                   10                  15

Val Val Ser Val Val Ser Ala Gly Pro Glu Ala Ile Glu Cys Trp Phe
                20                  25                  30

Val Glu Asp Ala Gly Gly Gly Leu Ser Lys Lys Pro Ala Thr Leu
            35                  40                  45

Leu Leu Arg His Gly Pro Arg Gly Pro Pro Arg Pro Asp Leu Asp
50                  55                  60

Pro Lys Leu Tyr Phe Lys Val Asp Asp Pro Ala Gly Met Leu Leu Ala
65                  70                  75                  80

Ala Phe Arg Arg Tyr Pro Ala Gly Ala Ser Ala Pro His Cys Glu Met
                85                  90                  95

Ser Arg Phe Ile Pro Phe Pro Ala Ser Ala Lys Trp Ala Arg Ser Leu
                100                 105                 110

Ser Pro Glu Gln Asn Cys Pro Arg Ala Leu Asp Gly Asp Trp Leu Leu
            115                 120                 125

Val Ser Val Ser Ser Thr Leu Phe Ser Leu Ser Ser Leu Leu Arg Pro
130                 135                 140

Gln Pro Glu Pro Leu Arg Glu Pro Val Val Ile Thr Met Ala Thr Val
145                 150                 155                 160

Val Leu Thr Val Leu Thr His Asn Pro Ala Pro Arg Val Gln Leu Gly
                165                 170                 175

Lys Asp Ala Val Leu Asp Leu Arg Phe Ala Tyr Ala Pro Ser Ala Leu
            180                 185                 190

Glu Gly Ser Pro Ser Leu Asp Ala Gly Pro Pro Phe Gly Leu Glu
        195                 200                 205

Trp Arg Arg Gln His Arg Gly Lys Gly His Leu Leu Ala Ala Thr
210                 215                 220

Pro Gly Leu Ala Gly Arg Met Pro Pro Ala Gln Glu Lys Ala Thr Ala
225                 230                 235                 240

Phe Ala Ala Trp Asp Asp Asp Glu Pro Trp Gly Pro Trp Thr Gly Asn
                245                 250                 255

Gly Thr Phe Trp Leu Pro Ala Val Lys Pro Ser Gln Glu Gly Val Tyr
            260                 265                 270

Leu Ala Thr Val His Leu Pro Tyr Leu Gln Gly Gln Val Ser Leu Glu
```

```
                    275                 280                 285
Leu Thr Val His Lys Ala Pro Arg Val Ser Leu Thr Pro Ala Pro Val
    290                 295                 300

Val Trp Ala Ala Pro Gly Glu Ala Pro Glu Leu Leu Cys Leu Ala
305                 310                 315                 320

Ser His Phe Phe Pro Ala Glu Gly Leu Glu Val Lys Trp Glu Leu Arg
                325                 330                 335

Gly Gly Pro Gly Gly Ser Ser Arg Lys Val Glu Gly Lys Thr Trp Leu
            340                 345                 350

Ser Thr Ile Arg His His Ser Asp Gly Ser Val Ser Gln Ser Gly His
        355                 360                 365

Leu Gln Leu Pro Pro Val Thr Ala Lys Gln His Gly Val His Tyr Val
    370                 375                 380

Cys Arg Val Tyr His Ser Ser Leu Pro Ala Ser Gly Arg Ser Ala Asp
385                 390                 395                 400

Val Thr Leu Glu Val Ala Gly Phe Ser Gly Pro Ser Ile Glu Asp Gly
                405                 410                 415

Ile Gly Leu Phe Leu Ser Ala Phe Leu Leu Leu Gly Leu Leu Lys Val
            420                 425                 430

Leu Gly Trp Leu Ala Ala Tyr Trp Thr Ile Pro Glu Val Ser Lys Glu
        435                 440                 445

Lys Ala Thr Ala Ala Ser Leu Thr Ile Pro Arg Asn Ser Lys Lys Ser
    450                 455                 460

Gln
465

<210> SEQ ID NO 41
<211> LENGTH: 5593
<212> TYPE: DNA
<213> ORGANISM: Homo sapiens

<400> SEQUENCE: 41
acggatccgc gttcagaaag gcgtgcactt cctacgcctg atccccgca tcgcaacctc      60 gcagcttccc cggcgtgcag cgctcattta ccaattccct tcctgggagt tgcggcttcc    120
ctcgctcggc cccactcccg tttacccttt ccccagctcc cgccttagcc aggggcttcc    180
ccgcctgccg ctagggctcg ggccgaagcg ccgctcagcg ccagcctgcc gctcccgggg    240
ctccactttc actttcggtc ctgggggagc taggccggcg gcagtggtgg tggcggcggc    300
gcaagggtga gggcggcccc agaacccag gtaggtagag caagaagatg gtgtttctgc    360
ccctcaaatg gtcccttgca accatgtcat ttctactttc ctcactgttg gctctcttaa    420
ctgtgtccac tccttcatgg tgtcagagca ctgaagcatc tccaaaacgt agtgatggga    480
caccatttcc ttggaataaa atacgacttc ctgagtacgt catcccagtt cattatgatc    540
tcttgatcca tgcaaacctt accacgctga ccttctgggg aaccacgaaa gtagaaatca    600
cagccagtca gccaccagc accatcatcc tgcatagtca ccacctgcag atatctaggg    660
ccacccctca gaagggagct ggagagaggc tatcggaaga accctgcag gtcctggaac    720 acccccgtca ggagcaaatt gcactgctgg ctcccgagcc cctccttgtc gggctcccgt    780
acacagttgt cattcactat gctggcaatc tttcggagac tttccacgga ttttacaaaa    840
gcacctacag aaccaaggaa ggggaactga ggatactagc atcaacacaa tttgaaccca    900
ctgcagctag aatggccttt ccctgctttg atgaacctgc cttcaaagca gtttctcaa     960 tcaaaattag aagagagcca aggcacctag ccatctccaa tatgccattg gtgaaatctg   1020
```

-continued

```
tgactgttgc tgaaggactc atagaagacc attttgatgt cactgtgaag atgagcacct    1080
atctggtggc cttcatcatt tcagattttg agtctgtcag caagataacc aagagtggag    1140
tcaaggtttc tgtttatgct gtgccagaca agataaatca agcagattat gcactggatg    1200
ctgcggtgac tcttctagaa ttttatgagg attatttcag cataccgtat cccctaccca    1260
aacaagatct tgctgctatt cccgactttc agtctggtgc tatggaaaac tggggactga    1320
caacatatag agaatctgct ctgttgtttg atgcagaaaa gtcttctgca tcaagtaagc    1380
ttggcatcac aatgactgtg gcccatgaac tggctcacca gtggtttggg aacctggtca    1440
ctatggaatg tgtggaatgat ctttggctaa atgaaggatt tgccaaattt atggagtttg    1500
tgtctgtcag tgtgacccat cctgaactga agttggaga ttatttctttt ggcaaatgtt     1560
ttgacgcaat ggaggtagat gctttaaatt cctcacaccc tgtgtctaca cctgtggaaa    1620
atcctgctca gatccgggag atgtttgatg atgtttctta tgataaggga gcttgtattc    1680
tgaatatgct aagggagtat cttagtgctg acgcatttaa aagtggtatt gtacagtatc    1740
tccagaagca tagctataaa aatacaaaaa acgaggacct gtgggatagt atggcaagta    1800
tttgccctac agatggtgta aaagggatgg atggcttttg ctctagaagt caacattcat    1860
cttcatcctc acattggcat caggaagggg tggatgtgaa aaccatgatg aacacttgga    1920
cactgcagaa gggttttccc ctaataacca tcacagtgag ggggaggaat gtacacatga    1980
agcaagagca ctacatgaag ggctctgacg gcgccccgga cactgggtac ctgtggcatg    2040
ttccattgac attcatcacc agcaaatccg acatggtcca tcgattttttg ctaaaaacaa    2100
aaacagatgt gctcatcctc ccagaagagg tggaatggat caaatttaat gtgggcatga    2160
atggctatta cattgtgcat tacgaggatg atggatggga ctctttgact ggcctttttaa    2220
aaggaacaca cacagcagtc agcagtaatg atcgggcgag tctcattaac aatgcatttc    2280
agctcgtcag cattgggaag ctgtccattg aaaaggcctt ggatttatcc ctgtacttga    2340
aacatgaaac tgaaattatg cccgtgtttc aaggtttgaa tgagctgatt cctatgtata    2400
agttaatgga gaaagagat atgaatgaag tggaaactca attcaaggcc ttcctcatca    2460
ggctgctaag ggacctcatt gataagcaga catggacaga cgagggctca gtctcagagc    2520
gaatgctgcg gagtcaacta ctactcctcg cctgtgtgca caactatcag ccgtgcgtac    2580
agagggcaga aggctatttc agaaagtgga aggaatccaa tggaaacttg agcctgcctg    2640
tcgacgtgac cttggcagtg tttgctgtgg gggcccagag cacagaaggc tgggattttc    2700
tttatagtaa atatcagttt tctttgtcca gtactgagaa aagccaaatt gaatttgccc    2760
tctgcagaac ccaaaataag gaaaagcttc aatggctact agatgaaagc tttaagggag    2820
ataaaataaa aactcaggag tttccacaaa ttcttacact cattggcagg aacccagtag    2880
gatacccact ggcctggcaa tttctgagga aaaactggaa caaacttgta caaaagtttg    2940
aacttggctc atcttccata gcccacatgg taatgggtac aacaaatcaa ttctccacaa    3000
gaacacggct tgaagaggta aaaggattct tcagctcttt gaaagaaaat ggttctcagc    3060
tccgttgtgt ccaacagaca attgaaacca ttgaagaaaa catcggttgg atggataaga    3120
attttgataa aatcagagtg tggctgcaaa gtgaaaagct tgaacatgat cctgaagctg    3180
acgcaacagg atgaaaatcc atcagaatct cagactacag cactaaatat gctttgatgc    3240
tacatcaaac ggaatggaag catagctgac ttcgctaaag ttacttcatc tccatctagc    3300
aaatgaggca ctgttctcaa ccaaaggaga tggggatctg gtttagggca atccctttat    3360
```

```
aatttgatgt gctgtggtct ccttggtaat gtataatttg gtattgcaca ggtgattagt    3420
caaggaagtc tggaaaagct ttggtcccac agccttgcct cacagcatgt aaataattaa    3480
aacaatattg atgctgaggt tcttctactg ctagtatgaa agtgacaaat ttttactggt    3540
gtgaattggg aagaaaacaa tgctattcca tgacgtttgt aaaatgtttg taaaagctca    3600
aacatgacga ttccataaaa taaacttgag gttaaataat gggtagtaaa ttatagaatg    3660
tataagaaaa aatataaagg agaaaatcaa ttatcaggaa agctaaagaa cttttcaaat    3720
ctagtaattt gaatatagac acaatgcact ttattgcact ttcaattctt ataaagcaac    3780
aataatatta aggtccttga ctatgtgtac aatgttttca catatatagt ttcatttaat    3840
catttcaaag ttaatctctg ccatctcgct aaatcatcag tctcggctct tctgaaatag    3900
aaggtgcctg atcttcctaa taattctgcc tattttcatt tgctttaaac aggcgcccta    3960
ttttctttct agttgtggct gcgcaaaaac atttatctcc caataagat gtgctgctta    4020 ccgaggtatc acggggtggg gctccagctt gggtcgttga agctgggggtt tgggaaacca    4080 cttcagagat ggcagcagca agtttagcat cttcaaattt cttttattga aaaaaatttt    4140
attagtaaca tgttgtatat aaaattatga gcacaatgcc atcacttaac tataactctt    4200
aaagatagct taatgactgt ttattctctt gaccaaatag actcataata acatataatt    4260
ttaaaagaaa tttaaattct ttcttctcta ttgtattatt ttatacaatt tgctatttct    4320
atttccttct catattgatt attctaaata ctatgcaata atataactta gagttccacg    4380
gtttgtttac acatttcctg ttgtacattt aggttattca agttttcag ctcttttaaa    4440 attgctctga ataagttcta gtgagtgagt tatggtgctg gctatatttt gctaaactgc    4500
cctctcaaat gttgctagga attcatactg cgaaaagcaa tgaataagca tgcctgtttt    4560
cccatggcct tgcttgccag aatttgactt ttattatgat aatcagtgta aaatgatata    4620
ctactattgc ttgtatattg tggtatacgg tgtcaggttt cagggttttt tttcaacgtt    4680
aaatattcta gaaactttct gaaataattt ctgtttaaaa atattgaata tttgcttcat    4740
ttcaaatact cccttttgac aaaaaaactt aggtataact gttgatgaaa aaccagaaaa    4800
aagtccagaa ctctttggtg actccaacta tggatagctt attttgaaaa aggagaattg    4860 caaatttttac caaaagatgg agaaaagcac attaaaaaga taccaacatt cagaaattca    4920
tttcagcatg ttattattgg aaattattta aactaattta gataactata agatacttat    4980
tgtccattta taccctgtaa agccgttta gaatgtaata ttttaggtaa tccaaaatgt    5040
actaaattaa attcattttt agttatgaga aatctttgct tatatgacaa atgaaaagaa    5100
taacaagttg tcaaatgaaa agaatgacat tgaaacattt gtattgtctc ttcttaaact    5160
atcttattga cttattattt aagccttta atactaagta tgaaacaacc tatggtctgg    5220
aaatttgtat cgcaaagcta tatgtgcata tgttatttaa ttcatctaat gctacacaaa    5280
agcataaaat aatgattttt cactctcttt aaaaatacta atcattat gtccatttct    5340 caatttttc attgatctat gctttgagtt tgctttctca acattattgt attttccact    5400
tattattact gtataacata tgctagtgtt tagttggatt aatcttacct aaaagtactg    5460
aaaaatgctt tttagtactt tttcatattt tatacatta tttccgaat gtatcattga    5520 ataatttat tgagttataa agtatctta ttgctattta ataaaaaatt aacacataaa    5580
atgaaaaaaa aaa                                                       5593
```

<210> SEQ ID NO 42
<211> LENGTH: 948

<212> TYPE: PRT
<213> ORGANISM: Homo sapiens

<400> SEQUENCE: 42

```
Met Val Phe Leu Pro Leu Lys Trp Ser Leu Ala Thr Met Ser Phe Leu
1               5                   10                  15

Leu Ser Ser Leu Leu Ala Leu Leu Thr Val Ser Thr Pro Ser Trp Cys
            20                  25                  30

Gln Ser Thr Glu Ala Ser Pro Lys Arg Ser Asp Gly Thr Pro Phe Pro
        35                  40                  45

Trp Asn Lys Ile Arg Leu Pro Glu Tyr Val Ile Pro Val His Tyr Asp
    50                  55                  60

Leu Leu Ile His Ala Asn Leu Thr Thr Leu Thr Phe Trp Gly Thr Thr
65                  70                  75                  80

Lys Val Glu Ile Thr Ala Ser Gln Pro Thr Ser Thr Ile Ile Leu His
                85                  90                  95

Ser His His Leu Gln Ile Ser Arg Ala Thr Leu Arg Lys Gly Ala Gly
            100                 105                 110

Glu Arg Leu Ser Glu Glu Pro Leu Gln Val Leu Glu His Pro Arg Gln
        115                 120                 125

Glu Gln Ile Ala Leu Leu Ala Pro Glu Pro Leu Leu Val Gly Leu Pro
    130                 135                 140

Tyr Thr Val Val Ile His Tyr Ala Gly Asn Leu Ser Glu Thr Phe His
145                 150                 155                 160

Gly Phe Tyr Lys Ser Thr Tyr Arg Thr Lys Glu Gly Glu Leu Arg Ile
                165                 170                 175

Leu Ala Ser Thr Gln Phe Glu Pro Thr Ala Ala Arg Met Ala Phe Pro
            180                 185                 190

Cys Phe Asp Glu Pro Ala Phe Lys Ala Ser Phe Ser Ile Lys Ile Arg
        195                 200                 205

Arg Glu Pro Arg His Leu Ala Ile Ser Asn Met Pro Leu Val Lys Ser
    210                 215                 220

Val Thr Val Ala Glu Gly Leu Ile Glu Asp His Phe Asp Val Thr Val
225                 230                 235                 240

Lys Met Ser Thr Tyr Leu Val Ala Phe Ile Ile Ser Asp Phe Glu Ser
                245                 250                 255

Val Ser Lys Ile Thr Lys Ser Gly Val Lys Val Ser Val Tyr Ala Val
            260                 265                 270

Pro Asp Lys Ile Asn Gln Ala Asp Tyr Ala Leu Asp Ala Ala Val Thr
        275                 280                 285

Leu Leu Glu Phe Tyr Glu Asp Tyr Phe Ser Ile Pro Tyr Pro Leu Pro
    290                 295                 300

Lys Gln Asp Leu Ala Ala Ile Pro Asp Phe Gln Ser Gly Ala Met Glu
305                 310                 315                 320

Asn Trp Gly Leu Thr Thr Tyr Arg Glu Ser Ala Leu Leu Phe Asp Ala
                325                 330                 335

Glu Lys Ser Ser Ala Ser Ser Lys Leu Gly Ile Thr Met Thr Val Ala
            340                 345                 350

His Glu Leu Ala His Gln Trp Phe Gly Asn Leu Val Thr Met Glu Trp
        355                 360                 365

Trp Asn Asp Leu Trp Leu Asn Glu Gly Phe Ala Lys Phe Met Glu Phe
    370                 375                 380

Val Ser Val Ser Val Thr His Pro Glu Leu Lys Val Gly Asp Tyr Phe
385                 390                 395                 400
```

-continued

Phe Gly Lys Cys Phe Asp Ala Met Glu Val Asp Ala Leu Asn Ser Ser
              405                 410                 415

His Pro Val Ser Thr Pro Val Glu Asn Pro Ala Gln Ile Arg Glu Met
              420                 425                 430

Phe Asp Asp Val Ser Tyr Asp Lys Gly Ala Cys Ile Leu Asn Met Leu
              435                 440                 445

Arg Glu Tyr Leu Ser Ala Asp Ala Phe Lys Ser Gly Ile Val Gln Tyr
              450                 455                 460

Leu Gln Lys His Ser Tyr Lys Asn Thr Lys Asn Glu Asp Leu Trp Asp
465                 470                 475                 480

Ser Met Ala Ser Ile Cys Pro Thr Asp Gly Val Lys Gly Met Asp Gly
              485                 490                 495

Phe Cys Ser Arg Ser Gln His Ser Ser Ser Ser His Trp His Gln
              500                 505                 510

Glu Gly Val Asp Val Lys Thr Met Met Asn Thr Trp Thr Leu Gln Lys
              515                 520                 525

Gly Phe Pro Leu Ile Thr Ile Thr Val Arg Gly Arg Asn Val His Met
              530                 535                 540

Lys Gln Glu His Tyr Met Lys Gly Ser Asp Gly Ala Pro Asp Thr Gly
545                 550                 555                 560

Tyr Leu Trp His Val Pro Leu Thr Phe Ile Thr Ser Lys Ser Asp Met
              565                 570                 575

Val His Arg Phe Leu Leu Lys Thr Lys Thr Asp Val Leu Ile Leu Pro
              580                 585                 590

Glu Glu Val Glu Trp Ile Lys Phe Asn Val Gly Met Asn Gly Tyr Tyr
              595                 600                 605

Ile Val His Tyr Glu Asp Asp Gly Trp Asp Ser Leu Thr Gly Leu Leu
              610                 615                 620

Lys Gly Thr His Thr Ala Val Ser Ser Asn Asp Arg Ala Ser Leu Ile
625                 630                 635                 640

Asn Asn Ala Phe Gln Leu Val Ser Ile Gly Lys Leu Ser Ile Glu Lys
              645                 650                 655

Ala Leu Asp Leu Ser Leu Tyr Leu Lys His Glu Thr Glu Ile Met Pro
              660                 665                 670

Val Phe Gln Gly Leu Asn Glu Leu Ile Pro Met Tyr Lys Leu Met Glu
              675                 680                 685

Lys Arg Asp Met Asn Glu Val Glu Thr Gln Phe Lys Ala Phe Leu Ile
              690                 695                 700

Arg Leu Leu Arg Asp Leu Ile Asp Lys Gln Thr Trp Thr Asp Glu Gly
705                 710                 715                 720

Ser Val Ser Glu Arg Met Leu Arg Ser Gln Leu Leu Leu Leu Ala Cys
              725                 730                 735

Val His Asn Tyr Gln Pro Cys Val Gln Arg Ala Glu Gly Tyr Phe Arg
              740                 745                 750

Lys Trp Lys Glu Ser Asn Gly Asn Leu Ser Leu Pro Val Asp Val Thr
              755                 760                 765

Leu Ala Val Phe Ala Val Gly Ala Gln Ser Thr Glu Gly Trp Asp Phe
              770                 775                 780

Leu Tyr Ser Lys Tyr Gln Phe Ser Leu Ser Ser Thr Glu Lys Ser Gln
785                 790                 795                 800

Ile Glu Phe Ala Leu Cys Arg Thr Gln Asn Lys Glu Lys Leu Gln Trp
              805                 810                 815

```
Leu Leu Asp Glu Ser Phe Lys Gly Asp Lys Ile Lys Thr Gln Phe
                820                 825                 830

Pro Gln Ile Leu Thr Leu Ile Gly Arg Asn Pro Val Gly Tyr Pro Leu
            835                 840                 845

Ala Trp Gln Phe Leu Arg Lys Asn Trp Asn Lys Leu Val Gln Lys Phe
    850                 855                 860

Glu Leu Gly Ser Ser Ile Ala His Met Val Met Gly Thr Thr Asn
865                 870                 875                 880

Gln Phe Ser Thr Arg Thr Arg Leu Glu Glu Val Lys Gly Phe Phe Ser
                885                 890                 895

Ser Leu Lys Glu Asn Gly Ser Gln Leu Arg Cys Val Gln Gln Thr Ile
            900                 905                 910

Glu Thr Ile Glu Glu Asn Ile Gly Trp Met Asp Lys Asn Phe Asp Lys
        915                 920                 925

Ile Arg Val Trp Leu Gln Ser Glu Lys Leu Glu His Asp Pro Glu Ala
    930                 935                 940

Asp Ala Thr Gly
945

<210> SEQ ID NO 43
<211> LENGTH: 5589
<212> TYPE: DNA
<213> ORGANISM: Homo sapiens

<400> SEQUENCE: 43
acggatccgc gttcagaaag gcgtgcactt cctacgcctg atcccccgca tcgcaacctc      60
gcagcttccc cggcgtgcag cgctcattta ccaattccct tcctgggagt tgcggcttcc     120
ctcgctcggc cccactcccg tttacccttt ccccagctcc cgccttagcc aggggcttcc     180
ccgcctgccg ctagggctcg ggccgaagcg ccgctcagcg ccagcctgcc gctcccggg      240 ctccactttc actttcggtc ctgggggagc taggccggcg cagtggtgg tggcggcggc      300 gcaagggtga gggcggcccc agaacccag gtagagcaag aagatggtgt ttctgcccct     360
caaatggtcc cttgcaacca tgtcatttct actttcctca ctgttggctc tcttaactgt     420
gtccactcct tcatggtgtc agagcactga agcatctcca aaacgtagtg atgggacacc     480
atttccttgg aataaaatac gacttcctga gtacgtcatc ccagttcatt atgatctctt     540
gatccatgca aaccttacca cgctgacctt ctggggaacc acgaaagtag aaatcacagc     600
cagtcagccc accagcacca tcatcctgca tagtcaccac ctgcagatat ctagggccac     660
cctcaggaag ggagctggag agaggctatc ggaagaaccc ctgcaggtcc tggaacaccc     720
ccgtcaggag caaattgcac tgctggctcc cgagcccctc cttgtcgggc tcccgtacac     780
agttgtcatt cactatgctg caatctttc ggagactttc acggatttt acaaaagcac     840 ctacagaacc aaggaagggg aactgaggat actagcatca acacaatttg aacccactgc     900
agctagaatg gcctttccct gctttgatga acctgccttc aaagcaagtt tctcaatcaa     960
aattagaaga gagccaaggc acctagccat ctccaatatg ccattggtga atctgtgac    1020 tgttgctgaa ggactcatag aagaccattt tgatgtcact gtgaagatga gcacctatct    1080
ggtggccttc atcatttcag attttgagtc tgtcagcaag ataaccaaga gtggagtcaa    1140
ggtttctgtt tatgctgtgc agacaagat aaatcaagca gattatgcac tggatgctgc    1200
ggtgactctt ctagaatttt atgaggatta tttcagcata ccgtatcccc tacccaaaca    1260
agatcttgct gctattcccg actttcagtc tggtgctatg gaaaactggg gactgacaac    1320
```

```
atatagagaa tctgctctgt tgtttgatgc agaaaagtct tctgcatcaa gtaagcttgg    1380
catcacaatg actgtggccc atgaactggc tcaccagtgg tttgggaacc tggtcactat    1440
ggaatggtgg aatgatcttt ggctaaatga aggatttgcc aaatttatgg agtttgtgtc    1500
tgtcagtgtg acccatcctg aactgaaagt tggagattat ttctttggca atgttttga    1560 cgcaatggag gtagatgctt taaattcctc acaccctgtg tctacacctg tggaaaatcc    1620
tgctcagatc cgggagatgt tgatgatgt ttcttatgat aagggagctt gtattctgaa    1680
tatgctaagg gagtatctta gtgctgacgc atttaaaagt ggtattgtac agtatctcca    1740
gaagcatagc tataaaaata caaaaaacga ggacctgtgg gatagtatgg caagtatttg    1800
ccctacagat ggtgtaaaag ggatggatgg cttttgctct agaagtcaac attcatcttc    1860
atcctcacat tggcatcagg aaggggtgga tgtgaaaacc atgatgaaca cttggacact    1920
gcagaagggt tttccctaa taaccatcac agtgaggggg aggaatgtac acatgaagca    1980
agagcactac atgaagggct ctgacggcgc cccggacact gggtacctgt ggcatgttcc    2040
attgacattc atcaccagca aatccgacat ggtccatcga tttttgctaa aaacaaaaac    2100
agatgtgctc atcctcccag aagaggtgga atggatcaaa tttaatgtgg gcatgaatgg    2160
ctattacatt gtgcattacg aggatgatgg atgggactct ttgactggcc ttttaaaagg    2220
aacacacaca gcagtcagca gtaatgatcg ggcgagtctc attaacaatg catttcagct    2280
cgtcagcatt gggaagctgt ccattgaaaa ggccttggat ttatccctgt acttgaaaca    2340
tgaaactgaa attatgcccg tgtttcaagg tttgaatgag ctgattccta tgtataagtt    2400
aatggagaaa agagatatga atgaagtgga aactcaattc aaggccttcc tcatcaggct    2460
gctaagggac ctcattgata agcagacatg gacagacgag ggctcagtct cagagcgaat    2520
gctgcggagt caactactac tcctcgcctg tgtgcacaac tatcagccgt gcgtacagag    2580
ggcagaaggc tatttcagaa agtggaagga atccaatgga aacttgagcc tgcctgtcga    2640
cgtgaccttg gcagtgtttg ctgtggggc ccagagcaca aaggctggg atttttcttta    2700 tagtaaatat cagttttctt tgtccagtac tgagaaaagc caaattgaat tgccctctg    2760 cagaacccaa aataaggaaa agcttcaatg gctactagat gaaagcttta agggagataa    2820
aataaaaact caggagtttc cacaaattct tacactcatt ggcaggaacc cagtaggata    2880
cccactggcc tggcaatttc tgaggaaaaa ctggaacaaa cttgtacaaa agtttgaact    2940
tggctcatct tccatagccc acatggtaat gggtacaaca aatcaattct ccacaagaac    3000
acggcttgaa gaggtaaaag gattcttcag ctctttgaaa gaaaatggt ctcagctccg    3060 ttgtgtccaa cagacaattg aaaccattga agaaacatc ggttggatgg ataagaattt    3120
tgataaaatc agagtgtggc tgcaaagtga aaagcttgaa catgatcctg aagctgacgc    3180
aacaggatga aaatccatca gaatctcaga ctacagcact aaatatgctt tgatgctaca    3240
tcaaacggaa tggaagcata gctgacttcg ctaaagttac ttcatctcca tctagcaaat    3300
gaggcactgt tctcaaccaa aggagatggg gatctggttt agggcaatcc ctttataatt    3360
tgatgtgctg tggtctcctt ggtaatgtat aatttggtat tgcacaggtg attagtcaag    3420
gaagtctgga aaagctttgg tcccacagcc ttgcctcaca gcatgtaaat aattaaaaca    3480
atattgatgc tgaggttctt ctactgctag tatgaaagtg acaaattttt actggtgtga    3540
attgggaaga aaacaatgct attccatgac gtttgtaaaa tgtttgtaaa agctcaaaca    3600
tgacgattcc ataaaataaa cttgaggtta ataatgggag agtaaattat agaatgtata    3660
agaaaaaata taaggagaaa atcaattat caggaaagct aaagaacttt tcaaatctag    3720
```

```
taatttgaat atagacacaa tgcactttat tgcactttca attcttataa agcaacaata    3780
atattaaggt ccttgactat gtgtacaatg ttttcacata tatagtttca tttaatcatt    3840
tcaaagttaa tctctgccat ctcgctaaat catcagtctc ggctcttctg aaatagaagg    3900
tgcctgatct tcctaataat tctgccatt ttcatttgct ttaaacaggc gccctatttt    3960
ctttctagtt gtggctgcgc aaaaacattt atctcccaaa taagatgtgc tgcttaccga    4020
ggtatcacgg ggtggggctc cagcttgggt cgttgaagct ggggtttggg aaaccacttc    4080
agagatggca gcagcaagtt tagcatcttc aaatttcttt tattgaaaaa aattttatta    4140
gtaacatgtt gtatataaaa ttatgagcac aatgccatca cttaactata actcttaaag    4200
atagcttaat gactgtttat tctcttgacc aaatagactc ataataacat ataattttaa    4260
aagaaattta aattctttct tctctattgt attattttat acaatttgct atttctattt    4320
ccttctcata ttgattattc taaatactat gcaataatat aacttagagt tccacggttt    4380
gtttacacat ttcctgttgt acatttaggt tattcaaagt tttcagctct tttaaaattg    4440
ctctgaataa gttctagtga gtgagttatg gtgctggcta tattttgcta aactgccctc    4500
tcaaatgttg ctaggaattc atactgcgaa aagcaatgaa taagcatgcc tgttttccca    4560
tggccttgct tgccagaatt tgactttat tatgataatc agtgtaaaat gatatactac    4620
tattgcttgt atattgtggt atacggtgtc aggtttcagg gttttttttc aacgttaaat    4680
attctagaaa ctttctgaaa taatttctgt ttaaaaatat tgaatatttg cttcatttca    4740
aatactccct tttgacaaaa aaacttaggt ataactgttg atgaaaaacc agaaaaaagt    4800
ccagaactct ttggtgactc caactatgga tagcttattt tgaaaaagga gaattgcaaa    4860
ttttaccaaa agatggagaa aagcacatta aaaagatacc aacattcaga aattcatttc    4920
agcatgttat tattggaaat tatttaaact aatttagata actataagat acttattgtc    4980
catttatacc ctgtaaagcc gttttagaat gtaatatttt aggtaatcca aaatgtacta    5040
aattaaattc attttagtt atgagaaatc tttgcttata tgacaaatga aagaataac     5100 aagttgtcaa atgaaaagaa tgacattgaa acatttgtat tgtctcttct taaactatct    5160
tattgactta ttatttaagc ctttaatac taagtatgaa acaacctatg gtctggaaat    5220
ttgtatcgca aagctatatg tgcatatgtt atttaattca tctaatgcta cacaaaagca    5280
taaaataatg attttcact ctcttaaaa atactaaatc atttatgtcc atttctcaat    5340
tttttcattg atctatgctt tgagtttgct ttctcaacat tattgtattt tccacttatt    5400
attactgtat aacatatgct agtgtttagt tggattaatc ttacctaaaa gtactgaaaa    5460
atgcttttta gtacttttc atattttata catttatttt ccgaatgtat cattgaataa    5520
ttttattgag ttataaaagt atcttattgc tatttaataa aaaattaaca cataaaatga    5580
aaaaaaaaa                                                            5589
```

<210> SEQ ID NO 44
<211> LENGTH: 5110
<212> TYPE: DNA
<213> ORGANISM: Homo sapiens

<400> SEQUENCE: 44

```
acggatccgc gttcagaaag gcgtgcactt cctacgcctg atccccgca tcgcaacctc      60 gcagcttccc cggcgtgcag cgctcattta ccaattccct tcctgggagt tgcggcttcc    120
ctcgctcggc cccactcccg tttacccttt ccccagctcc cgccttagcc aggggcttcc    180
```

-continued

```
ccgcctgccg ctagggctcg ggccgaagcg ccgctcagcg ccagcctgcc gctccccggg      240
ctccactttc actttcggtc ctggggagc taggccggcg gcagtggtgg tggcggcggc       300
gcaagggtga gggcggcccc agaacccag gtaggtagag caagaagatg gtgtttctgc      360
ccctcaaatg gtcccttgca accatgtcat ttctactttc ctcactgttg gctctcttaa     420
ctgtgtccac tccttcatgg tgtcagagca ctgaagcatc tccaaaacgt agtgatggga     480
caccatttcc ttggaataaa atacgacttc ctgagtacgt catcccagtt cattatgatc     540
tcttgatcca tgcaaacctt accacgctga ccttctgggg aaccacgaaa gtagaaatca     600
cagccagtca gcccaccagc accatcatcc tgcatagtca ccacctgcag atatctaggg     660
ccaccctcag gaagggagct ggagagaggc tatcggaaga acccctgcag gtcctggaac     720
acccccgtca ggagcaaatt gcactgctgg ctcccgagcc cctccttgtc gggctcccgt     780
acacagttgt cattcactat gctggcaatc tttcggagac ttttccacgga ttttacaaaa   840 gcacctacag aaccaaggaa ggggaactga ggatactagc atcaacacaa tttgaaccca     900
ctgcagctag aatggccttt ccctgctttg atgaacctgc cttcaaagca gtttctcaa     960 tcaaaattag aagagagcca aggcacctag ccatctccaa tatgccattg gtgaaatctg    1020
tgactgttgc tgaaggactc atagaagacc atttttgatgt cactgtgaag atgagcacct   1080
atctggtggc cttcatcatt tcagattttg agtctgtcag caagataacc aagagtggag    1140
tcaaggtttc tgtttatgct gtgccagaca agataaatca agcagattat gcactggatg    1200
ctgcggtgac tcttctagaa ttttatgagg attatttcag cataccgtat ccctaccca     1260 aacaagatct tgctgctatt cccgactttc agtctggtgc tatggaaaac tggggactga    1320
caacatatag agaatctgct ctgttgtttg atgcagaaaa gtcttctgca tcaagtaagc    1380
ttggcatcac aatgactgtg gcccatgaac tggctcacca gtggtttggg aacctggtca    1440
ctatggaatg gtggaatgat ctttggctaa atgaaggatt tgccaaattt atggagtttg   1500
tgtctgtcag tgtgacccat cctgaactga agttggaga ttatttcttt ggcaaatgtt    1560
ttgacgcaat ggaggtagat gctttaaatt cctcacaccc tgtgtctaca cctgtggaaa   1620
atcctgctca gatccgggag atgtttgatg atgtttctta tgataaggga gcttgtattc    1680
tgaatatgct aagggagtat cttagtgctg acgcatttaa aagtggtatt gtacagtatc    1740
tccagaagca tagctataaa aatacaaaaa acgaggacct gtgggatagt atggcaagta    1800
tttgccctac agatggtgta aaagggatgg atggcttttg ctctagaagt caacattcat    1860
cttcatcctc acattggcat caggaagggg tggatgtgaa aaccatgatg aacacttgga    1920
cactgcagaa gggtttttccc ctaataacca tcacagtgag ggggaggaat gtacacatga   1980
agcaagagca ctacatgaag ggctctgacg gcgccccgga cactgggtac ctgtggcatg    2040
ttccattgac attcatcacc agcaaatccg acatggtcca tcgattttttg ctaaaaacaa   2100 aaacagatgt gctcatcctc ccagaagagg tggaatggat caaatttaat gtgggcatga    2160
atggctatta cattgtgcat tacgaggatg atggatggga ctctttgact ggccttttaa    2220
aaggaacaca cacagcagtc agcagtaatg atcgggcgag tctcattaac aatgcatttc    2280
agctcgtcag cattgggaag ctgtccattg aaaaggcctt ggatttatcc ctgtacttga    2340
aacatgaaac tgaaattatg cccgtgtttc aaggtttgaa tgagctgatt cctatgtata   2400
agttaatgga gaaaagagat atgaatgaag tggaaactca attcaaggcc ttcctcatca    2460
ggctgctaag ggacctcatt gataagcaga catggacaga cgagggctca gtctcagagc    2520
gaatgctgcg gagtcaacta ctactcctcg cctgtgtgca caactatcag ccgtgcgtac    2580
```

```
agagggcaga aggctatttc agaaagtgga aggaatccaa tggaaacttg agcctgcctg   2640
tcgacgtgac cttggcagtg tttgctgtgg gggcccagag cacagaaggc tgggattttc   2700
tttatagtaa atatcagttt tctttgtcca gtactgagaa aagccaaatt gaatttgccc   2760
tctgcagaac ccaaaataag gaaaagcttc aatggctact agatgaaagc tttaagggag   2820
ataaaataaa aactcaggag tttccacaaa ttcttacact cattggcagg aacccagtag   2880
gatacccact ggcctggcaa tttctgagga aaaactggaa caaacttgta caaaagtttg   2940
aacttggctc atcttccata gcccacatgg taatgggtac aacaaatcaa ttctccacaa   3000
gaacacggct tgaagaggta aaaggattct tcagctcttt gaaagaaaat ggttctcagc   3060
tccgttgtgt ccaacagaca attgaaacca ttgaagaaaa catcggttgg atggataaga   3120
attttgataa aatcagagtg tggctgcaaa gtgaaaagct tgaacgtatg taaaaattcc   3180
tcccttgcca ggttcctgtt atctctaatc accaacattt tgttgagtgt attttcaaac   3240
tagagatggc tgtttggct ccaactggag atactttttt cccttcaact cattttttga   3300
ctatccctgt gaaaagaata gctgttagtt tttcatgaat gggctatcgc taccatgtgt   3360
tttgttcatc acaggtgttg ccctgcaacg taaacccaag tgttgggttc cctgccacag   3420
aagaataaag taccttattc ttctcattt atagtttatg cttaagcacc cgtgtccaaa   3480
accctgtacc ccatgtttat cattcataaa ctgtttcatc agtctcctcg aaagactctg   3540
aatagtcgac tactgaacaa tgaacacctg gatctgagac taagccggac gatgactggg   3600
ttaaagctct cccggctcac ccctccagac ccgctgccca tccctcttcc ttgctccatg   3660 cccagggct gacttgtaaa ggccaagtca tcaagctttc ttgccctttg gatgttggtc   3720
agtggggagc cggagagctg gagctggggt cggaggaggt agtaggtgga ggtgttcttc   3780
cctgattccc ttgcgggatg cctcgggctg gcctcccctg agggtcttag ctccgagagg   3840
ggaccctctt ttccacacag ccttctccac ctctggattt tggtaactgc tccctcctca   3900 tccccttcagg attagtggcc tcagtgggag tctggctttt actagtcctg gcggacttgt   3960
ggtttctaca taatgtgctc gcacttttgc aaaaaatctt tttatagaac cctcctcaga   4020
taattctgag tgagtgtcat ctatttccct gactggtaca gtatctcttc tgaaaaagca   4080
gagtgcattc aagtctgtag gaaaacccctt tcttaggga ggtgattttt tttctctctc   4140
tgcttcttat ttggcctact ttacaatttc taactaacta gttattggca tttactgaca   4200
gtaaattatt gcagtcacca ataaatgata gtacattgtg aaacaaaata tttgctcata   4260
ttagcaaata ggacattctt tggctttgaa gtctttcttt cttttgtgaa gacttcacac   4320
acggttgctt cagcacacag ttgctgctca ggttttatgt atagatgata ataatagaaa   4380
gcacagttta ctaacatggt aaaccaacgg agttcaagtc aagtcagtta ataccctaag   4440
aattagattt tatttcttat tctgaaaact tgctacacag ggacttatct aacccatagt   4500
gtgctctgtt gctgacttga ttcaagttgc agcgtgtttt gcgctgactc taaggtgcgg   4560
aaatcctcac acctggcaaa ggagaattca aactgaactt tttgaatata aggcaaaaac   4620
ttcaagataa gggaatatga ttgatgattg gtacgaaaaa tgtcaaaatg tgttccccta   4680
atacacgaca aaatagagtg acttctggac ataaatctgc catttattaa accattcact   4740
acaacaaata aataggtata aaagtggaat tggaatttt atacttattt gttgtagtga   4800
atggtttaat aaaaatagaa atcactggta atttccaccc caaactaaac tatttcccctt   4860 cttttaaaaa aatacacaac caagattta atgtaaaata ttttgcttta attgtatttt   4920
```

```
                                               -continued atgccttgat taatgaaaca tggaaatatt gattttcagt tttggtcacc tgaggaacct    4980
atctttgttt gcttttggaa aagcccattt tctaaacaga tacaatattg ccacaacaat    5040
gtgcagaaac cttttgata taaaaaatt gttctttgcc tctaaaaaaa aaaaaaaaaa      5100
aaaaaaaaaa                                                           5110

<210> SEQ ID NO 45
<211> LENGTH: 941
<212> TYPE: PRT
<213> ORGANISM: Homo sapiens

<400> SEQUENCE: 45

Met Val Phe Leu Pro Leu Lys Trp Ser Leu Ala Thr Met Ser Phe Leu
1               5                   10                  15

Leu Ser Ser Leu Leu Ala Leu Leu Thr Val Ser Thr Pro Ser Trp Cys
            20                  25                  30

Gln Ser Thr Glu Ala Ser Pro Lys Arg Ser Asp Gly Thr Pro Phe Pro
        35                  40                  45

Trp Asn Lys Ile Arg Leu Pro Glu Tyr Val Ile Pro Val His Tyr Asp
    50                  55                  60

Leu Leu Ile His Ala Asn Leu Thr Thr Leu Thr Phe Trp Gly Thr Thr
65                  70                  75                  80

Lys Val Glu Ile Thr Ala Ser Gln Pro Thr Ser Thr Ile Ile Leu His
                85                  90                  95

Ser His His Leu Gln Ile Ser Arg Ala Thr Leu Arg Lys Gly Ala Gly
            100                 105                 110

Glu Arg Leu Ser Glu Glu Pro Leu Gln Val Leu Glu His Pro Arg Gln
        115                 120                 125

Glu Gln Ile Ala Leu Leu Ala Pro Glu Pro Leu Leu Val Gly Leu Pro
    130                 135                 140

Tyr Thr Val Val Ile His Tyr Ala Gly Asn Leu Ser Glu Thr Phe His
145                 150                 155                 160

Gly Phe Tyr Lys Ser Thr Tyr Arg Thr Lys Glu Gly Glu Leu Arg Ile
                165                 170                 175

Leu Ala Ser Thr Gln Phe Glu Pro Thr Ala Ala Arg Met Ala Phe Pro
            180                 185                 190

Cys Phe Asp Glu Pro Ala Phe Lys Ala Ser Phe Ser Ile Lys Ile Arg
        195                 200                 205

Arg Glu Pro Arg His Leu Ala Ile Ser Asn Met Pro Leu Val Lys Ser
    210                 215                 220

Val Thr Val Ala Glu Gly Leu Ile Glu Asp His Phe Asp Val Thr Val
225                 230                 235                 240

Lys Met Ser Thr Tyr Leu Val Ala Phe Ile Ile Ser Asp Phe Glu Ser
                245                 250                 255

Val Ser Lys Ile Thr Lys Ser Gly Val Lys Val Ser Val Tyr Ala Val
            260                 265                 270

Pro Asp Lys Ile Asn Gln Ala Asp Tyr Ala Leu Asp Ala Ala Val Thr
        275                 280                 285

Leu Leu Glu Phe Tyr Glu Asp Tyr Phe Ser Ile Pro Tyr Pro Leu Pro
    290                 295                 300

Lys Gln Asp Leu Ala Ala Ile Pro Asp Phe Gln Ser Gly Ala Met Glu
305                 310                 315                 320

Asn Trp Gly Leu Thr Thr Tyr Arg Glu Ser Ala Leu Leu Phe Asp Ala
                325                 330                 335
```

-continued

```
Glu Lys Ser Ser Ala Ser Ser Lys Leu Gly Ile Thr Met Thr Val Ala
                340                 345                 350

His Glu Leu Ala His Gln Trp Phe Gly Asn Leu Val Thr Met Glu Trp
        355                 360                 365

Trp Asn Asp Leu Trp Leu Asn Glu Gly Phe Ala Lys Phe Met Glu Phe
    370                 375                 380

Val Ser Val Ser Val Thr His Pro Glu Leu Lys Val Gly Asp Tyr Phe
385                 390                 395                 400

Phe Gly Lys Cys Phe Asp Ala Met Glu Val Asp Ala Leu Asn Ser Ser
                405                 410                 415

His Pro Val Ser Thr Pro Val Glu Asn Pro Ala Gln Ile Arg Glu Met
            420                 425                 430

Phe Asp Asp Val Ser Tyr Asp Lys Gly Ala Cys Ile Leu Asn Met Leu
        435                 440                 445

Arg Glu Tyr Leu Ser Ala Asp Ala Phe Lys Ser Gly Ile Val Gln Tyr
    450                 455                 460

Leu Gln Lys His Ser Tyr Lys Asn Thr Lys Asn Glu Asp Leu Trp Asp
465                 470                 475                 480

Ser Met Ala Ser Ile Cys Pro Thr Asp Gly Val Lys Gly Met Asp Gly
                485                 490                 495

Phe Cys Ser Arg Ser Gln His Ser Ser Ser Ser His Trp His Gln
            500                 505                 510

Glu Gly Val Asp Val Lys Thr Met Met Asn Thr Trp Thr Leu Gln Lys
        515                 520                 525

Gly Phe Pro Leu Ile Thr Ile Thr Val Arg Gly Arg Asn Val His Met
530                 535                 540

Lys Gln Glu His Tyr Met Lys Gly Ser Asp Gly Ala Pro Asp Thr Gly
545                 550                 555                 560

Tyr Leu Trp His Val Pro Leu Thr Phe Ile Thr Ser Lys Ser Asp Met
                565                 570                 575

Val His Arg Phe Leu Leu Lys Thr Lys Thr Asp Val Leu Ile Leu Pro
            580                 585                 590

Glu Glu Val Glu Trp Ile Lys Phe Asn Val Gly Met Asn Gly Tyr Tyr
        595                 600                 605

Ile Val His Tyr Glu Asp Asp Gly Trp Asp Ser Leu Thr Gly Leu Leu
    610                 615                 620

Lys Gly Thr His Thr Ala Val Ser Ser Asn Asp Arg Ala Ser Leu Ile
625                 630                 635                 640

Asn Asn Ala Phe Gln Leu Val Ser Ile Gly Lys Leu Ser Ile Glu Lys
                645                 650                 655

Ala Leu Asp Leu Ser Leu Tyr Leu Lys His Glu Thr Glu Ile Met Pro
            660                 665                 670

Val Phe Gln Gly Leu Asn Glu Leu Ile Pro Met Tyr Lys Leu Met Glu
        675                 680                 685

Lys Arg Asp Met Asn Glu Val Glu Thr Gln Phe Lys Ala Phe Leu Ile
    690                 695                 700

Arg Leu Leu Arg Asp Leu Ile Asp Lys Gln Thr Trp Thr Asp Glu Gly
705                 710                 715                 720

Ser Val Ser Glu Arg Met Leu Arg Ser Gln Leu Leu Leu Leu Ala Cys
                725                 730                 735

Val His Asn Tyr Gln Pro Cys Val Gln Arg Ala Glu Gly Tyr Phe Arg
            740                 745                 750

Lys Trp Lys Glu Ser Asn Gly Asn Leu Ser Leu Pro Val Asp Val Thr
```

|  |  |  |  | 755 |  |  |  |  | 760 |  |  |  |  | 765 |  |
|--|--|--|--|--|--|--|--|--|--|--|--|--|--|--|--|

Leu Ala Val Phe Ala Val Gly Ala Gln Ser Thr Glu Gly Trp Asp Phe
 770                 775                 780

Leu Tyr Ser Lys Tyr Gln Phe Ser Leu Ser Ser Thr Glu Lys Ser Gln
785                 790                 795                 800

Ile Glu Phe Ala Leu Cys Arg Thr Gln Asn Lys Glu Lys Leu Gln Trp
                805                 810                 815

Leu Leu Asp Glu Ser Phe Lys Gly Asp Lys Ile Lys Thr Gln Glu Phe
            820                 825                 830

Pro Gln Ile Leu Thr Leu Ile Gly Arg Asn Pro Val Gly Tyr Pro Leu
        835                 840                 845

Ala Trp Gln Phe Leu Arg Lys Asn Trp Asn Lys Leu Val Gln Lys Phe
    850                 855                 860

Glu Leu Gly Ser Ser Ser Ile Ala His Met Val Met Gly Thr Thr Asn
865                 870                 875                 880

Gln Phe Ser Thr Arg Thr Arg Leu Glu Glu Val Lys Gly Phe Phe Ser
                885                 890                 895

Ser Leu Lys Glu Asn Gly Ser Gln Leu Arg Cys Val Gln Gln Thr Ile
            900                 905                 910

Glu Thr Ile Glu Glu Asn Ile Gly Trp Met Asp Lys Asn Phe Asp Lys
        915                 920                 925

Ile Arg Val Trp Leu Gln Ser Glu Lys Leu Glu Arg Met
    930                 935                 940

<210> SEQ ID NO 46
<211> LENGTH: 4868
<212> TYPE: DNA
<213> ORGANISM: Homo sapiens

<400> SEQUENCE: 46

```
ccttccttc tgctgggcct caggtgagac tgcagctcca gtcatcatct tgattgcagc      60
ccacagaaac taccaaccca cagaaactgt aggtagagca agaagatggt gtttctgccc    120
ctcaaatggt cccttgcaac catgtcattt ctactttcct cactgttggc tctcttaact    180
gtgtccactc cttcatggtg tcagagcact gaagcatctc caaaacgtag tgatgggaca    240
ccatttcctt ggaataaaat acgacttcct gagtacgtca tcccagttca ttatgatctc    300
ttgatccatg caaaccttac cacgctgacc ttctggggaa ccacgaaagt agaaatcaca    360
gccagtcagc ccaccagcac catcatcctg catagtcacc acctgcagat atctagggcc    420
accctcagga agggagctgg agagaggcta tcggaagaac ccctgcaggt cctggaacac    480
ccccgtcagg agcaaattgc actgctggct cccgagcccc tccttgtcgg gctcccgtac    540
acagttgtca ttcactatgc tggcaatctt tcggagactt ccacggatt ttacaaaagc    600
acctacagaa ccaaggaagg ggaactgagg atactagcat caacacaatt tgaacccact    660
gcagctagaa tggcctttcc ctgctttgat gaacctgcct tcaaagcaag tttctcaatc    720
aaaattagaa gagagccaag gcacctagcc atctccaata tgccattggt gaaatctgtg    780
actgttgctg aaggactcat agaagaccat tttgatgtca ctgtgaagat gagcacctat    840
ctggtggcct tcatcatttc agattttgag tctgtcagca agataaccaa gagtggagtc    900
aaggtttctg tttatgctgt gccagacaag ataaatcaag cagattatgc actggatgct    960
gcggtgactc ttctagaatt ttatgaggat tatttcagca taccgtatcc cctacccaaa   1020
caagatcttg ctgctattcc cgactttcag tctggtgcta tggaaaactg gggactgaca   1080
```

-continued

```
acatatagag aatctgctct gttgtttgat gcagaaaagt cttctgcatc aagtaagctt      1140
ggcatcacaa tgactgtggc ccatgaactg gctcaccagt ggtttgggaa cctggtcact      1200
atggaatggt ggaatgatct ttggctaaat gaaggatttg ccaaatttat ggagtttgtg      1260
tctgtcagtg tgacccatcc tgaactgaaa gttggagatt atttctttgg caaatgtttt      1320
gacgcaatgg aggtagatgc tttaaattcc tcacaccctg tgtctacacc tgtggaaaat      1380
cctgctcaga tccgggagat gttttgatgat gtttcttatg ataagggagc ttgtattctg      1440
aatatgctaa gggagtatct tagtgctgac gcatttaaaa gtggtattgt acagtatctc      1500
cagaagcata gctataaaaa tacaaaaaac gaggacctgt gggatagtat ggcaagtatt      1560
tgccctacag atggtgtaaa agggatggat ggcttttgct ctagaagtca acattcatct      1620
tcatcctcac attggcatca ggaaggggtg gatgtgaaaa ccatgatgaa cacttggaca      1680
ctgcagaagg gttttcccct aataaccatc acagtgaggg ggaggaatgt acacatgaag      1740
caagagcact acatgaaggg ctctgacggc gccccggaca ctgggtacct gtggcatgtt      1800
ccattgacat tcatcaccag caaatccgac atggtccatc gattttttgct aaaaacaaaa      1860 acagatgtgc tcatcctccc agaagaggtg gaatggatca aatttaatgt gggcatgaat      1920
ggctattaca ttgtgcatta cgaggatgat ggatgggact ctttgactgg ccttttaaaa      1980
ggaacacaca cagcagtcag cagtaatgat cgggcgagtc tcattaacaa tgcatttcag      2040
ctcgtcagca ttgggaagct gtccattgaa aaggccttgg atttatccct gtacttgaaa      2100
catgaaactg aaattatgcc cgtgtttcaa ggtttgaatg agctgattcc tatgtataag      2160
ttaatggaga aagagatat gaatgaagtg gaaactcaat tcaaggcctt cctcatcagg      2220
ctgctaaggg acctcattga taagcagaca tggacagacg agggctcagt ctcagagcga      2280
atgctgcgga gtcaactact actcctcgcc tgtgtgcaca actatcagcc gtgcgtacag      2340
agggcagaag gctatttcag aaagtggaag gaatccaatg gaaacttgag cctgcctgtc      2400
gacgtgacct tggcagtgtt tgctgtgggg gcccagagca cagaaggctg ggattttctt      2460
tatagtaaat atcagttttc tttgtccagt actgagaaaa gccaaattga atttgccctc      2520
tgcagaaccc aaaataagga aaagcttcaa tggctactag atgaaagctt taagggagat      2580
aaaataaaaa ctcaggagtt tccacaaatt cttacactca ttggcaggaa cccagtagga      2640
tacccactgg cctggcaatt tctgaggaaa aactggaaca aacttgtaca aaagtttgaa      2700
cttggctcat cttccatagc ccacatggta atgggtacaa caaatcaatt ctccacaaga      2760
acacggcttg aagaggtaaa aggattcttc agctctttga agaaaatgg ttctcagctc      2820 cgttgtgtcc aacagacaat tgaaaccatt gaagaaaaca tcggttggat ggataagaat      2880
tttgataaaa tcagagtgtg gctgcaaagt gaaaagcttg aacgtatgta aaaattcctc      2940
ccttgccagg ttcctgttat ctctaatcac caacattttg ttgagtgtat tttcaaacta      3000
gagatggctg ttttggctcc aactggagat acttttttcc cttcaactca ttttttgact      3060
atccctgtga aaagaatagc tgttagtttt tcatgaatgg ctatcgcta ccatgtgttt      3120 tgttcatcac aggtgttgcc ctgcaacgta aacccaagtg ttgggttccc tgccacagaa      3180
gaataaagta cctattctt tcatttttat agtttatgct taagcacccg tgtccaaaac      3240
cctgtacccc atgtttatca ttcataaact gtttcatcag tctcctcgaa agactctgaa      3300
tagtcgacta ctgaacaatg aacacctgga tctgagacta agccggacga tgactgggtt      3360
aaagctctcc cggctcaccc ctccagaccc gctgcccatc cctcttcctt gctccatgcc      3420
caggggctga cttgtaaagg ccaagtcatc aagctttctt gcccttttgga tgttggtcag      3480
```

```
tggggagccg gagagctgga gctggggtcg gaggaggtag taggtggagg tgttcttccc    3540
tgattcccct tgcgggatgcc tcgggctggc ctcccctgag ggtcttagct ccagagggg     3600 accctctttt ccacacagcc ttctccacct ctggattttg gtaactgctc cctcctcatc    3660
ccttcaggat tagtggcctc agtgggagtc tggcttttac tagtcctggc ggacttgtgg    3720
tttctacata atgtgctcgc acttttgcaa aaaatctttt tatagaaccc tcctcagata    3780
attctgagtg agtgtcatct atttccctga ctggtacagt atctcttctg aaaaagcaga    3840
gtgcattcaa gtctgtagga aaaccctttt cttagggagg tgatttttt  tctctctctg    3900 cttcttattt ggcctacttt acaatttcta actaactagt tattggcatt tactgacagt    3960
aaattattgc agtcaccaat aaatgatagt acattgtgaa acaaaatatt tgctcatatt    4020
agcaaatagg acattctttg ctttgaagt  cttttctttct tttgtgaaga cttcacacac    4080
ggttgcttca gcacacagtt gctgctcagg ttttatgtat agatgataat aatagaaagc    4140
acagtttact aacatggtaa accaacggag ttcaagtcaa gtcagttaat accctaagaa    4200 ttagattta  tttcttattc tgaaaacttg ctacacaggg acttatctaa cccatagtgt    4260
gctctgttgc tgacttgatt caagttgcag cgtgttttgc gctgactcta aggtgcggaa    4320
atcctcacac ctggcaaagg agaattcaaa ctgaactttt tgaatataag gcaaaaactt    4380
caagataagg gaatatgatt gatgattggt acgaaaaatg tcaaaatgtg ttcccctaat    4440
acacgacaaa atagagtgac ttctggacat aaatctgcca tttattaaac cattcactac    4500
aacaaataaa taggtataaa agtggaattg gaattttttat acttatttgt tgtagtgaat    4560
ggtttaataa aaatagaaat cactggtaat ttccacccca aactaaacta tttcccttct    4620
tttaaaaaaa tacacaacca agattttaat gtaaatatt  ttgctttaat tgtatttat     4680 gccttgatta atgaaacatg gaaatattga ttttcagttt tggtcacctg aggaacctat    4740
ctttgtttgc ttttggaaaa gcccattttc taaacagata caatattgcc acaacaatgt    4800
gcagaaacct ttttgataat aaaaaattgt tctttgcctc taaaaaaaaa aaaaaaaaaa    4860
aaaaaaaa                                                              4868
```

<210> SEQ ID NO 47
<211> LENGTH: 4014
<212> TYPE: DNA
<213> ORGANISM: Mus musculus

<400> SEQUENCE: 47

```
cagactggcg gctgtgatga aggtaatttg agcaagaaga tagtgtctct gctcctcaaa     60
tagccacttg caagcatgcc ctctcttctt cccctagtat tgacattttt atctgtgtca    120
tctccttctt ggtgtcagaa cagtgatata gaatctctaa aagctagtaa tggagactca    180
ttcccttgga ataatatgcg acttcctgag tatatgaccc cgattcatta tgatctcatg    240
atccatgcaa acctcagcac tctgactttc tggggaaaaa cagaagtaga aatcatagct    300
agccggccca ccagcaccat tattatgcat agtcaccacc tgcaaatatc taaggccacc    360
ctcagaagag gagctggaga gatgctgtct gaagaaccac tgaaggtcct ggaatatcct    420
gctcatgagc aagttgcact gctggctgcc cagccgcttc ttgctgggtc cctgtacaca    480
gttatcatcg actatgctgc caacctgtct gagagtttcc atggattcta taagagcacc    540
tacagaacac aggaaggtga aatgagaata cttgcagcaa cacagtttga acccacagct    600
gctagaatgg cttttccctg ctttgatgaa cctgccctca ggcaagtttt ttccatcaag    660
```

```
ataaagaggg atccaaggca cctggccatc tccaacatgc ccctggtgaa atctgtgaat    720
gttgctgaag gactcataga agaccatttt gacatcactg tgaagatgag tacctaccta    780
gtggccttca tcatttctga ttttaagtct gtgagcaaga tgactaagag tggagtcaag    840
gtttctgtgt atgctgtgcc agacaagata aatcaagccg attatgctct ggatgctgca    900
gtgactcttc tagagtttta tgaggattat ttcaacattc catatccttt acccaagcaa    960
gatcttgctg caatcccaga ctttcagtct ggtgctatgg aaaactgggg actgaccaca   1020
tacagagagt cctctctgtt atacgataaa gaaaagtctt ctgcatctag taagcttggc   1080
atcacaatga ttgtgtccca tgaactggct caccagtggt tcgggaacct ggtcaccatg   1140
gaatggtgga atgacctttg gctcaatgaa ggatttgcca aatttatgga gtttgtgtct   1200
gtcactgtga cccatcctga actaaaagtt gaagactatt tctttggcaa gtgttttaat   1260
gcaatggaag ttgatgcatt aaactcctct caccctgtat ccacacctgt ggagaatcct   1320
gcgcagattc gggagatgtt tgatgatgtt tcttatgaaa agggagcttg tattctgaat   1380
atgctaagag attatctgag tgcagataca tttaaaagag gaattgtaca gtatctccaa   1440
aagtatagtt ataaaaacac aaaaaacgag gacctgtgga atagcatgat gcatatttgc   1500
cctacagatg gcacacaaac aatggatggc ttctgctcta gaagccaaca ctcatcatca   1560
acctcacact ggcgtcagga ggttgtagat gtaaagacca tgatgaacac atggacactg   1620
cagaagggct ttcctctgat aaccatcact gtgagtgggc ggaatgtgca catgaagcaa   1680
gaacactaca tgaagggttc agaacgcttc ccagagactg ggtatttgtg gcatgttcca   1740
ctgacattca ttaccagcaa atcagactca gtccagagat ttttgctgaa gacaaagaca   1800
gatgtgctca tcctcccaga agcagtgcag tggatcaaat ttaacgtggg aatgaatggc   1860
tattacattg tgcattacgc ggatgatgga tgggcttctc tgagtggcct tttaaaagaa   1920
gcgcacacaa caatcagcag taatgatcgg gcaagtctca tcaacaatgc atttcagctg   1980
gtcagcattg aaaagttatc aatagaaaaa gccctggatt taaccctgta cttgaaaaat   2040
gaaactgaaa ttatgcccat attccaagct ttgaatgaac tcatacctat gtataagtta   2100
atggagaaaa gagatatgat tgaggtggaa actcaattta aggacttcct tctcaagttg   2160
ctgaaggacc ttattgataa gcagacttgg acagatgaag gctctgtctc agagaggatg   2220
ctcaggagcc agctcctcct cctcgcatgt gtgcgcaatt atcagccctg tgtgcagagg   2280
gcagagcgct atttcagaga gtggaagtca tctaatggaa acatgagcat ccctattgat   2340
gtgaccttgg ctgtgtttgc tgtcgggggcc caaaacacag aaggctggga ttttctttat   2400
agtaaatatc agtcttcttt gtctagtact gagaaaagcc aaattgaatt ttccctctgt   2460
acaagcaaag atccagaaaa acttcagtgg cttctagatc aaagtttaa gggagagata   2520 ataaaaactc aggaatttcc acatattctc acactcattg gcagaaaccc agtgggttat   2580
ccattggcct ggaagtttct gagggaaaat tggaataagc ttgtacagaa atttgaactt   2640
ggctcatcgt ccatagctca catggtaatg ggaacaacag accagttttc caccagagca   2700
cgtcttgaag aggtaaaagg attcttcagt tccttgaaag aaaacggttc tcagctccgt   2760
tgtgttcaac aaaccattga gaccattgaa gaaaacatac gatggatgga taagaatttt   2820
gataaaataa gactgtggct gcaaaaagaa aagccagagt tgctgtgaca atatgtttct   2880
tgccaagttc cagaatttat gatgagcaaa attttgttca atttgagtat ttttaaacta   2940
aagatagttg ttttggctac tactgaagat attttcttat ttcatttcac ttgattatgt   3000
ctgagaaaag cttcaatgac tgtgattgac aggtttaaac ccaagtgccc agctccttgc   3060
```

-continued

```
cacagaaaaa cccagggggc ttcttctcag tttatacttc agcttctgtg tcggccattc   3120
atcagtattt ttgtaagact gaatagtgag gcataactgt gcagtgaatg cttggctcct   3180
tagccatgct gggaagtggc tgtgcagcag ccctcctgtt gacctctctg gctctacagt   3240
cctgcagtct ctcttcctgg gttcactat gggtgctgcc ttgcaggatc cacttaatca   3300 gacactttg ccctctggat tttgttaata gtgtttggta gttgttatcc atgagggatt   3360
gcatagaggt gtttattttc ttgtacttgc ctctggctgg ctttcaacca ccgtaagtct   3420
tactcctaag aggtggcctt tccccccccc ccccccccgc actctgataa ctacttcctt   3480
ttcatccttt ggggcatggg gcaacagtgg aaacctgctg ataccagtca tggtagtact   3540
tgtcattttc actgaaccta cgtgcacatt tgtttttaaa aatattgtat atctataacc   3600
ctcgttggat aagtcaaata tgagagccac ttactttctt tggaaggtta tttttaaaaa   3660
tgcagagtgc attcagatct gtatcagaaa tatctcgttt taagatatac ttgtgagtca   3720
ctgatccctt aagtagggag tagggttgta aattcctaaa taactcataa tagcacttac   3780
tgaaaataaa tcattgagga ctcactaaca aaggacaata ttaataatat gtttatatta   3840
gtataaggaa agattccttta aatcttaaaa agatttttttt gatgtatggc ataaatgata   3900
ggaaaaatat caacatatgg tgctgtaata tactatgaaa taaagcgatt ttaggggttc   3960
aattatattt tcactggcct accaaaatac ttgagattaa atgaggaaag attt         4014
```

```
<210> SEQ ID NO 48
<211> LENGTH: 930
<212> TYPE: PRT
<213> ORGANISM: Mus musculus

<400> SEQUENCE: 48
```

```
Met Pro Ser Leu Leu Pro Leu Val Leu Thr Phe Leu Ser Val Ser Ser
 1               5                   10                  15

Pro Ser Trp Cys Gln Asn Ser Asp Ile Glu Ser Leu Lys Ala Ser Asn
            20                  25                  30

Gly Asp Ser Phe Pro Trp Asn Asn Met Arg Leu Pro Glu Tyr Met Thr
        35                  40                  45

Pro Ile His Tyr Asp Leu Met Ile His Ala Asn Leu Ser Thr Leu Thr
    50                  55                  60

Phe Trp Gly Lys Thr Glu Val Glu Ile Ile Ala Ser Arg Pro Thr Ser
65                  70                  75                  80

Thr Ile Ile Met His Ser His His Leu Gln Ile Ser Lys Ala Thr Leu
                85                  90                  95

Arg Arg Gly Ala Gly Glu Met Leu Ser Glu Pro Leu Lys Val Leu
            100                 105                 110

Glu Tyr Pro Ala His Glu Gln Val Ala Leu Leu Ala Ala Gln Pro Leu
        115                 120                 125

Leu Ala Gly Ser Leu Tyr Thr Val Ile Asp Tyr Ala Ala Asn Leu
    130                 135                 140

Ser Glu Ser Phe His Gly Phe Tyr Lys Ser Thr Tyr Arg Thr Gln Glu
145                 150                 155                 160

Gly Glu Met Arg Ile Leu Ala Ala Thr Gln Phe Glu Pro Thr Ala Ala
                165                 170                 175

Arg Met Ala Phe Pro Cys Phe Asp Glu Pro Ala Leu Lys Ala Ser Phe
            180                 185                 190

Ser Ile Lys Ile Lys Arg Asp Pro Arg His Leu Ala Ile Ser Asn Met
        195                 200                 205
```

```
Pro Leu Val Lys Ser Val Asn Val Ala Glu Gly Leu Ile Glu Asp His
    210                 215                 220

Phe Asp Ile Thr Val Lys Met Ser Thr Tyr Leu Val Ala Phe Ile Ile
225                 230                 235                 240

Ser Asp Phe Lys Ser Val Ser Lys Met Thr Lys Ser Gly Val Lys Val
                245                 250                 255

Ser Val Tyr Ala Val Pro Asp Lys Ile Asn Gln Ala Asp Tyr Ala Leu
            260                 265                 270

Asp Ala Ala Val Thr Leu Leu Glu Phe Tyr Glu Asp Tyr Phe Asn Ile
        275                 280                 285

Pro Tyr Pro Leu Pro Lys Gln Asp Leu Ala Ala Ile Pro Asp Phe Gln
    290                 295                 300

Ser Gly Ala Met Glu Asn Trp Gly Leu Thr Thr Tyr Arg Glu Ser Ser
305                 310                 315                 320

Leu Leu Tyr Asp Lys Glu Lys Ser Ser Ala Ser Ser Lys Leu Gly Ile
                325                 330                 335

Thr Met Ile Val Ser His Glu Leu Ala His Gln Trp Phe Gly Asn Leu
            340                 345                 350

Val Thr Met Glu Trp Trp Asn Asp Leu Trp Leu Asn Glu Gly Phe Ala
        355                 360                 365

Lys Phe Met Glu Phe Val Ser Val Thr Val Thr His Pro Glu Leu Lys
    370                 375                 380

Val Glu Asp Tyr Phe Phe Gly Lys Cys Phe Asn Ala Met Glu Val Asp
385                 390                 395                 400

Ala Leu Asn Ser Ser His Pro Val Ser Thr Pro Val Glu Asn Pro Ala
                405                 410                 415

Gln Ile Arg Glu Met Phe Asp Asp Val Ser Tyr Glu Lys Gly Ala Cys
            420                 425                 430

Ile Leu Asn Met Leu Arg Asp Tyr Leu Ser Ala Asp Thr Phe Lys Arg
        435                 440                 445

Gly Ile Val Gln Tyr Leu Gln Lys Tyr Ser Tyr Lys Asn Thr Lys Asn
    450                 455                 460

Glu Asp Leu Trp Asn Ser Met Met His Ile Cys Pro Thr Asp Gly Thr
465                 470                 475                 480

Gln Thr Met Asp Gly Phe Cys Ser Arg Ser Gln His Ser Ser Ser Thr
                485                 490                 495

Ser His Trp Arg Gln Glu Val Val Asp Val Lys Thr Met Met Asn Thr
            500                 505                 510

Trp Thr Leu Gln Lys Gly Phe Pro Leu Ile Thr Ile Thr Val Ser Gly
        515                 520                 525

Arg Asn Val His Met Lys Gln Glu His Tyr Met Lys Gly Ser Glu Arg
    530                 535                 540

Phe Pro Glu Thr Gly Tyr Leu Trp His Val Pro Leu Thr Phe Ile Thr
545                 550                 555                 560

Ser Lys Ser Asp Ser Val Gln Arg Phe Leu Leu Lys Thr Lys Thr Asp
                565                 570                 575

Val Leu Ile Leu Pro Glu Ala Val Gln Trp Ile Lys Phe Asn Val Gly
            580                 585                 590

Met Asn Gly Tyr Tyr Ile Val His Tyr Ala Asp Asp Gly Trp Ala Ser
        595                 600                 605

Leu Ser Gly Leu Leu Lys Glu Ala His Thr Thr Ile Ser Ser Asn Asp
    610                 615                 620
```

```
Arg Ala Ser Leu Ile Asn Asn Ala Phe Gln Leu Val Ser Ile Glu Lys
625                 630                 635                 640

Leu Ser Ile Glu Lys Ala Leu Asp Leu Thr Leu Tyr Leu Lys Asn Glu
            645                 650                 655

Thr Glu Ile Met Pro Ile Phe Gln Ala Leu Asn Glu Leu Ile Pro Met
                660                 665                 670

Tyr Lys Leu Met Glu Lys Arg Asp Met Ile Glu Val Glu Thr Gln Phe
            675                 680                 685

Lys Asp Phe Leu Leu Lys Leu Lys Asp Leu Ile Asp Lys Gln Thr
690                 695                 700

Trp Thr Asp Glu Gly Ser Val Ser Glu Arg Met Leu Arg Ser Gln Leu
705                 710                 715                 720

Leu Leu Leu Ala Cys Val Arg Asn Tyr Gln Pro Cys Val Gln Arg Ala
            725                 730                 735

Glu Arg Tyr Phe Arg Glu Trp Lys Ser Ser Asn Gly Asn Met Ser Ile
                740                 745                 750

Pro Ile Asp Val Thr Leu Ala Val Phe Ala Val Gly Ala Gln Asn Thr
            755                 760                 765

Glu Gly Trp Asp Phe Leu Tyr Ser Lys Tyr Gln Ser Ser Leu Ser Ser
770                 775                 780

Thr Glu Lys Ser Gln Ile Glu Phe Ser Leu Cys Thr Ser Lys Asp Pro
785                 790                 795                 800

Glu Lys Leu Gln Trp Leu Leu Asp Gln Ser Phe Lys Gly Glu Ile Ile
            805                 810                 815

Lys Thr Gln Glu Phe Pro His Ile Leu Thr Leu Ile Gly Arg Asn Pro
            820                 825                 830

Val Gly Tyr Pro Leu Ala Trp Lys Phe Leu Arg Glu Asn Trp Asn Lys
            835                 840                 845

Leu Val Gln Lys Phe Glu Leu Gly Ser Ser Ile Ala His Met Val
850                 855                 860

Met Gly Thr Thr Asp Gln Phe Ser Thr Arg Ala Arg Leu Glu Glu Val
865                 870                 875                 880

Lys Gly Phe Phe Ser Ser Leu Lys Glu Asn Gly Ser Gln Leu Arg Cys
            885                 890                 895

Val Gln Gln Thr Ile Glu Thr Ile Glu Glu Asn Ile Arg Trp Met Asp
            900                 905                 910

Lys Asn Phe Asp Lys Ile Arg Leu Trp Leu Gln Lys Glu Lys Pro Glu
            915                 920                 925

Leu Leu
    930

<210> SEQ ID NO 49
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 49
gcctgctgtc acttgctacg                                              20

<210> SEQ ID NO 50
<211> LENGTH: 20
<212> TYPE: DNA
<213> ORGANISM: Artificial Sequence
<220> FEATURE:
```

```
<223> OTHER INFORMATION: /note="Description of Artificial Sequence:
      Synthetic sgRNA targeting sequence"

<400> SEQUENCE: 50
aatcaaccag agaatttccg                                              20

<210> SEQ ID NO 51
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 51
ggtccagctc ccgttctaca                                              20

<210> SEQ ID NO 52
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 52
gtatggcagc aacgtcacga                                              20

<210> SEQ ID NO 53
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 53
tatagagctg aaaaaccgca                                              20

<210> SEQ ID NO 54
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 54
ccacattacg gacgatgcaa                                              20

<210> SEQ ID NO 55
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 55
tcttacgagg aggagaaagg                                              20

<210> SEQ ID NO 56
<211> LENGTH: 20
<212> TYPE: DNA
<213> ORGANISM: Artificial Sequence
<220> FEATURE:
<223> OTHER INFORMATION: /note="Description of Artificial Sequence:
```

-continued

Synthetic sgRNA targeting sequence"

<400> SEQUENCE: 56
gcaagtgtag tttcccacca                                            20

<210> SEQ ID NO 57
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 57
gcgaggtatt cggctccgcg                                            20

<210> SEQ ID NO 58
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 58
gctttcacgg aggttcgacg                                            20

<210> SEQ ID NO 59
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 59
atgttgcagt tcggctcgat                                            20

<210> SEQ ID NO 60
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 60
acgtgtaagg cgaacgcctt                                            20

<210> SEQ ID NO 61
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 61
attgttcgac cgtctacggg                                            20

<210> SEQ ID NO 62
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

```
<400> SEQUENCE: 62
tagccgacaa tgatgaaccg                                                    20

<210> SEQ ID NO 63
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 63
aggcctcctg acaatacccg                                                    20

<210> SEQ ID NO 64
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 64
ggaacttcag agtaaacctg                                                    20

<210> SEQ ID NO 65
<211> LENGTH: 8
<212> TYPE: PRT
<213> ORGANISM: Artificial Sequence
<220> FEATURE:
<223> OTHER INFORMATION: /note="Description of Artificial Sequence: OVA
      epitope peptide sequence"

<400> SEQUENCE: 65

Ser Ile Ile Asn Phe Glu Lys Leu
1               5
```